United States Patent
Bärfacker et al.

(10) Patent No.: US 9,682,995 B2
(45) Date of Patent: Jun. 20, 2017

(54) AMINO-SUBSTITUTED ISOTHIAZOLES

(71) Applicant: BAYER PHARMA AKTIENGESELLSCHAFT, Berlin (DE)

(72) Inventors: Lars Bärfacker, Düsseldorf (DE); Stefan Prechtl, Berlin (DE); Gerhard Siemeister, Berlin (DE); Antje Margret Wengner, Berlin (DE); Jens Ackerstaff, Düsseldorf (DE); Katrin Nowak-Reppel, Berlin (DE); Benjamin Bader, Berlin (DE); Philip Lienau, Berlin (DE); Detlef Stöckigt, Potsdam (DE); Tobias Heinrich, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/764,853

(22) PCT Filed: Jan. 28, 2014

(86) PCT No.: PCT/EP2014/051642
§ 371 (c)(1),
(2) Date: Jul. 30, 2015

(87) PCT Pub. No.: WO2014/118186
PCT Pub. Date: Aug. 7, 2014

(65) Prior Publication Data
US 2015/0368260 A1    Dec. 24, 2015

(30) Foreign Application Priority Data

Jan. 30, 2013 (EP) .................................. 13153278

(51) Int. Cl.
| | |
|---|---|
| *C07D 417/12* | (2006.01) |
| *C07D 417/14* | (2006.01) |
| *C07D 495/04* | (2006.01) |
| *C07D 487/04* | (2006.01) |
| *C07D 513/04* | (2006.01) |

(52) U.S. Cl.
CPC ......... *C07D 495/04* (2013.01); *C07D 417/12* (2013.01); *C07D 417/14* (2013.01); *C07D 487/04* (2013.01); *C07D 513/04* (2013.01)

(58) Field of Classification Search
CPC ............................. C07D 417/14; C07D 417/12
See application file for complete search history.

(56) References Cited

U.S. PATENT DOCUMENTS

2008/0275057 A1    11/2008    Kawabe et al.

FOREIGN PATENT DOCUMENTS

| CN | 101965339 | 2/2011 |
|---|---|---|
| WO | WO-2004007481 | 1/2004 |
| WO | WO-2009088990 | 7/2009 |

OTHER PUBLICATIONS

National Center for Biotechnology Information. PubChem Compound Database; CID=70069970, https://pubchem.ncbi.nlm.nih.gov/compound/70069970 (accessed Jul. 11, 2016).*
National Center for Biotechnology Information. PubChem Compound Database; CID=58158214, https://pubchem.ncbi.nlm.nih.gov/compound/58158214 (accessed Jul. 11, 2016).*
National Center for Biotechnology Information. PubChem Compound Database; CID=10084358, https://pubchem.ncbi.nlm.nih.gov/compound/10084358 (accessed Jul. 11, 2016).*
Burak, K. et al. (Jan. 1, 1992). "Synthesis of isothiazole derivatives with potential biological activity," *Die Pharmazie, Govi Verlag Pharmazeutischer Verlag GMBH* 47(7): 492-495.
International Search Report mailed Feb. 27, 2014 for PCT Application No. PCT/EP2014/051642, filed on Jan. 28, 2014, 5 pages.
Larson, G. et al. (2007). "Identification of novel, selective and potent Chk2 inhibitors," *Bioorganic & Medicinal Chemistry Letters* 17(1): 172-175.

* cited by examiner

*Primary Examiner* — Matthew Coughlin
(74) *Attorney, Agent, or Firm* — Morrison & Foerster LLP

(57) ABSTRACT

The present invention relates to isothiazoles of general formula (I) which inhibit the mitotic checkpoint: in which A, R1 and R2 are as defined in the claims, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of neoplasms, as a sole agent or in combination with other active ingredients.

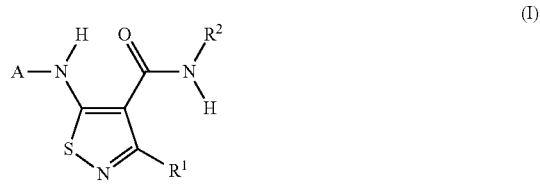

(I)

15 Claims, No Drawings

AMINO-SUBSTITUTED ISOTHIAZOLES

The present invention relates to amino-substituted isothiazole compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of neoplasms, as a sole agent or in combination with other active ingredients.

BACKGROUND OF THE INVENTION

The present invention relates to chemical compounds that inhibit the mitotic checkpoint (also known as spindle checkpoint, spindle assembly checkpoint). The mitotic checkpoint is a surveillance mechanism that ensures proper chromosome segregation during mitosis. Every dividing cell has to ensure equal separation of the replicated chromosomes into the two daughter cells. Upon entry into mitosis, chromosomes are attached at their kinetochores to the microtubules of the spindle apparatus. The mitotic checkpoint is active as long as unattached kinetochores are present and prevents mitotic cells from entering anaphase and thereby completing cell division with unattached chromosomes [Suijkerbuijk and Kops, Biochemica et Biophysica Acta, 2008, 1786, 24-31; Musacchio and Salmon, Nat Rev Mol Cell Biol., 2007, 8, 379-93]. Lack of attachment results in the production of a molecular inhibitor of the anaphase promoting complex/cyclosome (APC/C), an E3 ubiquitin ligase marking cyclin B and securin for proteasomal degradation [Pines J. Cubism and the cell cycle: the many faces of the APC/C. Nat. Rev. Mol. Cell Biol. 12, 427-438, 2012]. Once all kinetochores are attached in a correct amphitelic, i.e. bipolar, fashion with the mitotic spindle, the checkpoint is satisfied, APC/C gets active, and the cell enters anaphase and proceeds through mitosis. On a molecular basis the inhibitor of APC/C, the mitotic checkpoint complex (MCC) represents a complex of mitotic arrest deficient (Mad)-2, budding uninhibited by benzimidazole (Bub)-related-1 (BubR-1)/Mad-3, and Bub3 that directly binds and inactivates the essential APC/C stimulatory cofactor Cdc20. The protein kinase monopolar spindle-1 (Mps1) stimulates MCC assembly via Mad1 and, thus, represents the key activator of the spindle assembly checkpoint [recently reviewed in Vleugel at al. Evolution and function of the mitotic checkpoint. Dev. Cell 23, 239-250, 2012]. Furthermore, the protein kinase Bub1 contributes to APC/C inhibition by phosphorylation of Cdc20.

There is ample evidence linking reduced but incomplete mitotic checkpoint function with aneuploidy and tumorigenesis [Weaver and Cleveland, Cancer Research, 2007, 67, 10103-5; King, Biochimica et Biophysica Acta, 2008, 1786, 4-14]. In contrast, complete inhibition of the mitotic checkpoint, e.g. by knock-down of protein components of the checkpoint, has been recognised to result in severe chromosome missegregation and induction of apoptosis in tumour cells [Kops et al., Nature Reviews Cancer, 2005, 5, 773-85; Schmidt and Medema, Cell Cycle, 2006, 5, 159-63; Schmidt and Bastians, Drug Resistance Updates, 2007, 10, 162-81].

Interference with cell cycle regulation by chemical substances has long been recognized as a therapeutic strategy for the treatment of proliferative disorders including solid tumours such as carcinomas and sarcomas and leukaemias and lymphoid malignancies or other disorders associated with uncontrolled cellular proliferation. Classical approaches focus on the inhibition of mitotic progression (e.g. with antitubulin drugs, antimetabolites or CDK-inhibitors). Recently, a novel approach has gathered attention in inhibiting the mitotic checkpoint [Manchado et al., Cell Death and Differentiation, 2012, 19, 369-377; Colombo and Moll, Expert Opin. Ther. Targets, 2011, 15(5), 595-608; Janssen and Medema, Oncogene, 2011, 30(25), 2799-809]. Abrogation of the mitotic checkpoint is expected to increase erroneous chromosome segregation in cancer cells resulting in severe aneuploidy and cell death. Chemical inhibitors of Mps1 kinase activity have been published [Lan and Cleveland, J Cell Biol, 2010, 190, 21-24; Colombo et al., Cancer Res., 2010, 70, 10255-64; Tardif et al. Characterization of the cellular and antitumor effects of MPI-0479605, a small-molecule inhibitor of the mitotic kinase Mps1. Mol. Cancer Ther. 10, 2267-2275, 2011]. WO2011/063908 (Bayer Intellectual Property GmbH) relates to triazolopyridine compounds which are monopolar spindle 1 kinase (MPS-1 or UK) inhibitors. WO 2012/080230 (Bayer Intellectual Property GmbH) relates to substituted imidazopyrazine compounds which are monopolar spindle 1 kinase (MPS-1 or UK) inhibitors.

These Mps1-kinase directed compounds showed rapid inhibition of nocodazole-induced mitotic checkpoint activity, chromosome segregation defects and anti-proliferative activity in cellular assays, as well as tumor growth inhibitory effects in xenograft models.

The present invention relates to chemical compounds which inhibit the mitotic checkpoint in cellular assays without directly interfering with Mps1 kinase activity or with any other of the kinases reported of being involved in mitotic checkpoint such as Bub1, BubR1, Aurora A-C, or CDK1. Thus, the present invention discloses a novel approach for chemical intervention with mitotic checkpoint function.

WO 2011/003793 (BASF SE) relates to pyridazine compounds for controlling invertebrate pests, to a method for controlling invertebrate pests, to a method for protecting plant propagation material and/or the plants which grow therefrom, to plant propagation material, comprising at least one such compound, to a method for treating or protecting an animal from infestation or infection by parasites and to an agricultural composition containing at least one such compound.

WO 2002/068406 (Amgen Inc.) relates to substituted amine derivatives for the prophylaxis and treatment of diseases, such as angiogenesis mediated diseases.

However, the state of the art described above does not describe the specific substituted isothiazole compounds of general formula (I) of the present invention as defined herein, i.e. an isothiazole moiety, bearing:
in its 3-position, a $C_1$-$C_3$-alkyl-group, and
in its 4-position, a group of structure:

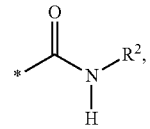

wherein:
\* indicates the point of attachment of said groups with the rest of the molecule, and R² represents phenyl or pyridinyl, which is optionally substituted as defined herein,
and
in its 5-position, a group of structure:

wherein:
* indicates the point of attachment of said groups with the rest of the molecule, and
A represents a heteroaryl group

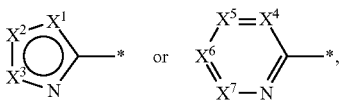

wherein * indicates the point of attachment of said heteroaryl group, which is as defined herein and which is optionally substituted as defined herein;
or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively inhibit the spindle assembly checkpoint and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

DESCRIPTION OF THE INVENTION

In accordance with a first aspect, the present invention covers compounds of general formula (I):

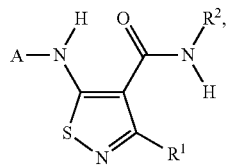

(I)

in which:
A represents a heteroaryl group selected from:

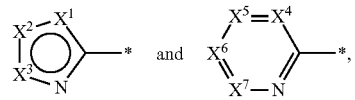

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, COOR³, CONR⁴R⁵, NR⁴R⁵,
said phenyl and 5-membered heteroaryl being optionally substituted, one or two times, identically or differently, with a substituent selected from:
a halogen atom, or a $C_1$-$C_3$-alkyl-, or a $C_1$-$C_3$-alkoxy- group,
R¹ represents a $C_1$-$C_3$-alkyl-group,
R² represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkyloxy, hydroxy, a halogen atom, phenyl, phenyloxy,
said phenyl and phenyloxy group being optionally substituted, one or two times, identically or differently, with a substituent selected from:
a halogen atom, or a $C_1$-$C_3$-alkyl-, or a $C_1$-$C_3$-alkoxy- group,
R³ represents:
a hydrogen atom, or a group selected from $C_1$-$C_6$-alkyl,
R⁴ represents:
a hydrogen atom, or a group selected from $C_1$-$C_6$-alkyl,
R⁵ represents:
a hydrogen atom, or a group selected from $C_1$-$C_6$-alkyl, or,
R⁴ and R⁵ together with the nitrogen to which they are attached represent:
a 5- to 6-membered heterocycloalkyl which optionally contains one further heteroatom selected from the group consisting of O, N and S,
or a stereoisomer, a tautomer, an N-oxide, a hydrate, a solvate, or a salt thereof, or a mixture of same.

The terms as mentioned in the present text have preferably the following meanings:

The term "halogen atom", "halo-" or "Hal-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "$C_1$-$C_6$-haloalkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said $C_1$-$C_6$-haloalkyl group is, for example, —$CF_3$, —$CHF_2$, —$CH_2F$, —$CF_2CF_3$, or —$CH_2CF_3$.

The term "$C_1$-$C_6$-alkoxy" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "$C_1$-$C_6$-haloalkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said $C_1$-$C_6$-haloalkoxy group is, for example, —$OCF_3$, —$OCHF_2$, —$OCH_2F$, —$OCF_2CF_3$, or —$OCH_2CF_3$.

The term "$C_3$-$C_6$-cycloalkyl" is to be understood as meaning a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl ring.

The term "$C_3$-$C_6$-cycloalkyloxy" is to be understood as meaning a saturated, monovalent, monocyclic hydrocarbon group of formula —O-cycloalkyl, in which the term "cycloalkyl" is defined supra, e.g. a. a cyclopropyloxy, cyclobutyloxy, cyclopentyloxy or cyclohexyloxy group.

The term "heteroaryl" is understood as meaning a monocyclic-, aromatic ring system having 5 or 6 ring atoms (a "5- or 6-membered heteroaryl" group), which contains one nitrogen atom, said "5-membered heteroaryl" containing one additional heteroatom being such as oxygen, nitrogen or sulfur, and said "6-membered heteroaryl" optionally containing one additional nitrogen atom, said "5- or 6-membered heteroaryl" optionally being condensed to a second 5- or 6-membered ring, this ring optionally containing one further heteroatom being such as oxygen, nitrogen or sulfur, and which second ring is unsaturated or partially saturated, thereby forming a bicyclic ring system. Particularly, "heteroaryl", which is a "5- or 6-membered heteroaryl" as defined above, which is condensed to another 5- or 6-membered ring, as defined above, thereby forming a bicyclic ring system, is selected from imidazolyl, oxazolyl, thiazolyl, pyrazolyl, isoxazolyl, isothiazolyl, pyridinyl, pyrimidinyl, pyridazinyl, pyrazinyl, and annelated derivatives thereof, such as, for example, benzoxazolyl, benzisoxazolyl, benzimidazolyl, benzothiazolyl, indazolyl, quinolinyl, quinazolinyl, isoquinolinyl, quinoxalinyl, cinnolinyl, thienopyrimidinyl, etc.

The term "5- to 6-membered heterocycloalkyl", is to be understood as meaning a saturated, monovalent, monocyclic ring which contains one nitrogen atom and 4 or 5 carbon atoms, wherein one carbon atom is optionally replaced by a further heteroatom selected from the group consisting of N, O and S, or by a heteroatom containing group S(=O), S(=O)$_2$, NR$^a$, in which R$^a$ represents a hydrogen atom or a $C_1$-$C_6$-alkyl group. Said 5- to 6-membered heterocycloalkyl is for example, a pyrrolidinyl, piperidinyl, morpholinyl, thiomorpholinyl, or piperazinyl.

In general, and unless otherwise mentioned, the heteroarylic radicals include all the possible isomeric forms thereof, e.g. the positional isomers thereof. Thus, for some illustrative non-restricting example, the term pyridinyl includes pyridin-2-yl, pyridin-3-yl and pyridin-4-yl.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence is preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of this invention optionally contain one or more asymmetric centre, depending upon the location and nature of the various substituents desired. Asymmetric carbon atoms is present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention optionally contain sulphur atoms which are asymmetric, such as an asymmetric sulfoxide, of structure:

for example,
in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, namely:

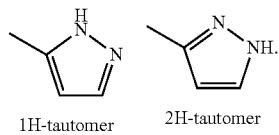

1H-tautomer   2H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt.

Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorph, or as a mixture of more than one polymorph, in any ratio.

In accordance with a second embodiment of the first aspect, the present invention covers compounds of general formula (I), supra, in which:

A represents a heteroaryl group selected from:

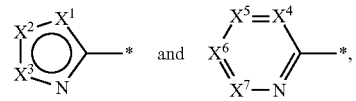

wherein one of $X^1$, $X^2$ and $X^3$ represents an N, O or S as ring atom and the others of $X^1$, $X^2$ and $X^3$ represent carbon as ring atoms, and wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and wherein * indicates the point of attachment of said groups with the rest of the molecule, said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, $COOR^3$, $CONR^4R^5$, $NR^4R^5$,
said phenyl and 5-membered heteroaryl being optionally substituted, one or two times, identically or differently, with a substituent selected from:
a halogen atom, or a $C_1$-$C_3$-alkyl-, or a $C_1$-$C_3$-alkoxy-group,
$R^1$ represents a methyl group,
$R^2$ represents a group selected from:
phenyl or pyridinyl, said phenyl and pyridinyl being optionally substituted, one or two times, identically or differently, with a substituent selected from:
$C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkyloxy, hydroxy, a halogen atom, phenyl, phenyloxy,
said phenyl and phenyloxy group being optionally substituted, one or two times, identically or differently, with a substituent selected from:
a halogen atom, or a $C_1$-$C_3$-alkyl-, or a $C_1$-$C_3$-alkoxy-group,
$R^3$ represents:
a hydrogen atom, or a group selected from $C_1$-$C_6$-alkyl,
$R^4$ represents:
a hydrogen atom, or a group selected from $C_1$-$C_6$-alkyl,
$R^5$ represents:
a hydrogen atom, or a group selected from $C_1$-$C_6$-alkyl, or,
$R^4$ and $R^5$ together with the nitrogen to which they are attached represent:
a 5- to 6-membered heterocycloalkyl which optionally contains one further heteroatom selected from the group consisting of O, N and S,
or a stereoisomer, a tautomer, an N-oxide, a hydrate, a solvate, or a salt thereof, or a mixture of same.

In accordance with a third embodiment of the first aspect, the present invention covers compounds of general formula (I), supra, in which:
A represents a heteroaryl group selected from:

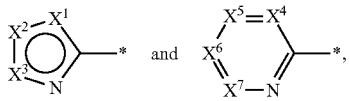

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, $COOR^3$, $CONR^4R^5$, $NR^4R^5$,
said phenyl and 5-membered heteroaryl being optionally substituted, one or two times, identically or differently, with a substituent selected from:
a halogen atom, or a $C_1$-$C_3$-alkyl-, or a $C_1$-$C_3$-alkoxy-group,
$R^1$ represents a methyl group,
$R^2$ represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-alkoxy, a halogen atom,
$R^3$ represents:
a hydrogen atom, or a group selected from $C_1$-$C_6$-alkyl,
$R^4$ represents:
a hydrogen atom, or a group selected from $C_1$-$C_6$-alkyl,
$R^5$ represents:
a hydrogen atom, or a group selected from $C_1$-$C_6$-alkyl, or,
$R^4$ and $R^5$ together with the nitrogen to which they are attached represent:
a 5- to 6-membered heterocycloalkyl which optionally contains one further heteroatom selected from the group consisting of O, N and S,
or a stereoisomer, a tautomer, an N-oxide, a hydrate, a solvate, or a salt thereof, or a mixture of same.

In accordance with a variant of the third embodiment of the first aspect, the present invention covers compounds of general formula (I), supra, in which:
A represents a heteroaryl group selected from:

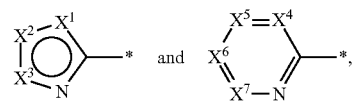

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, $COOR^3$, $CONR^4R^5$, $NR^4R^5$, said phenyl and 5-membered heteroaryl being optionally substituted, one or two times, identically or differently, with a substituent selected from:
a halogen atom, or a $C_1$-$C_3$-alkyl-, or a $C_1$-$C_3$-alkoxy-group,
$R^1$ represents a methyl group,
$R^2$ represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-alkoxy, $C_3$-$C_6$-cycloalkyloxy, a halogen atom, phenyloxy,
said phenyloxy group being optionally substituted, one or two times, identically or differently, with a substituent selected from:
a halogen atom, or a $C_1$-$C_3$-alkoxy-group,
$R^3$ represents:
a hydrogen atom, or a group selected from $C_1$-$C_6$-alkyl,
$R^4$ represents:
a hydrogen atom, or a group selected from $C_1$-$C_6$-alkyl,
$R^5$ represents:
a hydrogen atom, or a group selected from $C_1$-$C_6$-alkyl,
or,
$R^4$ and $R^5$ together with the nitrogen to which they are attached represent:
a 5- to 6-membered heterocycloalkyl which optionally contains one further heteroatom selected from the group consisting of O, N and S,
or a stereoisomer, a tautomer, an N-oxide, a hydrate, a solvate, or a salt thereof, or a mixture of same.

In accordance with a fourth embodiment of the first aspect, the present invention covers compounds of general formula (I), supra, in which:
A represents a heteroaryl group selected from:

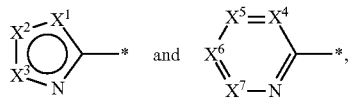

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, a halogen atom, cyano, phenyl, 5-membered heteroaryl, $COOR^3$, $CONR^4R^5$, $NR^4R^5$,
$R^1$ represents a methyl group,
$R^2$ represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-alkoxy, a halogen atom,
$R^3$ represents:
a group selected from $C_1$-$C_6$-alkyl,
$R^4$ represents:
a hydrogen atom,
$R^5$ represents:
a hydrogen atom, or a group selected from $C_1$-$C_6$-alkyl,
or a stereoisomer, a tautomer, an N-oxide, a hydrate, a solvate, or a salt thereof, or a mixture of same.

In accordance with a variant of the fourth embodiment of the first aspect, the present invention covers compounds of general formula (I), supra, in which:
A represents a heteroaryl group selected from:

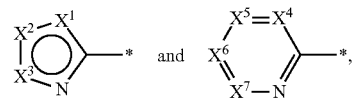

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, a halogen atom, cyano, phenyl, 5-membered heteroaryl, $COOR^3$, $CONR^4R^5$, $NR^4R^5$,
$R^1$ represents a methyl group,
$R^2$ represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-alkoxy, $C_3$-$C_6$-cycloalkyloxy, a halogen atom, phenyloxy,
said phenyloxy group being optionally substituted, one or two times, identically or differently, with a substituent selected from:
a halogen atom, or a $C_1$-$C_3$-alkoxy-group,
$R^3$ represents:
a group selected from $C_1$-$C_6$-alkyl,
$R^4$ represents:
a hydrogen atom, or a group selected from $C_1$-$C_6$-alkyl,
$R^5$ represents:
a hydrogen atom, or a group selected from $C_1$-$C_6$-alkyl,
or,
$R^4$ and $R^5$ together with the nitrogen to which they are attached represent:

a 5- to 6-membered heterocycloalkyl which 6-membered heterocycloalkyl contains one further heteroatom which is O, or a stereoisomer, a tautomer, an N-oxide, a hydrate, a solvate, or a salt thereof, or a mixture of same.

In accordance with a fifth embodiment of the first aspect, the present invention covers compounds of general formula (I), supra, in which:

A represents a heteroaryl group selected from:

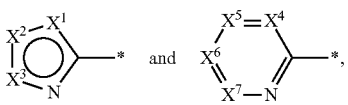

wherein $X^1$ represents an O or S as ring atom and $X^2$ and $X^3$ represent carbon as ring atoms, and wherein $X^4$, $X^5$, $X^6$ and $X^7$ represent carbon as ring atoms or one of $X^4$, $X^5$ and $X^6$ represent an N atom, and the others of $X^4$, $X^5$, $X^6$ and $X^7$ represent carbon as ring atoms, and wherein $X^2$ and $X^3$ or $X^4$ and $X^5$ or $X^6$ and $X^7$ optionally form part of an additional 5-membered or 6-membered ring, said 5-membered ring optionally containing one further heteroatom which is S, and being unsaturated, and said 6-membered ring being unsaturated, wherein * indicates the point of attachment of said groups with the rest of the molecule, said heteroaryl group, which is monocyclic or bicyclic, being optionally substituted, one or two times, identically or differently, with a substituent selected from:

a chlorine or a fluorine atom, or a methyl, ethyl, trifluoromethyl, methoxy, cyano, phenyl, imidazol-1-yl, COOR$^3$, CONR$^4$R$^5$, NR$^4$R$^5$-group, $R^1$ represents a methyl group, $R^2$ represents a group selected from:

phenyl or pyridin-3-yl, said phenyl and pyridinyl being optionally substituted, one or two times, identically or differently, with a substituent selected from:

ethyl, methoxy, a fluorine atom, $R^3$ represents a group selected from:

methyl or ethyl, $R^4$ represents:

a hydrogen atom, $R^5$ represents:

a hydrogen atom, or a methyl group, or a stereoisomer, a tautomer, an N-oxide, a hydrate, a solvate, or a salt thereof, or a mixture of same.

In accordance with a variant of the fifth embodiment of the first aspect, the present invention covers compounds of general formula (I), supra, in which:

A represents a heteroaryl group selected from:

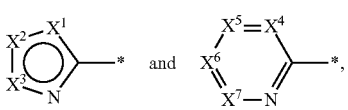

wherein $X^1$ represents an O or S as ring atom and $X^2$ and $X^3$ represent carbon as ring atoms, and wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and wherein $X^2$ and $X^3$ or $X^4$ and $X^5$ or $X^6$ and $X^7$ optionally form part of an additional 5-membered or 6-membered ring, said 5-membered ring optionally containing one further heteroatom which is selected from the group consisting of N and S, and being unsaturated, and said 6-membered ring optionally containing one further heteroatom which is N, and being unsaturated, wherein * indicates the point of attachment of said groups with the rest of the molecule, said heteroaryl group, which is monocyclic or bicyclic, being optionally substituted, one or two times, identically or differently, with a substituent selected from:

a chlorine, a fluorine or a bromine atom, or a methyl, ethyl, trifluoromethyl, methoxy, cyano, phenyl, imidazol-1-yl, 1,3-oxazol-2-yl, pyrazol-1-yl, COOR$^3$, CONR$^4$R$^5$, NR$^4$R$^5$-group, $R^1$ represents a methyl group, $R^2$ represents a group selected from:

phenyl or pyridin-3-yl, said phenyl and pyridinyl being optionally substituted, one or two times, identically or differently, with a substituent selected from:

methyl, ethyl, methoxy, ethoxy, isopropoxy, cyclohexyloxy, a chlorine or a fluorine atom, phenyloxy, said phenyloxy group being optionally substituted, one or two times, identically or differently, with a substituent selected from:

a fluorine atom, or methoxy, $R^3$ represents a group selected from:

methyl or ethyl, $R^4$ represents:

a hydrogen atom, or a methyl group, $R^5$ represents:

a hydrogen atom, or a methyl group, or an ethyl group, or, $R^4$ and $R^5$ together with the nitrogen to which they are attached represent:

a pyrrolidine ring, or a morpholine ring, or a stereoisomer, a tautomer, an N-oxide, a hydrate, a solvate, or a salt thereof, or a mixture of same.

In accordance with a sixth embodiment of the first aspect, the present invention covers compounds of general formula (I), supra, in which:

A represents a heteroaryl group selected from:

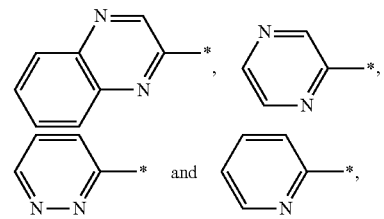

wherein * indicates the point of attachment of said groups with the rest of the molecule, said heteroaryl group being substituted with a substituent selected from:

a trifluoromethyl, cyano, or a CONR$^4$R$^5$-group, $R^1$ represents a methyl group, $R^2$ represents a group selected from:

phenyl or pyridin-3-yl, said phenyl and pyridinyl being substituted, one or two times, identically or differently, with a substituent selected from:

methoxy, a chlorine or a fluorine atom, $R^4$ represents:
 a hydrogen atom,
$R^5$ represents:
 a methyl group,
or a stereoisomer, a tautomer, an N-oxide, a hydrate, a solvate, or a salt thereof, or a mixture of same.

In accordance with a seventh embodiment of the first aspect, the present invention covers compounds of general formula (I), supra, in which:
A represents a heteroaryl group selected from:

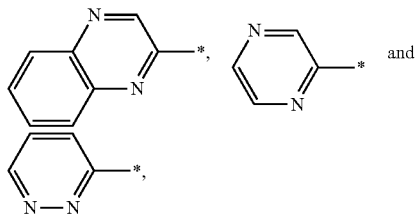

wherein * indicates the point of attachment of said groups with the rest of the molecule,
said heteroaryl group being substituted with a substituent selected from:
a trifluoromethyl, or a $CONR^4R^5$-group,
or,
A represents a:

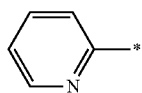

group, wherein * indicates the point of attachment of said group with the rest of the molecule,
said group being substituted with a cyano-group,
$R^1$ represents a methyl group,
$R^2$ represents a group selected from:
 phenyl or pyridin-3-yl,
 said phenyl being substituted, two times, identically or differently, with a substituent selected from:
  a chlorine or a fluorine atom,
 and,
 said pyridinyl being substituted with a substituent selected from:
  methoxy,
$R^4$ represents:
 a hydrogen atom,
$R^5$ represents:
 a methyl group,
or a stereoisomer, a tautomer, an N-oxide, a hydrate, a solvate, or a salt thereof, or a mixture of same.

In a further embodiment of the above-mentioned aspect, the invention relates to compounds of formula (I), wherein:
A represents a heteroaryl group selected from:

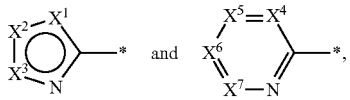

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, $COOR^3$, $CONR^4R^5$, $NR^4R^5$,
 said phenyl and 5-membered heteroaryl being optionally substituted, one or two times, identically or differently, with a substituent selected from:
  a halogen atom, or a $C_1$-$C_3$-alkyl-, or a $C_1$-$C_3$-alkoxy-group.

In a further embodiment of the above-mentioned aspect, the invention relates to compounds of formula (I), wherein:
A represents a heteroaryl group selected from:

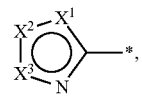

wherein one of $X^1$, $X^2$ and $X^3$ represents an N, O or S as ring atom and the others of $X^1$, $X^2$ and $X^3$ represent carbon as ring atoms, and
wherein $X^1$ and $X^2$ or $X^2$ and $X^3$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, $COOR^3$, $CONR^4R^5$, $NR^4R^5$,
 said phenyl and 5-membered heteroaryl being optionally substituted, one or two times, identically or differently, with a substituent selected from:
  a halogen atom, or a $C_1$-$C_3$-alkyl-, or a $C_1$-$C_3$-alkoxy-group.

In a further embodiment of the above-mentioned aspect, the invention relates to compounds of formula (I), wherein:
A represents a heteroaryl group selected from:

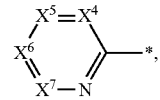

wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and wherein $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and wherein * indicates the point of attachment of said groups with the rest of the molecule, said heteroaryl group, which is monocyclic or bicyclic, being optionally substituted, one or two times, identically or differently, with a substituent selected from:

$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, COOR³, CONR⁴R⁵, NR⁴R⁵, said phenyl and 5-membered heteroaryl being optionally substituted, one or two times, identically or differently, with a substituent selected from:
a halogen atom, or a $C_1$-$C_3$-alkyl-, or a $C_1$-$C_3$-alkoxy-group.

In a further embodiment of the above-mentioned aspect, the invention relates to compounds of formula (I), wherein:
R¹ represents a $C_1$-$C_3$-alkyl-group.

In a further embodiment of the above-mentioned aspect, the invention relates to compounds of formula (I), wherein:
R² represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkyloxy, hydroxy, a halogen atom, phenyl, phenyloxy,
said phenyl and phenyloxy group being optionally substituted, one or two times, identically or differently, with a substituent selected from:
a halogen atom, or a $C_1$-$C_3$-alkyl-, or a $C_1$-$C_3$-alkoxy-group.

In a further embodiment of the above-mentioned aspect, the invention relates to compounds of formula (I), wherein:
R³ represents:
a hydrogen atom, or a group selected from $C_1$-$C_6$-alkyl.

In a further embodiment of the above-mentioned aspect, the invention relates to compounds of formula (I), wherein:
R⁴ represents:
a hydrogen atom, or a group selected from $C_1$-$C_6$-alkyl.

In a further embodiment of the above-mentioned aspect, the invention relates to compounds of formula (I), wherein:
R⁵ represents:
a hydrogen atom, or a group selected from $C_1$-$C_6$-alkyl, or,
R⁴ and R⁵ together with the nitrogen to which they are attached represent:
a 5- to 6-membered heterocycloalkyl which optionally contains one further heteroatom selected from the group consisting of O, N and S.

In a further embodiment of the above-mentioned aspect, the invention relates to compounds of formula (I), wherein:
R⁵ represents:
a hydrogen atom, or a group selected from $C_1$-$C_6$-alkyl.

In a further embodiment of the above-mentioned aspect, the invention relates to compounds of formula (I), wherein:
R⁴ and R⁵ together with the nitrogen to which they are attached represent:
a 5- to 6-membered heterocycloalkyl which optionally contains one further heteroatom selected from the group consisting of O, N and S.

In a further embodiment of the above-mentioned aspect, the invention relates to compounds of formula (I), wherein:
R¹ represents a methyl group.

In a further embodiment of the above-mentioned aspect, the invention relates to compounds of formula (I), wherein:
R² represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-alkoxy, a halogen atom.

In a further embodiment of the above-mentioned aspect, the invention relates to compounds of formula (I), wherein:
A represents a heteroaryl group selected from:

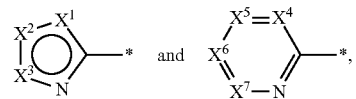

wherein one of $X^1$, $X^2$ and $X^3$ represents an N, O or S as ring atom and the others of $X^1$, $X^2$ and $X^3$ represent carbon as ring atoms, and wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and wherein * indicates the point of attachment of said groups with the rest of the molecule, said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, a halogen atom, cyano, phenyl, 5-membered heteroaryl, COOR³, CONR⁴R⁵, NR⁴R⁵.

In a further embodiment of the above-mentioned aspect, the invention relates to compounds of formula (I), wherein:
A represents a heteroaryl group selected from:

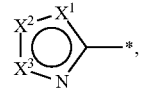

wherein one of $X^1$, $X^2$ and $X^3$ represents an N, O or S as ring atom and the others of $X^1$, $X^2$ and $X^3$ represent carbon as ring atoms, and wherein $X^1$ and $X^2$ or $X^2$ and $X^3$ optionally form part of an additional 5-membered or 6-membered ring, which optionally contains one further heteroatom selected from the group consisting of O, N and S, and which ring is unsaturated or partially saturated, and wherein * indicates the point of attachment of said groups with the rest of the molecule, said heteroaryl group, which is monocyclic or bicyclic, being optionally substituted, one or two times, identically or differently, with a substituent selected from:
C$_1$-C$_6$-alkyl, C$_1$-C$_6$-haloalkyl, C$_1$-C$_6$-alkoxy, a halogen atom, cyano, phenyl, 5-membered heteroaryl, COOR$^3$, CONR$^4$R$^5$, NR$^4$R$^5$.

In a further embodiment of the above-mentioned aspect, the invention relates to compounds of formula (I), wherein:
A represents a heteroaryl group selected from:

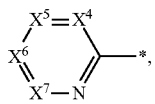

wherein X$^4$, X$^5$, X$^6$ and X$^7$ represent carbon as ring atoms or one of X$^4$, X$^5$, X$^6$ and X$^7$ represent an N atom, and the others of X$^4$, X$^5$, X$^6$ and X$^7$ represent carbon as ring atoms, and wherein X$^4$ and X$^5$ or X$^5$ and X$^6$ or X$^6$ and X$^7$ optionally form part of an additional 5-membered or 6-membered ring, which optionally contains one further heteroatom selected from the group consisting of O, N and S, and which ring is unsaturated or partially saturated, and wherein * indicates the point of attachment of said groups with the rest of the molecule, said heteroaryl group, which is monocyclic or bicyclic, being optionally substituted, one or two times, identically or differently, with a substituent selected from:
C$_1$-C$_6$-alkyl, C$_1$-C$_6$-haloalkyl, C$_1$-C$_6$-alkoxy, a halogen atom, cyano, phenyl, 5-membered heteroaryl, COOR$^3$, CONR$^4$R$^5$, NR$^4$R$^5$.

In a further embodiment of the above-mentioned aspect, the invention relates to compounds of formula (I), wherein:
A represents a heteroaryl group selected from:

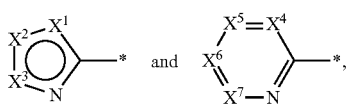

wherein X$^1$ represents an O or S as ring atom and X$^2$ and X$^3$ represent carbon as ring atoms, and wherein X$^4$, X$^5$, X$^6$ and X$^7$ represent carbon as ring atoms or one of X$^4$, X$^5$ and X$^6$ represent an N atom, and the others of X$^4$, X$^5$, X$^6$ and X$^7$ represent carbon as ring atoms, and wherein X$^2$ and X$^3$ or X$^4$ and X$^5$ or X$^6$ and X$^7$ optionally form part of an additional 5-membered or 6-membered ring, said 5-membered ring optionally containing one further heteroatom which is S, and being unsaturated, and said 6-membered ring being unsaturated, wherein * indicates the point of attachment of said groups with the rest of the molecule, said heteroaryl group, which is monocyclic or bicyclic, being optionally substituted, one or two times, identically or differently, with a substituent selected from:
a chlorine or a fluorine atom, or a methyl, ethyl, trifluoromethyl, methoxy, cyano, phenyl, imidazol-1-yl, COOR$^3$, CONR$^4$R$^5$, NR$^4$R$^5$-group.

In a further embodiment of the above-mentioned aspect, the invention relates to compounds of formula (I), wherein:
A represents a heteroaryl group selected from:

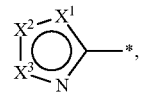

wherein X$^1$ represents an O or S as ring atom and X$^2$ and X$^3$ represent carbon as ring atoms, and wherein X$^2$ and X$^3$ optionally form part of an additional 5-membered or 6-membered ring, said 5-membered ring optionally containing one further heteroatom which is S, and being unsaturated, and said 6-membered ring being unsaturated, wherein * indicates the point of attachment of said groups with the rest of the molecule, said heteroaryl group, which is monocyclic or bicyclic, being optionally substituted, one or two times, identically or differently, with a substituent selected from:
a chlorine or a fluorine atom, or a methyl, ethyl, trifluoromethyl, methoxy, cyano, phenyl, imidazol-1-yl, COOR$^3$, CONR$^4$R$^5$, NR$^4$R$^5$-group.

In a further embodiment of the above-mentioned aspect, the invention relates to compounds of formula (I), wherein:
A represents a heteroaryl group selected from:

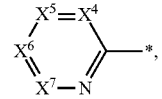

wherein X$^4$, X$^5$, X$^6$ and X$^7$ represent carbon as ring atoms or one of X$^4$, X$^5$ and X$^6$ represent an N atom, and the others of X$^4$, X$^5$, X$^6$ and X$^7$ represent carbon as ring atoms, and wherein X$^4$ and X$^5$ or X$^6$ and X$^7$ optionally form part of an additional 5-membered or 6-membered ring, said 5-membered ring optionally containing one further heteroatom which is S, and being unsaturated, and said 6-membered ring being unsaturated, wherein * indicates the point of attachment of said groups with the rest of the molecule, said heteroaryl group, which is monocyclic or bicyclic, being optionally substituted, one or two times, identically or differently, with a substituent selected from:
a chlorine or a fluorine atom, or a methyl, ethyl, trifluoromethyl, methoxy, cyano, phenyl, imidazol-1-yl, COOR$^3$, CONR$^4$R$^5$, NR$^4$R$^5$-group.

In a further embodiment of the above-mentioned aspect, the invention relates to compounds of formula (I), wherein:
R$^1$ represents a methyl group.

In a further embodiment of the above-mentioned aspect, the invention relates to compounds of formula (I), wherein:
R$^2$ represents a group selected from:
phenyl or pyridin-3-yl,
said phenyl and pyridinyl being optionally substituted, one or two times, identically or differently, with a substituent selected from:
ethyl, methoxy, a fluorine atom.

In a further embodiment of the above-mentioned aspect, the invention relates to compounds of formula (I), wherein:
R$^3$ represents a group selected from:
methyl or ethyl.

In a further embodiment of the above-mentioned aspect, the invention relates to compounds of formula (I), wherein:
R$^4$ represents:
  a hydrogen atom.

In a further embodiment of the above-mentioned aspect, the invention relates to compounds of formula (I), wherein:
R$^5$ represents:
  a hydrogen atom, or a methyl group.

In a further embodiment of the above-mentioned aspect, the invention relates to compounds of formula (I), wherein:
R$^1$ represents a C$_1$-C$_3$-alkyl-group.

In a further embodiment of the above-mentioned aspect, the invention relates to compounds of formula (I), wherein:
R$^2$ represents a group selected from:
  phenyl or pyridinyl.

In a further embodiment of the above-mentioned aspect, the invention relates to compounds of formula (I), wherein:
R$^2$ represents a phenyl group.

In a further embodiment of the above-mentioned aspect, the invention relates to compounds of formula (I), wherein:
R$^2$ represents a pyridin-3-yl group.

In a further embodiment of the above-mentioned aspect, the invention relates to compounds of formula (I), wherein:
R$^2$ represents a group selected from:
  phenyl or pyridinyl,
    said phenyl and pyridinyl being optionally substituted, one or two times, identically or differently, with a substituent selected from:
      C$_1$-C$_6$-alkyl, C$_1$-C$_6$-alkoxy, C$_3$-C$_6$-cycloalkyloxy, a halogen atom, phenyloxy,
    said phenyloxy group being optionally substituted, one or two times, identically or differently, with a substituent selected from:
      a halogen atom, or a C$_1$-C$_3$-alkoxy-group.

In a further embodiment of the above-mentioned aspect, the invention relates to compounds of formula (I), wherein:
R$^2$ represents a group selected from:
  phenyl,
    said phenyl being optionally substituted, one or two times, identically or differently, with a substituent selected from:
      C$_1$-C$_6$-alkyl, C$_1$-C$_6$-alkoxy, C$_3$-C$_6$-cycloalkyloxy, a halogen atom, phenyloxy,
    said phenyloxy group being optionally substituted, one or two times, identically or differently, with a substituent selected from:
      a halogen atom, or a C$_1$-C$_3$-alkoxy-group.

In a further embodiment of the above-mentioned aspect, the invention relates to compounds of formula (I), wherein:
R$^2$ represents a group selected from:
  pyridinyl,
    said pyridinyl being optionally substituted, one or two times, identically or differently, with a substituent selected from:
      C$_1$-C$_6$-alkyl, C$_1$-C$_6$-alkoxy, C$_3$-C$_6$-cycloalkyloxy, a halogen atom, phenyloxy,
    said phenyloxy group being optionally substituted, one or two times, identically or differently, with a substituent selected from:
      a halogen atom, or a C$_1$-C$_3$-alkoxy-group.

In a further embodiment of the above-mentioned aspect, the invention relates to compounds of formula (I), wherein:
A represents a heteroaryl group selected from:

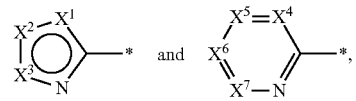

wherein X$^1$ represents an O or S as ring atom and X$^2$ and X$^3$ represent carbon as ring atoms, and
wherein X$^4$, X$^5$, X$^6$ and X$^7$ represent carbon as ring atoms or one of X$^4$, X$^5$, X$^6$ and X$^7$ represent an N atom, and the others of X$^4$, X$^5$, X$^6$ and X$^7$ represent carbon as ring atoms, and
wherein X$^2$ and X$^3$ or X$^4$ and X$^5$ or X$^6$ and X$^7$ optionally form part of an additional 5-membered or 6-membered ring, said 5-membered ring optionally containing one further heteroatom which is selected from the group consisting of N and S, and being unsaturated, and said 6-membered ring optionally containing one further heteroatom which is N, and being unsaturated,
wherein * indicates the point of attachment of said groups with the rest of the molecule,
said heteroaryl group, which is monocyclic or bicyclic, being optionally substituted, one or two times, identically or differently, with a substituent selected from:
a chlorine, a fluorine or a bromine atom, or a methyl, ethyl, trifluoromethyl, methoxy, cyano, phenyl, imidazol-1-yl, 1,3-oxazol-2-yl, pyrazol-1-yl, COOR$^3$, CONR$^4$R$^5$, NR$^4$R$^5$-group.

In a further embodiment of the above-mentioned aspect, the invention relates to compounds of formula (I), wherein:
A represents a heteroaryl group selected from:

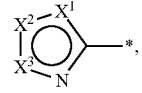

wherein X$^1$ represents an O or S as ring atom and X$^2$ and X$^3$ represent carbon as ring atoms, and
wherein X$^2$ and X$^3$ optionally form part of an additional 5-membered or 6-membered ring, said 5-membered ring optionally containing one further heteroatom which is selected from the group consisting of N and S, and being unsaturated, and said 6-membered ring optionally containing one further heteroatom which is N, and being unsaturated,
wherein * indicates the point of attachment of said groups with the rest of the molecule,
said heteroaryl group, which is monocyclic or bicyclic, being optionally substituted, one or two times, identically or differently, with a substituent selected from:
a chlorine, a fluorine or a bromine atom, or a methyl, ethyl, trifluoromethyl, methoxy, cyano, phenyl, imidazol-1-yl, 1,3-oxazol-2-yl, pyrazol-1-yl, COOR$^3$, CONR$^4$R$^5$, NR$^4$R$^5$-group.

In a further embodiment of the above-mentioned aspect, the invention relates to compounds of formula (I), wherein:
A represents a heteroaryl group selected from:

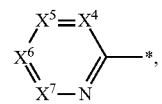

wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and wherein $X^4$ and $X^5$ or $X^6$ and $X^7$ optionally form part of an additional 5-membered or 6-membered ring, said 5-membered ring optionally containing one further heteroatom which is selected from the group consisting of N and S, and being unsaturated, and said 6-membered ring optionally containing one further heteroatom which is N, and being unsaturated, wherein * indicates the point of attachment of said groups with the rest of the molecule, said heteroaryl group, which is monocyclic or bicyclic, being optionally substituted, one or two times, identically or differently, with a substituent selected from:

a chlorine, a fluorine or a bromine atom, or a methyl, ethyl, trifluoromethyl, methoxy, cyano, phenyl, imidazol-1-yl, 1,3-oxazol-2-yl, pyrazol-1-yl, $COOR^3$, $CONR^4R^5$, $NR^4R^5$-group.

In a further embodiment of the above-mentioned aspect, the invention relates to compounds of formula (I), wherein:
$R^2$ represents a group selected from:
phenyl or pyridin-3-yl,
said phenyl and pyridinyl being optionally substituted, one or two times, identically or differently, with a substituent selected from:
methyl, ethyl, methoxy, ethoxy, isopropoxy, cyclohexyloxy, a chlorine or a fluorine atom, phenyloxy,
said phenyloxy group being optionally substituted, one or two times, identically or differently, with a substituent selected from:
a fluorine atom, or methoxy.

In a further embodiment of the above-mentioned aspect, the invention relates to compounds of formula (I), wherein:
$R^2$ represents a group selected from:
phenyl,
said phenyl being optionally substituted, one or two times, identically or differently, with a substituent selected from:
methyl, ethyl, methoxy, ethoxy, isopropoxy, cyclohexyloxy, a chlorine or a fluorine atom, phenyloxy,
said phenyloxy group being optionally substituted, one or two times, identically or differently, with a substituent selected from:
a fluorine atom, or methoxy.

In a further embodiment of the above-mentioned aspect, the invention relates to compounds of formula (I), wherein:
$R^2$ represents a group selected from:
pyridin-3-yl,
said phenyl being optionally substituted, one or two times, identically or differently, with a substituent selected from:
methyl, ethyl, methoxy, ethoxy, isopropoxy, cyclohexyloxy, a chlorine or a fluorine atom, phenyloxy,
said phenyloxy group being optionally substituted, one or two times, identically or differently, with a substituent selected from:
a fluorine atom, or methoxy.

In a further embodiment of the above-mentioned aspect, the invention relates to compounds of formula (I), wherein:
A represents a heteroaryl group selected from:

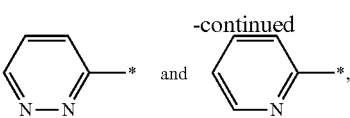

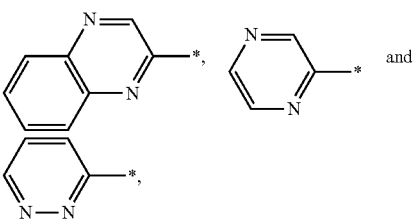

wherein * indicates the point of attachment of said groups with the rest of the molecule,
said heteroaryl group being substituted with a substituent selected from:
a trifluoromethyl, cyano, or a $CONR^4R^5$-group.

In accordance with a the sixth embodiment of the first aspect, the present invention covers compounds of general formula (I), supra, in which:
$R^2$ represents a group selected from:
phenyl or pyridin-3-yl,
said phenyl and pyridinyl being substituted, one or two times, identically or differently, with a substituent selected from:
methoxy, a chlorine or a fluorine atom.

In a further embodiment of the above-mentioned aspect, the invention relates to compounds of formula (I), wherein:
$R^5$ represents:
a methyl group.

In a further embodiment of the above-mentioned aspect, the invention relates to compounds of formula (I), wherein:
A represents a heteroaryl group selected from:

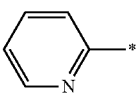 [SMILES: *c1ccccn1]

wherein * indicates the point of attachment of said groups with the rest of the molecule,
said heteroaryl group being substituted with a substituent selected from:
a trifluoromethyl, or a $CONR^4R^5$-group,
or,
A represents a:

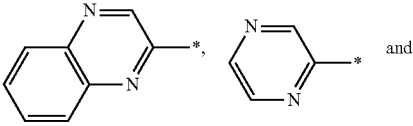

group, wherein * indicates the point of attachment of said group with the rest of the molecule,
said group being substituted with a cyano-group.

In a further embodiment of the above-mentioned aspect, the invention relates to compounds of formula (I), wherein:
A represents a heteroaryl group selected from:

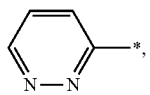

-continued wherein * indicates the point of attachment of said groups with the rest of the molecule,
said heteroaryl group being substituted with a substituent selected from:
a trifluoromethyl, or a CONR$^4$R$^5$-group.

In a further embodiment of the above-mentioned aspect, the invention relates to compounds of formula (I), wherein:
A represents a:

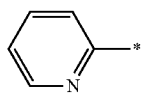

group, wherein * indicates the point of attachment of said group with the rest of the molecule,
said group being substituted with a cyano-group.

In a further embodiment of the above-mentioned aspect, the invention relates to compounds of formula (I), wherein:
R$^2$ represents a group selected from:
phenyl or pyridin-3-yl,
said phenyl being substituted, two times, identically or differently, with a substituent selected from:
a chlorine or a fluorine atom,
and,
said pyridinyl being substituted with a substituent selected from:
methoxy.

In a further embodiment of the above-mentioned aspect, the invention relates to compounds of formula (I), wherein:
R$^2$ represents a group selected from:
phenyl,
said phenyl being substituted, two times, identically or differently, with a substituent selected from:
a chlorine or a fluorine atom.

In a further embodiment of the above-mentioned aspect, the invention relates to compounds of formula (I), wherein:
R$^2$ represents a group selected from:
pyridin-3-yl,
said pyridinyl being substituted with a substituent selected from:
methoxy.

In a further embodiment of the above-mentioned aspect, the invention relates to compounds of formula (I), according to any of the above-mentioned embodiments, in the form of or a stereoisomer, a tautomer, an N-oxide, a hydrate, a solvate, or a salt thereof, or a mixture of same.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

In accordance with a further aspect, the present invention covers intermediate compounds which are useful in the preparation of compounds of the present invention of general formula (I), particularly in the method described herein. In particular, the present invention covers compounds of general formula (II):

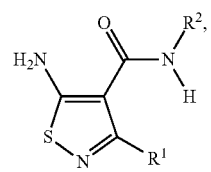

(II)

in which R1 and R2 are as defined for the compound of general formula (I) supra.

In accordance with yet another aspect, the present invention covers the use of the intermediate compounds of general formula (II):

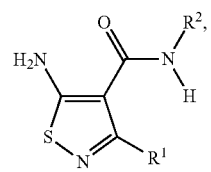

(II)

in which R1 and R2 are as defined for the compound of general formula (I) supra, for the preparation of a compound of general formula (I) as defined supra.

EXPERIMENTAL SECTION

The following table lists the abbreviations used in this paragraph and in the Intermediate Examples and Examples section as far as they are not explained within the text body. NMR peak forms are stated as they appear in the spectra, possible higher order effects have not been considered. Chemical names were generated using the ICS naming tool of ACD labs. In some cases generally accepted names of commercially available reagents were used in place of ICS naming tool generated names.

| Abbreviation | Meaning |
|---|---|
| br | Broad |
| CDI | 1,1'-carbonyl-diimidazol [CAS RN: 530-62-1] |
| CI | chemical ionisation |
| d | Doublet |
| dd | doublet of doublet |
| dquint | doublet of quintet |
| DAD | diode array detector |
| DavePhos | 2-Dicyclohexylphosphino-2'-(N,N-dimethylamino)-biphenyl [CAS RN: 213697-53-1] |
| DCM | Dichloromethane |
| DIPEA | N,N-diisopropylethylamine [CAS RN: 7087-68-5] |
| DMF | N,N-dimethylformamide |
| EtOAc | ethyl acetate |
| Eq. | Equivalent |
| ESI | electrospray (ES) ionisation |
| h | hour(s) |
| HATU | 2-(7-Aza-1H-benzotriazole-1-yl)-1,1,3,3-tetramethyluronium hexafluorophosphate [CAS RN: 148893-10-1] |
| HPLC | high performance liquid chromatography |
| LC-MS | liquid chromatography mass spectrometry |
| m | Multiplet |

| Abbreviation | Meaning |
| --- | --- |
| min | minute(s) |
| MPLC | medium performance liquid chromatography |
| MS | mass spectrometry |
| MTBE | methyl tert-butylether |
| NMR | nuclear magnetic resonance spectroscopy: chemical shifts (δ) are given in ppm. The chemical shifts were corrected by setting the DMSO signal to 2.50 ppm using unless otherwise stated. |
| q | Quartet |
| rt | room temperature |
| $R_t$ | retention time (as measured either with HPLC or UPLC) in minutes |
| s | Singlet |
| s br | singlet, broad (NMR) |
| t | triplet |
| tt | triplet of triplet |
| T3P | 2,4,6-tripropyl-1,3,5,2,4,6-trioxatriphosphinane 2,4,6-trioxide [CAS RN: 68957-94-8] |
| THF | Tetrahydrofuran |
| UPLC | ultra performance liquid chromatography |
| Xantphos | 4,5-Bis(diphenylphosphino)-9,9-dimethylxanthene (CAS-RN: 22131-51-7) |

Other abbreviations have their meanings customary per se to the skilled person.

The various aspects of the invention described in this application are illustrated by the following examples which are not meant to limit the invention in any way.

Syntheses of Compounds (Overview):

The compounds of the present invention can be prepared as descibed in the following section. Scheme 1 and the procedures described below illustrate general synthetic routes to the compounds of general formula (I) of the invention and are not intended to be limiting. It is clear to the person skilled in the art that the order of transformations as exemplified in Scheme 1 can be modified in various ways. The order of transformations exemplified in the Scheme 1 is therefore not intended to be limiting. In addition, interconversion of any of the substituents, A and R2 can be achieved before and/or after the exemplified transformations. These modifications can be such as the introduction of protecting groups, cleavage of protecting groups, exchange, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3$^{rd}$ edition, Wiley 1999). Specific examples are described in the subsequent paragraphs. Further, it is possible that two or more successive steps may be performed without work-up being performed between said steps, e.g. a "one-pot" reaction, as is well-known to the person skilled in the art.

Scheme 1:

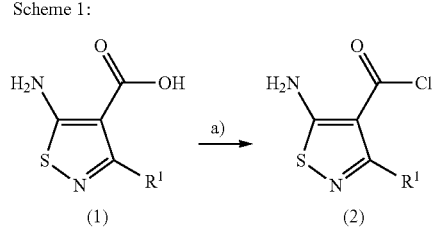

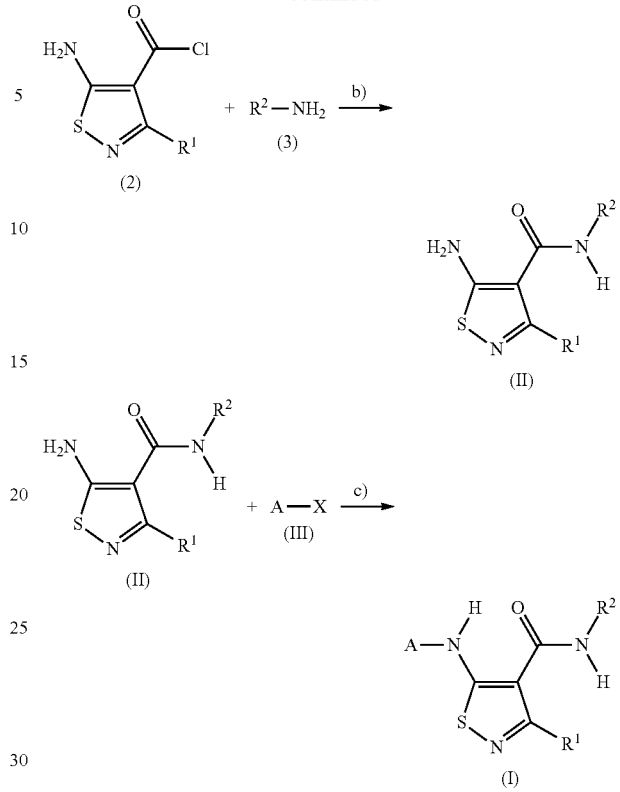

in which A, R1 and R2 are as defined supra, and X represents a halogen atom, for example a chlorine, bromine or iodine atom, or a perfluoroalkylsulfonate group, for example a trifluoromethylsulfonate group or a nonafluorobutylsulfonate group, or a boronic acid.

In the first step, a carboxylic acid of formula (I), which is either described in the literature [CAS-RN: 22131-51-7, for the synthesis, please see: J. Goerdeler, H. Horn, Chem. Ber. (1963), 96, 1551-1560.] or which can be prepared in analogy to procedures described in the literature, can be reacted with thionyl chloride at elevated temperature, for example at 80° C., to give, after removal of volatile components, the corresponding carboxylic acid chloride of formula (2).

In the second step, a compound of formula (2) reacts with an amine of formula (3), which is either commercially available or which is known [CAS-RN: 578-54-1, CAS-RN: 6628-77-9, CAS-RN: 3863-11-4] or which can be prepared by methods that are well known to the person skilled in the art, in the presence of a tertiary amine, as for example triethylamine, to give a compound of general formula (II).

In the third step, a compound of general formula (II) is reacted with a compound of general formula (III), which is either commercially available or which is known or which can be prepared by methods that are well known to the person skilled in the art, in a palladium catalyzed coupling reaction, employing, for example, palladium(II) acetate, in the presence of a suitable ligand, employing, for example, Xantphos, in the presence of cesium carbonate in solvents as for example dioxane, or DMF or mixtures thereof, at elevated temperatures, preferably using a microwave oven, which results in compounds of general formula (I). Alternatively, compounds of the present inventions are accessible by other palladium- or copper-catalysed N-arylation conditions or strategies as exemplified in the literature [for a review article on N-aryl bond formation for the synthesis of biologically active compounds please see, C. Fischer, B. Koenig, Beilstein J. Org. Chem. (2011), 7, 59-74].

Compounds of general formula (II) serve as central intermediates for the introduction of various heteroaryl groups A, which results in compounds of general formula (I). Depending on the nature of A and R2 it may be necessary to introduce A bearing suitable protecting groups on functional groups which may disturb the desired reaction. It also may be necessary to use protecting groups on functional groups at R2, which may disturb the desired reaction.

In accordance with an embodiment, the present invention also relates to a method of preparing a compound of general formula (I) as defined supra, said method comprising the step of allowing an intermediate compound of general formula (II):

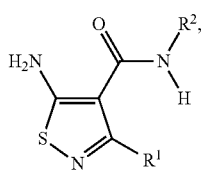
(II)

in which R1 and R2 are as defined for the compound of general formula (I) supra,
to react with a compound of general formula (III):

A-X  (III), in which A is as defined as for the compound of general formula (I), supra, and X represents a halogen atom, for example a chlorine, bromine or iodine atom, or a perfluoroalkylsulfonate group, for example a trifluoromethylsulfonate group or a nonafluorobutylsulfonate group, or a boronic acid,
thereby giving a compound of general formula (I):

(I)

in which A, R1 and R2 are as defined for the compound of general formula (I) supra.

General Part

UPLC-MS Standard Procedures

Analytical UPLC-MS was performed using UPLC-MS Method 1 unless otherwise stated. The masses (m/z) are reported from the positive mode electrospray ionisation unless the negative mode is indicated (ES−).

Method 1:
Instrument: Waters Acquity UPLC-MS SQD 3001; column: Acquity UPLC BEH C18 1.7 50×2.1 mm; eluent A: water+0.1% formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD Method 2:
Instrument: Waters Acquity UPLC-MS SQD 3001; column: Acquity UPLC BEH C18 1.7 50×2.1 mm; eluent A: water+0.2% ammonia, Eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD Method 3:
Instrument: Waters Acquity UPLC-MS SQD; column: Acquity UPLC BEH C18 1.7 50×2.1 mm; Eluent A: water+0.05% formic acid (98%), Eluent B: acetonitrile+0.05% formic acid (98%); Gradient: 0-1.6 min 1-99% B, 1.6-2.0 min 99% B; flow 0.8 ml/min; Temperature: 60° C.; Injection: 2 μl; DAD scan: 210-400 nm; ELSD Method 4:
Instrument: Waters Acquity UPLC-MS SQD; column: Acquity UPLC BEH C18 1.7 50×2.1 mm; Eluent A: water+0.1% Vol. formic acid (99%), Eluent B: acetonitrile; Gradient: 0-1.6 min 1-99% B, 1.6-2.0 min 99% B; Flow 0.8 ml/min; Temperature: 60° C.; Injection: 2 μl; DAD scan: 210-400 nm; ELSD Method 5:
Instrument: Waters Acquity UPLC-MS SQD; column: Acquity UPLC BEH C18 1.7 50×2.1 mm; Eluent A: Wasser+0.1% Vol. formic acid (99%), Eluent B: acetonitrile; Gradient: 0-1.6 min 1-99% B, 1.6-2.0 min 99% B; Flow 0.8 ml/min; Temperature: 60° C.; Injection: 2 μl; DAD scan: 210-400 nm; ELSD Preparative HPLC Standard Procedures Method A:
Instrument: Waters Autopurificationsystem SQD; column: Waters XBrigde C18 5μ 100×30 mm; Eluent A: water+0.1% Vol. formic acid (99%), Eluent B: acetonitrile; gradient: 1-100% B (the gradient was adapted individually as required by the samples separated).

Intermediates

Intermediate 1

5-Amino-N-(2-ethylphenyl)-3-methyl-1,2-thiazole-4-carboxamide

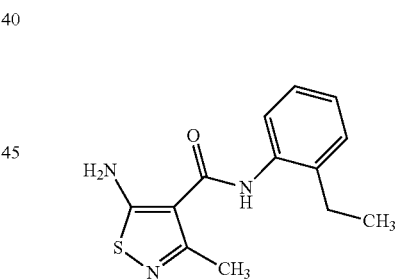

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (13.2 g, 56.6 mmol, 1.0 eq) and thionyl chloride (41.5 mL, 569 mmol, 9.0 eq) was stirred at 80° C. for 2 h. After cooling, the volatile components were removed in vacuo. The crude acid chloride was diluted with toluene and concentrated at the rotary evaporator. This process was repeated one more time. The acid chloride observed this way was diluted with THF (100 mL). Then 2-ethylaniline [CAS-RN: 578-54-1] (14.0 mL, 113 mmol, 2.0 eq) and triethyl amine (15.8 mL, 113 mmol, 2.0 eq) was added. The reaction mixture was stirred at rt overnight. After addition of water the crude reaction mixture was acidified with 1M hydrochloric acid and extracted with EtOAc. The organic phase was washed with brine and dried with sodium sulphate.

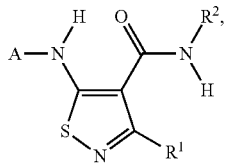

After removal of the volatile components by the use of a rotary evaporator the title compound was observed in >90% purity (UPLC-MS: area-%) (14.2 g, ~90% yield of theory) which was used without further purification.

UPLC-MS (Method 1): Rt=0.98 min; MS (EI$_{neg}$): m/z=260 [M−H]$^-$.

1H-NMR (400 MHz, CDCl3): δ [ppm]=1.27 (t, 3H), 2.67 (q, 2H), 2.70 (s, 3H), 6.70 (s br, 2H), 7.14-7.30 (m, 3H, partially covered by solvent signal), 7.36 (s br, 1H), 7.77-7.83 (m, 1H).

Intermediate 2

5-Amino-N-(6-methoxypyridin-3-yl)-3-methyl-1,2-thiazole-4-carboxamide

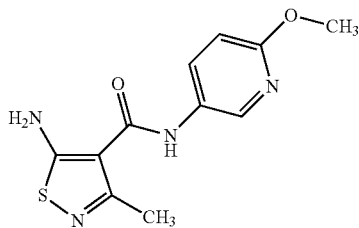 [SMILES: COc1ccc(NC(=O)c2c(C)nsc2N)cn1]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (7.50 g, 47.4 mmol, 1.0 eq) and thionyl chloride (38.0 mL, 522 mmol, 11.0 eq) was stirred at 90° C. for 5 h. After cooling, the volatile components were removed in vacuo. The crude acid chloride was diluted with toluene and concentrated at the rotary evaporator. This process was repeated two more times. The acid chloride observed this way [11.0 g, ~80% purity (LC-MS area-%), ~40 mmol] was diluted with THF (240 mL). Then, 6-methoxypyridin-3-amine [CAS-RN: 6628-77-9] (6.62 g, 50.7 mmol, 1.2 eq) and triethyl amine (17.7 mL, 127 mmol, 3.0 eq) was added. The reaction mixture was stirred at rt overnight. After addition of water the crude reaction mixture was extracted with dichloromethane (2×). The combined organic phases were dried with sodium sulphate. After removal of the volatile components by the use of a rotary evaporator the crude material was purified via preparative MPLC (Biotage Isolera; 100 g SNAP cartridge: hexane/ethyl acetate 6/4->ethyl acetate) to give 6.80 g (~61% yield of theory, based on the intermediate acid chlorid) of the title compound.

UPLC-MS (Method 1): Rt=0.73 min; MS (EI$_{neg}$): m/z=263 [M−H]$^-$.

1H-NMR (400 MHz, DMSO-d6): δ [ppm]=2.36 (s, 3H), 2.79 (s, 3H), 6.77 (d, 1H), 7.22 (s br, 2H), 7.89 (dd, 1H), 8.36 (d, 1H), 9.43 (s, 1H).

Intermediate 3

5-Amino-N-(3,4-difluorophenyl)-3-methyl-1,2-thiazole-4-carboxamide

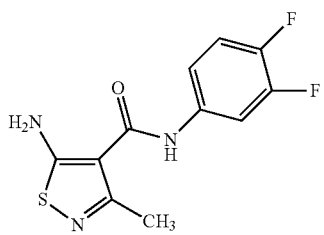 [SMILES: Cc1nsc(N)c1C(=O)Nc1ccc(Cl)c(F)c1]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (15.0 g, 94.8 mmol, 1.0 eq) and thionyl chloride (62.3 mL, 522 mmol, 9.0 eq) was stirred at 100° C. for 2 h. After cooling, the volatile components were removed in vacuo. The crude acid chloride was diluted with toluene and concentrated at the rotary evaporator. This process was repeated two more times. The acid chloride observed this way (21.9 g) was diluted with THF (140 mL). Then, 3,4-difluoroaniline [CAS-RN: 3863-11-4] (9.33 mL, 94.1 mmol, 1.5 eq) and triethyl amine (21.9 mL, 157 mmol, 2.5 eq) was added. The reaction mixture was stirred at rt overnight. After addition of 1 L water the crude reaction mixture was extracted with ethyl acetate (3×). The organic phase was washed with half-concentrated sodium chloride solution and dried with magnesium sulphate. After removal of the volatile components the crude product was diluted with 200 mL methyl tert-butylether and heated to 50° C. for 20 min. The remaining solids were removed by filtration. Then, the solvent was removed in vacuo to give 10.0 g (55% yield of theory, based on the intermediate acid chlorid) of the title compound in about 90%-purity (H-NMR).

UPLC-MS (Method 3): Rt=0.96 min; MS (EI$_{neg}$): m/z=268 [M−H]$^-$.

$^1$H-NMR (400 MHz, DMSO-d6): δ [ppm]=2.34 (s, 3H), 7.22 (s br, 2H), 7.-29-7.41 (m, 2H), 8.36 (m, 1H), 9.67 (s, 1H).

Intermediate 4

5-Amino-N-(4-chloro-3-fluorophenyl)-3-methyl-1,2-thiazole-4-carboxamide

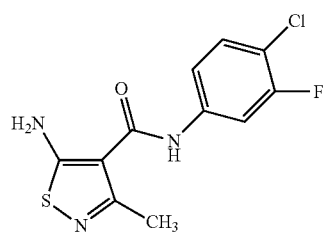

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (5.00 g, 9.93 mmol, 1.0 eq) and thionyl chloride (20.7 mL, 284 mmol, 9.0 eq) was stirred at 80° C. for 2 h. After cooling, the volatile components were removed in vacuo. The crude acid chloride was diluted with toluene and concentrated at the rotary evaporator. This process was repeated one more time. The acid chloride (1.75 g, 9.93 mmol, 1.0 eq) observed this way was dissolved in THF (15 mL). Then, 4-chloro-3-fluoroaniline [CAS-RN: 367-22-6] (2.89 mL, 19.9 mmol, 2.0 eq) and triethyl amine (2.01 mL, 19.9 mmol, 2.0 eq) was added. The reaction mixture was stirred at rt overnight. After addition of water the crude reaction mixture was acidified with 1M hydrochloric acid and extracted with EtOAc. The organic phase was washed with brine and dried with sodium sulfate. After removal of the volatile components the product was crystallized from dichloromethane and methanol. The precipitate was isolated by filtration and dried under high vacuum to give the title compound (600 mg, ~21% yield of theory based on the intermediate acid chloride).

UPLC-MS (Method 2): Rt=1.06 min; MS (EI$_{neg}$): m/z=284 [M−H]⁻.

$^1$H-NMR (400 MHz, DMSO-d6): δ [ppm]=2.36 (s, 3H), 7.28 (s br, 2H), 7.41 (dd, 1H), 7.51 (t, 1H), 7.81 (dd, 1H), 9.82 (s, 1H).

Intermediate 5

5-Amino-N-(3-fluoro-4-methoxyphenyl)-3-methyl-1,2-thiazole-4-carboxamide

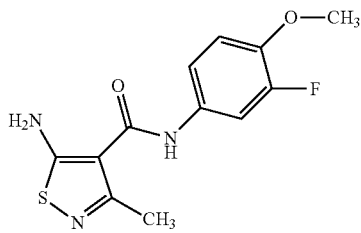 [SMILES: COc1ccc(NC(=O)c2c(C)nsc2N)cc1F]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (1.00 g, 6.32 mmol, 1.0 eq) and thionyl chloride (4.15 mL, 56.8 mmol, 9.0 eq) was stirred at 80° C. for 2 h. After cooling, the volatile components were removed in vacuo. The crude acid chloride was diluted with toluene and concentrated at the rotary evaporator. This process was repeated one more time. The acid chloride (650 mg, 3.68 mmol, 1.0 eq) observed this way was dissolved in THF (18 mL). Then, 3-fluoro-4-methoxyaniline [CAS-RN: 366-99-4] (1.06 g, 7.36 mmol, 2.0 eq) and triethyl amine (0.75 mL, 7.36 mmol, 2.0 eq) was added. The reaction mixture was stirred at rt overnight. After addition of water the crude reaction mixture was acidified with 1M hydrochloric acid and extracted with EtOAc. The organic phase was washed with brine. After phase separation via a Whatman-filter the volatile components were removed. The crude material was purified via preparative MPLC (Biotage Isolera; 50 g NH2-SNAP cartridge: hexane->hexane/ethyl acetate 1/1) to give 650 mg (~37% yield of theory, based on the intermediate acid chlorid) of the title compound in about 30% purity. The material observed this way was used without further purification.

UPLC-MS (Method 1): Rt=0.90 min; MS (EI$_{neg}$): m/z=280 [M−H]⁻.

$^1$H-NMR (400 MHz, DMSO-d6): δ [ppm]=2.36 (s, 3H), 3.79 (s, 3H), 7.11 (t, 1H), 7.21 (s br, 2H), 7.32 (m, 1H), 7.62 (dd, 1H), 9.50 (s, 1H).

Intermediate 6

2-Chloro-N,N-dimethyl-1,3-thiazole-5-carboxamide

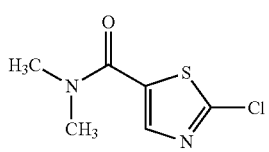

A mixture of 2-chloro-1,3-thiazole-5-carboxylic acid [CAS-RN: 5198-87-8] (1.00 g, 6.11 mmol, 1.0 eq), dimethylamine [CAS-RN: 124-40-3] (3.67 mL, 2M solution in THF, 7.34 mmol, 1.2 eq), HATU (2.79 g, 7.34 mmol, 1.2 eq) and DIPEA (3.19 mL, 18.3 mmol, 3.0 eq) was dissolved in 28 mL DMF and stirred at rt overnight. The reaction mixture was partitioned between ethyl acetate and water. The organic phase was washed with brine and separated by the use of a Whatman filter. The volatile components were removed in vacuo and the crude material obtained was purified via preparative MPLC (Biotage Isolera; 50 g NH2-SNAP cartridge: hexane->hexane/ethyl acetate 1/1) to give 800 mg (56% yield of theory) of the title compound.

$^1$H-NMR (400 MHz, DMSO-d6): δ [ppm]=2.99 (s, 3H), 3.20 (s, 3H), 8.06 (s, 1H).

Intermediate 7

5-Amino-N-(3,4-dichlorophenyl)-3-methyl-1,2-thiazole-4-carboxamide

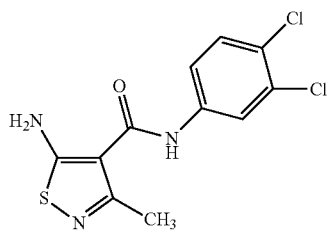 [SMILES: Cc1nsc(N)c1C(=O)Nc1ccc(Cl)c(Cl)c1]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (11.0 g, 69.5 mmol, 1.0 eq) and thionyl chloride (45.7 mL, 626 mmol, 9.0 eq) was stirred at 80° C. for 2 h. After cooling, the volatile components were removed in vacuo. The crude acid chloride was diluted with toluene and concentrated at the rotary evaporator. This process was repeated two times. The acid chloride (11.0 g, 62.3 mmol, 1.0 eq) observed this way was dissolved in THF (400 mL). Then, 3,4-dichloroaniline [CAS-RN: 95-76-1] (20.2 g, 125 mmol, 2.0 eq) and triethyl amine (17.4 mL, 125 mmol, 2.0 eq) was added. The reaction mixture was stirred at rt overnight. After addition of water the crude reaction mixture was extracted with EtOAc. The organic phase was washed with brine. The phases were separated by the use of a Whatman filter. During this process a white precipitate remained on the filter. This solid was dried under high vacuum to give the title compound (6.69 g, 26% yield) in 93% purity (based on UPLC-MS area-%).

UPLC-MS (Method 1): Rt=1.16 min; MS (EI$_{neg}$): m/z=300 [M−H]⁻.

$^1$H-NMR (400 MHz, DMSO-d6): δ [ppm]=2.36 (s, 3H), 7.29 (s br, 2H), 7.55-7.59 (m, 2H), 8.02 (s, 1H), 9.78 (s, 1H).

Intermediate 8

6-Chloro-N-ethylpyrazine-2-carboxamide

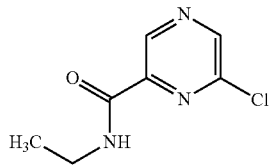

A mixture of 6-chloropyrazine-2-carbonyl chloride [CAS-RN: 148673-71-6, for the synthesis, please see: M. J. C. Scanio et al., J. Med. Chem. (2011), 54, 7678-7692.] (400 mg, 2.26 mmol, 1.0 eq), triethylamine (0.79 mL, 5.65 mmol, 2.5 eq), and ethylamine [CAS-RN: 75-04-7] (2.26 mL, 2M solution in THF, 4.52 mmol, 2.0 eq) in 15 mL THF was stirred at rt overnight. The reaction mixture was partitioned between ethyl acetate and water. The organic phase was washed with brine and separated by the use of a Whatman filter. The volatile components were removed in vacuo and the crude material obtained was purified via preparative MPLC (Biotage Isolera; 25 g SNAP cartridge: hexane/ethyl acetate 8/2->hexane/ethyl acetate 1/1) to give 90 mg (19% yield of theory) of the title compound.

UPLC-MS (Method 1): $R_t$=0.76 min; MS ($EI_{pos}$): m/z=186 [M]$^+$.

$^1$H-NMR (400 MHz, DMSO-d6): δ [ppm]=1.12 (t, 3H), 3.31 (m, 2H), 8.90 (m, 1H), 8.99 (s, 1H), 9.11 (s, 1H).

Intermediate 9

5-Chloro-N-methylpyrazine-2-carboxamide

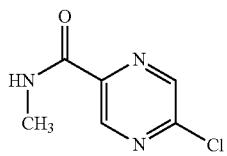

5-Hydroxypyrazine-2-carboxylic acid [CAS RN: 34604-60-9] (500 mg, 3.57 mmol, 1.0 eq) was treated with thionyl chloride (3.90 mL, 53.5 mmol, 15 eq) and 0.04 mL DMF. Then, the reaction mixture was heated to reflux temperature for 4 h. On cooling, the volatile components were removed in vacuo. The crude material remaining was diluted with toluene and the resulting solution was concentrated by the use of a rotary evaporator. This procedure was repeated two more times. Then, the remaining material was treated with 4 ml DMF and with 2-methoxy-N-methylethanamine [CAS-RN: 38256-93-8] (795 mg, 8.92 mmol, 2.5 eq). The reaction mixture was stirred at rt overnight. The volatile components were removed in vacuo and the crude material was purified via preparative MPLC (Biotage Isolera; 25 g SNAP cartridge: hexane->hexane/ethyl acetate 2/1->ethyl acetate) to give 300 mg (49% yield of theory) of the title compound.

UPLC-MS (Method 1): $R_t$=0.64 min; MS ($EI_{pos}$): m/z=172 [M+H]$^+$.

$^1$H-NMR (400 MHz, DMSO-d6): δ [ppm]=2.82 (d, 3H), 8.85 (d, 1H), 8.89 (m, 1H), 8.98 (d, 1H).

Intermediate 10

6-Bromo-N-methylpyridazine-3-carboxamide

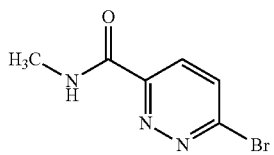

6-Bromopyridazine-3-carboxylic acid [CAS RN: 65202-51-9] (250 mg, 1.23 mmol, 1.0 eq) was dissolved in 9.3 mL THF and CDI (200 mg, 1.23 mmol, 1.0 eq) was added. Then, the reaction mixture was heated to 70° C. for 1 h. Then, methylamine [CAS RN: 74-89-5] (2M in THF, 0.63 mL, 1.27 mmol, 1.03 eq) was added and the reaction mixture was heated to 70° C. for 2 h. The volatile components were removed in vacuo and the crude material was purified via preparative MPLC (Biotage Isolera; 25 g SNAP cartridge: hexane->hexane/ethyl acetate 2/1) to give 94 mg (34% yield of theory) of the title compound.

UPLC-MS (Method 1): $R_t$=0.60 min; MS ($EI_{pos}$): m/z=216 [M]$^+$.

$^1$H-NMR (400 MHz, DMSO-d6): δ [ppm]=2.84 (d, 3H), 8.09 (d, 1H), 8.20 (d, 1H), 9.20 (m, 1H).

Intermediate 11

(2-Chloro-1,3-thiazol-5-yl)(morpholin-4-yl)methanone

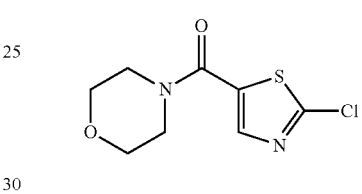

A mixture of 2-chloro-1,3-thiazole-5-carboxylic acid [CAS-RN: 101012-12-8] (500 mg, 3.06 mmol, 1.0 eq), morpholine [CAS-RN: 110-91-8] (270 µL, 3.06 mmol, 1.0 eq), HATU (1.40 g, 3.67 mmol, 1.2 eq) and DIPEA (1.60 mL, 9.17 mmol, 3.0 eq) was dissolved in 14 mL DMF and stirred at rt overnight. The reaction mixture was partitioned between ethyl acetate and water. The organic phase was washed with brine and filtered through a Whatman filter. The volatile components were removed in vacuo and the crude material obtained was purified via preparative MPLC (Biotage Isolera; 25 g SNAP cartridge: hexane/ethyl acetate 8/2->hexane/ethyl acetate 4/6) to give 600 mg (84% yield of theory) of the title compound.

UPLC-MS (Method 1): $R_t$=0.73 min; MS ($EI_{pos}$): m/z=233 [M+H]$^+$.

$^1$H-NMR (400 MHz, DMSO-d6): δ [ppm]=3.62 (s, 8H), 8.01 (s, 1H).

Intermediate 12

2-Chloro-N-ethyl-1,3-thiazole-4-carboxamide

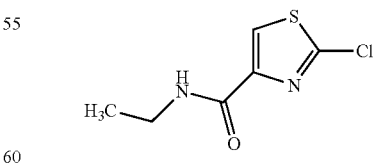

A mixture of 2-chloro-1,3-thiazole-4-carboxylic acid [CAS-RN: 5198-87-8] (500 mg, 3.06 mmol, 1.0 eq), ethylamine [CAS-RN: 75-04-7] (2M solution in THF, 1.83 mL, 3.67 mmol, 1.2 eq), HATU (1.40 g, 3.67 mmol, 1.2 eq) and DIPEA (1.60 mL, 9.17 mmol, 3.0 eq) was dissolved in 14 mL DMF and stirred at rt overnight. The reaction mixture was partitioned between ethyl acetate and water. The organic phase was washed with brine and filtered through a Whatman filter. The volatile components of the resulting organic phase were removed in vacuo and the crude material obtained was purified via preparative MPLC (Biotage Isolera; 25 g SNAP cartridge: hexane->hexane/ethyl acetate 2/1) to give 380 mg (59% yield of theory) of the title compound in 90% purity (UPLC-MS area-%), which was used in the following step without further purification.

UPLC-MS (Method 1): $R_t$=0.83 min; MS (EI$_{pos}$): m/z=191 [M+1]$^+$.

$^1$H-NMR (400 MHz, DMSO-d6): δ [ppm]=1.08 (t, 3H), 3.24 (m, 2H), 8.20 (s, 1H), 8.48 (m, 1H).

Intermediate 13

6-Chloro-N,N-dimethylpyrazine-2-carboxamide

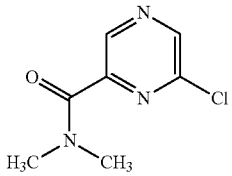

A mixture of 6-chloropyrazine-2-carboxylic acid [CAS-RN: 23688-89-3] (510 mg, 3.22 mmol, 1.0 eq), dimethylamine [CAS-RN: 124-40-3] (1.61 mL, 2M solution in THF, 3.22 mmol, 1.0 eq), HATU (1.47 g, 3.86 mmol, 1.2 eq) and DIPEA (1.78 mL, 9.65 mmol, 3.0 eq) was dissolved in 15 mL DMF and stirred at rt overnight. The reaction mixture was partitioned between ethyl acetate and water. The organic phase was washed with brine and separated by the use of a Whatman filter. The volatile components were removed in vacuo and the crude material obtained was purified via preparative MPLC (Biotage Isolera; 25 g SNAP cartridge: hexane/ethyl acetate 8/2->hexane/ethyl acetate 4/6) to give 330 mg (50% yield of theory) of the title compound.

UPLC-MS (Method 1): $R_t$=0.67 min; MS (EI$_{pos}$): m/z=186 [M]$^+$.

Intermediate 14

5-Amino-3-methyl-N-(6-phenoxypyridin-3-yl)-1,2-thiazole-4-carboxamide

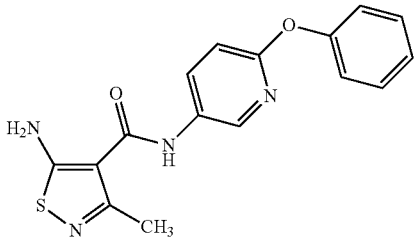 [SMILES: Cc1nsc(N)c1C(=O)Nc1ccc(Oc2ccccc2)nc1]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (3 g, 19 mmol, 1.0 eq) and thionyl chloride (15 mL, 209 mmol, 11.0 eq) was stirred at 80° C. for 5 h. After cooling, the volatile components were removed in vacuo. The crude acid chloride was diluted with toluene and concentrated at the rotary evaporator. This process was repeated two more times. The acid chloride observed this way [4 g, ~80% purity (LC-MS area-%), ~18 mmol] was diluted with THF (54 mL) and 9 mL of this acid chloride solution were reacted with 6-phenoxypyridin-3-amine [CAS-RN: 25194-67-6] (692 mg, 3.7 mmol, 1.2 eq) and triethyl amine (1.3 mL, 9.3 mmol, 3.0 eq) was added. The reaction mixture was stirred at rt 2 hours. After removal of the volatile components by the use of a rotary evaporator the crude material was purified via preparative MPLC (Biotage Isolera; 100 g SNAP cartridge: dichloromethane/methanol 95/5) and was purified again via preparative MPLC (Biotage Isolera; 100 g SNAP cartridge: hexane/ethyl acetate 70/30->50/50) to yield 155 mg (15% yield of theory) of the title compound.

UPLC-MS (Method 1): Rt=1.02 min; MS (EI$_{neg}$): m/z=325 [M−H]$^-$.

Intermediate 15

5-Amino-N-[6-(2,4-difluorophenoxyl)pyridin-3-yl]-3-methyl-1,2-thiazole-4-carboxamide

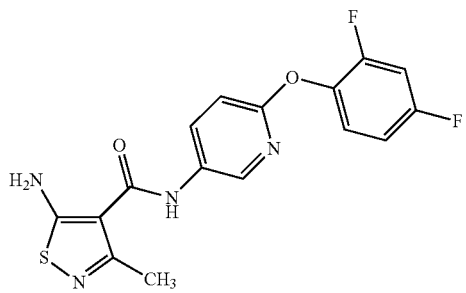 [SMILES: Cc1nsc(N)c1C(=O)Nc1ccc(Oc2ccc(F)cc2F)nc1]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (3 g, 19 mmol, 1.0 eq) and thionyl chloride (15 mL, 209 mmol, 11.0 eq) was stirred at 80° C. for 5 h. After cooling, the volatile components were removed in vacuo. The crude acid chloride was diluted with toluene and concentrated at the rotary evaporator. This process was repeated two more times. The acid chloride observed this way [4 g, ~80% purity (LC-MS area-%), ~18 mmol] was diluted with THF (54 mL) and 9 mL of this acid chloride solution were reacted with 6-(2,4-difluorophenoxyl)pyridin-3-amine [CAS-RN: 219865-86-8] (806 mg, 3.6 mmol, 1.2 eq) and triethyl amine (1.3 mL, 9.1 mmol, 3.0 eq) was added. The reaction mixture was stirred at rt 2 hours and 3 mL of the acid chloride solution were added and the reaction mixture was stirred for additional 45 min at rt. After removal of the volatile components by the use of a rotary evaporator the crude material was purified via preparative MPLC (Biotage Isolera; 100 g SNAP cartridge: hexane/ethyl acetate 70/30->50/50) to yield 170 mg (16% yield of theory) of the title compound.

UPLC-MS (Method 1): Rt=1.09 min; MS (EI$_{neg}$): m/z=361 [M−H]$^-$.

Intermediate 16

5-Amino-N-[6-(cyclohexyloxy)pyridin-3-yl]-3-methyl-1,2-thiazole-4-carboxamide

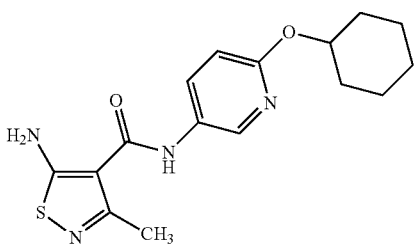 [SMILES: Cc1nsc(N)c1C(=O)Nc1ccc(OC2CCCCC2)nc1]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (5 g, 31.6 mmol, 1.0 eq) and thionyl chloride (25 mL, 348 mmol, 11.0 eq) was stirred at 80° C. for 5 h. After cooling, the volatile components were removed in vacuo. The crude acid chloride was diluted with toluene and concentrated at the rotary evaporator. This process was repeated two more times. The acid chloride observed this way [6.6 g, ~80% purity (LC-MS area-%), ~31 mmol] was diluted with THF (48 mL) and 6 mL of this acid chloride solution were reacted with 6-(cyclohexyloxy)pyridin-3-amine (for the synthesis, please see: H. L. Friedmann et. al, JACS. (1947), 69, 1204-1206.] (740 mg, 3.9 mmol, 1.0 eq) and triethyl amine (1.6 mL, 11.6 mmol, 3.0 eq) was added. The reaction mixture was stirred at rt 2.5 hours. After removal of the volatile components by the use of a rotary evaporator the crude material was purified via preparative MPLC (Biotage Isolera; 100 g SNAP cartridge: hexane/ethyl acetate 70/30→50/50) to yield 560 mg (44% yield of theory) of the title compound.

UPLC-MS (Method 1): Rt=1.18 min; MS (EI$_{pos}$): m/z=333 [M+H]$^+$.

Intermediate 17

5-Amino-N-[6-(4-methoxyphenoxyl)pyridin-3-yl]-3-methyl-1,2-thiazole-4-carboxamide

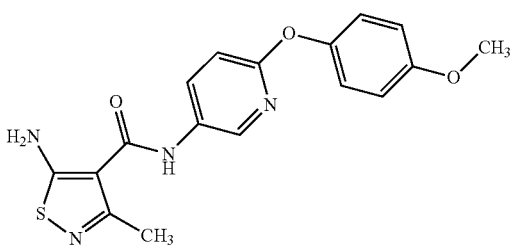 [SMILES: COc1ccc(Oc2ccc(NC(=O)c3c(C)nsc3N)cn2)cc1]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (3.5 g, 22.1 mmol, 1.0 eq) and thionyl chloride (17.8 mL, 243 mmol, 11.0 eq) was stirred at 80° C. for 5 h. After cooling, the volatile components were removed in vacuo. The crude acid chloride was diluted with toluene and concentrated at the rotary evaporator. This process was repeated two more times. The acid chloride observed this way [3.6 g, ~80% purity (LC-MS area-%), ~31 mmol] was diluted with THF (35 mL) and 5 mL of this acid chloride solution were reacted with 6-(4-methoxyphenoxyl)pyridin-3-amine [CAS-RN: 219865-99-3] (609 mg, 2.8 mmol, 1.2 eq) and triethyl amine (1 mL, 7 mmol, 3.0 eq) was added. The reaction mixture was stirred at rt 2.5 hours. After removal of the volatile components by the use of a rotary evaporator the crude material was purified via preparative MPLC (Biotage Isolera; 100 g SNAP cartridge: hexane/ethyl acetate 70/30→50/50→100/0) to yield 340 mg (41% yield of theory) of the title compound.

UPLC-MS (Method 1): Rt=1.01 min; MS (EI$_{pos}$): m/z=357 [M+H]$^+$.

Intermediate 18

5-Amino-N-(6-ethoxypyridin-3-yl)-3-methyl-1,2-thiazole-4-carboxamide

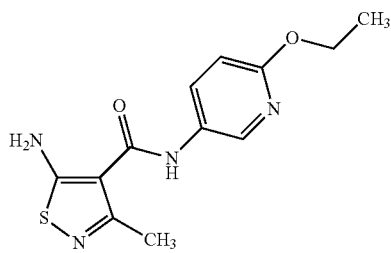 [SMILES: CCOc1ccc(NC(=O)c2c(C)nsc2N)cn1]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (2 g, 12.6 mmol, 1.0 eq) and thionyl chloride (10.1 mL, 139.1 mmol, 11.0 eq) was stirred at 80° C. for 4.5 h. After cooling, the volatile components were removed in vacuo. The crude acid chloride was diluted with toluene and concentrated at the rotary evaporator. This process was repeated two more times. The acid chloride observed this way [2.6 g, ~80% purity (LC-MS area-%), ~12 mmol] was diluted with THF (40 mL) and 8 mL of this acid chloride solution were reacted with 6-ethoxypyridin-3-amine [CAS-RN: 52025-34-0] (405 mg, 2.9 mmol, 1.2 eq) and triethyl amine (1 mL, 7.3 mmol, 3.0 eq) was added. The reaction mixture was stirred at rt 2.5 hours. After removal of the volatile components by the use of a rotary evaporator the crude material was purified via preparative MPLC (Biotage Isolera; 100 g SNAP cartridge: hexane/ethyl acetate 1/1) and afterwards purified via preparative HPLC (method A) to yield 120 mg (18% yield of theory) of the title compound.

UPLC-MS (Method 1): Rt=0.85 min; MS (EI$_{pos}$): m/z=279 [M+H]$^+$.

Intermediate 19

5-Amino-N-(6-methoxy-5-methylpyridin-3-yl)-3-methyl-1,2-thiazole-4-carboxamide

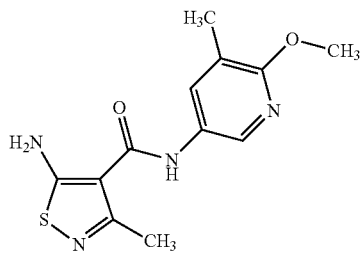 [SMILES: COc1ncc(NC(=O)c2c(C)nsc2N)cc1C]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (2 g, 12.6 mmol, 1.0 eq) and thionyl chloride (10.1 mL, 139.1 mmol, 11.0 eq) was stirred at 80° C. for 4.5 h. After cooling, the volatile components were removed in vacuo. The crude acid chloride was diluted with toluene and concentrated at the rotary evaporator. This process was repeated two more times. The acid chloride observed this way [2.6 g, ~80% purity (LC-MS area-%), ~12 mmol] was diluted with THF (40 mL) and 8 mL of this acid chloride solution were reacted with 6-methoxy-5-methylpyridin-3-amine [CAS-RN: 867012-70-2] (405 mg, 2.9 mmol, 1.2 eq) and triethyl amine (1 mL, 7.3 mmol, 3.0 eq) was added. The reaction mixture was stirred at rt 2.5 hours. After removal of the volatile components by the use of a rotary evaporator the crude material was purified via preparative MPLC (Biotage Isolera; 100 g SNAP cartridge: dichloromethane/methanol 95/5) to yield 270 mg (40% yield of theory) of the title compound.

UPLC-MS (Method 3): Rt=0.89 min; MS (EI$_{pos}$): m/z=279 [M+H]$^+$.

Intermediate 20

5-Amino-N-(6-isopropoxypyridin-3-yl)-3-methyl-1,2-thiazole-4-carboxamide

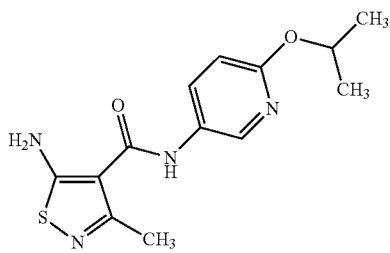 [SMILES: Cc1nsc(N)c1C(=O)Nc1ccc(OC(C)C)nc1]

A mixture of 5-amino-3-methyl-1,2-thiazole-4-carboxylic acid [CAS-RN: 22131-51-7, for the synthesis, please see: J. Goerdeler, H. Horn, Chem. Ber. (1963), 96, 1551-1560.] (2 g, 12.6 mmol, 1.0 eq) and thionyl chloride (10.1 mL, 139.1 mmol, 11.0 eq) was stirred at 80° C. for 4.5 h. After cooling, the volatile components were removed in vacuo. The crude acid chloride was diluted with toluene and concentrated at the rotary evaporator. This process was repeated two more times. The acid chloride observed this way [2.6 g, ~80% purity (LC-MS area-%), ~12 mmol] was diluted with THF (40 mL) and 8 mL of this acid chloride solution were reacted with 6-isopropoxypyridin-3-amine [CAS-RN: 52025-36-2] (446 mg, 2.9 mmol, 1.2 eq) and triethyl amine (1 mL, 7.3 mmol, 3.0 eq) was added. The reaction mixture was stirred at rt 2.5 hours. After removal of the volatile components by the use of a rotary evaporator the crude material was purified via preparative MPLC (Biotage Isolera; 100 g SNAP cartridge: dichloromethane/methanol 95/5) to yield 220 mg (31% yield of theory) of the title compound.

UPLC-MS (Method 1): Rt=0.95 min; MS (EI$_{neg}$): m/z=291 [M−H]$^-$.

EXAMPLES

Example 1

N-(2-Ethylphenyl)-3-methyl-5-(pyrazin-2-ylamino)-1,2-thiazole-4-carboxamide

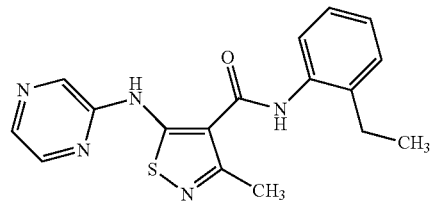 [SMILES: CCc1ccccc1NC(=O)c1c(C)nsc1Nc1cnccn1]

A mixture of 5-amino-N-(2-ethylphenyl)-3-methyl-1,2-thiazole-4-carboxamide [Intermediate 1] (150 mg, 0.57 mmol, 1.4 eq), 2-chloropyrazine [CAS-RN: 14508-49-7] (47 mg, 0.41 mmol, 1.0 eq) and cesium carbonate (307 mg, 0.94 mmol, 2.3 eq) in 3.5 mL dioxane was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via MPLC (Biotage Isolera; 50 g SNAP cartridge: hexane/ethyl acetate 9/1->hexane/ethyl acetate 4/6). The product fractions obtained were crystallised from diethylether to give 51 mg (26% yield of theory) of the title compound.

UPLC-MS (Method 1): R$_t$=1.22 min; MS (EI$_{neg}$): m/z=338 [M−H]$^-$.

$^1$H-NMR (400 MHz, CDCl$_3$): δ [ppm]=1.30 (t, 3H), 2.71 (q, 2H), 2.85 (s, 3H), 7.24-7.28 (m, 1H, partially covered by solvent signal), 7.30-7.36 (m, 2H), 7.62 (s br, 1H), 7.78 (m, 1H), 8.19 (d, 1H), 8.37 (dd, 1H), 8.43 (d, 1H), 12.03 (s br, 1H).

Example 2

N-(2-Ethylphenyl)-3-methyl-5-(pyrimidin-4-ylamino)-1,2-thiazole-4-carboxamide

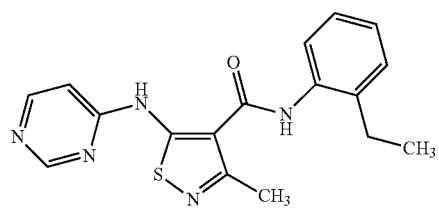 [SMILES: CCc1ccccc1NC(=O)c1c(C)nsc1Nc1ccncn1]

A mixture of 5-amino-N-(2-ethylphenyl)-3-methyl-1,2-thiazole-4-carboxamide [Intermediate 1] (150 mg, 0.57 mmol, 1.4 eq), 4-chloropyrimidine [CAS-RN: 17180-93-7] (47 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium (II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to yield 20 mg (10% yield of theory) of the title compound.

UPLC-MS (Method 3): $R_t$=1.12 min; MS ($EI_{pos}$): m/z=340 [M+H]$^+$.

$^1$H-NMR (400 MHz, DMSO-d$_6$): δ [ppm]=1.16 (t, 3H), 2.56 (s, 3H), 2.60-2.75 (m, 2H), 7.07-7.39 (m, 4H), 7.57 (s br, 1H), 8.41 (s br, 1H), 8.88 (s, 1H), 9.54 (s br, 1H), 10.96 (s br, 1H).

Example 3

N-(2-Ethylphenyl)-3-methyl-5-{[3-(trifluoromethyl)pyridin-2-yl]amino}-1,2-thiazole-4-carboxamide

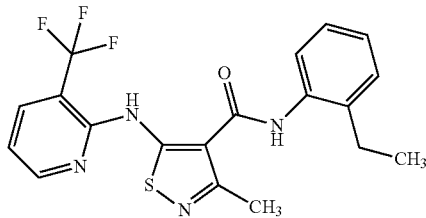 [SMILES: CCc1ccccc1NC(=O)c1c(C)nsc1Nc1ncccc1C(F)(F)F]

A mixture of 5-amino-N-(2-ethylphenyl)-3-methyl-1,2-thiazole-4-carboxamide [Intermediate 1] (150 mg, 0.57 mmol, 1.4 eq), 2-bromo-3-(trifluoromethyl)pyridine [CAS-RN: 175205-82-0] (93 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5) to deliver 45 mg (19% yield of theory) of the title compound.

UPLC-MS (Method 1): $R_t$=1.48 min; MS ($EI_{neg}$): m/z=405 [M−H]$^-$.

$^1$H-NMR (400 MHz, CDCl$_3$): δ [ppm]=1.30 (t, 3H), 2.70 (q, 2H), 2.84 (s, 3H), 7.05 (dd, 1H), 7.17-7.37 (m, 3H, partially covered by solvent signal), 7.61 (s br, 1H), 7.95 (d, 2H), 8.61 (d, 1H), 12.55 (s br, 1H).

Example 4

5-[(4-Cyanopyridin-2-yl)amino]-N-(2-ethylphenyl)-3-methyl-1,2-thiazole-4-carboxamide

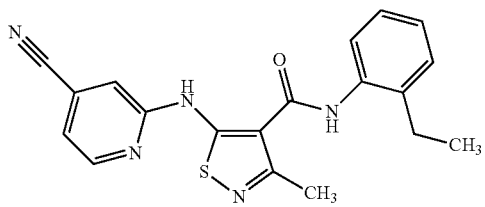 [SMILES: CCc1ccccc1NC(=O)c1c(C)nsc1Nc1cc(C#N)ccn1]

A mixture of 5-amino-N-(2-ethylphenyl)-3-methyl-1,2-thiazole-4-carboxamide [Intermediate 1] (150 mg, 0.57 mmol, 1.4 eq), 2-iodoisonicotinonitrile [CAS-RN: 114821-24-8] (94 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5). Then, the resulting product fractions were combined, concentrated in vacuo and crystallised from diethyl ether to deliver 83 mg (40% yield of theory) of the title compound.

UPLC-MS (Method 1): $R_t$=1.35 min; MS ($EI_{neg}$): m/z=362 [M−H]$^-$.

$^1$H-NMR (400 MHz, CDCl$_3$): δ [ppm]=1.29 (t, 3H), 2.70 (q, 2H), 2.84 (s, 3H), 7.11 (dd, 1H), 7.16 (m, 1H), 7.21-7.28 (m, 1H, partially covered by solvent signal), 7.29-7.36 (m, 2H), 7.62 (s br, 1H), 7.79 (m, 1H), 8.58 (d, 1H), 12.07 (s br, 1H).

Example 5

N-(2-Ethylphenyl)-3-methyl-5-[(4-phenylpyrimidin-2-yl)amino]-1,2-thiazole-4-carboxamide

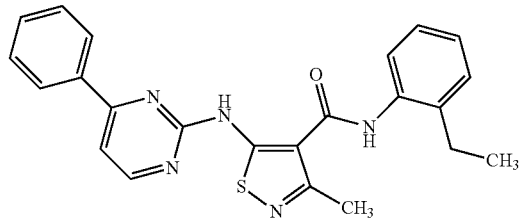 [SMILES: CCc1ccccc1NC(=O)c1c(C)nsc1Nc1nccc(-c2ccccc2)n1]

A mixture of 5-amino-N-(2-ethylphenyl)-3-methyl-1,2-thiazole-4-carboxamide [Intermediate 1] (150 mg, 0.57 mmol, 1.4 eq), 2-chloro-4-phenylpyrimidine [CAS-RN: 13036-50-5] (78 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5) to deliver 30 mg (13% yield of theory) of the title compound.

UPLC-MS (Method 3): $R_t$=1.50 min; MS ($EI_{neg}$): m/z=414 [M−H]$^-$.

$^1$H-NMR (400 MHz, CDCl$_3$): δ [ppm]=1.33 (t, 3H), 2.74 (q, 2H), 2.87 (s, 3H), 7.23-7.30 (m, 1H, partially covered by solvent signal), 7.31-7.39 (m, 3H), 7.51-7.56 (m, 4H), 7.93 (d, 1H), 8.22 (s br, 2H), 8.67 (d, 1H), 11.82 (s br, 1H).

Example 6

5-[(2-Cyanopyrimidin-4-yl)amino]-N-(2-ethylphenyl)-3-methyl-1,2-thiazole-4-carboxamide

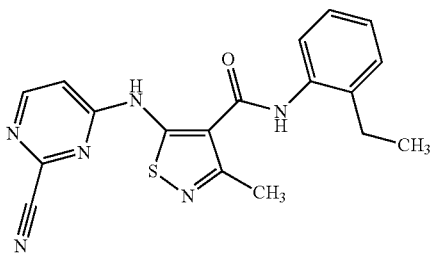 [SMILES: CCc1ccccc1NC(=O)c1c(C)nsc1Nc1ccnc(C#N)n1]

A mixture of 5-amino-N-(2-ethylphenyl)-3-methyl-1,2-thiazole-4-carboxamide [Intermediate 1] (150 mg, 0.57 mmol, 1.4 eq), 4-chloropyrimidine-2-carbonitrile [CAS-RN: 898044-48-9] (57 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5) to deliver 10 mg (5% yield of theory) of the title compound.

UPLC-MS (Method 1): $R_t$=1.29 min; MS ($EI_{neg}$): m/z=363 [M−H]⁻.

$^1$H-NMR (400 MHz, DMSO-$d_6$): δ [ppm]=1.15 (t, 3H), 2.57 (s, 3H), 2.65 (m, 2H), 7.13-7.24 (m, 2H), 7.27 (dd, 1H), 7.47-7.21 (m, 2H), 8.58 (d, 1H), 9.66 (s br, 1H), 11.36 (s br, 1H).

Example 7

5-[(5-Cyanopyridin-2-yl)amino]-N-(2-ethylphenyl)-3-methyl-1,2-thiazole-4-carboxamide

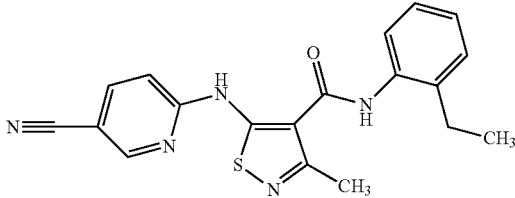 [SMILES: CCc1ccccc1NC(=O)c1c(C)nsc1Nc1ccc(C#N)cn1]

A mixture of 5-amino-N-(2-ethylphenyl)-3-methyl-1,2-thiazole-4-carboxamide [Intermediate 1] (150 mg, 0.57 mmol, 1.4 eq), 6-iodonicotinonitrile [CAS-RN: 289470-22-0] (94 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via MPLC (Biotage Isolera; 50 g SNAP cartridge: hexane/ethyl acetate 9/1->hexane/ethyl acetate 4/6) to give 66 mg (32% yield) of the title compound.

UPLC-MS (Method 1): $R_t$=1.37 min; MS ($EI_{neg}$): m/z=362 [M−H]⁻.

$^1$H-NMR (400 MHz, CDCl$_3$): δ [ppm]=1.30 (t, 3H), 2.71 (q, 2H), 2.84 (s, 3H), 7.11 (dd, 1H), 7.16 (s, 1H), 7.22-7.29 (m, 1H, partially covered by solvent signal), 7.30-7.35 (m, 2H), 7.62 (s br, 1H), 7.79 (m, 1H), 8.58 (d, 1H), 12.08 (s br, 1H).

Example 8

5-[(3-Cyanopyridin-2-yl)amino]-N-(2-ethylphenyl)-3-methyl-1,2-thiazole-4-carboxamide

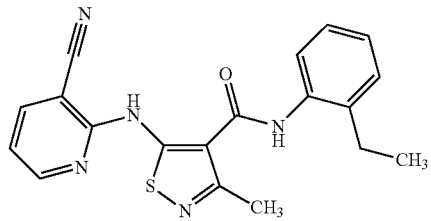 [SMILES: CCc1ccccc1NC(=O)c1c(C)nsc1Nc1ncccc1C#N]

A mixture of 5-amino-N-(2-ethylphenyl)-3-methyl-1,2-thiazole-4-carboxamide [Intermediate 1] (150 mg, 0.57 mmol, 1.4 eq), 2-chloronicotinonitrile [CAS-RN: 6602-54-6] (57 mg, 0.41 mmol, 1.0 eq) and cesium carbonate (307 mg, 0.94 mmol, 2.3 eq) in 3.5 mL dioxane was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5). The product fractions obtained were crystallised from diethylether to give 51 mg (26% yield of theory) of the title compound.

UPLC-MS (Method 1): $R_t$=1.33 min; MS ($EI_{neg}$): m/z=362 [M−H]⁻.

$^1$H-NMR (400 MHz, CDCl$_3$): δ [ppm]=1.30 (t, 3H), 2.71 (q, 2H), 2.86 (s, 3H), 7.02 (dd, 1H), 7.15-7.35 (m, 3H, partially covered by solvent signal), 7.65 (s br, 1H), 7.95 (dd, 1H), 8.03 (d, 1H), 8.63 (dd, 1H), 12.76 (s br, 1H).

Example 9

N-(2-Ethylphenyl)-5-{[6-(1H-imidazol-1-yl)pyrimidin-4-yl]amino}-3-methyl-1,2-thiazole-4-carboxamide

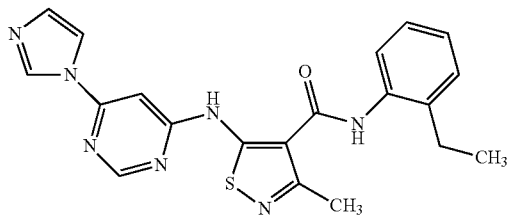 [SMILES: CCc1ccccc1NC(=O)c1c(C)nsc1Nc1cc(-n2ccnc2)ncn1]

A mixture of 5-amino-N-(2-ethylphenyl)-3-methyl-1,2-thiazole-4-carboxamide [Intermediate 1] (150 mg, 0.57 mmol, 1.4 eq), 4-chloro-6-(1H-imidazol-1-yl)pyrimidine [CAS-RN: 114834-02-5] (74 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to yield 10 mg (4% yield of theory) of the title compound.

UPLC-MS (Method 3): $R_t$=1.10 min; MS ($EI_{neg}$): m/z=404 [M–H]$^-$.

$^1$H-NMR (400 MHz, DMSO-d$_6$): δ [ppm]=1.16 (t, 3H), 2.59-2.69 (m, 5H), 7.18-7.25 (m, 2H), 7.26-7.31 (m, 2H), 7.52 (m, 1H), 7.75 (s, 1H), 7.94 (s br, 1H), 8.75 (s br, 1H), 8.90 (s, 1H), 9.50 (s, 1H), 11.23 (s br, 1H).

Example 10

N-(2-Ethylphenyl)-3-methyl-5-(quinazolin-4-ylamino)-1,2-thiazole-4-carboxamide

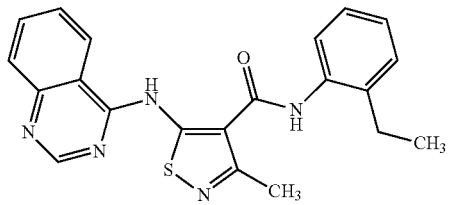 [SMILES: CCc1ccccc1NC(=O)c1c(C)nsc1Nc1ncnc2ccccc12]

A mixture of 5-amino-N-(2-ethylphenyl)-3-methyl-1,2-thiazole-4-carboxamide [Intermediate 1] (150 mg, 0.57 mmol, 1.4 eq), 4-chloroquinazoline [CAS-RN: 5190-68-1] (67 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5) to give 30 mg (13% yield of theory) of the title compound.

UPLC-MS (Method 1): $R_t$=1.24 min; MS ($EI_{neg}$): m/z=388 [M–H]$^-$.

$^1$H-NMR (400 MHz, DMSO-d$_6$): δ [ppm]=1.06 (t, 3H), 2.59 (s, 3H), 2.65 (q, 2H), 7.17 (t, 1H), 7.23 (t, 1H), 7.31 (dd, 1H), 7.54 (t, 1H), 7.60 (d, 2H), 7.81 (t, 1H), 8.11 (d, 1H), 8.84 (s, 1H), 11.69 (s br, 1H), 13.50 (s br, 1H).

Example 11

5-(1,3-Benzoxazol-2-ylamino)-N-(2-ethylphenyl)-3-methyl-1,2-thiazole-4-carboxamide

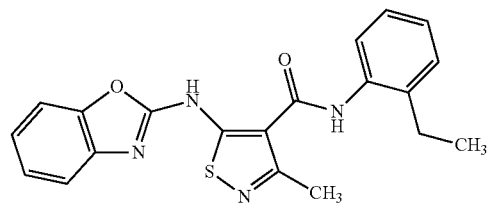

A mixture of 5-amino-N-(2-ethylphenyl)-3-methyl-1,2-thiazole-4-carboxamide [Intermediate 1] (150 mg, 0.57 mmol, 1.4 eq), 2-chloro-1,3-benzoxazole [CAS-RN: 615-18-9] (63 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to yield 30 mg (14% yield of theory) of the title compound.

UPLC-MS (Method 1): $R_t$=1.50 min; MS ($EI_{neg}$): m/z=377 [M–H]$^-$.

$^1$H-NMR (400 MHz, DMSO-d$_6$): δ [ppm]=1.26 (t, 3H), 2.70 (s, 3H), 2.85 (q, 2H), 7.05 (t, 1H), 7.18 (t, 2H), 7.22-7.31 (m, 2H), 7.45-7.58 (m, 2H), 8.17 (s br, 1H), 11.66 (s br, 1H).

Example 12

N-(2-Ethylphenyl)-3-methyl-5-(thieno[2,3-d]pyrimidin-4-ylamino)-1,2-thiazole-4-carboxamide

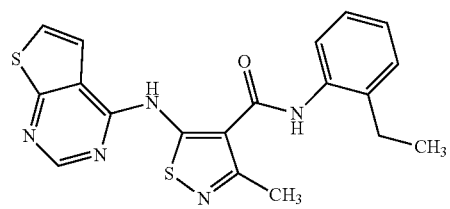 [SMILES: CCc1ccccc1NC(=O)c1c(C)nsc1Nc1ncnc2sccc12]

A mixture of 5-amino-N-(2-ethylphenyl)-3-methyl-1,2-thiazole-4-carboxamide [Intermediate 1] (150 mg, 0.57 mmol, 1.4 eq), 4-chlorothieno[2,3-d]pyrimidine [CAS-RN: 14080-59-2] (70 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to yield 10 mg (3% yield of theory) of the title compound.

UPLC-MS (Method 1): $R_t$=1.42 min; MS (EI$_{neg}$): m/z=394 [M−H]$^−$.

$^1$H-NMR (400 MHz, CDCl$_3$): δ [ppm]=1.31 (t, 3H), 2.73 (q, 2H), 2.87 (s, 3H), 7.24-7.30 (m, 1H, partially covered by solvent signal), 7.31-7.38 (m, 2H), 7.49 (d, 1H), 7.52 (d, 1H), 7.68 (s br, 1H), 7.83 (d, 1H), 8.87 (s, 1H), 12.61 (s br, 1H).

Example 13

N-(2-Ethylphenyl)-3-methyl-5-(thieno[3,2-d]pyrimidin-4-ylamino)-1,2-thiazole-4-carboxamide

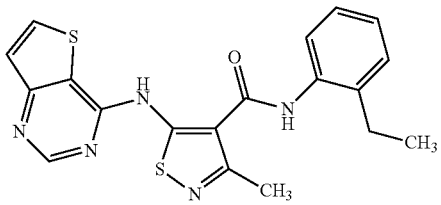 [SMILES: CCc1ccccc1NC(=O)c1c(C)nsc1Nc1ncnc2ccsc12]

A mixture of 5-amino-N-(2-ethylphenyl)-3-methyl-1,2-thiazole-4-carboxamide [Intermediate 1] (150 mg, 0.57 mmol, 1.4 eq), 4-chlorothieno[3,2-d]pyrimidine [CAS-RN: 16269-66-2] (70 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to yield 20 mg (7% yield of theory) of the title compound.

UPLC-MS (Method 1): $R_t$=1.27 min; MS (EI$_{neg}$): m/z=394 [M−H]$^−$.

$^1$H-NMR (400 MHz, DMSO-d$_6$): δ [ppm]=1.13 (t, 3H), 2.65 (s, 3H), 2.79 (m, 2H), 7.10-7.26 (m, 2H), 7.30 (d, 1H), 7.47 (s br, 1H), 7.64 (d, 1H), 8.23 (s br, 1H), 8.92 (s, 1H), 11.74 (s br, 1H).

Example 14

5-(1,3-Benzothiazol-2-ylamino)-N-(2-ethylphenyl)-3-methyl-1,2-thiazole-4-carboxamide

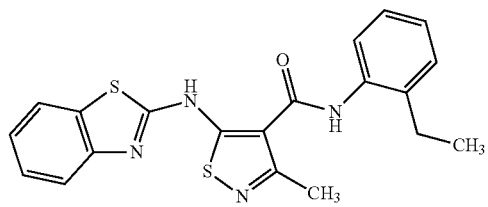 [SMILES: CCc1ccccc1NC(=O)c1c(C)nsc1Nc1nc2ccccc2s1]

A mixture of 5-amino-N-(2-ethylphenyl)-3-methyl-1,2-thiazole-4-carboxamide [Intermediate 1] (150 mg, 0.57 mmol, 1.4 eq), 2-chloro-1,3-benzothiazole [CAS-RN: 615-20-3] (70 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to yield 20 mg (9% yield of theory) of the title compound.

UPLC-MS (Method 1): $R_t$=1.60 min; MS (EI$_{neg}$): m/z=393 [M−H]$^−$.

$^1$H-NMR (400 MHz, CDCl$_3$): δ [ppm]=1.30 (t, 3H), 2.71 (q, 2H), 2.85 (s, 3H), 7.20-7.66 (m, 6H, partially covered by solvent signal), 7.71 (d, 1H), 7.79 (d, 1H), 7.87 (d, 1H), 12.20 (s br, 1H).

Example 15

N-(2-Ethylphenyl)-3-methyl-5-{[6-(methylamino)pyrimidin-4-yl]amino}-1,2-thiazole-4-carboxamide

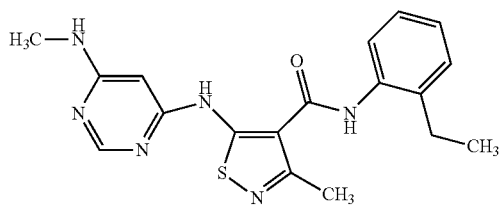 [SMILES: CCc1ccccc1NC(=O)c1c(C)nsc1Nc1cc(NC)ncn1]

A mixture of 5-amino-N-(2-ethylphenyl)-3-methyl-1,2-thiazole-4-carboxamide [Intermediate 1] (150 mg, 0.57 mmol, 1.4 eq), 6-chloro-N-methylpyrimidin-4-amine [CAS-RN: 65766-32-7] (59 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to yield 10 mg (5% yield of theory) of the title compound.

UPLC-MS (Method 4): $R_t$=1.15 min; MS (EI$_{neg}$): m/z=367 [M−H]$^-$.

$^1$H-NMR (400 MHz, CDCl$_3$): δ [ppm]=1.29 (t, 3H), 2.70 (q, 2H), 2.81 (s, 3H), 2.90 (d, 3H), 5.21 (s br, 1H), 5.80 (s, 1H), 7.20-7.66 (m, 3H, partially covered by solvent signal), 7.59 (s br, 1H), 7.77 (d, 1H), 8.43 (s, 1H), 11.69 (s br, 1H).

Example 16

N-(2-Ethylphenyl)-5-[(4-methoxypyrimidin-2-yl)amino]-3-methyl-1,2-thiazole-4-carboxamide

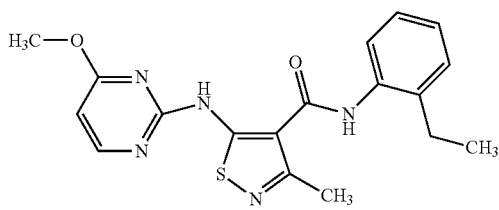

A mixture of 5-amino-N-(2-ethylphenyl)-3-methyl-1,2-thiazole-4-carboxamide [Intermediate 1] (150 mg, 0.57 mmol, 1.4 eq), 2-chloro-4-methoxypyrimidine [CAS-RN: 22536-63-6] (59 mg, 0.41 mmol, 1.0 eq) and cesium carbonate (307 mg, 0.94 mmol, 2.3 eq) in 3.5 mL dioxane was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5). The product fractions obtained were crystallised from diethylether to give 22 mg (10% yield of theory) of the title compound.

UPLC-MS (Method 1): $R_t$=1.36 min; MS (EI$_{neg}$): m/z=368 [M−H]$^-$.

$^1$H-NMR (400 MHz, DMSO-d$_6$): δ [ppm]=1.14 (t, 3H), 2.56-2.72 (m, 5H), 3.29 (s, 3H), 6.53 (d, 1H), 7.09-7.34 (m, 3H), 7.48 (m, 1H), 8.39 (d, 1H), 9.28 (s, 1H), 10.82 (s, 1H).

Example 17

N-(2-Ethylphenyl)-5-[(4-ethylpyrimidin-2-yl)amino]-3-methyl-1,2-thiazole-4-carboxamide

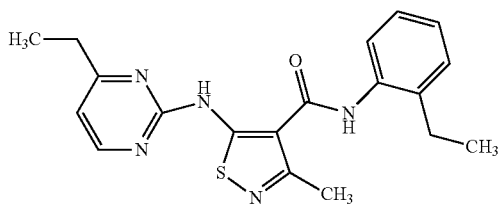 [SMILES: CCc1ccccc1NC(=O)c1c(C)nsc1Nc1nccc(OC)n1]

A mixture of 5-amino-N-(2-ethylphenyl)-3-methyl-1,2-thiazole-4-carboxamide [Intermediate 1] (150 mg, 0.57 mmol, 1.4 eq), 2-chloro-4-ethylpyrimidine [CAS-RN: 188707-99-5] (58 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to yield 50 mg (24% yield of theory) of the title compound.

UPLC-MS (Method 4): $R_t$=1.37 min; MS (EI$_{neg}$): m/z=366 [M−H]$^-$.

$^1$H-NMR (400 MHz, CDCl$_3$): δ [ppm]=1.23-1.46 (m, 6H), 2.70 (q, 2H), 2.75-2.90 (m, 5H), 6.78 (d, 1H), 7.21-7.35 (m, 3H, partially covered by solvent signal), 7.56 (s br, 1H), 7.90 (d, 1H), 8.46 (d, 1H), 11.67 (s br, 1H).

Example 18

N-(2-Ethylphenyl)-3-methyl-5-{[4-(trifluoromethyl)pyridin-2-yl]amino}-1,2-thiazole-4-carboxamide

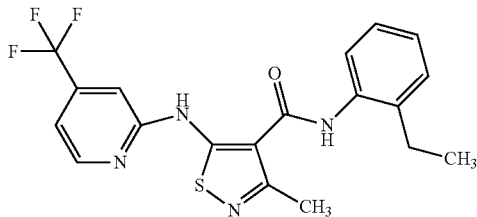 [SMILES: CCc1ccccc1NC(=O)c1c(C)nsc1Nc1cc(C(F)(F)F)ccn1]

A mixture of 5-amino-N-(2-ethylphenyl)-3-methyl-1,2-thiazole-4-carboxamide [Intermediate 1] (150 mg, 0.57 mmol, 1.4 eq), 2-bromo-4-(trifluoromethyl)pyridine [CAS-RN: 175205-81-9] (93 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to yield 10 mg (4% yield of theory) of the title compound.

UPLC-MS (Method 3): $R_t$=1.47 min; MS (EI$_{neg}$): m/z=405 [M−H]$^-$.

$^1$H-NMR (400 MHz, CDCl$_3$): δ [ppm]=1.29 (t, 3H), 2.71 (q, 2H), 2.84 (s, 3H), 7.12 (d, 1H), 7.16 (s, 1H), 7.21-7.37 (m, 3H, partially covered by solvent signal), 7.61 (s br, 1H), 7.80 (d, 1H), 8.60 (d, 1H), 12.05 (s br, 1H).

Example 19

N-(2-Ethylphenyl)-3-methyl-5-(quinoxalin-2-ylamino)-1,2-thiazole-4-carboxamide

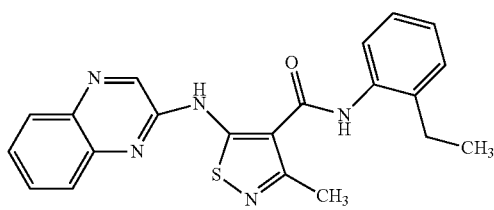 [SMILES: CCc1ccccc1NC(=O)c1c(C)nsc1Nc1cnc2ccccc2n1]

A mixture of 5-amino-N-(2-ethylphenyl)-3-methyl-1,2-thiazole-4-carboxamide [Intermediate 1] (150 mg, 0.57 mmol, 1.4 eq), 2-chloroquinoxaline [CAS-RN: 1448-87-9] (67 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium (II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5). The product fractions obtained were crystallised from diethylether to give 0.05 g (22% yield of theory) of the title compound.

UPLC-MS (Method 1): $R_t$=1.42 min; MS ($EI_{neg}$): m/z=388 [M−H]⁻.

¹H-NMR (400 MHz, CDCl₃): δ [ppm]=1.31 (t, 3H), 2.73 (q, 2H), 2.88 (s, 3H), 7.24-7.33 (m, 1H, partially covered by solvent signal), 7.30-7.38 (m, 2H), 7.61 (t, 1H), 7.66 (s br, 1H), 7.75 (t, 1H), 7.81 (d, 1H), 8.04 (d, 1H), 8.06 (d, 1H), 8.66 (s, 1H), 12.27 (s br, 1H).

Example 20

N-(2-Ethylphenyl)-5-[(6-fluoroquinoxalin-2-yl)amino]-3-methyl-1,2-thiazole-4-carboxamide

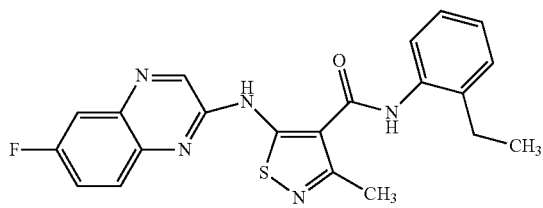 [SMILES: CCc1ccccc1NC(=O)c1c(C)nsc1Nc1cnc2cc(F)ccc2n1]

A mixture of 5-amino-N-(2-ethylphenyl)-3-methyl-1,2-thiazole-4-carboxamide [Intermediate 1] (150 mg, 0.57 mmol, 1.4 eq), 2-chloro-6-fluoroquinoxaline [CAS-RN: 55687-33-7] (75 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5). The product fractions obtained were crystallised from diethylether to give 40 mg (17% yield of theory) of the title compound.

UPLC-MS (Method 1): $R_t$=1.48 min; MS ($EI_{neg}$): m/z=406 [M−H]⁻.

¹H-NMR (400 MHz, DMSO-d₆): δ [ppm]=1.18 (m, 3H), 2.56-2.79 (m, 5H), 7.10-7.34 (m, 3H), 7.56 (s br, 1H), 7.67 (dt, 1H), 7.76 (dd, 1H), 8.03 (m, 1H), 9.08 (s br, 1H), 9.55 (s br, 1H), 11.33 (s br, 1H).

Example 21

N-(2-Ethylphenyl)-3-methyl-5-[(3-methylquinoxalin-2-yl)amino]-1,2-thiazole-4-carboxamide

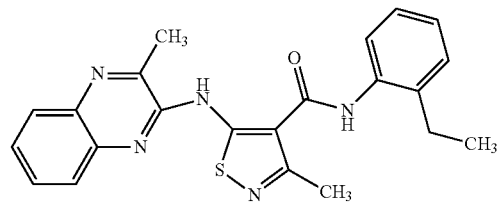 [SMILES: CCc1ccccc1NC(=O)c1c(C)nsc1Nc1nc2ccccc2nc1C]

A mixture of 5-amino-N-(2-ethylphenyl)-3-methyl-1,2-thiazole-4-carboxamide [Intermediate 1] (150 mg, 0.57 mmol, 1.4 eq), 2-chloro-3-methylquinoxaline [CAS-RN: 32601-86-8] (73 mg, 0.41 mmol, 1.0 eq) and cesium carbonate (307 mg, 0.94 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5). The product fractions obtained were crystallised from diethylether to give 3 mg (1.3% yield of theory) of the title compound.

UPLC-MS (Method 3): $R_t$=1.48 min; MS ($EI_{neg}$): m/z=402 [M−H]⁻.

¹H-NMR (400 MHz, CDCl₃): δ [ppm]=1.31 (t, 3H), 2.73 (q, 2H), 2.85 (s, 3H), 2.89 (s, 3H), 7.21-7.29 (m, 1H, partially covered by solvent signal), 7.30-7.39 (m, 2H), 7.58 (t, 1H), 7.64-7.74 (m, 2H), 7.87 (d, 1H), 7.97 (d, 1H), 8.05 (d, 1H), 12.45 (s br, 1H).

Example 22

N-(6-methoxypyridin-3-yl)-3-methyl-5-[(8-methylquinoxalin-2-yl)amino]-1,2-thiazole-4-carboxamide

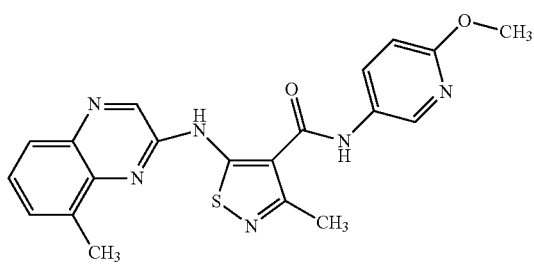 [SMILES: COc1ccc(NC(=O)c2c(C)nsc2Nc2cnc3cccc(C)c3n2)cn1]

A mixture of 5-amino-N-(6-methoxypyridin-3-yl)-3-methyl-1,2-thiazole-4-carboxamide [Intermediate 2] (150 mg, 0.57 mmol, 1.4 eq), 2-chloro-8-methylquinoxaline [CAS-RN: 61148-40-1] (72 mg, 0.41 mmol, 1.0 eq) and cesium carbonate (304 mg, 0.93 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (23 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallised from dichloromethane/ethyl acetate to give 65 mg (28% yield of theory) of the title compound in 99% purity (LC-MS area-%).

UPLC-MS (Method 1): $R_t$=1.25 min; MS ($EI_{neg}$): m/z=405 [M−H]−.

$^1$H-NMR (400 MHz, DMSO-d$_6$): δ [ppm]=2.77 (s, 3H), 3.82 (s, 3H), 6.85 (d, 1H), 7.51 (t, 1H), 7.65 (d, 1H), 7.81 (d, 1H), 8.05 (d, 1H), 8.52 (s br, 1H), 9.02 (s, 1H), 10.23 (s br, 1H), 11.36 (s br, 1H), 1×CH$_3$ covered by solvent signal.

Example 23

5-[(6-Chloroquinoxalin-2-yl)amino]-N-(6-methoxypyridin-3-yl)-3-methyl-1,2-thiazole-4-carboxamide

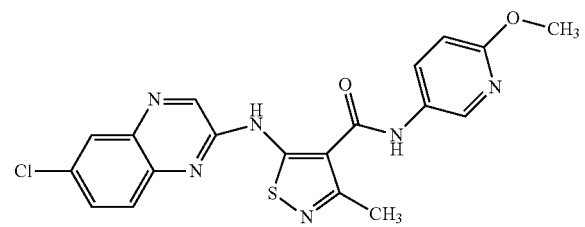 [SMILES: COc1ccc(NC(=O)c2c(C)nsc2Nc2cnc3cc(Cl)ccc3n2)cn1]

A mixture of 5-amino-N-(6-methoxypyridin-3-yl)-3-methyl-1,2-thiazole-4-carboxamide [Intermediate 2] (150 mg, 0.57 mmol, 1.4 eq), 2,6-dichloroquinoxaline [CAS-RN: 18671-97-1] (81 mg, 0.41 mmol, 1.0 eq) and cesium carbonate (304 mg, 0.93 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (23 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallised from dichloromethane/ethyl acetate to give 70 mg (29% yield of theory) of the title compound in 99% purity (LC-MS area-%).

UPLC-MS (Method 1): $R_t$=1.32 min; MS ($EI_{neg}$): m/z=425 [M−H]−.

$^1$H-NMR (400 MHz, DMSO-d$_6$): δ [ppm]=3.82 (s, 3H), 6.84 (d, 1H), 7.77 (dd, 1H), 7.96 (d, 1H), 8.00-8.10 (m, 2H), 8.52 (s br, 1H), 9.03 (s, 1H), 10.24 (s br, 1H), 11.39 (s br, 1H), 1×CH$_3$ covered by solvent signal.

Example 24

5-[(3-Cyanopyrazin-2-yl)amino]-N-(6-methoxypyridin-3-yl)-3-methyl-1,2-thiazole-4-carboxamide

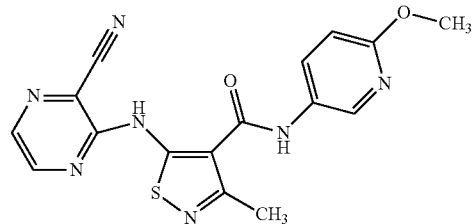 [SMILES: COc1ccc(NC(=O)c2c(C)nsc2Nc2nccnc2C#N)cn1]

A mixture of 5-amino-N-(6-methoxypyridin-3-yl)-3-methyl-1,2-thiazole-4-carboxamide [Intermediate 2] (100 mg, 0.38 mmol, 1.2 eq), 3-chloropyrazine-2-carbonitrile [CAS-RN: 55557-52-3] (44 mg, 0.32 mmol, 1.0 eq) and cesium carbonate (236 mg, 0.73 mmol, 2.3 eq) in 3 mL dioxane/DMF (7/1) was placed in a microwave vial and flushed with argon. Then, palladium(II) acetate (7 mg, 0.03 mmol, 0.1 eq) and Xantphos (18 mg, 0.03 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallised from dichloromethane/ethyl acetate to give 30 mg (21% yield of theory) of the title compound in 99% purity (LC-MS area-%).

UPLC-MS (Method 1): $R_t$=1.09 min; MS ($EI_{neg}$): m/z=366 [M−H]−.

$^1$H-NMR (400 MHz, DMSO-d$_6$): δ [ppm]=2.53 (s, 3H), 3.79 (s, 3H), 6.72 (d, 1H), 7.75 (s, 1H), 8.24 (dd, 1H), 8.42 (d, 1H), 8.61 (d, 1H), 12.54 (s br, 1H).

Example 25

5-[(4-Cyanopyridin-2-yl)amino]-N-(6-methoxypyridin-3-yl)-3-methyl-1,2-thiazole-4-carboxamide

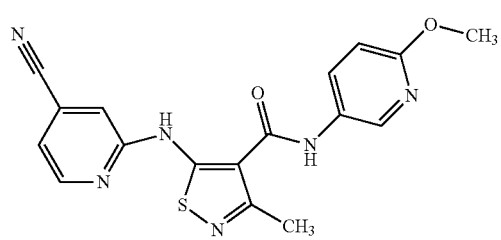 [SMILES: COc1ccc(NC(=O)c2c(C)nsc2Nc2cc(C#N)ccn2)cn1]

A mixture of 5-amino-N-(6-methoxypyridin-3-yl)-3-methyl-1,2-thiazole-4-carboxamide [Intermediate 2] (150 mg, 0.57 mmol, 1.4 eq), 2-iodoisonicotinonitrile [CAS-RN: 114821-24-8] (93 mg, 0.41 mmol, 1.0 eq) and cesium carbonate (304 mg, 0.93 mmol, 2.3 eq) in 4 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallised from dichloromethane/ethyl acetate and washed subsequently with a small portion of ethyl acetate to give 69 mg (33% yield of theory) of the title compound in 99% purity (LC-MS area-%).

UPLC-MS (Method 1): $R_t$=1.10 min; MS (EI$_{neg}$): m/z=365 [M−H]$^-$.

$^1$H-NMR (400 MHz, CDCl$_3$): δ [ppm]=2.82 (s, 3H), 3.96 (s, 3H), 6.83 (d, 1H), 7.12 (dd, 1H), 7.20 (t, 1H), 7.57 (s br, 1H), 7.89 (dd, 1H), 8.25 (d, 1H), 8.58 (dd, 1H), 11.90 (s br, 1H).

Example 26

Ethyl 2-({4-[(2-ethylphenyl)carbamoyl]-3-methyl-1,2-thiazol-5-yl}amino)-4-methyl-1,3-thiazole-5-carboxylate

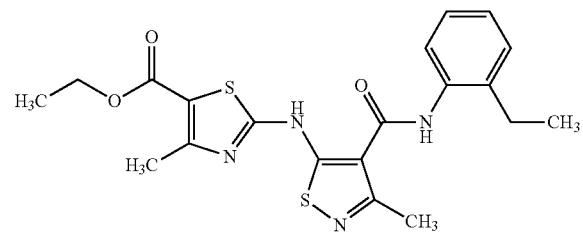 [SMILES: CCOC(=O)c1sc(Nc2snc(C)c2C(=O)Nc2ccccc2CC)nc1C]

A mixture of 5-amino-N-(2-ethylphenyl)-3-methyl-1,2-thiazole-4-carboxamide [Intermediate 1] (180 mg, 0.69 mmol, 1.0 eq), ethyl 2-bromo-4-methyl-1,3-thiazole-5-carboxylate [CAS-RN: 22900-83-0] (207 mg, 0.83 mmol, 1.2 eq) and cesium carbonate (516 mg, 1.58 mmol, 2.3 eq) in 5.7 mL dioxane/DMF (7/1) was placed in a microwave vial and flushed with argon. Then, palladium(II) acetate (15 mg, 0.07 mmol, 0.1 eq) and Xantphos (40 mg, 0.07 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallised from diethyl ether and washed subsequently with a small portion of ethyl acetate to give 116 mg (40% yield of theory) of the title compound in 99% purity (LC-MS area-%).

UPLC-MS (Method 1): $R_t$=1.55 min; MS (EI$_{neg}$): m/z=429 [M−H]$^-$.

$^1$H-NMR (400 MHz, DMSO-d6): δ [ppm]=1.12-1.34 (m, 3H), 1.25 (t, 3H), 2.59 (s, 3H), 2.53-2.85 (m, 5H), 4.22 (q, 2H), 7.06 (s br, 1H), 7.18 (t, 1H), 7.24 (d, 1H), 8.30 (d, 1H), 11.70 (s br, 1H).

Example 27

5-[(4-Cyanopyridin-2-yl)amino]-N-(3,4-difluorophenyl)-3-methyl-1,2-thiazole-4-carboxamide

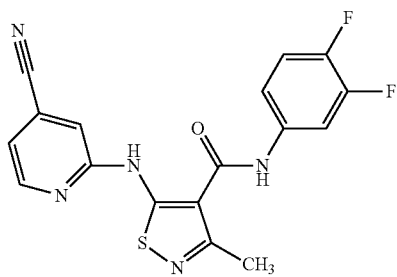 [SMILES: Cc1nsc(Nc2cc(C#N)ccn2)c1C(=O)Nc1ccc(F)c(F)c1]

A mixture of 5-amino-N-(3,4-difluorophenyl)-3-methyl-1,2-thiazole-4-carboxamide [Intermediate 3] (150 mg, 0.56 mmol, 1.0 eq), 2-iodoisonicotinonitrile [CAS-RN: 114821-24-8] (154 mg, 0.67 mmol, 1.2 eq) and cesium carbonate (417 mg, 1.28 mmol, 2.3 eq) in 5.4 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5). The product fractions obtained were crystallised from diethylether to give 32 mg (15% yield of theory) of the title compound.

UPLC-MS (Method 3): $R_t$=1.27 min; MS (EI$_{neg}$): m/z=370 [M−H]$^-$.

$^1$H-NMR (400 MHz, DMSO-d6): δ [ppm]=2.44 (s, 3H), 7.36 (s br, 1H), 7.40-7.50 (m, 2H), 7.74 (s, 1H), 7.93 (m, 1H), 8.60 (d, 1H), 10.40 (s br, 1H), 10.89 (s br, 1H).

Example 28

5-[(5-Cyanopyridin-2-yl)amino]-N-(3,4-difluorophenyl)-3-methyl-1,2-thiazole-4-carboxamide

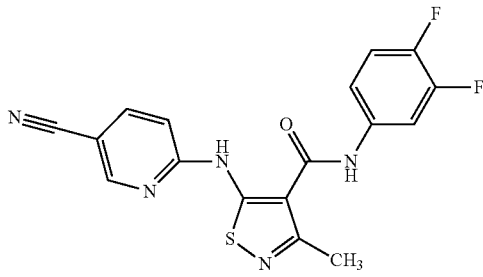 [SMILES: Cc1nsc(Nc2ccc(C#N)cn2)c1C(=O)Nc1ccc(F)c(F)c1]

A mixture of 5-amino-N-(3,4-difluorophenyl)-3-methyl-1,2-thiazole-4-carboxamide [Intermediate 3] (150 mg, 0.56 mmol, 1.0 eq), 6-bromonicotinonitrile [CAS-RN: 139585-70-9] (122 mg, 0.67 mmol, 1.2 eq) and cesium carbonate (417 mg, 1.28 mmol, 2.3 eq) in 5.4 mL dioxane/DMF (7/1)

was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A). The product fractions obtained were crystallised from diethylether to give 28 mg (13% yield of theory) of the title compound.

UPLC-MS (Method 3): $R_t$=1.24 min; MS (EI$_{neg}$): m/z=370 [M−H]$^−$.

$^1$H-NMR (400 MHz, DMSO-d6): δ [ppm]=2.40 (s, 3H), 7.33-7.48 (m, 3H), 7.91 (m, 1H), 8.10 (dd, 1H), 8.84 (d, 1H), 10.45 (s br, 1H), 11.05 (s br, 1H).

Example 29

Ethyl 2-({4-[(6-methoxypyridin-3-yl)carbamoyl]-3-methyl-1,2-thiazol-5-yl}amino)-1,3-thiazole-5-carboxylate

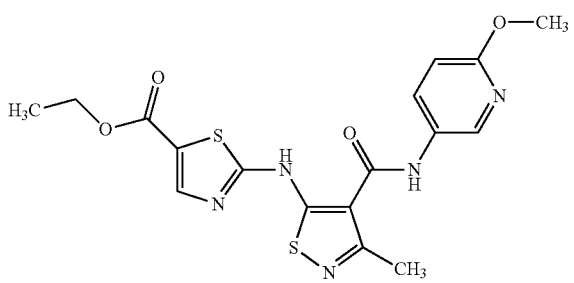 [SMILES: CCOC(=O)c1cnc(Nc2snc(C)c2C(=O)Nc2ccc(OC)nc2)s1]

A mixture of 5-amino-N-(6-methoxypyridin-3-yl)-3-methyl-1,2-thiazole-4-carboxamide [Intermediate 2] (180 mg, 0.68 mmol, 1.0 eq), ethyl 2-bromo-1,3-thiazole-5-carboxylate [CAS-RN: 41731-83-3] (193 mg, 0.82 mmol, 1.2 eq) and cesium carbonate (510 mg, 1.57 mmol, 2.3 eq) in 6.6 mL dioxane/DMF (7/1) was placed in a microwave vial and flushed with argon. Then, palladium(II) acetate (15 mg, 0.07 mmol, 0.1 eq) and Xantphos (39 mg, 0.07 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallised from diethyl ether to give 90 mg (30% yield of theory) of the title compound in 95% purity (LC-MS area-%).

UPLC-MS (Method 1): $R_t$=1.25 min; MS (EI$_{neg}$): m/z=418 [M−H]$^−$.

$^1$H-NMR (400 MHz, DMSO-d$_6$): δ [ppm]=1.27 (t, 3H), 3.84 (s, 3H), 4.27 (q, 2H), 6.85 (d, 1H), 8.03 (d, 1H), 8.13 (s br, 1H), 8.50 (d, 1H), 10.35 (s br, 1H), 11.95 (s br, 1H), 1×CH$_3$ covered by solvent signal.

Example 30

Ethyl 2-({4-[(6-methoxypyridin-3-yl)carbamoyl]-3-methyl-1,2-thiazol-5-yl}amino)-4-methyl-1,3-thiazole-5-carboxylate

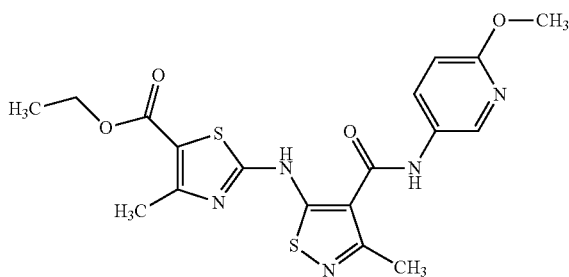 [SMILES: CCOC(=O)c1sc(Nc2snc(C)c2C(=O)Nc2ccc(OC)nc2)nc1C]

A mixture of 5-amino-N-(6-methoxypyridin-3-yl)-3-methyl-1,2-thiazole-4-carboxamide [Intermediate 2] (180 mg, 0.68 mmol, 1.0 eq), ethyl 2-bromo-4-methyl-1,3-thiazole-5-carboxylate [CAS-RN: 22900-83-0] (204 mg, 0.82 mmol, 1.2 eq) and cesium carbonate (510 mg, 1.57 mmol, 2.3 eq) in 6.6 mL dioxane/DMF (7/1) was placed in a microwave vial and flushed with argon. Then, palladium(II) acetate (15 mg, 0.07 mmol, 0.1 eq) and Xantphos (39 mg, 0.07 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to give 16 mg (5% yield of theory) of the title compound.

UPLC-MS (Method 3): $R_t$=1.32 min; MS (EI$_{neg}$): m/z=432 [M−H]$^−$.

$^1$H-NMR (400 MHz, DMSO-d$_6$): δ [ppm]=1.27 (t, 3H), 2.59 (s, 3H), 3.83 (s, 3H), 4.23 (q, 2H), 6.85 (d, 1H), 8.03 (d, 1H), 8.50 (s, 1H), 10.33 (s br, 1H), 11.83 (s br, 1H), 1×CH$_3$ covered by solvent signal.

Example 31

Methyl 6-({4-[(6-methoxypyridin-3-yl)carbamoyl]-3-methyl-1,2-thiazol-5-yl}amino)-nicotinate

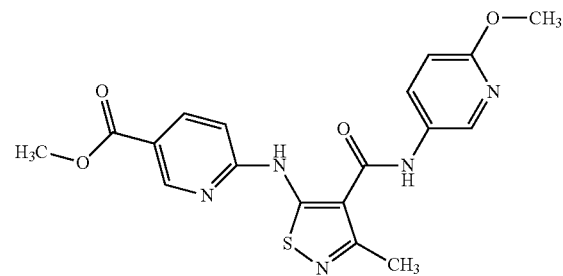

A mixture of 5-amino-N-(6-methoxypyridin-3-yl)-3-methyl-1,2-thiazole-4-carboxamide [Intermediate 2] (180 mg, 0.68 mmol, 1.4 eq), methyl 6-chloronicotinate [CAS-RN: 73781-91-6] (83 mg, 0.82 mmol, 1.0 eq) and cesium carbonate (365 mg, 1.12 mmol, 2.3 eq) in 4.7 mL dioxane/

DMF (7/1) was placed in a microwave vial and flushed with argon. Then, palladium(II) acetate (11 mg, 0.05 mmol, 0.1 eq) and Xantphos (28 mg, 0.05 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallised from diethyl ether to give 20 mg (7% yield of theory) of the title compound in 99% purity (LC-MS area-%).

UPLC-MS (Method 1): $R_t$=1.13 min; MS (EI$_{neg}$): m/z=398 [M−H]$^-$.

$^1$H-NMR (400 MHz, CDCl$_3$): δ [ppm]=2.82 (s, 3H), 3.93 (s, 3H), 3.98 (s, 3H), 6.82 (d, 1H), 6.97 (d, 1H), 7.58 (s br, 1H), 7.89 (dd, 1H), 8.21-8.28 (m, 2H), 9.08 (d, 1H), 11.61 (s br, 1H).

Example 32

Methyl 5-({4-[(6-methoxypyridin-3-yl)carbamoyl]-3-methyl-1,2-thiazol-5-yl}amino)-pyrazine-2-carboxylate

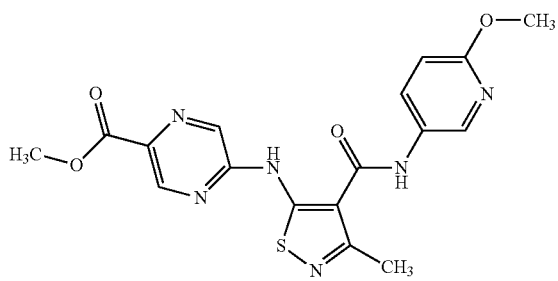

A mixture of 5-amino-N-(6-methoxypyridin-3-yl)-3-methyl-1,2-thiazole-4-carboxamide [Intermediate 2] (150 mg, 0.57 mmol, 1.4 eq), methyl 5-chloropyrazine-2-carboxylate [CAS-RN: 33332-25-1] (70 mg, 0.41 mmol, 1.0 eq) and cesium carbonate (304 mg, 0.93 mmol, 2.3 eq) in 4.0 mL dioxane/DMF (7/1) was placed in a microwave vial and flushed with argon. Then, palladium(II) acetate (9 mg, 0.04 mmol, 0.1 eq) and Xantphos (23 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to give 6 mg (3% yield of theory) of the title compound.

UPLC-MS (Method 1): $R_t$=0.98 min; MS (EI$_{neg}$): m/z=399 [M−H]$^-$.

$^1$H-NMR (400 MHz, DMSO-d$_6$): δ [ppm]=3.81 (s, 3H), 3.84 (s, 3H), 6.83 (d, 1H), 8.03 (d, 1H), 8.49 (d, 1H), 8.74 (s br, 1H), 8.94 (d, 1H), 10.27 (s br, 1H), 11.39 (s br, 1H), 1×C$\underline{H}_3$ covered by solvent signal.

Example 33

N-(2-Ethylphenyl)-3-methyl-5-[(8-methylquinoxalin-2-yl)amino]-1,2-thiazole-4-carboxamide

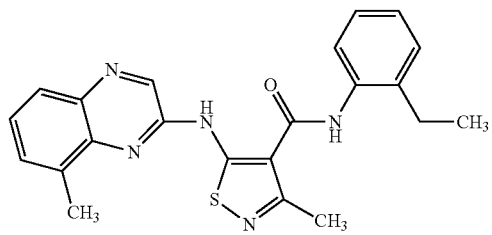 [SMILES: CCc1ccccc1NC(=O)c1c(C)nsc1Nc1cnc2cccc(C)c2n1]

A mixture of 5-amino-N-(2-ethylphenyl)-3-methyl-1,2-thiazole-4-carboxamide [Intermediate 1] (150 mg, 0.57 mmol, 1.4 eq), 2-chloro-8-methylquinoxaline [CAS-RN: 61148-40-1] (73 mg, 0.41 mmol, 1.0 eq) and cesium carbonate (307 mg, 0.94 mmol, 2.3 eq) in 4.0 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallized by the use of dichloromethane/ethyl acetate. The solid was separated by filtration and washed with ethyl acetate to give 58 mg (25% yield of theory) of the title compound.

UPLC-MS (Method 1): $R_t$=1.46 min; MS (EI$_{neg}$): m/z=402 [M−H]$^-$.

$^1$H-NMR (400 MHz, DMSO-d$_6$): δ [ppm]=1.17 (t, 3H), 2.62 (s, 3H), 2.69 (m, 2H), 2.77 (s, 3H), 7.16-7.25 (m, 2H), 7.29 (dd, 1H), 7.51 (m, 1H), 7.58 (m, 1H), 7.65 (d, 1H), 7.81 (d, 1H), 9.07 (s, 1H), 9.52 (s br, 1H), 11.39 (s br, 1H).

Example 34

5-[(3-Cyanopyrazin-2-yl)amino]-N-(2-ethylphenyl)-3-methyl-1,2-thiazole-4-carboxamide

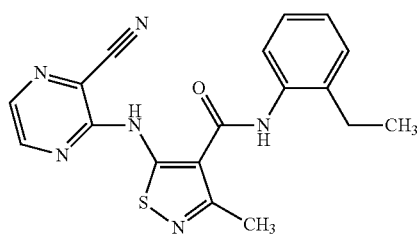 [SMILES: CCc1ccccc1NC(=O)c1c(C)nsc1Nc1nccnc1C#N]

A mixture of 5-amino-N-(2-ethylphenyl)-3-methyl-1,2-thiazole-4-carboxamide [Intermediate 1] (150 mg, 0.57 mmol, 1.4 eq), 3-chloropyrazine-2-carbonitrile [CAS-RN: 55557-52-3] (57 mg, 0.41 mmol, 1.0 eq) and cesium carbonate (307 mg, 0.94 mmol, 2.3 eq) in 4.0 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to give 47 mg (22% yield of theory) of the title compound.

UPLC-MS (Method 1): $R_t$=1.24 min; MS ($EI_{neg}$): m/z=363 [M−H]⁻.

$^1$H-NMR (400 MHz, DMSO-$d_6$): δ [ppm]=1.11 (t, 3H), 2.61-2.82 (m, 5H), 7.09-7.31 (m, 3H), 7.46 (d, 1H), 8.20 (s br, 1H), 8.77 (d, 1H), 11.72 (s br, 1H).

Example 35

N-(2-Ethylphenyl)-3-methyl-5-[(2-methylquinazolin-4-yl)amino]-1,2-thiazole-4-carboxamide

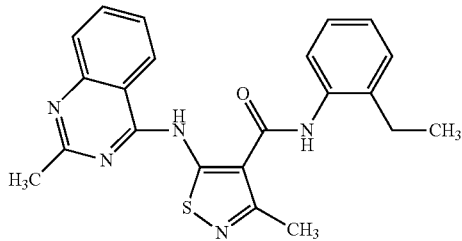 [SMILES: CCc1ccccc1NC(=O)c1c(C)nsc1Nc1nc(C)nc2ccccc12]

A mixture of 5-amino-N-(2-ethylphenyl)-3-methyl-1,2-thiazole-4-carboxamide [Intermediate 1] (150 mg, 0.57 mmol, 1.4 eq), 4-chloro-2-methylquinazoline [CAS-RN: 6484-24-8] (73 mg, 0.41 mmol, 1.0 eq) and cesium carbonate (307 mg, 0.94 mmol, 2.3 eq) in 4.0 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallized by the use of dichloromethane/ethyl acetate. The solid was separated by filtration and washed with ethyl acetate to give 100 mg (43% yield of theory) of the title compound.

UPLC-MS (Method 1): $R_t$=1.13 min; MS ($EI_{neg}$): m/z=402 [M−H]⁻.

$^1$H-NMR (400 MHz, DMSO-$d_6$): δ [ppm]=1.04 (t, 3H), 2.58 (s, 3H), 2.60-2.68 (m, 5H), 7.16 (dt, 1H), 7.23 (dt, 1H), 7.30 (dd, 1H), 7.50 (d, 1H), 7.55 (d, 1H), 7.61 (d, 1H), 7.780 (t, 1H), 8.06 (d, 1H), 11.78 (s br, 1H), 13.26 (s br, 1H).

Example 36

5-[(3-Cyanopyridin-2-yl)amino]-N-(6-methoxypyridin-3-yl)-3-methyl-1,2-thiazole-4-carboxamide

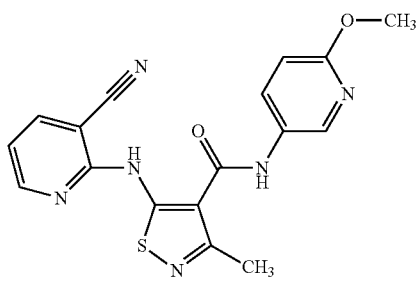 [SMILES: COc1ccc(NC(=O)c2c(C)nsc2Nc2ncccc2C#N)cn1]

A mixture of 5-amino-N-(6-methoxypyridin-3-yl)-3-methyl-1,2-thiazole-4-carboxamide [Intermediate 2] (150 mg, 0.57 mmol, 1.4 eq), 2-chloronicotinonitrile [CAS-RN: 6602-54-6] (56 mg, 0.41 mmol, 1.0 eq) and cesium carbonate (304 mg, 0.93 mmol, 2.3 eq) in 3.9 mL dioxane/DMF (7/1) was placed in a microwave vial and flushed with argon. Then, palladium(II) acetate (9 mg, 0.04 mmol, 0.1 eq) and Xantphos (23 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5). The product fractions obtained were crystallised from diethylether to give 3 mg (1.3% yield of theory) of the title compound.

UPLC-MS (Method 1): $R_t$=1.15 min; MS ($EI_{neg}$): m/z=365 [M−H]⁻.

$^1$H-NMR (400 MHz, DMF-$d_7$): δ [ppm]=2.61 (s, 3H), 3.87 (s, 3H), 6.81 (d, 1H), 7.07 (m, 1H), 8.25-8.46 (m, 2H), 8.70-8.87 (m, 2H), 11.63 (s br, 1H).

Example 37

5-[(6-Cyanopyridin-2-yl)amino]-N-(6-methoxypyridin-3-yl)-3-methyl-1,2-thiazole-4-carboxamide

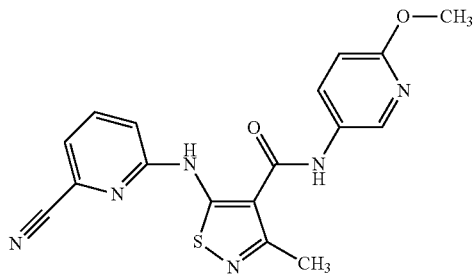 [SMILES: COc1ccc(NC(=O)c2c(C)nsc2Nc2cccc(C#N)n2)cn1]

A mixture of 5-amino-N-(6-methoxypyridin-3-yl)-3-methyl-1,2-thiazole-4-carboxamide [Intermediate 2] (150 mg, 0.57 mmol, 1.4 eq), 6-chloropyridine-2-carbonitrile [CAS-RN: 33252-29-8] (56 mg, 0.41 mmol, 1.0 eq) and cesium carbonate (304 mg, 0.93 mmol, 2.3 eq) in 3.9 mL dioxane/DMF (7/1) was placed in a microwave vial and flushed with argon. Then, palladium(II) acetate (9 mg, 0.04 mmol, 0.1 eq) and Xantphos (23 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC (method A) to give 47 mg (22% yield of theory) of the title compound.

UPLC-MS (Method 1): $R_t$=1.09 min; MS ($EI_{neg}$): m/z=365 [M−H]⁻.

$^1$H-NMR (400 MHz, DMF-$d_7$): δ [ppm]=2.71 (s, 3H), 4.06 (s, 3H), 7.04 (s, 1H), 7.81 (d, 1H), 7.90 (d, 1H), 8.28 (dd, 1H), 8.74 (d, 1H), 10.22 (s br, 1H), 11.37 (s br, 1H), 1H covered by solvent signal.

Example 38

N-(2-Ethylphenyl)-3-methyl-5-[(2-methylthieno[2,3-d]pyrimidin-4-yl)amino]-1,2-thiazole-4-carboxamide

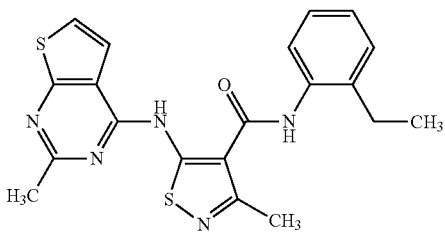 [SMILES: CCc1ccccc1NC(=O)c1c(C)nsc1Nc1nc(C)nc2sccc12]

A mixture of 5-amino-N-(2-ethylphenyl)-3-methyl-1,2-thiazole-4-carboxamide [Intermediate 1] (150 mg, 0.57 mmol, 1.4 eq), 4-chloro-2-methylthieno[2,3-d]pyrimidine [CAS-RN: 56843-79-9] (76 mg, 0.41 mmol, 1.0 eq) and cesium carbonate (307 mg, 0.94 mmol, 2.3 eq) in 4.0 mL dioxane/DMF (7/1) was placed in a microwave vial and flushed with argon. Then, palladium(II) acetate (9 mg, 0.04 mmol, 0.1 eq) and Xantphos (24 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallized by the use of diethyl ether to give 1.6 mg (1% yield of theory) of the title compound.

UPLC-MS (Method 4): $R_t$=1.44 min; MS (EI$_{neg}$): m/z=408 [M−H]$^-$.

$^1$H-NMR (400 MHz, DMSO-d$_6$): δ [ppm]=1.14 (t, 3H), 2.55-2.75 (m, 8H), 7.18-7.26 (m, 2H), 7.29 (d, 1H), 7.61 (t, 1H), 7.73 (d, 1H), 9.44 (s br, 1H), 11.56 (s br, 1H).

Example 39

5-[(5-Cyanopyridin-2-yl)amino]-N-(6-methoxypyridin-3-yl)-3-methyl-1,2-thiazole-4-carboxamide

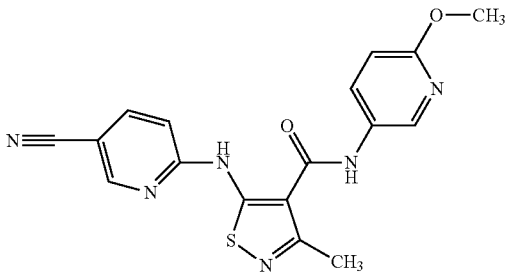 [SMILES: COc1ccc(NC(=O)c2c(C)nsc2Nc2ccc(C#N)cn2)cn1]

A mixture of 5-amino-N-(6-methoxypyridin-3-yl)-3-methyl-1,2-thiazole-4-carboxamide [Intermediate 2] (150 mg, 0.57 mmol, 1.4 eq), 6-bromonicotinonitrile [CAS-RN: 139585-70-9] (74 mg, 0.41 mmol, 1.0 eq) and cesium carbonate (304 mg, 0.93 mmol, 2.3 eq) in 3.9 mL dioxane/DMF (7/1) was placed in a microwave vial and flushed with argon. Then, palladium(II) acetate (9 mg, 0.04 mmol, 0.1 eq) and Xantphos (23 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under acidic conditions (column: Chromatorex C18, eluent: acetonitrile/0.1% aqueous formic acid 20:80→95:5). The product fractions concentrated in vacuo and again purified via preparative HPLC (method A) to give 2.2 mg (1% yield of theory) of the title compound.

UPLC-MS (Method 1): $R_t$=1.06 min; MS (EI$_{neg}$): m/z=365 [M−H]$^-$.

$^1$H-NMR (400 MHz, CDCl$_3$): δ [ppm]=2.83 (s, 3H), 3.96 (s, 3H), 6.83 (d, 1H), 7.02 (d, 1H), 7.61 (s, 1H), 7.86 (dt, 2H), 8.25 (d, 1H), 8.73 (d, 1H), 11.96 (s br, 1H).

Example 40

N-(4-Chloro-3-fluorophenyl)-3-methyl-5-(quinoxalin-2-ylamino)-1,2-thiazole-4-carboxamide

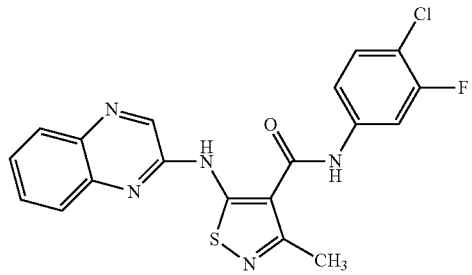 [SMILES: Cc1nsc(Nc2cnc3ccccc3n2)c1C(=O)Nc1ccc(Cl)c(F)c1]

A mixture of 5-amino-N-(4-chloro-3-fluorophenyl)-3-methyl-1,2-thiazole-4-carboxamide [Intermediate 4] (150 mg, 0.50 mmol, 1.2 eq), 2-chloroquinoxaline [CAS-RN: 1448-87-9] (74 mg, 0.42 mmol, 1.0 eq) and cesium carbonate (315 mg, 0.97 mmol, 2.3 eq) in 3.5 mL dioxane/DMF (7/1) was placed in a microwave vial and flushed with argon. Then, palladium(II) acetate (9 mg, 0.04 mmol, 0.1 eq) and Xantphos (23 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative HPLC under basic conditions (column: Chromatorex C18, eluent: acetonitrile/0.1% aqueous formic acid 20:80→95:5). The product fractions concentrated in vacuo and again purified via preparative HPLC under acidic conditions (column: Chromatorex C18, eluent: acetonitrile/water (2/1)→acetonitrile) to give 7.6 mg (4% yield of theory) of the title compound.

UPLC-MS (Method 2): $R_t$=0.89 min; MS (EI$_{neg}$): m/z=412 [M−H]$^-$.

$^1$H-NMR (400 MHz, DMSO-d$_6$): δ [ppm]=7.43-7.66 (m, 2H), 7.73 (m, 1H), 7.84-8.10 (m, 2H), 8.97 (s, 1H), 10.61 (s br, 1H), 11.36 (s br, 1H), 1×C$\underline{H}_3$ covered by solvent signal, 2H not assigned.

Example 41

5-[(7-Chloroquinoxalin-2-yl)amino]-N-(2-ethylphenyl)-3-methyl-1,2-thiazole-4-carboxamide

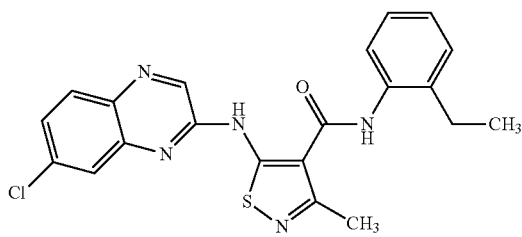 [SMILES: CCc1ccccc1NC(=O)c1c(C)nsc1Nc1cnc2ccc(Cl)cc2n1]

A mixture of 5-amino-N-(2-ethylphenyl)-3-methyl-1,2-thiazole-4-carboxamide [Intermediate 1] (100 mg, 0.38 mmol, 1.4 eq), 2,7-dichloroquinoxaline [CAS-RN: 59489-31-5, H. Wear, J. Am. Chem. Soc. (1950), 72, 2393.] (54 mg, 0.27 mmol, 1.0 eq) and cesium carbonate (204 mg, 0.63 mmol, 2.3 eq) in 2.7 mL dioxane/DMF (7/1) was placed in a microwave vial and flushed with argon. Then, palladium (II) acetate (6 mg, 0.03 mmol, 0.1 eq) and Xantphos (16 mg, 0.03 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallized by the use of dichloromethane/methanol. The precipitate was washed with dichloromethane, isolated by filtration and dried under high vacuum to deliver 70 mg of the title compound (43% yield of theory).

UPLC-MS (Method 1): $R_t$=1.56 min; MS (EI$_{neg}$): m/z=422 [M−H]⁻.

$^1$H-NMR (400 MHz, DMSO-d$_6$): δ [ppm]=1.19 (m, 3H), 2.55-2.88 (m, 5H), 7.11-7.25 (m, 2H), 7.28 (d, 1H), 7.52-7.65 (m, 2H), 7.96 (d, 1H), 8.01 (s br, 1H), 9.05 (s, 1H), 9.56 (s br, 1H), 11.41 (s br, 1H).

Example 42

5-[(7-Chloroquinoxalin-2-yl)amino]-N-(6-methoxypyridin-3-yl)-3-methyl-1,2-thiazole-4-carboxamide

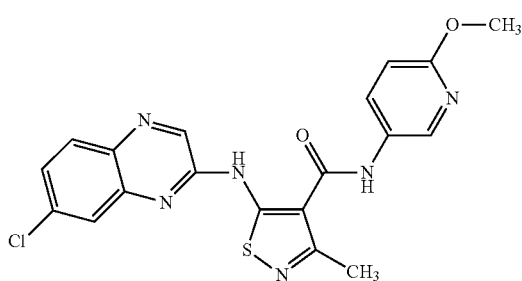 [SMILES: COc1ccc(NC(=O)c2c(C)nsc2Nc2cnc3ccc(Cl)cc3n2)cn1]

A mixture of 5-amino-N-(6-methoxypyridin-3-yl)-3-methyl-1,2-thiazole-4-carboxamide [Intermediate 2] (100 mg, 0.38 mmol, 1.4 eq), 2,7-dichloroquinoxaline [CAS-RN: 59489-31-5, H. Wear, J. Am. Chem. Soc. (1950), 72, 2393.] (54 mg, 0.27 mmol, 1.0 eq) and cesium carbonate (204 mg, 0.63 mmol, 2.3 eq) in 2.7 mL dioxane/DMF (7/1) was placed in a microwave vial and flushed with argon. Then, palladium (II) acetate (6 mg, 0.03 mmol, 0.1 eq) and Xantphos (16 mg, 0.03 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallized by the use of dichloromethane/methanol. The precipitate was washed with dichloromethane, isolated by filtration and dried under high vacuum to deliver 59 mg of the title compound (35% yield of theory).

UPLC-MS (Method 1): $R_t$=1.33 min; MS (EI$_{neg}$): m/z=425 [M−H]⁻.

$^1$H-NMR (400 MHz, DMSO-d$_6$): δ [ppm]=3.82 (s, 3H), 6.84 (d, 1H), 7.61 (dd, 1H), 7.97 (d, 1H), 8.00 (d, 1H), 8.04 (d, 1H), 8.51 (s br, 1H), 9.01 (s, 1H), 10.26 (s br, 1H), 11.40 (s br, 1H), 1×C$\underline{H}_3$ covered by solvent signal.

Example 43

5-[(5,6-Difluoroquinoxalin-2-yl)amino]-N-(6-methoxypyridin-3-yl)-3-methyl-1,2-thiazole-4-carboxamide

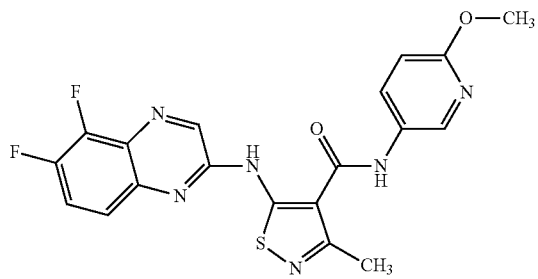 [SMILES: COc1ccc(NC(=O)c2c(C)nsc2Nc2cnc3c(F)c(F)ccc3n2)cn1]

A mixture of 5-amino-N-(6-methoxypyridin-3-yl)-3-methyl-1,2-thiazole-4-carboxamide [Intermediate 2] (71 mg, 0.27 mmol, 1.0 eq), 2-chloro-5,6-difluoroquinoxaline [WO 2012/85857 (Actelion Pharmaceuticals)] (60 mg, 0.30 mmol, 1.1 eq) and cesium carbonate (203 mg, 0.62 mmol, 2.3 eq) in 2.6 mL dioxane/DMF (7/1) was placed in a microwave vial and flushed with argon. Then, palladium(II) acetate (6 mg, 0.03 mmol, 0.1 eq) and Xantphos (16 mg, 0.03 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallized by the use of diethylether. The precipitate was isolated by filtration and dried under high vacuum to deliver 21 mg of the title compound (18% yield of theory).

UPLC-MS (Method 1): $R_t$=1.25 min; MS (EI$_{neg}$): m/z=427 [M−H]⁻.

$^1$H-NMR (400 MHz, DMSO-d$_6$): δ [ppm]=3.82 (s, 3H), 6.84 (d, 1H), 7.77-7.93 (m, 2H), 8.05 (d, 1H), 8.52 (s br, 1H), 9.08 (s, 1H), 10.27 (s br, 1H), 11.45 (s br, 1H), 1×C$\underline{H}_3$ covered by solvent signal.

Example 44

5-[(7-Fluoroquinoxalin-2-yl)amino]-N-(6-methoxy-pyridin-3-yl)-3-methyl-1,2-thiazole-4-carboxamide

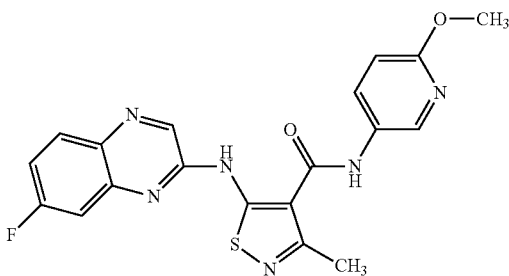 [SMILES: COc1ccc(NC(=O)c2c(C)nsc2Nc2cnc3ccc(F)cc3n2)cn1]

A mixture of 5-amino-N-(6-methoxypyridin-3-yl)-3-methyl-1,2-thiazole-4-carboxamide [Intermediate 2] (163 mg, 0.62 mmol, 1.0 eq), 2-chloro-7-fluoroquinoxaline [WO 2010/84152 (Basilea Pharmaceutica AG)] (124 mg, 0.68 mmol, 1.1 eq) and cesium carbonate (461 mg, 1.42 mmol, 2.3 eq) in 6.0 mL dioxane/DMF (7/1) was placed in a microwave vial and flushed with argon. Then, palladium(II) acetate (14 mg, 0.06 mmol, 0.1 eq) and Xantphos (36 mg, 0.06 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The product fractions concentrated in vacuo and again purified via preparative HPLC under acidic conditions (column: Chromatorex C18, eluent: acetonitrile/water (2/1)→acetonitrile). The product fractions were combined and the solvent removed. Crystallization was achieved by the use of diethylether. The precipitate was isolated by filtration and dried under high vacuum to deliver 20 mg of the title compound (6% yield of theory).

UPLC-MS (Method 1): $R_t$=1.24 min; MS ($EI_{neg}$): m/z=409 [M–H]⁻.

$^1$H-NMR (400 MHz, DMSO-d$_6$): δ [ppm]=3.82 (s, 3H), 6.84 (d, 1H), 7.48 (m, 1H), 7.71 (d, 1H), 7.95-8.14 (m, 2H), 8.52 (s, 1H), 8.96 (s, 1H), 10.26 (s br, 1H), 11.36 (s br, 1H), 1×C$\underline{H}_3$ covered by solvent signal.

Example 45

N-(6-Methoxypyridin-3-yl)-3-methyl-5-{[6-(trifluoromethyl)quinoxalin-2-yl]amino}-1,2-thiazole-4-carboxamide

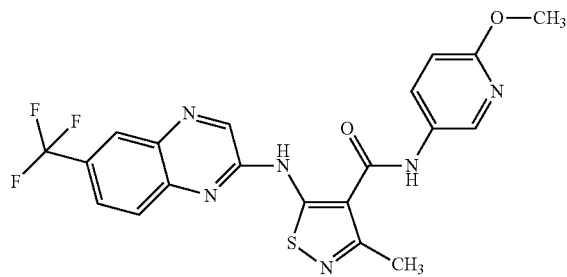 [SMILES: COc1ccc(NC(=O)c2c(C)nsc2Nc2cnc3cc(C(F)(F)F)ccc3n2)cn1]

A mixture of 5-amino-N-(6-methoxypyridin-3-yl)-3-methyl-1,2-thiazole-4-carboxamide [Intermediate 2] (100 mg, 0.38 mmol, 1.2 eq), 2-chloro-6-(trifluoromethyl)quinoxaline [W. Lumma, J. Med. Chem. (1981), 24, 93-101.] (81 mg, 0.32 mmol, 1.0 eq) and cesium carbonate (236 mg, 0.73 mmol, 2.3 eq) in 2.1 mL dioxane/DMF (7/1) was placed in a microwave vial and flushed with argon. Then, palladium (II) acetate (7 mg, 0.03 mmol, 0.1 eq) and Xantphos (18 mg, 0.03 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallized by the use of dichloromethane/methanol. The precipitate was isolated by filtration, washed with dichloromethane and dried under high vacuum to deliver 64 mg of the title compound (35% yield of theory).

UPLC-MS (Method 1): $R_t$=1.38 min; MS ($EI_{neg}$): m/z=459 [M–H]⁻.

$^1$H-NMR (400 MHz, DMSO-d$_6$): δ [ppm]=3.82 (s, 3H), 6.85 (d, 1H), 8.00 (m, 1H), 8.05 (m, 1H), 8.14 (d, 1H), 8.29 (s, 1H), 8.52 (s br, 1H), 9.11 (s, 1H), 10.31 (s br, 1H), 11.56 (s br, 1H), 1×C$\underline{H}_3$ covered by solvent signal.

Example 46

N-(3,4-Difluorophenyl)-5-[(6-fluoroquinoxalin-2-yl)amino]-3-methyl-1,2-thiazole-4-carboxamide

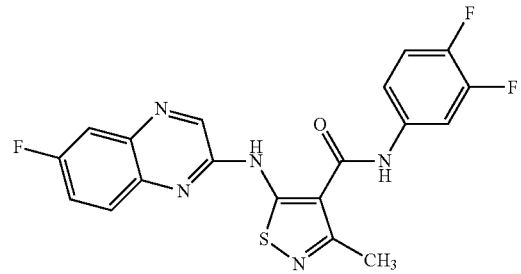 [SMILES: Cc1nsc(Nc2cnc3cc(F)ccc3n2)c1C(=O)Nc1ccc(F)c(F)c1]

A mixture of 5-amino-N-(3,4-difluorophenyl)-3-methyl-1,2-thiazole-4-carboxamide [Intermediate 3] (150 mg, 0.56 mmol, 1.0 eq), 2-chloro-6-fluoroquinoxaline [W. Lumma, J. Med. Chem. (1981), 24, 93-101.] (122 mg, 0.67 mmol, 1.2 eq) and cesium carbonate (417 mg, 1.28 mmol, 2.3 eq) in 4.4 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product purified via preparative HPLC under acidic conditions (column: Chromatorex C18, eluent: acetonitrile/water (2/1)→acetonitrile) to give 24 mg (10% yield of theory) of the title compound.

UPLC-MS (Method 1): $R_t$=1.39 min; MS ($EI_{neg}$): m/z=414 [M–H]⁻.

$^1$H-NMR (400 MHz, DMSO-d$_6$): δ [ppm]=7.35-7.52 (m, 2H), 7.68 (dt, 1H), 7.77 (dd, 1H), 7.95 (m, 1H), 8.01 (dd, 1H), 9.03 (s, 1H), 10.48 (s br, 1H), 11.32 (s br, 1H), 1×C$\underline{H}_3$ covered by solvent signal.

Example 47

N-(3-Fluoro-4-methoxyphenyl)-3-methyl-5-{[4-(trifluoromethyl)-1,3-benzothiazol-2-yl]amino}-1,2-thiazole-4-carboxamide

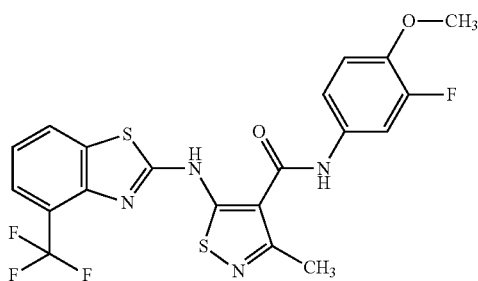 [SMILES: COc1ccc(NC(=O)c2c(C)nsc2Nc2nc3c(C(F)(F)F)cccc3s2)cc1F]

A mixture of 5-amino-N-(3-fluoro-4-methoxyphenyl)-3-methyl-1,2-thiazole-4-carboxamide [Intermediate 5] (150 mg, 0.53 mmol, 1.2 eq), 2-chloro-4-(trifluoromethyl)-1,3-benzothiazole [CAS-RN: 898784-15-7] (105 mg, 0.44 mmol, 1.0 eq) and cesium carbonate (333 mg, 1.02 mmol, 2.3 eq) in 4.5 mL dioxane/DMF (7/1) was placed in a microwave vial and flushed with argon. Then, palladium(II) acetate (10 mg, 0.04 mmol, 0.1 eq) and Xantphos (26 mg, 0.04 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product purified via preparative HPLC under acidic conditions (column: Chromatorex C18, eluent: acetonitrile/water (2/1)→acetonitrile) to give 20 mg (7% yield of theory) of the title compound.

UPLC-MS (Method 1): Rt=1.49 min; MS (EI$_{neg}$): m/z=481 [M−H]$^-$.

$^1$H-NMR (400 MHz, DMSO-d6): δ [ppm]=2.42 (s, 3H), 3.82 (s, 3H), 7.18 (t, 1H), 7.32-7.48 (m, 2H), 7.68-7.84 (m, 2H), 8.23 (d, 1H), 10.42 (s br, 1H), 12.10 (s br, 1H).

Example 48

N-(6-Methoxypyridin-3-yl)-3-methyl-5-{[4-(trifluoromethyl)-1,3-benzothiazol-2-yl]-amino}-1,2-thiazole-4-carboxamide

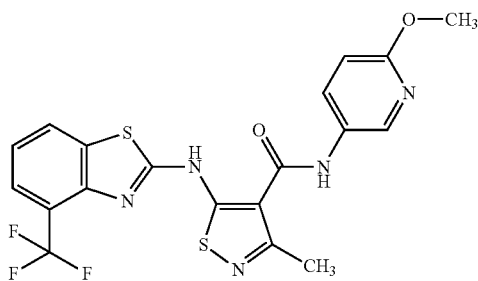 [SMILES: COc1ccc(NC(=O)c2c(C)nsc2Nc2nc3c(C(F)(F)F)cccc3s2)cn1]

A mixture of 5-amino-N-(6-methoxypyridin-3-yl)-3-methyl-1,2-thiazole-4-carboxamide [Intermediate 2] (100 mg, 0.38 mmol, 1.2 eq), 2-chloro-4-(trifluoromethyl)-1,3-benzothiazole [CAS-RN: 898784-15-7] (75 mg, 0.32 mmol, 1.0 eq) and cesium carbonate (236 mg, 0.73 mmol, 2.3 eq) in 4.1 mL dioxane/DMF (7/1) was placed in a microwave vial and flushed with argon. Then, palladium(II) acetate (7 mg, 0.03 mmol, 0.1 eq) and Xantphos (18 mg, 0.03 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallized by the use of dichloromethane/methanol. The precipitate was isolated by filtration, washed with dichloromethane and dried under high vacuum to deliver 74 mg of the title compound (42% yield of theory).

UPLC-MS (Method 1): Rt=1.42 min; MS (EI$_{neg}$): m/z=464 [M−H]$^-$.

$^1$H-NMR (400 MHz, DMSO-d6): δ [ppm]=3.82 (s, 3H), 6.84 (d, 1H), 7.37 (t, 1H), 7.71 (d, 1H), 8.02 (dd, 1H), 8.21 (d, 1H), 8.49 (s, 1H), 10.36 (s br, 1H), 12.05 (s br, 1H), 1×CH$_3$ covered by solvent signal.

Example 49

N-(3,4-Difluorophenyl)-5-{[5-(dimethylcarbamoyl)-1,3-thiazol-2-yl]amino}-3-methyl-1,2-thiazole-4-carboxamide

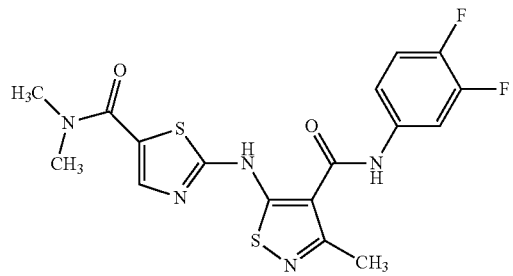 [SMILES: Cc1nsc(Nc2ncc(C(=O)N(C)C)s2)c1C(=O)Nc1ccc(F)c(F)c1]

A mixture of 5-amino-N-(3,4-difluorophenyl)-3-methyl-1,2-thiazole-4-carboxamide [Intermediate 3] (65 mg, 0.24 mmol, 1.2 eq), 2-chloro-N,N-dimethyl-1,3-thiazole-5-carboxamide [Intermediate 6] (38 mg, 0.20 mmol, 1.0 eq) and cesium carbonate (151 mg, 0.46 mmol, 2.3 eq) in 2.0 mL dioxane/DMF (7/1) was placed in a microwave vial and flushed with argon. Then, palladium(II) acetate (5 mg, 0.02 mmol, 0.1 eq) and Xantphos (12 mg, 0.02 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product purified via preparative HPLC under basic conditions (column: Chromatorex C18, eluent: acetonitrile/water (2/1) acetonitrile) to give 15 mg (15% yield of theory) of the title compound.

UPLC-MS (Method 2): R$_t$=0.76 min; MS (EI$_{neg}$): m/z=422 [M−H]$^-$.

$^1$H-NMR (400 MHz, DMSO-d$_6$): δ [ppm]=2.40 (s, 3H), 3.11 (s br, 6H), 7.37-7.49 (m, 2H), 7.85-8.00 (m, 2H), 10.53 (s br, 1H), 11.77 (s br, 1H).

Example 50

N-(3,4-Difluorophenyl)-3-methyl-5-(quinoxalin-2-ylamino)-1,2-thiazole-4-carboxamide

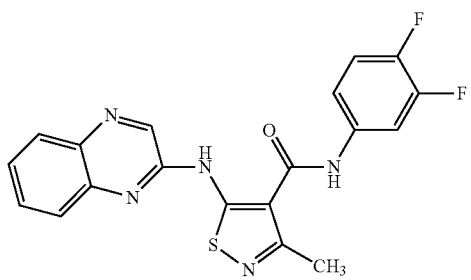

A mixture of 5-amino-N-(3,4-difluorophenyl)-3-methyl-1,2-thiazole-4-carboxamide [Intermediate 3] (150 mg, 0.56 mmol, 1.0 eq), 2-chloroquinoxaline [CAS-RN: 1448-87-9] (110 mg, 0.67 mmol, 1.2 eq) and cesium carbonate (417 mg, 1.28 mmol, 2.3 eq) in 5.4 mL dioxane/DMF (7/1) was placed in a microwave vial and flushed with argon. Then, palladium (II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the reaction mixture was partitioned between dichloromethane and water. The water phase was extracted with dichloromethane/isopropanol (4/1) (3×). The combined organic phases were washed with brine and the volatile components were removed in vacuo to give 115 mg (52% yield of theory) of the title compound in 98% purity (UPLC area-%) after drying.

UPLC-MS (Method 3): $R_t$=1.33 min; MS ($EI_{neg}$): m/z=396 [M–H]⁻.

¹H-NMR (400 MHz, DMSO-d₆): δ [ppm]=7.39-7.54 (m, 2H), 7.62 (dt, 1H), 7.78 (dt, 1H), 7.91-8.08 (m, 3H), 9.03 (s, 1H), 10.53 (s br, 1H), 11.36 (s br, 1H), 1×C$\underline{H}_3$ covered by solvent signal.

Example 51

N-(3,4-Difluorophenyl)-3-methyl-5-{[4-(trifluoromethyl)-1,3-benzothiazol-2-yl]-amino}-1,2-thiazole-4-carboxamide

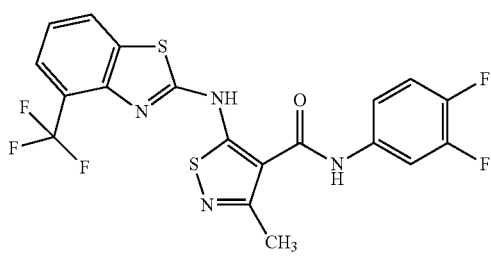 [SMILES: Cc1nsc(Nc2nc3c(C(F)(F)F)cccc3s2)c1C(=O)Nc1ccc(F)c(F)c1]

A mixture of 5-amino-N-(3,4-difluorophenyl)-3-methyl-1,2-thiazole-4-carboxamide [Intermediate 3] (200 mg, 0.71 mmol, 1.2 eq), 2-chloro-4-(trifluoromethyl)-1,3-benzothiazole [CAS-RN: 898784-15-7] (140 mg, 0.59 mmol, 1.0 eq) and cesium carbonate (441 mg, 1.35 mmol, 2.3 eq) in 6.1 mL dioxane/DMF (7/1) was placed in a microwave vial and flushed with argon. Then, palladium(II) acetate (13 mg, 0.06 mmol, 0.1 eq) and Xantphos (34 mg, 0.06 mmol, 0.1 eq) were added. The vial was capped and the reaction mixture was stirred at an environmental temperature of 110° C. overnight. On cooling, the reaction mixture was partitioned between dichloromethane and water. The water phase was extracted with dichloromethane/isopropanol (4/1) (3×). The combined organic phases were washed with brine and the volatile components were removed in vacuo. The crude compound was crystallized by the use of dichloromethane and methanol under ice-cooling to give 154 mg (46% yield of theory) of the title compound in 95% purity (UPLC area-%) after drying.

UPLC-MS (Method 3): $R_t$=1.55 min; MS ($EI_{neg}$): m/z=469 [M–H]⁻.

¹H-NMR (400 MHz, DMSO-d₆): δ [ppm]=2.44 (s, 3H), 7.35-7.50 (m, 3H), 7.74 (d, 1H), 7.95 (dd, 1H), 8.23 (d, 1H), 10.62 (s br, 1H), 12.10 (s br, 1H).

Example 52

N-(4-Chloro-3-fluorophenyl)-5-[(5-cyanopyridin-2-yl)amino]-3-methyl-1,2-thiazole-4-carboxamide

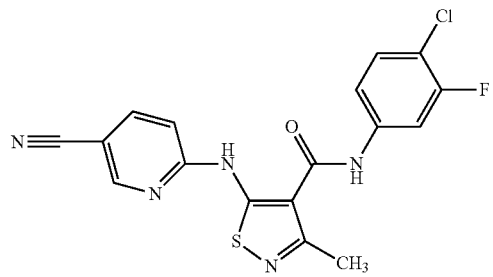 [SMILES: Cc1nsc(Nc2ccc(C#N)cn2)c1C(=O)Nc1ccc(Cl)c(F)c1]

A mixture of 5-amino-N-(4-chloro-3-fluorophenyl)-3-methyl-1,2-thiazole-4-carboxamide [Intermediate 4] (200 mg, 0.70 mmol, 1.4 eq), 6-bromopyridine-3-carbonitrile [CAS-RN: 139585-70-9] (92 mg, 0.50 mmol, 1.0 eq) and cesium carbonate (375 mg, 1.15 mmol, 2.3 eq) in 4.9 mL dioxane/DMF (7/1) was placed in a microwave vial and flushed with argon. Then, palladium(II) acetate (11 mg, 0.05 mmol, 0.1 eq) and Xantphos (29 mg, 0.05 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was purified via preparative MPLC (Biotage Isolera; 50 g SNAP cartridge: hexane->hexane/ethyl acetate 1/1) to give 26.4 mg (9% yield of theory) of the title compound.

UPLC-MS (Method 1): $R_t$=1.32 min; MS ($EI_{neg}$): m/z=386 [M–H]⁻.

¹H-NMR (400 MHz, DMSO-d₆): δ [ppm]=2.42 (s, 3H), 7.42 (d, 1H), 7.49 (dd, 1H), 7.57 (t, 1H), 7.93 (dd, 1H), 8.12 (dd, 1H), 8.87 (s, 1H), 10.57 (s br, 1H), 11.10 (s br, 1H).

Example 53

N-(4-Chloro-3-fluorophenyl)-3-methyl-5-{[4-(trifluoromethyl)-1,3-benzothiazol-2-yl]amino}-1,2-thiazole-4-carboxamide

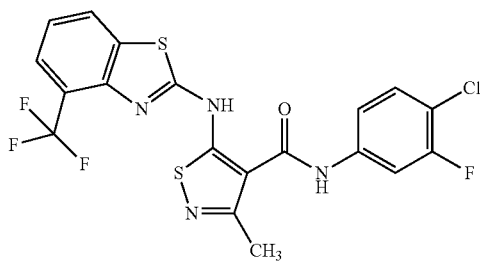 [SMILES: Cc1nsc(Nc2nc3c(C(F)(F)F)cccc3s2)c1C(=O)Nc1ccc(Cl)c(F)c1]

A mixture of 5-amino-N-(4-chloro-3-fluorophenyl)-3-methyl-1,2-thiazole-4-carboxamide [Intermediate 4] (200 mg, 0.56 mmol, 80% purity, 1.2 eq), 2-chloro-4-(trifluoromethyl)-1,3-benzothiazole [CAS-RN: 898784-15-7] (111 mg, 0.47 mmol, 1.0 eq) and cesium carbonate (350 mg, 1.07 mmol, 2.3 eq) in 4.8 mL dioxane/DMF (7/1) was placed in a microwave vial and flushed with argon. Then, palladium (II) acetate (10 mg, 0.05 mmol, 0.1 eq) and Xantphos (27 mg, 0.05 mmol, 0.1 eq) were added. The vial was capped and the reaction mixture was stirred at an environmental temperature of 110° C. overnight. On cooling, the volatile components were removed in vacuo. The crude material was treated with dichloromethane and methanol and the solids were removed by filtration. The resulting solution was concentrated by the use of a rotary evaporator. The crude material was then subjected to preparative HPLC (column: Chromatorex C18, eluent: acetonitrile/water (2/1) acetonitrile). Finally, 69 mg (25% yield of theory) of the title compound in 98% purity (UPLC area-%) were obtained after crystallization using of dichloromethane and methanol.

UPLC-MS (Method 1): $R_t$=1.66 min; MS ($EI_{neg}$): m/z=485 [M−H]−.

$^1$H-NMR (400 MHz, DMSO-d$_6$): δ [ppm]=2.44 (s, 3H), 7.40 (t, 1H), 7.48 (m, 1H), 7.58 (t, 1H), 7.74 (d, 1H), 7.95 (dd, 1H), 8.23 (d, 1H), 10.71 (s br, 1H), 12.11 (s br, 1H).

Example 54

N-(4-Chloro-3-fluorophenyl)-5-[(4-cyanopyridin-2-yl)amino]-3-methyl-1,2-thiazole-4-carboxamide

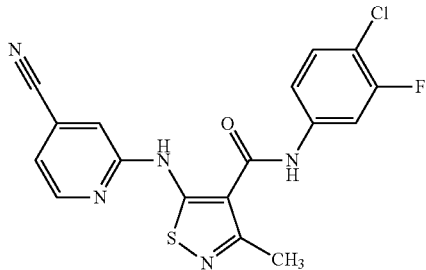 [SMILES: Cc1nsc(Nc2cc(C#N)ccn2)c1C(=O)Nc1ccc(Cl)c(F)c1]

A mixture of 5-amino-N-(4-chloro-3-fluorophenyl)-3-methyl-1,2-thiazole-4-carboxamide [Intermediate 4] (200 mg, 0.70 mmol, 1.2 eq), 2-iodopyridine-4-carbonitrile [CAS-RN: 114821-24-8] (115 mg, 0.50 mmol, 1.0 eq) and cesium carbonate (375 mg, 1.07 mmol, 2.3 eq) in 4.8 mL dioxane/DMF (7/1) was placed in a microwave vial and flushed with argon. Then, palladium(II) acetate (11 mg, 0.05 mmol, 0.1 eq) and Xantphos (29 mg, 0.05 mmol, 0.1 eq) were added. The vial was capped and the reaction mixture was stirred at an environmental temperature of 110° C. overnight. On cooling, the volatile components were removed in vacuo. The crude material was treated with water and a little amount of acetone. The resulting solution was passed through a phase separator while a solid was formed.

The solid obtained like that way was isolated and dried to give 9 mg (3% yield of theory) the title compound in 95% purity (UPLC area-%).

UPLC-MS (Method 1): $R_t$=1.35 min; MS ($EI_{neg}$): m/z=386 [M−H]−.

$^1$H-NMR (400 MHz, DMSO-d$_6$): δ [ppm]=7.35 (m, 1H), 7.46-7.61 (m, 2H), 7.72 (s, 1H), 7.96 (m, 1H), 8.58 (d, 1H), 10.51 (s br, 1H), 10.94 (s br, 1H), 1×C$\underline{H}_3$ covered by solvent signal.

Example 55

Ethyl 5-({4-[(3,4-difluorophenyl)carbamoyl]-3-methyl-1,2-thiazol-5-yl}amino)-pyrazolo[1,5-a]pyrimidine-3-carboxylate

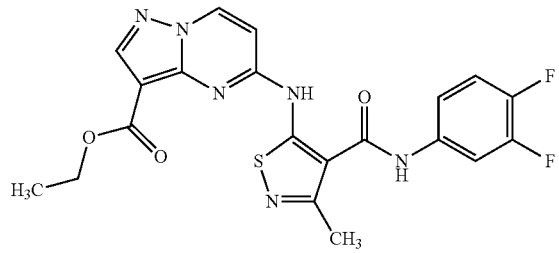 [SMILES: CCOC(=O)c1cnn2ccc(Nc3snc(C)c3C(=O)Nc3ccc(F)c(F)c3)nc12]

A mixture of 5-amino-N-(3,4-difluorophenyl)-3-methyl-1,2-thiazole-4-carboxamide [Intermediate 3] (150 mg, 0.56 mmol, 1.0 eq), ethyl 5-chloropyrazolo[1,5-a]pyrimidine-3-carboxylate [CAS-RN: 1224944-77-7] (126 mg, 0.56 mmol, 1.0 eq) and cesium carbonate (417 mg, 1.28 mmol, 2.3 eq) in 4.5 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the volatile components were removed in vacuo. The crude product was purified via preparative MPLC (Biotage Isolera; 50 g SNAP cartridge: hexane->hexane/ethyl acetate 1/1). The combined product fractions were treated with dichloromethane/methanol to give 20 mg (8% yield of theory) of crystallized title compound after drying under high vacuum.

UPLC-MS (Method 1): $R_t$=1.22 min; MS ($EI_{neg}$): m/z=457 [M−H]−.

$^1$H-NMR (400 MHz, DMSO-d$_6$): δ [ppm]=1.42 (t, 3H), 2.45 (s, 3H), 4.37 (q, 2H), 7.17 (d, 1H), 7.37-7.51 (m, 2H), 7.95 (dd, 1H), 8.42 (s, 1H), 8.97 (d, 1H), 10.55 (s br, 1H), 11.30 (s, 1H).

Example 56

N-(4-Chloro-3-fluorophenyl)-3-methyl-5-(pyrazin-2-ylamino)-1,2-thiazole-4-carboxamide

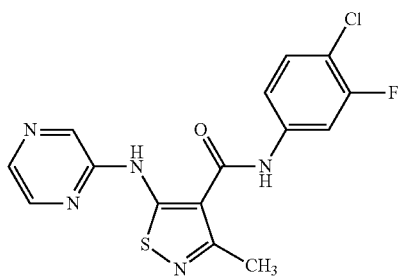 [SMILES: Cc1nsc(Nc2cnccn2)c1C(=O)Nc1ccc(Cl)c(F)c1]

A mixture of 5-amino-N-(4-chloro-3-fluorophenyl)-3-methyl-1,2-thiazole-4-carboxamide [Intermediate 4] (150 mg, 0.53 mmol, 1.0 eq), 2-chloropyrazine [CAS-RN: 14508-49-7] (72 mg, 0.63 mmol, 1.2 eq) and cesium carbonate (393 mg, 1.21 mmol, 2.3 eq) in 5.1 mL dioxane/DMF (7/1) was placed in a microwave vial and flushed with argon. Then, palladium(II) acetate (12 mg, 0.05 mmol, 0.1 eq) and Xantphos (30 mg, 0.05 mmol, 0.1 eq) were added. The vial was capped and the reaction mixture was stirred at an environmental temperature of 110° C. overnight. On cooling, the volatile components were removed in vacuo. The crude material was treated with water and partitioned by the use of dichloromethane/isopropanol (4/1). The organic phase was washed with brine and was passed through a phase separator. The volatile components were removed. Crystallization was achieved by the use of dichloromethane/methanol to give 92 mg (47% yield of theory) of solid title compound after drying under high vacuum.

UPLC-MS (Method 1): $R_t$=1.24 min; MS ($EI_{neg}$): m/z=362[M-H]$^-$.

$^1$H-NMR (400 MHz, DMSO-d$_6$): δ [ppm]=2.45 (s, 3H), 7.44-7.65 (m, 2H), 7.96 (d, 1H), 8.18 (s, 1H), 8.40 (s, 1H), 8.73 (s, 1H), 10.55 (s br, 1H), 10.99 (s br, 1H).

Example 57

N-(3,4-Difluorophenyl)-3-methyl-5-(pyrazolo[1,5-a]pyrimidin-5-ylamino)-1,2-thiazole-4-carboxamide

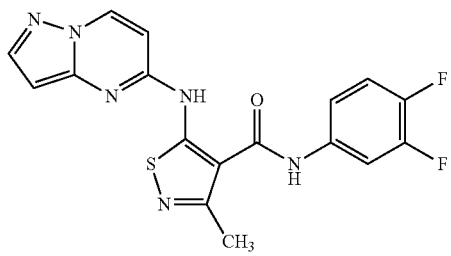 [SMILES: Cc1nsc(Nc2ccn3nccc3n2)c1C(=O)Nc1ccc(F)c(F)c1]

A mixture of 5-amino-N-(3,4-difluorophenyl)-3-methyl-1,2-thiazole-4-carboxamide [Intermediate 3] (150 mg, 0.56 mmol, 1.0 eq), 5-chloropyrazolo[1,5-a]pyrimidine [CAS-RN: 29274-24-6] (86 mg, 0.56 mmol, 1.0 eq) and cesium carbonate (417 mg, 1.28 mmol, 2.3 eq) in 4.5 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the volatile components were removed in vacuo. The crude product was partitioned between water and dichloromethane/isopropanol (4/1). The organic phase was washed with brine and the phases were separated by the use of a Whatman filter. Purification was conducted via preparative MPLC (Biotage Isolera; 50 g SNAP cartridge: hexane->hexane/ethyl acetate 1/1) to give 20 mg (9% yield of theory) of the title compound after drying under high vacuum.

UPLC-MS (Method 1): $R_t$=1.18 min; MS ($EI_{neg}$): m/z=385 [M-H]$^-$.

$^1$H-NMR (400 MHz, DMSO-d$_6$): δ [ppm]=2.90 (s, 3H), 6.44 (s, 1H), 6.98 (d, 1H), 7.32-7.52 (m, 2H), 7.95 (dd, 1H), 8.03 (s, 1H), 8.86 (d, 1H), 10.49 (s br, 1H), 11.02 (s, 1H).

Example 58

N-(3,4-Difluorophenyl)-3-methyl-5-{[7-(trifluoromethyl)[1,3]thiazolo[5,4-b]pyridin-2-yl]amino}-1,2-thiazole-4-carboxamide

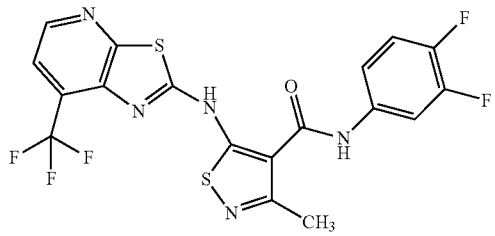 [SMILES: Cc1nsc(Nc2nc3c(C(F)(F)F)ccnc3s2)c1C(=O)Nc1ccc(F)c(F)c1]

A mixture of 5-amino-N-(3,4-difluorophenyl)-3-methyl-1,2-thiazole-4-carboxamide [Intermediate 3] (150 mg, 0.56 mmol, 1.0 eq), 2-chloro-7-(trifluoromethyl)-[1,3]thiazolo[5,4-b]pyridine [please see, L. Zhu, J. Heterocycl. Chem. (2005), 42, 727-730] (166 mg, 0.56 mmol, 1.0 eq) and cesium carbonate (417 mg, 1.28 mmol, 2.3 eq) in 4.5 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the volatile components were removed in vacuo. The crude product was purified via preparative HPLC (method A) to give 40 mg (14% yield of theory) of the title compound.

UPLC-MS (Method 1): $R_t$=1.51 min; MS ($EI_{neg}$): m/z=470 [M-H]$^-$.

$^1$H-NMR (400 MHz, DMSO-d$_6$): δ [ppm]=2.53 (s, 3H), 7.37-7.52 (m, 2H), 7.76 (dd, 1H), 7.95 (ddd, 1H), 8.53 (d, 1H), 10.82 (s br, 1H), 12.34 (s, 1H).

Example 59

Methyl 5-({4-[(3,4-difluorophenyl)carbamoyl]-3-methyl-1,2-thiazol-5-yl}amino)-pyrazine-2-carboxylate

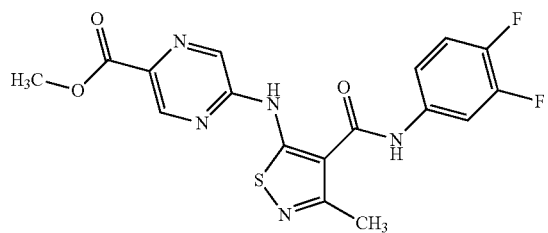 [SMILES: COC(=O)c1cnc(Nc2snc(C)c2C(=O)Nc2ccc(F)c(F)c2)cn1]

A mixture of 5-amino-N-(3,4-difluorophenyl)-3-methyl-1,2-thiazole-4-carboxamide [Intermediate 3] (150 mg, 0.56 mmol, 1.0 eq), methyl 5-chloropyrazine-2-carboxylate [CAS-RN: 33332-25-1] (115 mg, 0.67 mmol, 1.2 eq) and cesium carbonate (417 mg, 1.28 mmol, 2.3 eq) in 5.4 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the volatile components were removed in vacuo. The crude product was partitioned between water and dichloro-methane/isopropanol (4/1). The organic phase was washed with brine and the phases were separated by the use of a Whatman filter. The crude product was treated with dichloromethane/methanol to induce crystallization. After filtration and drying under high vacuum, 80 mg (34% yield of theory) of the title compound were obtained.

UPLC-MS (Method 1): $R_t$=1.16 min; MS ($EI_{neg}$): m/z=404 [M−H]−.

$^1$H-NMR (400 MHz, DMSO-d$_6$): δ [ppm]=3.86 (s, 3H), 7.36-7.53 (m, 2H), 7.98 (m, 1H), 8.75 (s, 1H), 8.96 (s, 1H), 10.58 (s br, 1H), 11.48 (s, 1H), 1×CH$_3$ not assigned.

Example 60

N-(3,4-Difluorophenyl)-3-methyl-5-{[6-(trifluoromethyl)quinoxalin-2-yl]amino}-1,2-thiazole-4-carboxamide

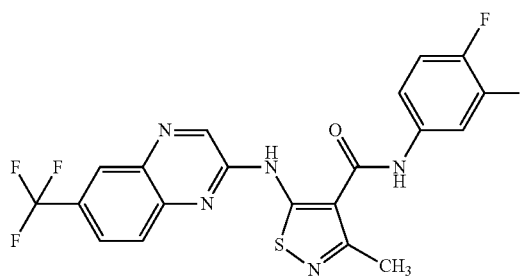

A mixture of 5-amino-N-(3,4-difluorophenyl)-3-methyl-1,2-thiazole-4-carboxamide [Intermediate 3] (150 mg, 0.56 mmol, 1.0 eq), 2-chloro-6-(trifluoromethyl)-quinoxaline [W. Lumma, J. Med. Chem. (1981), 24, 93-101.] (162 mg, 0.56 mmol, 80% purity, 1.0 eq) and cesium carbonate (417 mg, 1.28 mmol, 2.3 eq) in 5.4 mL dioxane/DMF (7/1) was placed in a microwave vial and flushed with argon. Then, palladium(II) acetate (7 mg, 0.03 mmol, 0.1 eq) and Xantphos (18 mg, 0.03 mmol, 0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was crystallized by the use of ice-cooled dichloromethane/methanol. The precipitate was isolated by filtration, washed with dichloromethane and dried under high vacuum to deliver 97 mg of the title compound (37% yield of theory).

UPLC-MS (Method 1): $R_t$=1.50 min; MS ($EI_{neg}$): m/z=464 [M−H]−.

$^1$H-NMR (400 MHz, DMSO-d$_6$): δ [ppm]=7.38-7.58 (m, 2H), 7.92-8.07 (m, 2H), 8.14 (d, 1H), 8.31 (s, 1H), 9.12 (s, 1H), 10.63 (s br, 1H), 11.64 (s br, 1H), 1×CH$_3$ covered by solvent signal.

Example 61

N-(3,4-Dichlorophenyl)-3-methyl-5-{[6-(trifluoromethyl)quinoxalin-2-yl]amino}-1,2-thiazole-4-carboxamide

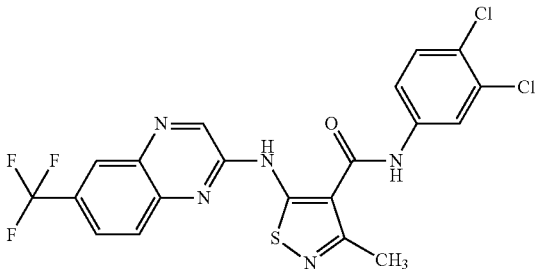 [SMILES: Cc1nsc(Nc2cnc3cc(C(F)(F)F)ccc3n2)c1C(=O)Nc1ccc(Cl)c(Cl)c1]

A mixture of 5-amino-N-(3,4-dichlorophenyl)-3-methyl-1,2-thiazole-4-carboxamide [Intermediate 7] (200 mg, 0.62 mmol, 1.0 eq), 2-chloro-6-(trifluoromethyl)-quinoxaline [W. Lumma, J. Med. Chem. (1981), 24, 93-101.] (162 mg, 0.62 mmol, 1.0 eq) and cesium carbonate (461 mg, 1.42 mmol, 2.3 eq) in 6.0 mL dioxane/DMF (7/1) was placed in a microwave vial and flushed with argon. Then, palladium(II) acetate (14 mg, 0.06 mmol, 0.1 eq) and Xantphos (36 mg, 0.06 mmol, 0.1 eq) were added. The vial was capped and the reaction mixture was stirred at an environmental temperature of 110° C. overnight. On cooling, the reaction mixture was partitioned between dichloromethane/isopropanol (4/1) and water. The water phase was extracted two more times with dichloromethane/isopropanol (4/1) and the combined organic phases were concentrated in vacuo. The crude product was crystallized by the use of ice-cooled dichloromethane/methanol. The precipitate was isolated by filtration, washed with dichloromethane and dried under high vacuum to deliver 152 mg of the title compound (49% yield of theory).

UPLC-MS (Method 1): $R_t$=1.61 min; MS ($EI_{neg}$): m/z=496 [M−H]−.

$^1$H-NMR (400 MHz, DMSO-d$_6$): δ [ppm]=7.59-7.72 (m, 2H), 8.03 (dd, 1H), 8.15 (d, 1H), 8.22 (s, 1H), 8.32 (s, 1H), 9.13 (s, 1H), 10.64 (s br, 1H), 11.62 (s br, 1H), 1×CH$_3$ covered by solvent signal.

Example 62

5-[(5-Cyanopyridin-2-yl)amino]-N-(3,4-dichlorophenyl)-3-methyl-1,2-thiazole-4-carboxamide

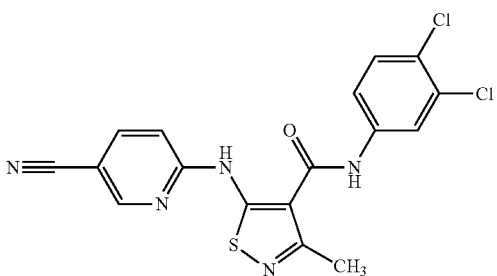 [SMILES: Cc1nsc(Nc2ccc(C#N)cn2)c1C(=O)Nc1ccc(Cl)c(Cl)c1]

A mixture of 5-amino-N-(3,4-dichlorophenyl)-3-methyl-1,2-thiazole-4-carboxamide [Intermediate 7] (200 mg, 0.66 mmol, 1.4 eq), 6-bromonicotinonitrile [CAS-RN: 139585-70-9] (87 mg, 0.47 mmol, 1.0 eq) and cesium carbonate (354 mg, 1.09 mmol, 2.3 eq) in 4.6 mL dioxane/DMF (7/1) was placed in a microwave vial and flushed with argon. Then, palladium(II) acetate (11 mg, 0.05 mmol, 0.1 eq) and Xantphos (27 mg, 0.05 mmol, 0.1 eq) were added. The vial was capped and the reaction mixture was stirred at an environmental temperature of 110° C. overnight. On cooling, the reaction mixture was evaporated in vacuo. The crude product was subjected to preparative MPLC (Biotage Isolera; 50 g SNAP cartridge: hexane->hexane/ethyl acetate 1/1->ethyl acetate) to give 29 mg (11% yield of theory) of the title compound.

UPLC-MS (Method 1): $R_t$=1.37 min; MS ($EI_{neg}$): m/z=402 [M−H]⁻.

$^1$H-NMR (400 MHz, DMSO-d$_6$): δ [ppm]=2.42 (s, 3H), 7.42 (d, 1H), 7.61-7.64 (m, 2H), 8.13 (dd, 1H), 8.17 (s, 1H), 8.87 (d, 1H), 10.56 (s br, 1H), 11.11 (s br, 1H).

Example 63

N-(4-Chloro-3-fluorophenyl)-3-methyl-5-{[6-(1,3-oxazol-2-yl)pyrazin-2-yl]amino}-1,2-thiazole-4-carboxamide

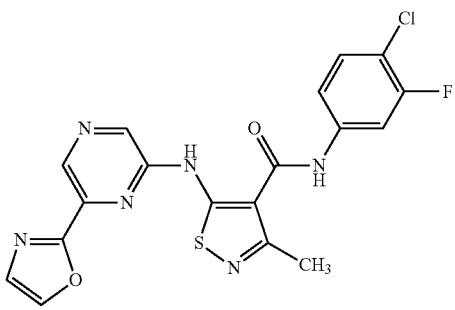 [SMILES: Cc1nsc(Nc2cncc(-c3ncco3)n2)c1C(=O)Nc1ccc(Cl)c(F)c1]

A mixture of 5-amino-N-(4-chloro-3-fluorophenyl)-3-methyl-1,2-thiazole-4-carboxamide [Intermediate 4] (107 mg, 0.37 mmol, 1.0 eq), 2-chloro-6-(1,3-oxazol-2-yl)-pyrazine [for the synthesis, please see: EP 2090570, 2009 (Kyowa Hakko Kirin Co, Ltd.)] (68 mg, 0.37 mmol, 1.0 eq) and cesium carbonate (281 mg, 0.86 mmol, 2.3 eq) in 3.9 mL dioxane/DMF (7/1) was placed in a microwave vial and flushed with argon. Then, palladium(II) acetate (8 mg, 0.04 mmol, 0.1 eq) and Xantphos (22 mg, 0.04 mmol, 0.1 eq) were added. The vial was capped and the reaction mixture was stirred at an environmental temperature of 110° C. overnight. On cooling, the volatile components were removed in vacuo. The crude material was treated with water and partitioned by the use of dichloromethane/isopropanol (4/1). The resulting organic phase was washed with brine and passed through a Whatman filter. The volatile components were removed. The crude product was purified via preparative HPLC (method A). The product fractions were combined and the solvent was removed. The remaining solid was stirred with a small amount of diethyl ether and the remaining solid was separated by the use of a filter to give 12 mg (7% yield of theory) of the title compound after drying under high vacuum.

UPLC-MS (Method 1): $R_t$=1.27 min; MS ($EI_{neg}$): m/z=429 [M−H]⁻.

$^1$H-NMR (400 MHz, DMSO-d$_6$): δ [ppm]=7.47-7.65 (m, 3H), 7.95 (d, 1H), 8.50 (s, 1H), 8.82 (s, 2H), 10.57 (s br, 1H), 11.21 (s br, 1H), 1×C$\underline{H}_3$ not assigned.

Example 64

N-(3,4-Difluorophenyl)-3-methyl-5-{[6-(1H-pyrazol-1-yl)pyrazin-2-yl]amino}-1,2-thiazole-4-carboxamide

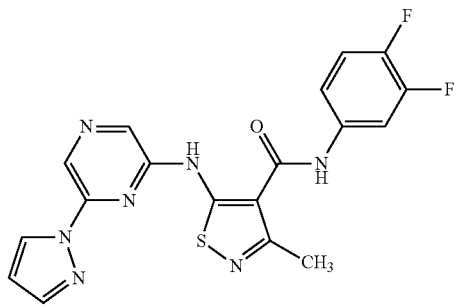 [SMILES: Cc1nsc(Nc2cncc(-n3cccn3)n2)c1C(=O)Nc1ccc(F)c(F)c1]

A mixture of 5-amino-N-(3,4-difluorophenyl)-3-methyl-1,2-thiazole-4-carboxamide [Intermediate 3] (150 mg, 0.56 mmol, 1.0 eq), 2-chloro-6-(1H-pyrazol-1-yl)-pyrazine [CAS RN: 642459-09-4; for the synthesis, see also: WO 2004/4730, 2004 (Astex Technology, Ltd.)] (80 mg, 0.45 mmol, 0.8 eq) and cesium carbonate (417 mg, 1.28 mmol, 2.3 eq) in 4.5 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the volatile components were removed in vacuo. The crude material was dissolved in a small amount DMSO and filtered. Purification was conducted via preparative HPLC (method A) to give 18 mg (7% yield of theory) of the title compound.

UPLC-MS (Method 2): $R_t$=0.83 min; MS ($EI_{neg}$): m/z=402 [M−H]⁻.

$^1$H-NMR (400 MHz, DMSO-d$_6$): δ [ppm]=2.47 (s, 3H), 6.75 (t, 1H), 7.39-7.51 (m, 2H), 7.89-8.02 (m, 2H), 8.63 (s, 1H), 8.67-8.73 (m, 2H), 10.54 (s br, 1H), 11.23 (s br, 1H).

Example 65

N-(3,4-Difluorophenyl)-3-methyl-5-(pyrazin-2-ylamino)-1,2-thiazole-4-carboxamide

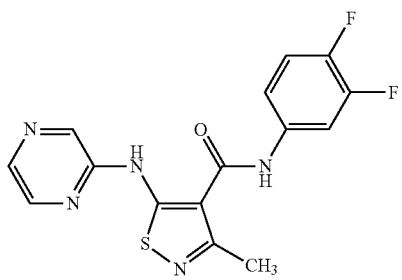

A mixture of 5-amino-N-(3,4-difluorophenyl)-3-methyl-1,2-thiazole-4-carboxamide [Intermediate 3] (150 mg, 0.56 mmol, 1.0 eq), 2-chloropyrazine [CAS RN: 14508-49-7] (77 mg, 0.67 mmol, 1.2 eq) and cesium carbonate (417 mg, 1.28 mmol, 2.3 eq) in 5.4 mL dioxane/DMF (7/1) was placed in a microwave vial and flushed with argon. Then, palladium (II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, water was added. Then, the aqueous phase was extracted three times with dichloromethane/isopropanol (4/1). The combined organic phases were washed with brine, passed through a Whatman filter and concentrated in vacuo. The crude material was crystallized by the use of ice-cooled dichloromethane/methanol. The precipitate was filtered and dried to give 5 mg (3% yield of theory) of the title compound.

UPLC-MS (Method 1): $R_t$=1.15 min; MS ($EI_{neg}$): m/z=346 [M−H]⁻.

$^1$H-NMR (400 MHz, DMSO-$d_6$): δ [ppm]=7.31-7.48 (m, 2H), 7.95 (s br, 1H), 8.02 (dd, 1H), 8.29 (s, 1H), 8.59 (s, 1H), 11.43 (s br, 1H), 1×C$\underline{H}_3$ & 1H not assigned.

Example 66

Methyl 6-({4-[(3,4-difluorophenyl)carbamoyl]-3-methyl-1,2-thiazol-5-yl}amino)-pyrazine-2-carboxylate

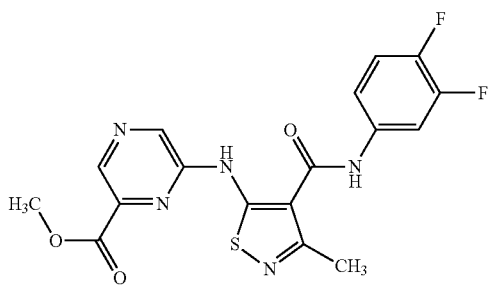 [SMILES: COC(=O)c1cncc(Nc2snc(C)c2C(=O)Nc2ccc(F)c(F)c2)n1]

A mixture of 5-amino-N-(3,4-difluorophenyl)-3-methyl-1,2-thiazole-4-carboxamide [Intermediate 3] (150 mg, 0.56 mmol, 1.0 eq), methyl 6-chloropyrazine-2-carboxylate [CAS RN: 23611-75-8] (120 mg, 0.56 mmol, 1.0 eq) and cesium carbonate (417 mg, 1.28 mmol, 2.3 eq) in 5.4 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the volatile components were removed in vacuo. The crude material was dissolved in a small amount DMSO and filtered. Purification was conducted via preparative HPLC (method A) to give 10 mg (4% yield of theory) of the title compound.

UPLC-MS (Method 1): $R_t$=1.20 min; MS ($ESI_{neg}$): m/z=404 [M−H]⁻.

$^1$H-NMR (400 MHz, DMSO-$d_6$): δ [ppm]=3.98 (s, 3H), 7.38-7.53 (m, 2H), 7.95 (m, 1H), 8.73 (s, 1H), 8.84 (s, 1H), 10.48 (s, 1H), 11.22 (s br, 1H), 1×C$\underline{H}_3$ not assigned.

Example 67

N-(4-Chloro-3-fluorophenyl)-3-methyl-5-{[6-(1H-pyrazol-1-yl)pyrazin-2-yl]amino}-1,2-thiazole-4-carboxamide

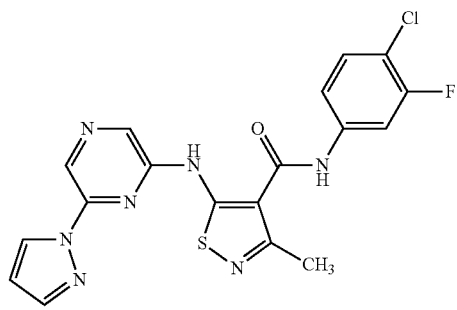 [SMILES: Cc1nsc(Nc2cncc(-n3cccn3)n2)c1C(=O)Nc1ccc(Cl)c(F)c1]

A mixture of 5-amino-N-(4-chloro-3-fluorophenyl)-3-methyl-1,2-thiazole-4-carboxamide [Intermediate 4] (150 mg, 0.53 mmol, 1.0 eq), 2-chloro-6-(1H-pyrazol-1-yl)-pyrazine [for the synthesis, please see: WO 20044730, 2004 (Astex Technology Ltd.)] (95 mg, 0.53 mmol, 1.0 eq) and cesium carbonate (393 mg, 1.21 mmol, 2.3 eq) in 5.4 mL dioxane/DMF (7/1) was placed in a microwave vial and flushed with argon. Then, palladium(II) acetate (12 mg, 0.05 mmol, 0.1 eq) and Xantphos (30 mg, 0.05 mmol, 0.1 eq) were added. The vial was capped and the reaction mixture was stirred at an environmental temperature of 110° C. overnight. On cooling, the volatile components were removed in vacuo. The crude material was treated with DMSO and filtered. The crude material was purified via preparative HPLC (method A) to give 6 mg (3% yield of theory) of the title compound.

UPLC-MS (Method 1): $R_t$=1.34 min; MS ($ESI_{neg}$): m/z=428 [M−H]⁻.

$^1$H-NMR (400 MHz, DMSO-$d_6$): δ [ppm]=2.46 (s, 3H), 6.75 (dd, 1H), 7.51 (dd, 1H), 7.59 (t, 1H), 7.95 (dt, 2H), 8.62 (s, 1H), 8.70 (s br, 2H), 10.64 (s, 1H), 11.24 (s br, 1H).

Example 68

N-(4-Chloro-3-fluorophenyl)-3-methyl-5-{[6-(trifluoromethyl)quinoxalin-2-yl]amino}-1,2-thiazole-4-carboxamide

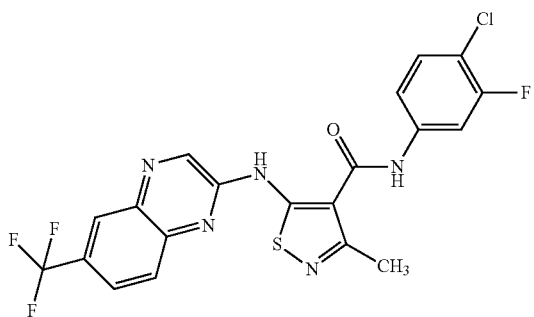 [SMILES: Cc1nsc(Nc2cnc3cc(C(F)(F)F)ccc3n2)c1C(=O)Nc1ccc(Cl)c(F)c1]

A mixture of 5-amino-N-(4-chloro-3-fluorophenyl)-3-methyl-1,2-thiazole-4-carboxamide [Intermediate 4] (180 mg, 0.50 mmol, ~80% purity, 1.0 eq), 2-chloro-6-(trifluoromethyl)quinoxaline [W. Lumma, J. Med. Chem. (1981), 24, 93-101.] (146 mg, 0.50 mmol, ~80% purity, 1.0 eq) and cesium carbonate (378 mg, 1.16 mmol, 2.3 eq) in 5.0 mL dioxane/DMF (7/1) was placed in a microwave vial and flushed with argon. Then, palladium(II) acetate (11 mg, 0.05 mmol, 0.1 eq) and Xantphos (29 mg, 0.05 mmol, 0.1 eq) were added. The vial was capped and the reaction mixture was stirred at an environmental temperature of 110° C. overnight. On cooling, the volatile components were removed in vacuo. The crude material was treated with DMSO and filtered. The crude material was purified first via preparative MPLC (Biotage Isolera; 50 g NH2-SNAP cartridge: hexane->hexane/ethyl acetate 2/1) and the product fractions in the following via preparative HPLC (method A) to give 4 mg (2% yield of theory) of the title compound.

UPLC-MS (Method 1): $R_t$=1.57 min; MS (ESI$_{neg}$): m/z=480 [M−H]$^-$.

$^1$H-NMR (400 MHz, DMSO-d$_6$): δ [ppm]=7.43-7.69 (m, 2H), 7.88-8.09 (m, 2H), 8.15 (d, 1H), 8.32 (s, 1H), 9.12 (s, 1H), 10.66 (s br, 1H), 11.61 (s br, 1H), 1×CH$_3$ not assigned.

Example 69

N-(4-Chloro-3-fluorophenyl)-3-methyl-5-[(6-methylpyrazin-2-yl)amino]-1,2-thiazole-4-carboxamide

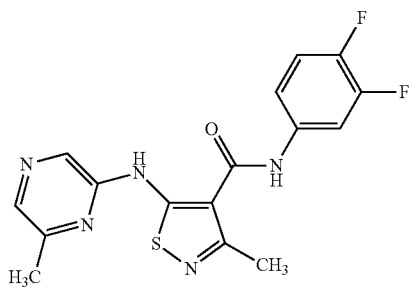 [SMILES: Cc1cncc(Nc2snc(C)c2C(=O)Nc2ccc(F)c(F)c2)n1]

A mixture of 5-amino-N-(3,4-difluorophenyl)-3-methyl-1,2-thiazole-4-carboxamide [Intermediate 3] (150 mg, 0.56 mmol, 1.0 eq), 2-chloro-6-methylpyrazine [CAS RN: 38557-71-0] (72 mg, 0.56 mmol, 1.0 eq) and cesium carbonate (417 mg, 1.28 mmol, 2.3 eq) in 5.4 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the volatile components were removed in vacuo. The crude material was treated with water and extracted three times with dichloromethane/methanol (~5/1). The combined organic phases were washed with brine, passed through a Whatman filter and concentrated in vacuo. The crude material was purified first via preparative MPLC (Biotage Isolera; 50 g SNAP cartridge: hexane/ethyl acetate 4/1->ethyl acetate). The product fractions were concentrated in vacuo and crystallized with dichloromethane to give 23 mg (11% yield of theory) of the title compound after filtration and subsequent drying.

UPLC-MS (Method 4): $R_t$=1.18 min; MS (ESI$_{neg}$): m/z=360 [M−H]$^-$.

$^1$H-NMR (400 MHz, DMSO-d$_6$): δ [ppm]=2.44 (s, 3H), 2.51 (s, 3H), 7.37-7.49 (m, 2H), 7.94 (dd, 1H), 8.07 (s, 1H), 8.52 (s, 1H), 10.38 (s br, 1H), 10.87 (s br, 1H).

Example 70

6-({4-[(3,4-Difluorophenyl)carbamoyl]-3-methyl-1,2-thiazol-5-yl}amino)-N-methylpyrazine-2-carboxamide

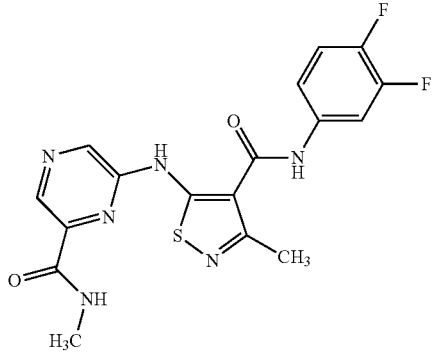 [SMILES: CNC(=O)c1cncc(Nc2snc(C)c2C(=O)Nc2ccc(F)c(F)c2)n1]

A mixture of 5-amino-N-(3,4-difluorophenyl)-3-methyl-1,2-thiazole-4-carboxamide [Intermediate 3] (150 mg, 0.56 mmol, 1.0 eq), 6-chloro-N-methylpyrazine-2-carboxamide [for the synthesis, please see: WO 2008144062, 2008 (Novartis AG)] (106 mg, 0.56 mmol, 90% purity, 1.0 eq) and cesium carbonate (417 mg, 1.28 mmol, 2.3 eq) in 5.4 mL dioxane/DMF (7/1) was placed in a microwave vial and flushed with argon. Then, palladium(II) acetate (13 mg, 0.06 mmol, 0.1 eq) and Xantphos (32 mg, 0.06 mmol, 0.1 eq) were added. The vial was capped and the reaction mixture was stirred at an environmental temperature of 110° C. overnight. On cooling, the volatile components were removed in vacuo. The crude material was treated with water and extracted three times with dichloromethane/isopropanol (~5/1). The combined organic phases were washed with brine, passed through a Whatman filter and concentrated in vacuo. The crude material was purified via preparative MPLC (Biotage Isolera; 50 g SNAP cartridge: hexane/ethyl acetate 8/2->ethyl acetate). Subsequently, the product fractions were crystallized by the use of dichloromethane to give 28 mg (12% yield of theory) of the title compound after drying.

UPLC-MS (Method 1): $R_t$=1.07 min; MS (ESI$_{neg}$): m/z=403 [M−H]$^-$.

¹H-NMR (400 MHz, DMSO-d₆): δ [ppm]=2.47 (s, 3H), 2.97 (d, 3H), 7.37-7.52 (m, 2H), 7.89-8.01 (m, 2H), 8.64 (s, 1H), 8.88 (s, 1H), 10.46 (s br, 1H), 11.17 (s br, 1H).

Example 71

5-[(6-Chloropyrazin-2-yl)amino]-N-(3,4-difluorophenyl)-3-methyl-1,2-thiazole-4-carboxamide

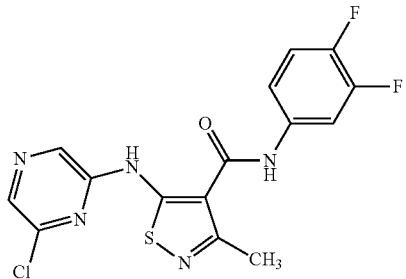 [SMILES: Cc1nsc(Nc2cncc(Cl)n2)c1C(=O)Nc1ccc(F)c(F)c1]

A mixture of 5-amino-N-(3,4-difluorophenyl)-3-methyl-1,2-thiazole-4-carboxamide [Intermediate 3] (3.19 g, 11.85 mmol, 1.0 eq), 2,6-dichloropyrazine [CAS RN: 4774-14-5] (3.31 g, 17.8 mmol, 1.5 eq) and cesium carbonate (8.88 g, 27.3 mmol, 2.3 eq) in 101 mL dioxane/DMF (7/1) was placed in a reaction flask and flushed with argon. Then, palladium(II) acetate (266 mg, 1.19 mmol, 0.1 eq) and Xantphos (685 mg, 1.19 mmol, 0.1 eq) were added. The reaction mixture was stirred at reflux temperature overnight. On cooling, the reaction mixture was partitioned between ethyl acetate and water. The aqueous phase was extracted with ethyl acetate and the combined organic phases were washed with brine. Phase separation was conducted by the use of a Whatman filter. The crude material crystallized with dichloromethane/methanol (~5/1). The precipitate was isolated by filtration and washed with dichloromethane. The filtrate was concentrated in vacuo and again crystallized with dichloromethane/methanol (~15/1). The resulting precipitate was again washed with dichloromethane. The two samples were combined to yield 1.58 g (31% yield of theory) of the title compound after drying.

UPLC-MS (Method 1): $R_t$=1.29 min; MS (ESI$_{neg}$): m/z=380 [M−H]⁻.

¹H-NMR (400 MHz, DMSO-d₆): δ [ppm]=2.45 (s, 3H), 7.41-7.50 (m, 2H), 7.94 (t, 1H), 8.27 (s, 1H), 8.67 (s, 1H), 10.48 (s br, 1H), 11.22 (s br, 1H).

Example 72

N-(3,4-Difluorophenyl)-5-[(6-methoxypyrazin-2-yl)amino]-3-methyl-1,2-thiazole-4-carboxamide

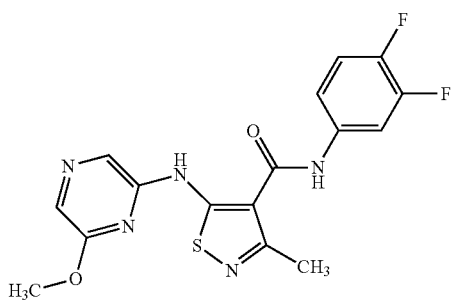 [SMILES: COc1cncc(Nc2snc(C)c2C(=O)Nc2ccc(F)c(F)c2)n1]

A mixture of 5-[(6-chloropyrazin-2-yl)amino]-N-(3,4-difluorophenyl)-3-methyl-1,2-thiazole-4-carboxamide [Example 71] (100 mg, 0.26 mmol, 1.0 eq) and a sodium methoxide solution [CAS RN: 16114-47-9] (25%-w/w in methanol, 0.18 mL, 0.79 mmol, 3.0 eq) in 1 mL 1-methyl-2-pyrrolidon was heated to 50° C. for 2 h. Only traces of product could be detected by LC/MS. Then, the reaction mixture was heated in a single microwave oven to 150° C. for 5 h. On cooling, the crude material was partitioned between ethyl acetate and water. The organic phase was washed with brine and the phases were separated by the use of a Whatman filter. Purification was conducted via preparative HPLC (column: Chromatorex C18, eluent: acetonitrile/0.1% formic acid, 40/60→80/20) to give 10 mg (10% yield of theory) of the title compound.

UPLC-MS (Method 1): $R_t$=1.24 min; MS (ESI$_{neg}$): m/z=376 [M−H]⁻.

¹H-NMR (400 MHz, DMSO-d₆): δ [ppm]=2.43 (s, 3H), 4.09 (s, 3H), 7.40-7.50 (m, 2H), 7.82 (s, 1H), 7.94 (m, 1H), 8.22 (s, 1H), 10.44 (s br, 1H), 10.86 (s br, 1H).

Example 73

6-({4-[(3,4-Difluorophenyl)carbamoyl]-3-methyl-1,2-thiazol-5-yl}amino)-N-ethylpyrazine-2-carboxamide

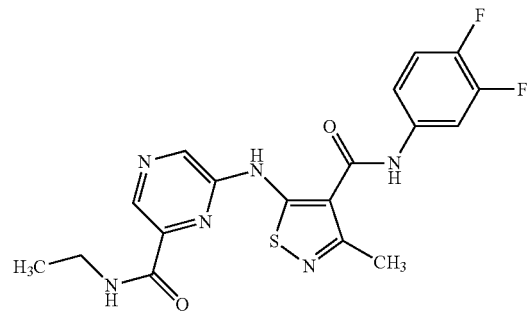 [SMILES: CCNC(=O)c1cncc(Nc2snc(C)c2C(=O)Nc2ccc(F)c(F)c2)n1]

A mixture of 5-amino-N-(3,4-difluorophenyl)-3-methyl-1,2-thiazole-4-carboxamide [Intermediate 3] (77 mg, 0.29 mmol, 1.0 eq), 6-chloro-N-ethylpyrazine-2-carboxamide [Intermediate 8] (53 mg, 0.29 mmol, 1.0 eq) and cesium carbonate (214 mg, 0.66 mmol, 2.3 eq) in 2.8 mL dioxane/DMF (7/1) was placed in a microwave vial and flushed with argon. Then, palladium(II) acetate (6 mg, 0.03 mmol, 0.1 eq) and Xantphos (13 mg, 0.03 mmol, 0.1 eq) were added. The vial was capped and the reaction mixture was stirred at an environmental temperature of 110° C. overnight. On cooling, the volatile components were removed in vacuo. The crude material was dissolved in 2 mL of DMSO and purified by preparative HPLC (column: X-bridge, eluent: acetonitrile/0.1% ammonia in water, 15/85→55/45) to give 7 mg (6% yield of theory) of the title compound.

UPLC-MS (Method 2): $R_t$=0.79 min; MS (ESI$_{neg}$): m/z=417 [M−H]⁻.

¹H-NMR (400 MHz, DMSO-d₆): δ [ppm]=1.23 (t, 3H), 3.45 (m, 2H), 7.38-7.51 (m, 2H), 7.89-8.03 (m, 2H), 8.65 (s, 1H), 8.88 (s, 1H), 10.47 (s br, 1H), 11.20 (s br, 1H), 1×CH₃ not assigned.

Example 74

5-[(5-Chloropyrazin-2-yl)amino]-N-(3,4-difluorophenyl)-3-methyl-1,2-thiazole-4-carboxamide

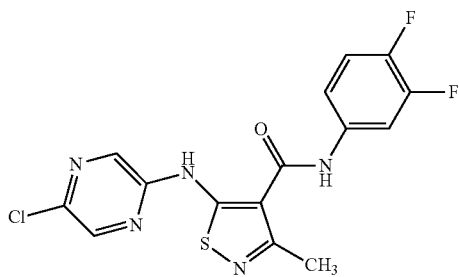 [SMILES: Cc1nsc(Nc2cnc(Cl)cn2)c1C(=O)Nc1ccc(F)c(F)c1]

A mixture of 5-amino-N-(3,4-difluorophenyl)-3-methyl-1,2-thiazole-4-carboxamide [Intermediate 3] (300 mg, 1.11 mmol, 1.0 eq), 2,5-dichloropyrazine [CAS RN: 19745-07-4] (166 mg, 1.11 mmol, 1.0 eq) and cesium carbonate (835 mg, 2.56 mmol, 2.3 eq) in 11 mL dioxane/DMF (7/1) was placed in a microwave vial and flushed with argon. Then, palladium (II) acetate (25 mg, 0.11 mmol, 0.1 eq) and Xantphos (64 mg, 0.11 mmol, 0.1 eq) were added. The vial was capped and the reaction mixture was stirred at an environmental temperature of 110° C. overnight. On cooling, the reaction mixture was partitioned between dichloro-methane/methanol (5/1) and water. The organic phase was washed with brine and the phases were separated by the use of a Whatman filter. The crude material was crystallized with dichloromethane/methanol and the precipitate was isolated via filtration. After drying, 192 mg (6% yield of theory) of the title compound were obtained.

UPLC-MS (Method 3): $R_t$=1.29 min; MS (ESI$_{neg}$): m/z=380 [M−H]$^-$.

$^1$H-NMR (400 MHz, DMSO-d$_6$): δ [ppm]=2.44 (s, 3H), 7.38-7.53 (m, 2H), 7.94 (dd, 1H), 8.56 (s, 2H), 10.47 (s br, 1H), 11.10 (s br, 1H).

Example 75

5-({4-[(3,4-Difluorophenyl)carbamoyl]-3-methyl-1,2-thiazol-5-yl}amino)-N-methylpyrazine-2-carboxamide

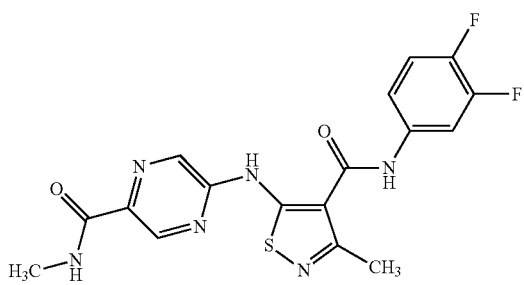 [SMILES: CNC(=O)c1cnc(Nc2snc(C)c2C(=O)Nc2ccc(F)c(F)c2)cn1]

A mixture of 5-amino-N-(3,4-difluorophenyl)-3-methyl-1,2-thiazole-4-carboxamide [Intermediate 3] (150 mg, 0.56 mmol, 1.5 eq), 5-chloro-N-methylpyrazine-2-carboxamide [Intermediate 9] (83 mg, 0.37 mmol, 1.0 eq) and potassium phosphate (102 mg, 0.48 mmol, 1.3 eq) in 3 mL tert-butanol was placed in a microwave vial and flushed with argon. Then, tris(dibenzylidenaceton)-dipalladium(0) (10 mg, 0.01 mmol, 0.03 eq) and di-tert-butyl[3,4,5,6-tetramethyl-2',4',6'-tri(propan-2-yl)biphenyl-2-yl]phosphane [CAS RN: 857356-94-6] (13 mg, 0.03 mmol, 0.1 eq) were added. The vial was capped and the reaction mixture was stirred at an environmental temperature of 100° C. overnight. On cooling, volatile components were removed in vacuo and the crude material was purified via preparative MPLC (Biotage Isolera; 25 g SNAP cartridge: hexane->hexane/ethyl acetate 2/1->ethyl acetate). None of the fractions isolated contained the product. The column was washed with ethanol to give the title compound in around 70% purity after removal of the solvent. Final purification was achieved by crystallization with dichloromethane/methanol to give 92 mg (40% yield of theory) of the title compound after filtration and drying.

UPLC-MS (Method 1): $R_t$=1.11 min; MS (ESI$_{neg}$): m/z=403 [M−H]$^-$.

$^1$H-NMR (400 MHz, DMSO-d$_6$): δ [ppm]=2.80 (d, 3H), 7.37-7.51 (m, 2H), 7.98 (m, 1H), 8.60 (s br, 1H), 8.70 (s br, 1H), 8.87 (s, 1H), 10.54 (s br, 1H), 11.29 (s br, 1H), 1×CH$_3$ obscured by solvent signal.

Example 76

N-(3,4-Difluorophenyl)-5-[(6-ethylpyrazin-2-yl)amino]-3-methyl-1,2-thiazole-4-carboxamide

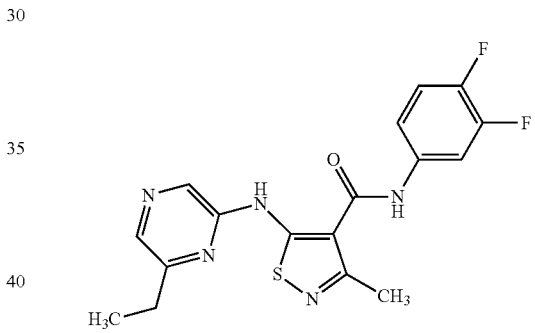

A mixture of 5-[(6-chloropyrazin-2-yl)amino]-N-(3,4-difluorophenyl)-3-methyl-1,2-thiazole-4-carboxamide [Example 71] (1.00 g, 2.62 mmol, 1.0 eq), trivinylboroxin-pyridine complex [CAS RN: 95010-17-6] (423 mg, 2.62 mmol, 1.0 eq), potassium carbonate (1.09 g, 7.86 mmol, 3.0 eq), DavePhos (103 mg, 0.26 mmol, 0.1 eq) and palladium (II) acetate (29 mg, 0.13 mmol, 0.05 eq) were dissolved in 20 mL acetonitrile and 15 mL of water. Then, the reaction vessel was flushed with argon and the reaction mixture was stirred for 5 h at reflux temperature. Palladium(II) acetate, DavePhos and trivinylboroxin-pyridine complex in the amount mentioned above were added and stirring was prolonged for another 5 h at reflux temperature. On cooling, the reaction mixture was partitioned between ethyl acetate and water. The aqueous phase was extracted with ethyl acetate and the combined organic phases were washed with brine. Phase separation was conducted by the use of a Whatman filter and the volatile components of the organic phase were removed in vacuo. The crude material was diluted with dichloromethane and the resulting solid was isolated to give 380 mg (35% yield of theory) of N-(3,4-difluorophenyl)-3-methyl-5-[(6-vinylpyrazin-2-yl)amino]-1,2-thiazole-4-carboxamide. The remaining mother liquor was concentrated by the use of a rotary evaporator and purified via preparative MPLC (Biotage Isolera; 25 g SNAP cartridge: hexan/ethyl acetate 9/1->hexane/ethyl acetate 1/1) to give another 340 mg (30% yield of theory) of N-(3,4-difluorophenyl)-3-methyl-5-[(6-vinylpyrazin-2-yl)amino]-1,2-thiazole-4-carboxamide. The N-(3,4-difluorophenyl)-3-methyl-5-[(6-vinylpyrazin-2-yl)amino]-1,2-thiazole-4-carboxamide (110 mg, 0.30 mmol, 1.0 eq) observed this way was dissolved in 10 mL methanol and palladium on carbon (10%, ~30 mg) was added. The reaction mixture was placed under a hydrogen atmosphere (balloon, 1 atm). After stirring for 4 h at rt, the catalyst was removed by filtration over Celite. After washing with ethanol the volatile components were removed in vacuo. Purification was conducted via preparative HPLC (column: Chromatorex C18, eluent: acetonitrile/0.1% formic acid, 15/85→55/45) to give 35 mg (31% yield of theory) of the title compound.

UPLC-MS (Method 1): $R_t$=1.29 min; MS ($ESI_{neg}$): m/z=374 [M−H]−.

$^1$H-NMR (400 MHz, DMSO-d$_6$): δ [ppm]=1.35 (t, 3H), 2.44 (s, 3H), 2.82 (q, 2H), 7.37-7.51 (m, 2H), 7.95 (dd, 1H), 8.09 (s, 1H), 8.53 (s, 1H), 10.41 (s, 1H), 10.91 (s, 1H).

Example 77

5-[(5-Bromopyrazin-2-yl)amino]-N-(3,4-difluorophenyl)-3-methyl-1,2-thiazole-4-carboxamide

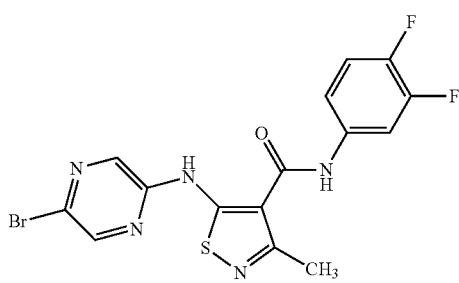

A mixture of 5-amino-N-(3,4-difluorophenyl)-3-methyl-1,2-thiazole-4-carboxamide [Intermediate 3] (1.00 g, 3.71 mmol, 1.0 eq), 2,5-dibromopyrazine [CAS RN: 23229-26-7] (883 mg, 3.71 mmol, 1.0 eq) and cesium carbonate (2.78 g, 8.54 mmol, 2.3 eq) in 35 mL dioxane/DMF (7/1) was placed in a reaction flask and flushed with argon. Then, palladium (II) acetate (83 mg, 0.37 mmol, 0.1 eq) and Xantphos (215 mg, 0.37 mmol, 0.1 eq) were added. The reaction mixture was stirred at an temperature of 110° C. (oil bath) overnight. On cooling, the reaction mixture was partitioned between dichloromethane/methanol (5/1) and water. The organic phase was washed with brine. The phases were separated by the use of a Whatman filter. Purification was achieved via preparative MPLC (Biotage Isolera; 25 g SNAP cartridge: hexane->hexane/ethyl acetate 2/1->ethyl acetate) yielding 312 mg (19% yield of theory) of the title compound.

UPLC-MS (Method 1): $R_t$=1.33 min; MS ($ESI_{neg}$): m/z=426 [M]−.

$^1$H-NMR (400 MHz, DMSO-d$_6$): δ [ppm]=2.43 (s, 3H), 7.37-7.52 (m, 2H), 7.94 (dd, 1H), 8.56 (d, 1H), 8.61 (d, 1H), 10.47 (s, 1H), 11.08 (s, 1H).

Example 78

N-(3,4-Difluorophenyl)-5-{[6-(ethylamino)pyrazin-2-yl]amino}-3-methyl-1,2-thiazole-4-carboxamide

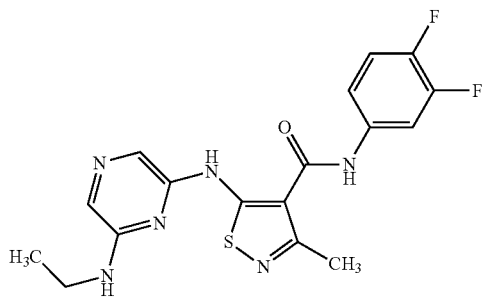 [SMILES: CCNc1cncc(Nc2snc(C)c2C(=O)Nc2ccc(F)c(F)c2)n1]

A mixture of 5-[(6-chloropyrazin-2-yl)amino]-N-(3,4-difluorophenyl)-3-methyl-1,2-thiazole-4-carboxamide [Example 71] (100 mg, 0.26 mmol, 1.0 eq), ethylamine hydrochloride [CAS-RN: 557-66-4] (214 mg, 2.62 mmol, 10.0 eq) and DIPEA (0.43 mL, 2.62 mmol, 10.0 eq) in 2.5 mL 2-butanol was placed in a microwave vial that was flushed with argon. The reaction mixture was heated to 170° C. for 5 h in a single mode microwave wave oven. On cooling, the volatile components were removed in vacuo. Purification was conducted via preparative HPLC (column: Chromatorex C18, eluent: acetonitrile/0.1% formic acid, 30/70→70/30) to give 10 mg (10% yield of theory) of the title compound.

UPLC-MS (Method 1): $R_t$=1.20 min; MS ($ESI_{neg}$): m/z=389 [M−H]−.

$^1$H-NMR (400 MHz, DMSO-d$_6$): δ [ppm]=1.22 (m, 3H), 2.41 (s, 3H), 3.46 (m, 2H), 7.22 (t, 1H), 7.36-7-49 (m, 3H), 7.65 (s, 1H), 7.92 (m, 1H), 10.31 (s br, 1H), 10.42 (s br, 1H).

Example 79

N-(3,4-Difluorophenyl)-5-[(5-ethylpyrazin-2-yl)amino]-3-methyl-1,2-thiazole-4-carboxamide

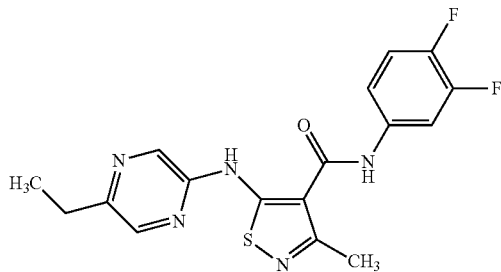 [SMILES: CCc1cnc(Nc2snc(C)c2C(=O)Nc2ccc(F)c(F)c2)cn1]

A mixture of 5-[(5-bromopyrazin-2-yl)amino]-N-(3,4-difluorophenyl)-3-methyl-1,2-thiazole-4-carboxamide [Example 77] (225 mg, 0.53 mmol, 1.0 eq), 2,4,6-trivinyl-boroxin-pyridine complex [CAS RN: 95010-17-6] (127 mg, 0.53 mmol, 1.0 eq), DavePhos (21 mg, 0.53 mmol, 0.1 eq), palladium(II) acetate (5.9 mg, 0.26 mmol, 0.05 eq) and potassium carbonate (219 mg, 1.58 mmol, 3.0 eq) in 4.3 mL acetonitrile was placed in a reaction flask and flushed with argon. The reaction mixture was stirred at a temperature of 150° C. in a single mode microwave oven for 2 h. On cooling, the reaction mixture was partitioned between ethyl acetate and water. The aqueous phase was washed with ethyl acetate and the combined organic phases were washed with brine. The phases were separated by the use of a Whatman filter. Purification was achieved via preparative MPLC (Biotage Isolera; 25 g SNAP cartridge: hexane->hexane/ethyl acetate 2/1) to yield 39 mg (18% yield of theory) of N-(3,4-difluorophenyl)-3-methyl-5-[(5-vinylpyrazin-2-yl)amino]-1,2-thiazole-4-carboxamide. A mixture of N-(3,4-difluorophenyl)-3-methyl-5-[(5-vinylpyrazin-2-yl)amino]-1,2-thiazole-4-carboxamide, samples of repeated experiments (80 mg, 167 µmol, 1.0 eq, 78% purity), was dissolved in 6 mL ethanol and platinum(IV) oxide (7 mg, 31 µmol) was added. The reaction mixture was placed under a hydrogen atmosphere (balloon, 1 atm). After stirring for 72 h at rt, the catalyst was removed by filtration over Celite. After washing with ethanol the volatile components were removed in vacuo. Purification was conducted via preparative HPLC (Method A) to give 8 mg (13% yield of theory) of the title compound.

UPLC-MS (Method 1): $R_t$=1.31 min; MS ($ESI_{pos}$): m/z=376 [M+H]$^+$.

$^1$H-NMR (400 MHz, DMSO-d$_6$): δ [ppm]=1.22 (t, 3H), 2.43 (s, 3H), 2.73 (q, 2H), 7.36-7.52 (m, 2H), 7.94 (dd, 1H), 8.29 (s, 1H), 8.56 (s, 1H), 10.38 (s, 1H), 10.83 (s, 1H).

Example 80

6-({4-[(3,4-Difluorophenyl)carbamoyl]-3-methyl-1,2-thiazol-5-yl}amino)-N-methylpyridazine-3-carboxamide

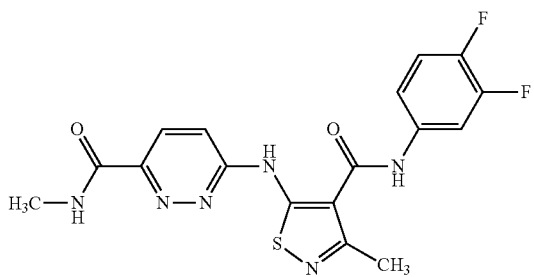 [SMILES: CNC(=O)c1ccc(Nc2snc(C)c2C(=O)Nc2ccc(F)c(F)c2)nn1]

A mixture of 5-amino-N-(3,4-difluorophenyl)-3-methyl-1,2-thiazole-4-carboxamide [Intermediate 3] (113 mg, 0.42 mmol, 1.0 eq), 6-bromo-N-methylpyridazine-3-carboxamide [Intermediate 10] (91 mg, 0.42 mmol, 1.0 eq) and cesium carbonate (316 mg, 0.97 mmol, 2.3 eq) in 4.1 mL dioxane/DMF (7/1) was placed in a microwave vial that was flushed with argon. Then, palladium(II) acetate (9.5 mg, 0.04 mmol, 0.1 eq) and Xantphos (24 mg, 0.04 mmol, 0.1 eq) were added. Afterwards, the vial was sealed and the reaction mixture was stirred at an environmental temperature of 110° C. for 2.5 h. On cooling, the reaction mixture was partitioned between dichloro-methane/isopropanol (4/1) and water. The organic phase was separated and the water phase was extracted three times with dichloro-methane/isopropanol (4/1). The combined organic phases were washed with brine and the phases were separated by the use of a Whatman filter. The volatile components of the organic phase were removed in vacuo. The crude material was dissolved in methanol and dichloromethane was added to initiate crystallization under ice-cooling. The precipitate observed was isolated by filtration and dried under high vacuum to give 90 mg (52% yield of theory) of the title compound.

UPLC-MS (Method 1): $R_t$=1.08 min; MS ($ESI_{neg}$): m/z=403 [M–H]$^-$.

$^1$H-NMR (400 MHz, DMSO-d6): δ [ppm]=2.44 (s, 3H), 2.83 (d, 3H), 7.38-7.51 (m, 2H), 7.77 (d, 1H), 7.94 (dd, 1H), 8.11 (d, 1H), 9.09 (m, 1H), 10.50 (s br, 1H), 11.08 (s br, 1H).

Example 81

N-(3,4-Difluorophenyl)-3-methyl-5-{[5-(trifluoromethyl)pyrazin-2-yl]amino}-1,2-thiazole-4-carboxamide

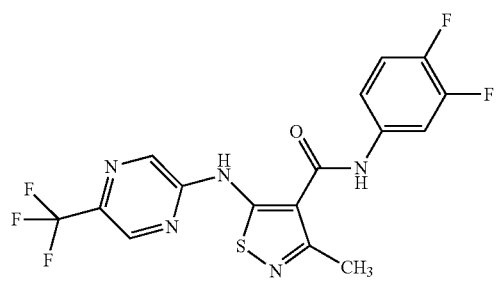 [SMILES: Cc1nsc(Nc2cnc(C(F)(F)F)cn2)c1C(=O)Nc1ccc(F)c(F)c1]

A mixture of 5-amino-N-(3,4-difluorophenyl)-3-methyl-1,2-thiazole-4-carboxamide [Intermediate 3] (100 mg, 0.37 mmol, 1.0 eq), 2-bromo-5-(trifluoromethyl)-pyrazine [CAS-RN: 1196152-38-1] (105 mg, 0.45 mmol, 1.2 eq) and cesium carbonate (242 mg, 0.74 mmol, 2.0 eq) in 4.0 mL dioxane/DMF (7/1) was placed in a microwave vial that was flushed with argon. Then, palladium(II) acetate (8 mg, 0.04 mmol, 0.1 eq) and Xantphos (21 mg, 0.04 mmol, 0.1 eq) were added. Afterwards, the vial was sealed and the reaction mixture was stirred at an environmental temperature of 110° C. for 4 h. On cooling, the reaction mixture was partitioned between ethyl acetate and water. The organic phase was washed with brine and the phases were separated by the use of a Whatman filter. The volatile components of the organic phase were removed in vacuo. Purification was conducted via preparative HPLC (Method A) to give 36 mg (22% yield of theory) of the title compound.

UPLC-MS (Method 1): $R_t$=1.36 min; MS ($ESI_{neg}$): m/z=414 [M–H]$^-$.

$^1$H-NMR (400 MHz, DMSO-d$_6$): δ [ppm]=2.46 (s, 3H), 7.34-7.54 (m, 2H), 7.95 (dd, 1H), 8.82 (s, 1H), 8.91 (s, 1H), 10.53 (s, 1H), 11.46 (s, 1H).

Example 82

N-(3,4-Difluorophenyl)-3-methyl-5-{[6-(trifluoromethyl)pyrazin-2-yl]amino}-1,2-thiazole-4-carboxamide

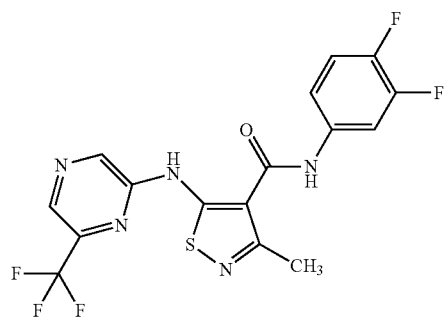 [SMILES: Cc1nsc(Nc2cncc(C(F)(F)F)n2)c1C(=O)Nc1ccc(F)c(F)c1]

A mixture of 5-amino-N-(3,4-difluorophenyl)-3-methyl-1,2-thiazole-4-carboxamide [Intermediate 3] (120 mg, 0.45 mmol, 1.0 eq), 2-iodo-6-(trifluoromethyl)pyrazine [CAS-RN: 141492-94-6] (187 mg, 0.67 mmol, 1.5 eq) and cesium carbonate (290 mg, 0.89 mmol, 2.0 eq) in 4.9 mL dioxane/DMF (7/1) was placed in a microwave vial that was flushed with argon. Then, palladium(II) acetate (10 mg, 0.05 mmol, 0.1 eq) and Xantphos (26 mg, 0.05 mmol, 0.1 eq) were added. Afterwards, the vial was sealed and the reaction mixture was stirred at an environmental temperature of 110° C. for 5 h. On cooling, the reaction mixture was partitioned between ethyl acetate and water. The organic phase was washed with brine and the phases were separated by the use of a Whatman filter. The volatile components of the organic phase were removed in vacuo. Purification was conducted via preparative HPLC (Method A) to give 87 mg (47% yield of theory) of the title compound.

UPLC-MS (Method 3): $R_t$=1.32 min; MS (ESI$_{neg}$): m/z=414 [M−H]⁻.

¹H-NMR (400 MHz, DMSO-d₆): δ [ppm]=7.38-7.52 (m, 2H), 7.95 (dd, 1H), 8.64 (s, 1H), 8.98 (s, 1H), 10.50 (s, 1H), 11.42 (s, 1H), 1×CH₃ obscured by solvent signal.

Example 83

N-(3,4-Difluorophenyl)-3-methyl-5-{[6-(trifluoromethyl)pyridazin-3-yl]amino}-1,2-thiazole-4-carboxamide

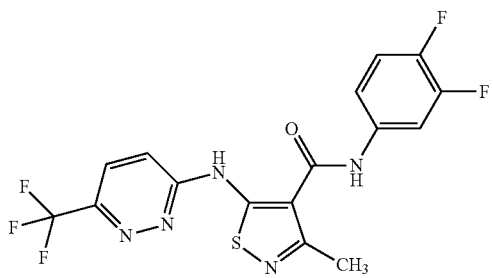 [SMILES: Cc1nsc(Nc2ccc(C(F)(F)F)nn2)c1C(=O)Nc1ccc(F)c(F)c1]

A mixture of 5-amino-N-(3,4-difluorophenyl)-3-methyl-1,2-thiazole-4-carboxamide [Intermediate 3] (200 mg, 0.74 mmol, 1.0 eq), 3-chloro-6-(trifluoromethyl)-pyridazine [CAS-RN: 258506-68-2] (135 mg, 0.74 mmol, 1.1 eq) and cesium carbonate (557 mg, 1.71 mmol, 2.3 eq) in 7.4 mL dioxane/DMF (7/1) was placed in a microwave vial that was flushed with argon. Then, palladium(II) acetate (17 mg, 0.07 mmol, 0.1 eq) and Xantphos (43 mg, 0.07 mmol, 0.1 eq) were added. Afterwards, the vial was sealed and the reaction mixture was stirred at an environmental temperature of 110° C. for 6 h. On cooling, the reaction mixture was partitioned between dichloromethane/isopropanol (4/1) and water. The organic phase was washed with brine and the phases were separated by the use of a Whatman filter. The volatile components of the organic phase were removed up to a volume of 3-5 mL. The precipitate observed was isolated by filtration to give 209 mg (64% yield of theory) of the title compound after drying under high vacuum.

UPLC-MS (Method 1): $R_t$=1.27 min; MS (EI$_{neg}$): m/z=414 [M−H]⁻.

¹H-NMR (400 MHz, DMSO-d6): δ [ppm]=7.38-7.51 (m, 2H), 7.86 (d, 1H), 7.97 (m, 1H), 8.09 (m, 1H), 10.55 (s br, 1H), 11.23 (s br, 1H), 1×CH₃ not assigned.

Example 84

N-(6-methoxypyridin-3-yl)-3-methyl-5-{[6-(trifluoromethyl)pyrazin-2-yl]amino}-1,2-thiazole-4-carboxamide

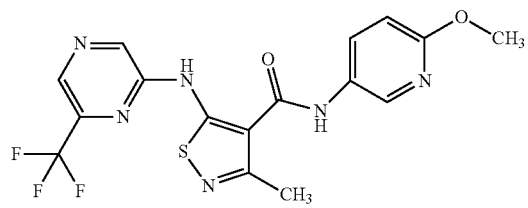 [SMILES: COc1ccc(NC(=O)c2c(C)nsc2Nc2cncc(C(F)(F)F)n2)cn1]

A mixture of 5-amino-N-(6-methoxypyridin-3-yl)-3-methyl-1,2-thiazole-4-carboxamide [Intermediate 2] (100 mg, 0.38 mmol, 1.2 eq), 2-iodo-6-(trifluoromethyl)pyrazine [CAS-RN: 141492-94-6] (86 mg, 0.31 mmol, 1.0 eq) and cesium carbonate (236 mg, 0.73 mmol, 2.3 eq) in 3 mL dioxane/DMF (5/1) was placed in a microwave vial and flushed with argon. Then, palladium(II) acetate (7 mg, 0.03 mmol, 0.1 eq) and Xantphos (18 mg, 0.03 mmol, 0.1 eq) were added. The vial was capped and the reaction mixture was stirred at an environmental temperature of 110° C. overnight. The volatile components were removed in vacuo. Purification of this crude material was achieved via preparative MPLC (Biotage Isolera; 25 g SNAP cartridge: dicloromethan->dichloromethane/ethanol 100:0/97:3/94:6). The volatile components of the collected fractions were removed in vacuo. Final purification was conducted via preparative HPLC (Method A) to give 47 mg (33% yield of theory) of the title compound.

UPLC-MS (Method 2): $R_t$=0.79 min; MS (EI$_{pos}$): m/z=411 [M+H]⁺.

¹H-NMR (400 MHz, CDCl₃): δ [ppm]=3.84 (s, 3H), 6.86 (d, 1H), 8.05 (d, 1H), 8.52 (br. s., 1H), 8.64 (s, 1H), 9.00 (s, 1H), 10.26 (s, 1H), 11.40 (s, 1H), 1×CH₃ obscured by solvent signal.

Example 85

N-(6-methoxypyridin-3-yl)-3-methyl-5-{[5-(trifluoromethyl)pyrazin-2-yl]amino}-1,2-thiazole-4-carboxamide

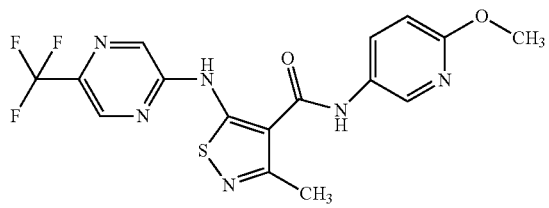 [SMILES: COc1ccc(NC(=O)c2c(C)nsc2Nc2cnc(C(F)(F)F)cn2)cn1]

A mixture of 5-amino-N-(6-methoxypyridin-3-yl)-3-methyl-1,2-thiazole-4-carboxamide [Intermediate 2] (100 mg, 0.38 mmol, 1.2 eq), 2-chloro-5-(trifluoromethyl)pyrazine [CAS-RN: 799557-87-2] (58 mg, 0.32 mmol, 1.0 eq) and cesium carbonate (236 mg, 0.73 mmol, 2.3 eq) in 3 mL dioxane/DMF (5/1) was placed in a microwave vial and flushed with argon. Then, palladium(II) acetate (7 mg, 0.03 mmol, 0.1 eq) and Xantphos (18 mg, 0.03 mmol, 0.1 eq)

were added. The vial was capped and the reaction mixture was stirred at an environmental temperature of 110° C. overnight. The volatile components were removed in vacuo. Purification of this crude material was achieved via preparative MPLC (Biotage Isolera; 25 g SNAP cartridge: dicloromethan->dichloromethane/ethanol 100:0/97:3/94:6) to give 125 mg (87% yield of theory) of the title compound.

UPLC-MS (Method 2): $R_t$=0.81 min; MS ($EI_{pos}$): m/z=411 [M+H]$^+$.

$^1$H-NMR (300 MHz, CDCl$_3$): δ [ppm]=3.84 (s, 3H), 6.87 (d, 1H), 8.06 (d, 1H), 8.53 (s br, 1H), 8.83 (s, 1H), 8.91 (s, 1H), 10.29 (s, 1H), 11.46 (s br, 1H), 1×CH$_3$ obscured by solvent signal.

The compounds listed in Table A were prepared according to the procedure outlined below from the starting materials named in the following SM1 and SM2. A typical reaction was usually run on 0.5 mmol scale:

A mixture of SM1 (0.5 mmol, 1.0 eq), SM2 (0.8-1.2 eq) and cesium carbonate (2.3 eq) in ~5.5 mL dioxane/DMF (7/1) was placed in a microwave vial and flushed with argon. Then, palladium(II) acetate (0.1 eq) and Xantphos (0.1 eq) were added. The vial was capped and the reaction mixture was stirred at an environmental temperature of 110° C. overnight. On cooling, the reaction mixture was partitioned between dichloromethane and water. After filtration over Celite, the organic phase was separated and concentrated in vacuo. The crude product was usually purified via preparative HPLC or via crystallization from a suitable solvent.

TABLE A

| Example No, SM1, SM2 | Structure, Name, yield of theory | Analytical data |
|---|---|---|
| Example 86<br>SM1: Intermediate 1<br>SM2: 2,6-dichloro-quinoxaline<br>[CAS RN: 1867-97-1] | 5-[(6-Chloroquinoxalin-2-yl)amino]-N-(2-ethylphenyl)-3-methyl-1,2-thiazole-4-carboxamide, 19% | UPLC-MS (Method 1): $R_t$ = 1.56 min; MS ($EI_{neg}$): m/z = 422 [M − H]$^-$.<br>$^1$H-NMR (400 MHz, DMSO-d6): δ [ppm] = 1.17 (m, 3H), 2.56-2.77 (m, 5H), 7.09-7.33 (m, 3H), 7.56 (s br, 1H), 7.96-8.08 (m, 2H), 9.08 (s br, 1H), 9.57 (s br, 1H), 11.38 (s br, 1H), 1×H not assigned. |
| Example 87<br>SM1: Intermediate 2<br>SM2: 2-chloro-6-methoxy-1,3-benzothiazole<br>[CAS RN: 2605-14-3] | 5-[(6-Methoxy-1,3-benzothiazol-2-yl)amino]-N-(6-methoxypyridin-3-yl)-3-methyl-1,2-thiazole-4-carboxamide, 3% | $ESI_{pos}$: m/z = 428 [M + H]$^+$.<br>$^1$H-NMR (400 MHz, DMSO-d6: δ [ppm] = 3.76 (s, 3H), 3.81 (s, 3H), 6.84 (d, 1H), 6.97 (dd, 1H), 7.51 (d, 1H), 7.62 (d, 1H), 8.02 (dd, 1H), 8.49 (d, 1H), 10.34 (s br, 1H), 11.67 (s br, 1H), 1×CH$_3$ covered by solvent signal. |
| Example 88<br>SM1: Intermediate 2<br>SM2: 2-chloro-6-fluoro-1,3-benzothiazole<br>[CAS RN: 399-74-6] | 5-[(6-Fluoro-1,3-benzothiazol-2-yl)amino]-N-(6-methoxypyridin-3-yl)-3-methyl-1,2-thiazole-4-carboxamide, 32% | UPLC-MS (Method 1): $R_t$ = 1.34 min; MS ($EI_{neg}$): m/z = 414 [M − H]$^-$.<br>$^1$H-NMR (400 MHz, DMSO-d6): δ [ppm] = 3.81 (s, 3H), 6.83 (d, 1H), 7.18 (m, 1H), 7.52-7.83 (m, 2H), 8.01 (dd, 1H), 8.46 (s, 1H), 10.40 (s br, 1H), 11.82 (s br, 1H), 1×CH$_3$ covered by solvent signal. |

TABLE A-continued

| Example No, SM1, SM2 | Structure, Name, yield of theory | Analytical data |
|---|---|---|
| Example 89<br>SM1: Intermediate 2<br>SM2: 2-chloro[1,3]-thiazolo[5,4-b]-pyridine<br>[CAS RN: 91524-96-8] | 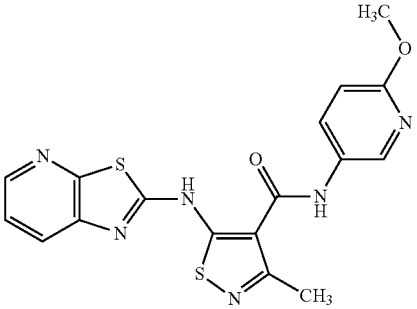 [SMILES: COc1ccc(NC(=O)c2c(C)nsc2Nc2nc3cccnc3s2)cn1]<br>N-(6-Methoxypyridin-3-yl)-3-methyl-5-([1,3]thiazolo[5,4-b]pyridin-2-ylamino)-1,2-thiazole-4-carboxamide, 11% | UPLC-MS (Method 1): Rt = 1.13 min; MS (EI$_{neg}$): m/z = 397 [M − H]⁻.<br>¹H-NMR (400 MHz, DMSO-d6): δ [ppm] = 3.82 (s, 3H), 6.84 (d, 1H), 7.43 (dd, 1H), 7.97-8.10 (m, 2H), 8.33 (dd, 1H), 8.49 (d, 1H), 10.41 (s br, 1H), 12.01 (s br, 1H), 1xCH₃ covered by solvent signal. |
| Example 90<br>SM1: Intermediate 2<br>SM2: 2-chloro-6-methyl-1,3-benzothiazole<br>[CAS RN: 350774-26-4] | 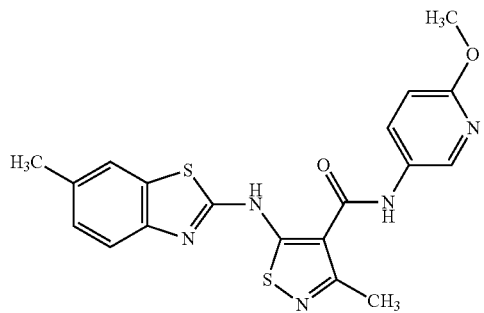 [SMILES: COc1ccc(NC(=O)c2c(C)nsc2Nc2nc3ccc(C)cc3s2)cn1]<br>N-(6-Methoxypyridin-3-yl)-3-methyl-5-[(6-methyl-1,3-benzothiazol-2-yl)amino]-1,2-thiazole-4-carboxamide, 5% | UPLC-MS (Method 1): Rt = 1.41 min; MS (EI$_{neg}$): m/z = 410 [M − H]⁻.<br>¹H-NMR (400 MHz, DMSO-d6): δ [ppm] = 2.38 (s, 3H), 3.82 (s, 3H), 6.84 (d, 1H), 7.20 (d, 1H), 7.59 (d, 1H), 7.67 (s, 1H), 8.02 (d, 1H), 8.49 (s, 1H), 10.33 (s br, 1H), 11.72 (s br, 1H), 1xCH₃ covered by solvent signal. |
| Example 91<br>SM1: Intermediate 1<br>SM2: methyl 2-chloro-1,3-oxazole-4-carboxylate<br>[CAS RN: 934236-35-8] | 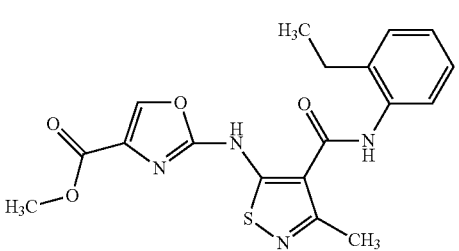 [SMILES: CCc1ccccc1NC(=O)c1c(C)nsc1Nc1nc(C(=O)OC)co1]<br>Methyl 2-({4-[(2-ethylphenyl)carbamoyl]-3-methyl-1,2-thiazol-5-yl}amino)-1,3-oxazole-4-carboxylate, 5% | UPLC-MS (Method 4): Rt = 1.31 min; MS (EI$_{neg}$): m/z = 385 [M − H]⁻.<br>¹H-NMR (400 MHz, DMSO-d6): δ [ppm] = 1.21 (t, 3H), 2.70 (s, 3H), 2.80 (q, 2H), 3.80 (s, 3H), 7.01 (t, 1H), 7.16 (dt, 1H), 7.21 (dd, 1H), 8.25 (s br, 1H), 8.47 (s, 1H), 11.69 (s br, 1H), 1H not assigned. |
| Example 92<br>SM1: Intermediate 1<br>SM2: ethyl 2-bromo-1,3-thiazole-5-carboxylate<br>[CAS RN: 41731-83-3] | 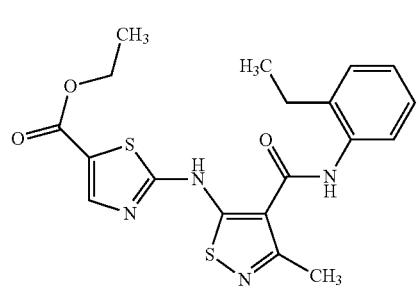 [SMILES: CCOC(=O)c1cnc(Nc2snc(C)c2C(=O)Nc2ccccc2CC)s1]<br>Ethyl 2-({4-[(2-ethylphenyl)-carbamoyl]-3-methyl-1,2-thiazol-5-yl}amino)-1,3-thiazole-5-carboxylate, 26% | UPLC-MS (Method 1): Rt = 1.49 min; MS (EI$_{neg}$): m/z = 415 [M − H]⁻.<br>¹H-NMR (400 MHz, DMSO-d6): δ [ppm] = 1.15-1.31 (m, 6H), 2.56-2.83 (m, 5H), 4.24 (q, 2H), 7.06 (s br, 1H), 7.18 (t, 1H), 7.24 (d, 1H), 8.09-8.41 (m, 2H), 11.73 (s br, 1H), 1xH not assigned. |

TABLE A-continued

| Example No, SM1, SM2 | Structure, Name, yield of theory | Analytical data |
|---|---|---|
| Example 93<br>SM1: Intermediate 5<br>SM2: Intermediate 11 | 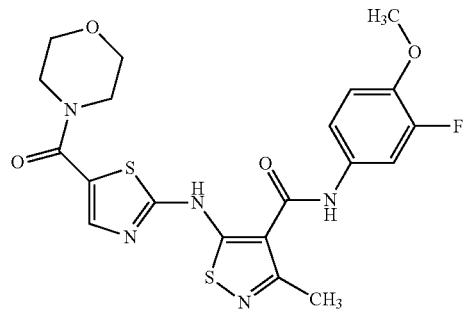 [SMILES: COc1ccc(NC(=O)c2c(C)nsc2Nc2ncc(C(=O)N3CCOCC3)s2)cc1F]<br>N-(3-Fluoro-4-methoxyphenyl)-3-methyl-5-{[5-(morpholin-4-ylcarbonyl)-1,3-thiazol-2-yl]amino}-1,2-thiazole-4-carboxamide, 12% | UPLC-MS (Method 2): Rt = 0.70 min; MS (EI$_{neg}$): m/z = 476 [M − H]$^-$.<br>$^1$H-NMR (400 MHz, DMSO-d6): δ [ppm] = 3.58-3.70 (m, 8H), 3.82 (s, 3H), 7.16 (t, 1H), 7.38 (m, 1H), 7.74 (d, 1H), 7.84 (s, 1H), 10.31 (s br, 1H), 11.77 (s br, 1H), 1xCH3 not assigned. |
| Example 94<br>SM1: Intermediate 2<br>SM2: 2-chloroquinoxaline<br>[CAS-RN: 1448-87-9] | 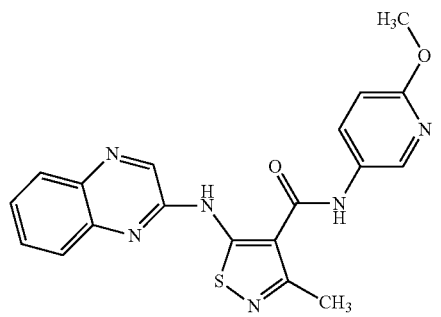 [SMILES: COc1ccc(NC(=O)c2c(C)nsc2Nc2cnc3ccccc3n2)cn1]<br>N-(6-Methoxypyridin-3-yl)-3-methyl-5-(quinoxalin-2-ylamino)-1,2-thiazole-4-carboxamide, 59% | UPLC-MS (Method 1): Rt = 1.19 min; MS (EI$_{neg}$): m/z = 391 [M − H]$^-$.<br>$^1$H-NMR (400 MHz, DMSO-d6): δ [ppm] = 3.84 (s, 3H), 6.87 (d, 1H), 7.62 (m, 1H), 7.78 (t, 1H), 7.97 (d, 2H), 8.09 (m, 1H), 8.56 (s, 1H), 9.05 (s, 1H), 10.36 (s br, 1H), 11.37 (s br, 1H), 1xCH$_3$ not assigned. |
| Example 95<br>SM1: Intermediate 4<br>SM2: ethyl 2-chloro-4-methyl-1,3-thiazole-5-carboxylate<br>[CAS-RN: 7238-62-2] | 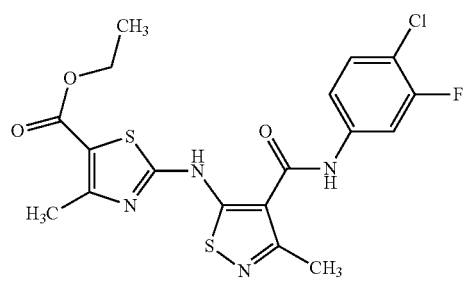 [SMILES: CCOC(=O)c1sc(Nc2snc(C)c2C(=O)Nc2ccc(Cl)c(F)c2)nc1C]<br>Ethyl 2-({4-[(4-chloro-3-fluoro-phenyl)carbamoyl]-3-methyl-1,2-thiazol-5-yl}amino)-4-methyl-1,3-thiazole-5-carboxylate, 4% | UPLC-MS (Method 1): Rt = 1.57 min; MS (EI$_{neg}$): m/z = 453 [M − H]$^-$.<br>$^1$H-NMR (400 MHz, DMSO-d6): δ [ppm] = 1.27 (t, 3H), 2.59 (s, 3H), 4.24 (q, 2H), 7.48 (m, 1H), 7.56 (t, 1H), 7.93 (d, 1H), 10.66 (s br, 1H), 11.87 (s br, 1H), 1xCH$_3$ not assigned. |
| Example 96<br>SM1: Intermediate 3<br>SM2: ethyl 2-chloro-1,3-oxazole-5-carboxylate<br>[CAS RN: 862599-47-1] | 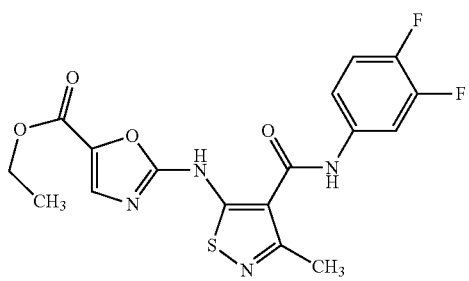 [SMILES: CCOC(=O)c1cnc(Nc2snc(C)c2C(=O)Nc2ccc(F)c(F)c2)o1]<br>Ethyl 2-({4-[(3,4-difluorophenyl)carbamoyl]-3-methyl-1,2-thiazol-5-yl}amino)-1,3-oxazole-5-carboxylate, 16% | UPLC-MS (Method 1): Rt = 1.31 min; MS (EI$_{neg}$): m/z = 407 [M − H]$^-$.<br>$^1$H-NMR (400 MHz, DMSO-d6): δ [ppm] = 1.28 (t, 3H), 4.28 (q, 2H), 7.28-7.52 (m, 2H), 7.93 (ddd, 1H), 8.08 (s br, 1H), 11.28 (s br, 1H), 1xCH$_3$ and 1H not assigned. |

TABLE A-continued

| Example No, SM1, SM2 | Structure, Name, yield of theory | Analytical data |
|---|---|---|
| Example 97<br>SM1: Intermediate 3<br>SM2: methyl 2-chloro-1,3-oxazole-5-carboxylate<br>[CAS RN: 934236-41-6] | Methyl 2-({4-[(3,4-difluoro-phenyl)carbamoyl]-3-methyl-1,2-thiazol-5-yl}amino)-1,3-oxazole-5-carboxylate, 46% | UPLC-MS (Method 1): Rt = 1.26 min; MS (EI$_{neg}$): m/z = 393 [M − H]$^-$.<br>$^1$H-NMR (400 MHz, DMSO-d6): δ [ppm] = 3.76 (s, 3H), 7.13 (m, 1H), 7.41 (dd, 1H), 7.84 (s, 1H), 8.00 (ddd, 1H), 12.67 (s br, 1H), 1xCH$_3$ and 1H not assigned. |
| Example 98<br>SM1: Intermediate 3<br>SM2: ethyl 2-chloro-1,3-oxazole-4-carboxylate<br>[CAS RN: 460081-18-9] | Ethyl 2-({4-[(3,4-difluoro-phenyl)carbamoyl]-3-methyl-1,2-thiazol-5-yl}amino)-1,3-oxazole-4-carboxylate, 22% | UPLC-MS (Method 1): Rt = 1.34 min; MS (EI$_{neg}$): m/z = 407 [M − H]$^-$.<br>$^1$H-NMR (400 MHz, DMSO-d6): δ [ppm] = 1.29 (t, 3H), 2.52 (s, 3H), 4.26 (q, 2H), 7.20 (m, 1H), 7.38 (dd, 1H), 7.98 (ddd, 1H), 8.26 (s, 1H), 12.39 (s br, 1H), 1H not assigned. |
| Example 99<br>SM1: Intermediate 3<br>SM2: Intermediate 12 | N-(3,4-Difluorophenyl)-5-{[4-(ethylcarbamoyl)-1,3-thiazol-2-yl]amino}-3-methyl-1,2-thiazole-4-carboxamide, 13% | UPLC-MS (Method 1): Rt = 1.20 min; MS (EI$_{neg}$): m/z = 422 [M − H]$^-$.<br>$^1$H-NMR (400 MHz, DMSO-d6): δ [ppm] = 1.16 (t, 3H), 3.34 (m, 2H), 7.13-7.50 (m, 3H), 7.55 (s br, 1H), 7.98 (dd, 1H), 11.71 (s br, 1H), 12.88 (s br, 1H), 1xCH3 not assigned. |
| Example 100<br>SM1: Intermediate 2<br>SM2: ethyl 2-chloro-1,3-oxazole-4-carboxylate<br>[CAS RN: 460081-18-9] | Ethyl 2-({4-[(6-methoxypyridin-3-yl)carbamoyl]-3-methyl-1,2-thiazol-5-yl}amino)-1,3-oxazole-4-carboxylate, 5% | UPLC-MS (Method 1): Rt = 1.15 min; MS (EI$_{neg}$): m/z = 402 [M − H]$^-$.<br>$^1$H-NMR (400 MHz, DMSO-d6): δ [ppm] = 1.30 (t, 3H), 2.57 (s, 3H), 3.83 (s, 3H), 4.29 (q, 2H), 6.84 (d, 1H), 7.99 (dd, 1H), 8.41-8.55 (m, 2H), 11.79 (s br, 1H), 1H not assigned. |

TABLE A-continued

| Example No, SM1, SM2 | Structure, Name, yield of theory | Analytical data |
|---|---|---|
| Example 101<br>SM1: Intermediate 2<br>SM2: Methyl 6-chloropyrazine-2-carboxylate<br>[CAS RN: 23611-75-8] | Methyl 6-({4-[(6-methoxypyridin-3-yl)carbamoyl]-3-methyl-1,2-thiazol-5-yl}amino)pyrazine-2-carboxylate, 17% | UPLC-MS (Method 1): Rt = 0.99 min; MS (EI$_{neg}$): m/z = 399 [M − H]$^-$.<br>$^1$H-NMR (400 MHz, DMSO-d6): δ [ppm] = 3.84 (s, 3H), 3.87 (s, 3H), 6.87 (d, 1H), 8.06 (d, 1H), 8.52 (s, 1H), 8.78 (s, 1H), 8.97 (s, 1H), 10.32 (s, 1H), 11.44 (s br, 1H), 1xCH$_3$ not assigned. |
| Example 102<br>SM1: Intermediate 7<br>SM2: 2-chloro-4-(trifluoromethyl)-1,3-benzothiazole<br>[CAS RN: 898748-15-7] | N-(3,4-Dichlorophenyl)-3-methyl-5-{[4-(trifluoromethyl)-1,3-benzothiazol-2-yl]amino}-1,2-thiazole-4-carboxamide, 54% | UPLC-MS (Method 1): Rt = 1.71 min; MS (EIneg): m/z = 501 [M − H]$^-$.<br>$^1$H-NMR (400 MHz, DMSO-d6): δ [ppm] = 7.37 (t, 1H), 7.54-7.67 (m, 2H), 7.72 (d, 1H), 8.15-8.27 (m, 2H), 10.79 (s br, 1H), 12.13 (s br, 1H), 1xCH$_3$ not assigned. |
| Example 103<br>SM1: Intermediate 4<br>SM2: 2-chloro-7-(trifluoromethyl)[1,3]-thiazolo[5,4-b]pyridine<br>[please see, L. Zhu, J. Heterocycl. Chem. (2005), 727-730.] | N-(4-Chloro-3-fluorophenyl)-3-methyl-5-{[7-(trifluoromethyl)[1,3]thiazolo[5,4-b]pyridin-2-yl]amino}-1,2-thiazole-4-carboxamide, 42% | UPLC-MS (Method 4): Rt = 1.58 min; MS (EIneg): m/z = 486 [M − H]$^-$.<br>$^1$H-NMR (400 MHz, DMSO-d6): δ [ppm] = 7.40 (d, 1H), 7.57 (t, 1H), 7.69 (s, 1H), 7.97 (m, 1H), 8.45 (s, 1H), 1xCH3 Et 2xH not assigned. |
| Example 104<br>SM1: Intermediate 3<br>SM2: Intermediate 13 | 6-({4-[(3,4-Difluorophenyl)-carbamoyl]-3-methyl-1,2-thiazol-5-yl}amino)-N,N-dimethyl-pyrazine-2-carboxamide, 37% | UPLC-MS (Method 1): Rt = 1.06 min; MS (EI$_{neg}$): m/z = 417 [M − H]$^-$.<br>$^1$H-NMR (400 MHz, DMSO-d6): δ [ppm] = 2.44 (s, 3H), 3.01 (s, 3H), 3.06 (s, 3H), 7.38-7.51 (m, 2H), 7.94 (dd, 1H), 8.28 (s, 1H), 8.76 (s, 1H), 10.45 (s, 1H), 11.12 (s, 1H). |

TABLE A-continued

| Example No, SM1, SM2 | Structure, Name, yield of theory | Analytical data |
|---|---|---|
| Example 105<br>SM1: Intermediate 3<br>SM2: 6-chloro-N,N-dimethylpyrazin-2-amine<br>[CAS RN: 898748-15-7] | 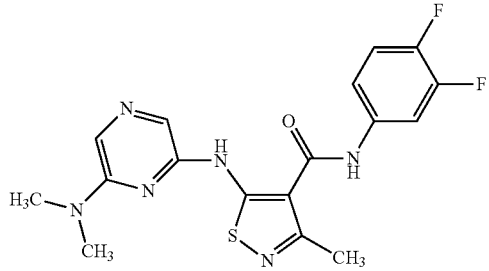 [SMILES: Cc1nsc(Nc2cncc(N(C)C)n2)c1C(=O)Nc1ccc(F)c(F)c1]<br>N-(3,4-Difluorophenyl)-5-{[6-(dimethylamino)pyrazin-2-yl]amino}-3-methyl-1,2-thiazole-4-carboxamide, 25% | UPLC-MS (Method 1): Rt = 1.25 min; MS (EI$_{neg}$): m/z = 389 [M − H]⁻.<br>¹H-NMR (400 MHz, DMSO-d6): δ [ppm] = 2.42 (s, 3H), 3.30 (s, 6H), 7.39-7.48 (m, 2H), 7.60 (s, 1H), 7.79 (s, 1H), 7.92 (dd, 1H), 10.32 (s, 1H), 10.49 (s, 1H). |
| Example 106<br>SM1: Intermediate 3<br>SM2: (6-chloropy-razin-2-yl)(pyrrolidin-1-yl)-methanone<br>[CAS RN: 959241-31-7] | 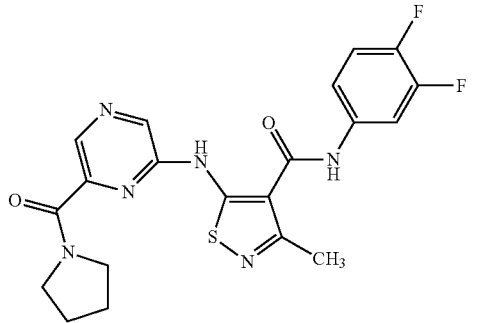 [SMILES: Cc1nsc(Nc2cncc(C(=O)N3CCCC3)n2)c1C(=O)Nc1ccc(F)c(F)c1]<br>N-(3,4-Difluorophenyl)-3-methyl-5-{[6-(pyrrolidin-1-ylcarbonyl)pyrazin-2-yl]amino}-1,2-thiazole-4-carboxamide, 20% | UPLC-MS (Method 1): Rt = 1.12 min; MS (EI$_{neg}$): m/z = 443 [M − H]⁻.<br>¹H-NMR (400 MHz, DMSO-d6): δ [ppm] = 1.80-1.97 (m, 4H), 2.44 (s, 3H), 3.55 (q, 4H), 7.39-7.50 (m, 2H), 7.94 (dd, 1H), 8.32 (s, 1H), 8.78 (s, 1H), 10.45 (s, 1H), 11.11 (s, 1H). |
| Example 107<br>SM1: Intermediate 3<br>SM2: (6-chloropyrazin-2-yl)(morpholin-4-yl)-methanone<br>[CAS RN: 24079-32-1] | 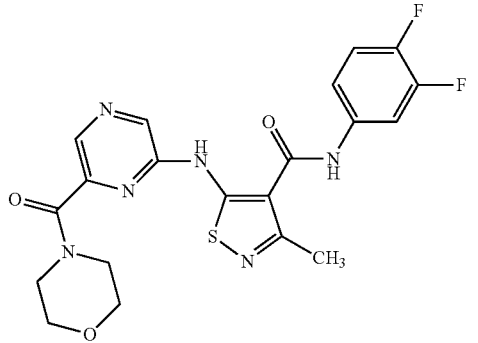 [SMILES: Cc1nsc(Nc2cncc(C(=O)N3CCOCC3)n2)c1C(=O)Nc1ccc(F)c(F)c1]<br>N-(3,4-Difluorophenyl)-3-methyl-5-{[6-(morpholin-4-ylcarbonyl)pyrazin-2-yl]amino}-1,2-thiazole-4-carboxamide, 12% | UPLC-MS (Method 1): Rt = 1.05 min; MS (EI$_{neg}$): m/z = 459 [M − H]⁻.<br>¹H-NMR (400 MHz, DMSO-d6): δ [ppm] = 2.44 (s, 3H), 3.44 (m, 2H), 3.60 (m, 2H), 3.71 (m, 4H), 7.38-7.51 (m, 2H), 7.94 (dd, 1H), 8.30 (s, 1H), 8.78 (s, 1H), 10.46 (s, 1H), 11.14 (s, 1H). |
| Example 108<br>SM1: Intermediate 3<br>SM2: 2-bromo-N-methylisonicotinamide<br>[CAS RN: 337536-01-3] | 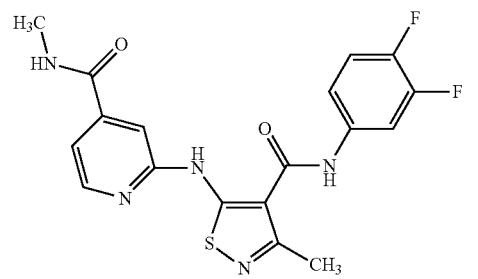 [SMILES: CNC(=O)c1ccnc(Nc2snc(C)c2C(=O)Nc2ccc(F)c(F)c2)c1]<br>2-({4-[(3,4-Difluorophenyl)-carbamoyl]-3-methyl-1,2-thiazol-5-yl}amino)-N-methyliso-nicotinamide, 37% | UPLC-MS (Method 1): Rt = 1.08 min; MS (EI$_{neg}$): m/z = 402 [M − H]⁻.<br>¹H-NMR (400 MHz, DMSO-d6): δ [ppm] = 2.41 (s, 3H), 2.78 (d, 3H), 7.30 (d, 1H), 7.37-7.50 (m, 2H), 7.69 (s, 1H), 7.94 (dd, 1H), 8.47 (d, 1H), 8.66 (d, 1H), 10.37 (s, 1H), 10.78 (s, 1H). |

TABLE A-continued

| Example No, SM1, SM2 | Structure, Name, yield of theory | Analytical data |
|---|---|---|
| Example 109<br>SM1: Intermediate 3<br>SM2: 5-chloro-N,N-dimethylpyrazine-2-carboxamide, see WO2010/103438 (Pfizer Inc.) | 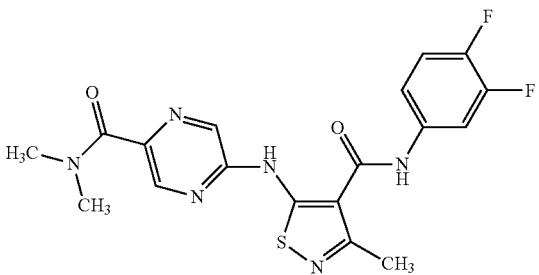 [SMILES: Cc1nsc(Nc2cnc(C(=O)N(C)C)cn2)c1C(=O)Nc1ccc(F)c(F)c1]<br>5-({4-[(3,4-Difluorophenyl)carbamoyl]-3-methyl-1,2-thiazol-5-yl}amino)-N,N-dimethylpyrazine-2-carboxamide, 2% | UPLC-MS (Method 1): Rt = 1.10 min; MS (EI$_{neg}$): m/z = 417 [M − H]$^-$.<br>$^1$H-NMR (400 MHz, DMSO-d6): δ [ppm] = 2.44 (s, 3H), 3.01 (s, 3H), 3.04 (s, 3H), 7.37-7.53 (m, 2H), 7.95 (dd, 1H), 8.62 (s, 1H), 8.67 (s, 1H), 10.48 (s, 1H), 11.19 (s, 1H). |
| Example 110<br>SM1: Intermediate 20<br>SM2: 6-chloronicotinonitrile<br>[CAS RN: 33252-28-7] | 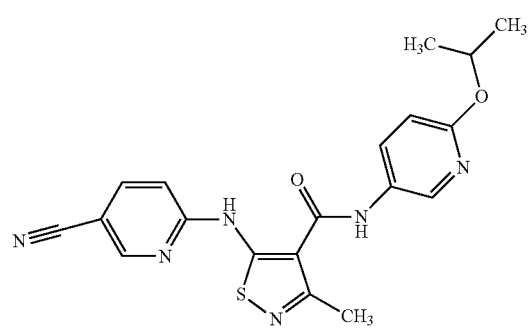 [SMILES: Cc1nsc(Nc2ccc(C#N)cn2)c1C(=O)Nc1ccc(OC(C)C)nc1]<br>5-[(5-Cyanopyridin-2-yl)amino]-N-(6-isopropoxyridin-3-yl)-3-methyl-1,2-thiazole-4-carboxamide, 6% | UPLC-MS (Method 2): Rt = 1.24 min; MS (EI$_{pos}$): m/z = 395 [M + H]$^+$.<br>$^1$H NMR (300 MHz, DMSO-d$_6$) δ [ppm] = 1.27 (d, 6 H), 2.44 (s, 3 H), 5.08-5.30 (m, 1 H), 6.77 (d, 1 H), 7.43 (d, 1 H), 8.00 (d, 1 H), 8.13 (dd, 1 H), 8.48 (d, 1 H), 8.86 (d, 1 H), 10.23 (s, 1 H), 11.08 (s, 1 H). |
| Example 111<br>SM1: Intermediate 14<br>SM2: 2-chloroisonicotinonitrile<br>[CAS RN: 33252-30-1] | 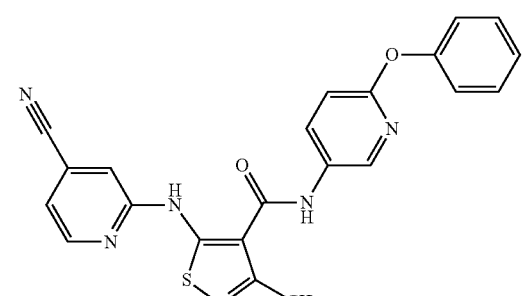<br>5-[(4-Cyanopyridin-2-yl)amino]-3-methyl-N-(6-phenoxypyridin-3-yl)-1,2-thiazole-4-carboxamide, 21% | UPLC-MS (Method 2): Rt = 1.28 min; MS (ESI$_{pos}$): m/z = 429 [M + H]$^+$.<br>$^1$H NMR (400 MHz, CDCl$_3$-d) δ [ppm] = 2.84 (s, 3 H), 7.01 (d, 1 H), 7.13-7.21 (m, 3 H), 7.21-7.27 (m, 2 H), 7.44 (t, 2 H), 7.67 (s, 1 H), 8.09 (dd, 1 H), 8.29 (d, 1 H), 8.60 (d, 1 H), 11.85 (s, 1 H). |
| Example 112<br>SM1: Intermediate 14<br>SM2: 2-chloroquinoxaline<br>[CAS RN: 1448-87-9] | 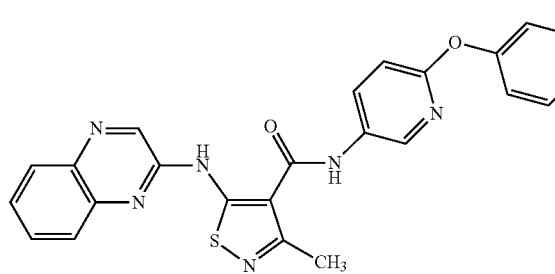<br>3-Methyl-N-(6-phenoxypyridin-3-yl)-5-(quinoxalin-2-ylamino)-1,2-thiazole-4-carboxamide, 6% | UPLC-MS (Method 2): Rt = 1.35 min; MS (ESI$^{pos}$): m/z = 455 [M + H]$^+$.<br>$^1$H NMR (300 MHz, CDCl$_3$-d) δ [ppm] = 2.89 (s, 3 H), 7.03 (d, 1 H), 7.19 (d, 2 H), 7.22-7.28 (m, 1 H), 7.39-7.51 (m, 2 H), 7.57-7.74 (m, 2 H), 7.79 (t, 1 H), 7.99-8.19 (m, 3 H), 8.30 (d, 1 H), 8.72 (s, 1 H), 12.05 (s, 1 H). |

TABLE A-continued

| Example No, SM1, SM2 | Structure, Name, yield of theory | Analytical data |
|---|---|---|
| Example 113<br>SM1: Intermediate 15<br>SM2: 2-chloroquinoxaline<br>[CAS RN: 1448-87-9] | 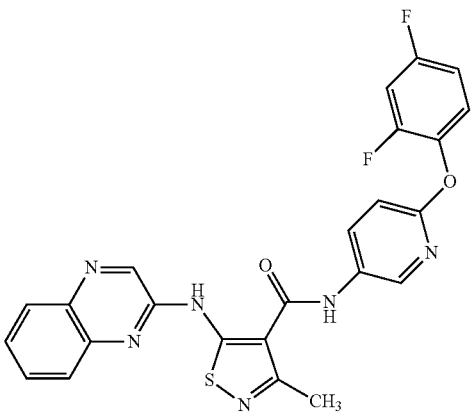 [SMILES: Cc1nsc(Nc2cnc3ccccc3n2)c1C(=O)Nc1ccc(Oc2ccc(F)cc2F)nc1]<br>N-[6-(2,4-Difluorophenoxy)pyridin-3-yl]-3-methyl-5-(quinoxalin-2-ylamino)-1,2-thiazole-4-carboxamide, 19% | UPLC-MS (Method 2): Rt = 1.39 min; MS (ESI$_{pos}$): m/z = 491 [M + H]$^+$.<br>$^1$H NMR (400 MHz, DMSO-d$_6$): δ [ppm] = 7.09-7.26 (m, 2 H), 7.29-7.53 (m, 3 H), 7.62 (s br, 1 H), 7.71-7.86 (m, 1 H), 7.90-8.05 (m, 2 H), 8.16-8.34 (m, 1 H), 8.44 (s br, 1 H), 9.01 (s, 1 H), 10.42 (s br, 1 H), 11.33 (s br, 1 H), 1xCH$_3$ obscured by solvent signal. |
| Example 114<br>SM1: Intermediate 15<br>SM2: 2-chloroisonicotinonitrile<br>[CAS RN: 33252-30-1] | 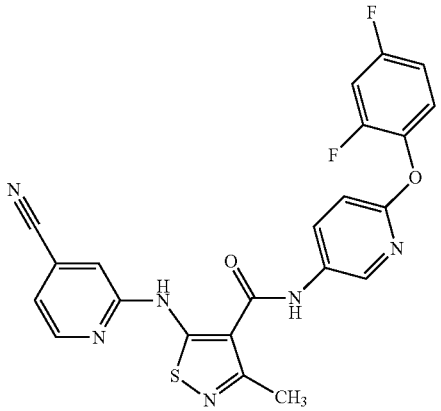<br>5-[(4-Cyanopyridin-2-yl)amino]-N-[6-(2,4-difluorophenoxy)pyridin-3-yl]-3-methyl-1,2-thiazole-4-carboxamide, 32% | UPLC-MS (Method 2): Rt = 1.39 min; MS (ESI$_{pos}$): m/z = 491 [M + H]$^+$.<br>$^1$H NMR (400 MHz, DMSO-d$_6$) δ [ppm] = 2.46 (s, 3 H), 7.04-7.26 (m, 2 H), 7.26-7.51 (m, 3 H), 7.74 (s br, 1 H), 8.22 (d, 1 H), 8.40 (s br, 1 H), 8.60 (d, 1 H), 10.31 (s br, 1 H), 10.88 (s br, 1 H). |
| Example 115<br>SM1: Intermediate 16<br>SM2: 2-chloroquinoxaline<br>[CAS RN: 1448-87-9] | 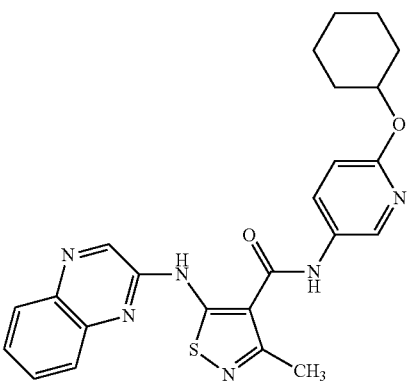 [SMILES: Cc1nsc(Nc2cnc3ccccc3n2)c1C(=O)Nc1ccc(OC2CCCCC2)nc1]<br>N-[6-(Cyclohexyloxy)pyridin-3-yl]-3-methyl-5-(quinoxalin-2-ylamino)-1,2-thiazole-4-carboxamide, 11% | UPLC-MS (Method 2): Rt = 1.31 min; MS (ESI$_{pos}$): m/z = 461 [M + H]$^+$.<br>$^1$H NMR (300 MHz, DMSO-d$_6$) δ [ppm] = 1.15-1.60 (m, 6 H), 1.62-1.82 (m, 2 H), 1.95 (d, 2 H), 4.78-5.08 (m, 1 H), 6.80 (d, 1 H), 7.52-7.70 (m, 1 H), 7.78 (t, 1 H), 7.89-8.11 (m, 2 H), 8.49 (s br, 1 H), 9.03 (s, 1 H), 10.26 (s br, 1 H), 11.33 (s br, 1 H), 1 NH not detected, 1xCH$_3$ obscured by solvent signal. |

TABLE A-continued

| Example No, SM1, SM2 | Structure, Name, yield of theory | Analytical data |
| --- | --- | --- |
| Example 116<br>SM1: Intermediate 17<br>SM2: 2-chloroquinoxaline<br>[CAS RN: 1448-87-9] | 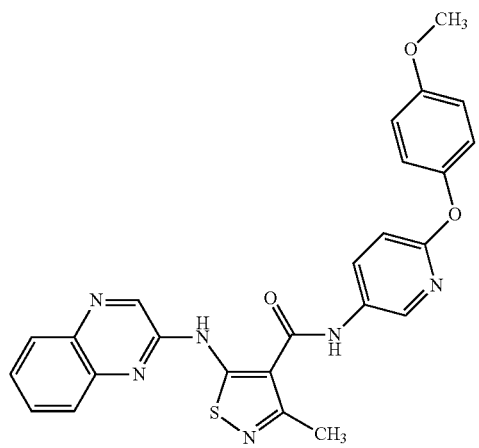 [SMILES: COc1ccc(Oc2ccc(NC(=O)c3c(C)nsc3Nc3cnc4ccccc4n3)cn2)cc1]<br>N-[6-(4-Methoxyphenoxy)pyridin-3-yl]-3-methyl-5-(quinoxaline-2-ylamino)-1,2-thiazole-4-carboxamide, 11% | UPLC-MS (Method 1): Rt = 1.34 min; MS (ESI$_{neg}$): m/z = 483 [M − H]$^-$.<br>$^1$H NMR (300 MHz, DMSO-d$_6$) δ [ppm] = 3.76 (s, 3 H), 6.87-7.18 (m, 5 H), 7.63 (d, 1 H), 7.78 (t, 1 H), 7.97 (d, 2 H), 8.21 (d, 1 H), 8.49 (s br, 1 H), 9.02 (s, 1 H), 10.42 (s br, 1 H), 11.35 (s br, 1 H), 1xCH$_3$ obscured by solvent signal. |
| Example 117<br>SM1: Intermediate 17<br>SM2: 2-chloroisonicotinonitrile<br>[CAS RN: 33252-30-1] | 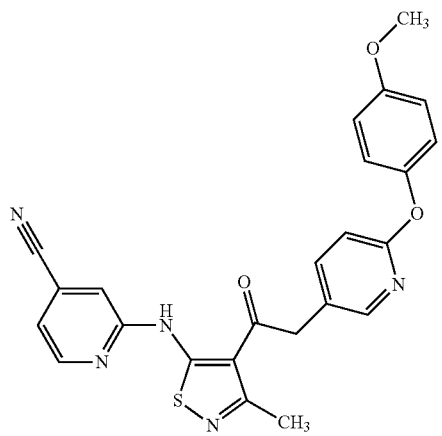 [SMILES: COc1ccc(Oc2ccc(CC(=O)c3c(C)nsc3Nc3cc(C#N)ccn3)cn2)cc1]<br>5-[(4-Cyanopyridin-2-yl)amino]-N-[6-(4-methoxyphenoxy)pyridin-3-yl]-3-methyl-1,2-thiazole-4-carboxamide, 11% | UPLC-MS (Method 2): Rt = 0.85 min; MS (ESI$_{pos}$): m/z = 459 [M + H]$^+$.<br>$^1$H NMR (300 MHz, DMSO-d$_6$) δ [ppm] = 2.44 (s br, 3 H), 3.76 (s, 3 H), 6.83-7.11 (m, 5 H), 7.36 (d, 1 H), 7.75 (s, 1 H), 8.16 (d, 1 H), 8.45 (s br, 1 H), 8.60 (d, 1 H), 10.29 (s br, 1 H), 10.90 (s br, 1 H). |
| Example 118<br>SM1: Intermediate 16<br>SM2: 2-chloroisonicotinonitrile<br>[CAS RN: 33252-30-1] | 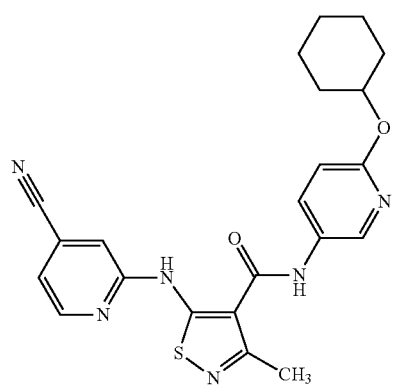 [SMILES: Cc1nsc(Nc2cc(C#N)ccn2)c1C(=O)Nc1ccc(OC2CCCCC2)nc1]<br>5-[(4-Cyanopyridin-2-yl)amino]-N-[6-(cyclohexyloxy)pyridin-3-yl]-3-methyl-1,2-thiazole-4-carboxamide, 15% | UPLC-MS (Method 1): Rt = 1.44 min; MS (ESI$_{pos}$): m/z = 435 [M + H]$^+$.<br>$^1$H NMR (400 MHz, DMSO-d$_6$) δ [ppm] = 1.15-1.31 (m, 1H), 1.31-1.48 (m, 4 H), 1.48-1.62 (m, 1 H), 1.72 (dd, 2 H), 1.88-2.02 (m, 2 H), 2.46 (s br, 3 H), 4.79-5.07 (m, 1 H), 6.78 (d, 1 H), 7.35 (d, 1 H), 7.76 (s br, 1 H), 8.01 (d, 1 H), 8.45 (s br, 1 H), 8.60 (d, 1 H), 10.13 (s br, 1 H), 10.88 (s br, 1 H). |

TABLE A-continued

| Example No, SM1, SM2 | Structure, Name, yield of theory | Analytical data |
|---|---|---|
| Example 119<br>SM1: Intermediate 18<br>SM2: 2-chloroquinoxaline<br>[CAS RN: 1448-87-9] | 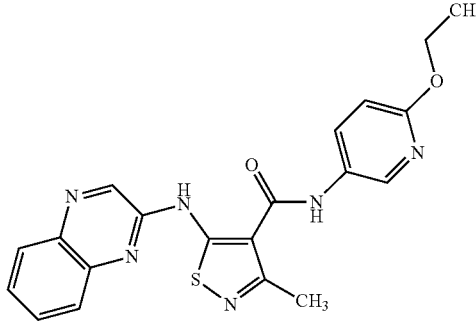<br>N-(6-Ethoxypyridin-3-yl)-3-methyl-5-(quinoxalin-2-ylamino)-1,2-thiazole-4-carboxamide, 27% | UPLC-MS (Method 1): Rt = 1.27 min; MS (ESI$_{neg}$): m/z = 405 [M − H]$^-$.<br>$^1$H NMR (300 MHz, DMSO-d$_6$) δ [ppm] = 1.31 (t, 3 H), 4.28 (q, 2 H), 6.84 (d, 1 H), 7.56-7.70 (m, 1 H), 7.78 (t, 1 H), 7.98 (d, 2 H), 8.06 (d, 1 H), 8.52 (s br, 1 H), 9.04 (s, 1 H), 10.27 (s br, 1 H), 11.34 (s br, 1 H), 1xCH$_3$ obscured by solvent signal. |
| Example 120<br>SM1: Intermediate 19<br>SM2: 6-chloronicotinonitrile<br>[CAS RN: 33252-28-7] | 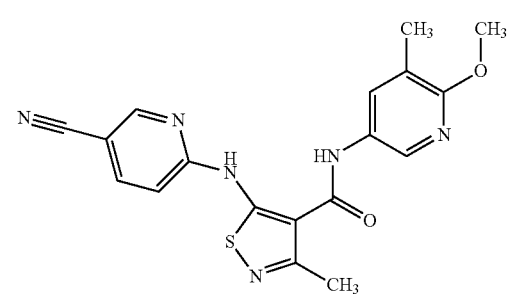 [SMILES: COc1ncc(NC(=O)c2c(C)nsc2Nc2ccc(C#N)cn2)cc1C]<br>5-[(5-Cyanopyridin-2-yl)amino]-N-(6-methoxy-5-methylpyridin-3-yl)-3-methyl-1,2-thiazole-4-carboxamide, 13% | UPLC-MS (Method 1): Rt = 1.20 min; MS (ESI$_{pos}$): m/z = 381 [M + H]$^+$.<br>$^1$H NMR (300 MHz, DMSO-d$_6$) δ [ppm] = 2.16 (s, 3 H), 2.45 (s, 3 H), 3.86 (s, 3 H), 7.45 (d, 1 H), 7.92 (s, 1 H), 8.04-8.19 (m, 1 H), 8.32 (s, 1 H), 8.86 (d, 1 H), 10.17 (s br, 1 H), 11.08 (s br, 1 H). |
| Example 121<br>SM1: Intermediate 19<br>SM2: 2-chloroquinoxaline<br>[CAS RN: 1448-87-9] | 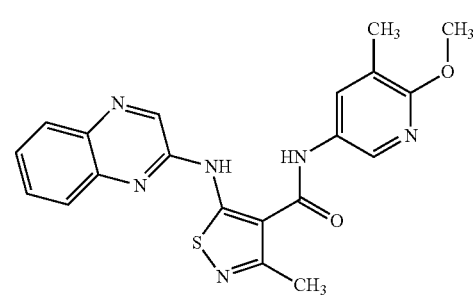 [SMILES: COc1ncc(NC(=O)c2c(C)nsc2Nc2cnc3ccccc3n2)cc1C]<br>N-(6-Methoxy-5-methylpyridin-3-yl)-3-methyl-5-(quinoxalin-2-ylamino)-1,2-thiazole-4-carboxamide, 11% | UPLC-MS (Method 1): Rt = 1.29 min; MS (ESI$_{neg}$): m/z = 405 [M − H]$^-$.<br>$^1$H NMR (300 MHz, DMSO-d$_6$) δ [ppm] = 2.18 (s, 3 H), 3.87 (s, 3 H), 7.54-7.69 (m, 1 H), 7.69-7.87 (m, 1 H), 7.69-7.87 (m, 1 H), 7.98 (d, 3 H), 8.36 (s br, 1 H), 9.05 (s, 1 H), 10.21 (s br, 1 H), 11.33 (s br, 1 H), 1xCH$_3$ obscured by solvent signal. |
| Example 122<br>SM1: Intermediate 20<br>SM2: 2-chloroquinoxaline<br>[CAS RN: 1448-87-9] | 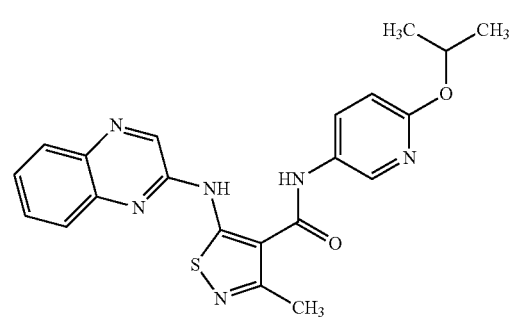 [SMILES: Cc1nsc(Nc2cnc3ccccc3n2)c1C(=O)Nc1ccc(OC(C)C)nc1]<br>N-(6-Isopropoxypyridin-3-yl)-3-methyl-5-(quinoxalin-2-ylamino)-1,2-thiazole-4-carboxamide, 28% | UPLC-MS (Method 1): Rt = 1.35 min; MS (ESI$_{pos}$): m/z = 421 [M + H]$^+$.<br>$^1$H NMR (300 MHz, DMSO-d$_6$) δ [ppm] = 1.17-1.43 (m, 6 H), 5.21 (quin, 1 H), 6.79 (d, 1 H), 7.55-7.70 (m, 1 H), 7.78 (t, 1 H), 7.89-8.12 (m, 3 H), 8.52 (s br, 1 H), 9.04 (s, 1 H), 10.26 (s br, 1 H), 11.33 (s br, 1 H), 1xCH$_3$ obscured by solvent signal. |

The compounds listed in Table B were prepared according to the procedures outlined above, using starting materials which were described above or which are known in the art.

TABLE B

| Example No | Structure, Name | Analytical data |
| --- | --- | --- |
| Example 123 | 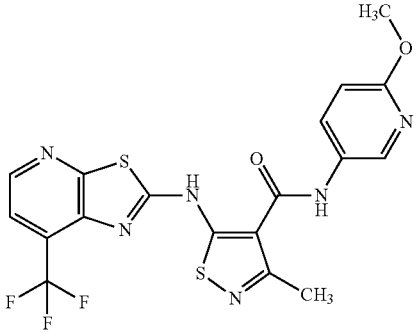<br>N-(6-Methoxypyridin-3-yl)-3-methyl-5-{[7-(trifluoromethyl)-[1,3]thiazolo[5,4-b]pyridin-2-yl]amino}-1,2-thiazole-4-carboxamide | UPLC-MS (Method 1): Rt = 1.35 min; MS (Elneg): m/z = 465 [M − H]⁻. |
| Example 124 | 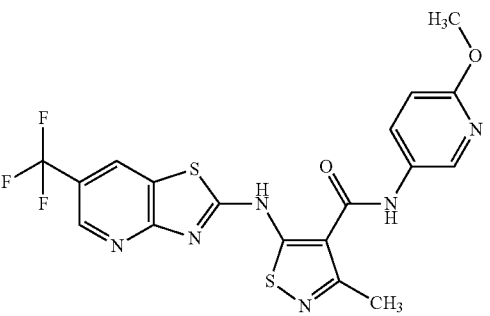<br>N-(6-Methoxypyridin-3-yl)-3-methyl-5-{[6-(trifluoromethyl)-[1,3]thiazolo[5,4-b]pyridin-2-yl]amino}-1,2-thiazole-4-carboxamide | UPLC-MS (Method 1): Rt = 1.30 min; MS (Elneg): m/z = 465 [M − H]⁻. |
| Example 125 | 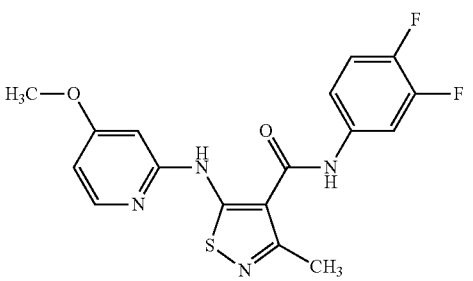<br>N-(3,4-Difluorophenyl)-5-[(4-methoxypyridin-2-yl)amino]-3-methyl-1,2-thiazole-4-carboxamide | UPLC-MS (Method 1): Rt = 1.30 min; MS (Elneg): m/z = 375 [M − H]⁻. |

TABLE B-continued

| Example No | Structure, Name | Analytical data |
| --- | --- | --- |
| Example 126 | 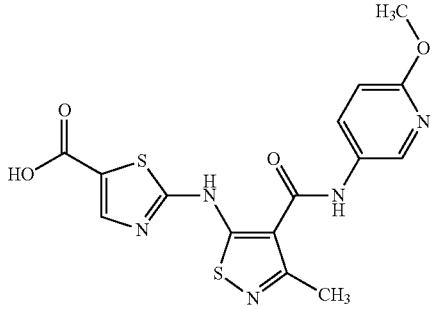<br>2-({4-[(6-Methoxypyridin-3-yl)carbamoyl]-3-methyl-1,2-thiazol-5-yl}amino)-1,3-thiazole-5-carboxylic acid | UPLC-MS (Method 1): Rt = 0.93 min; MS (Elneg): m/z = 390 [M − H]⁻. |
| Example 127 | 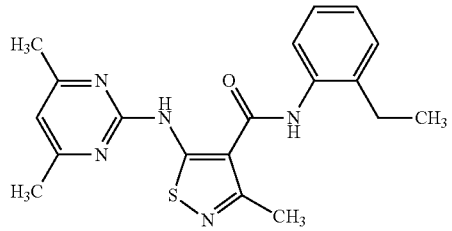<br>5-[(4,6-Dimethylpyrimidin-2-yl)amino]-N-(2-ethylphenyl)-3-methyl-1,2-thiazole-4-carboxamide | UPLC-MS (Method 4): Rt = 1.35 min; MS (Elneg): m/z = 366 [M − H]⁻. |
| Example 128 | 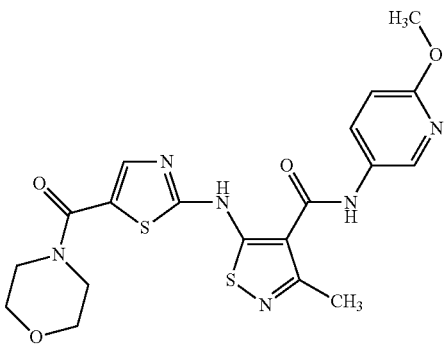<br>N-(6-Methoxypyridin-3-yl)-3-methyl-5-{[5-(morpholin-4-ylcarbonyl)-1,3-thiazol-2-yl]amino}-1,2-thiazole-4-carboxamide | UPLC-MS (Method 1): Rt = 0.97 min; MS (Elneg): m/z = 459 [M − H]⁻. |

TABLE B-continued

| Example No | Structure, Name | Analytical data |
|---|---|---|
| Example 129 | 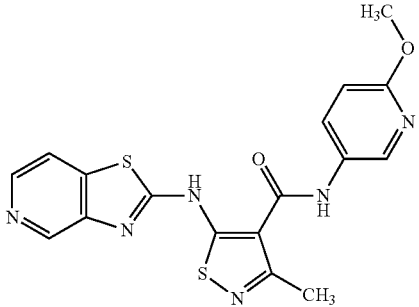<br>N-(6-Methoxypyridin-3-yl)-3-methyl-5-([1,3]thiazolo[4,5-c]pyridin-2-ylamino)-1,2-thiazole-4-carboxamide | UPLC-MS (Method 1): Rt = 0.85 min; MS (Elneg): m/z = 397 [M − H]−. |
| Example 130 | 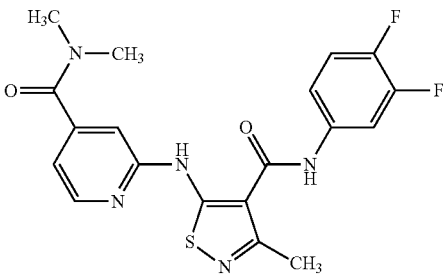<br>2-({4-[(3,4-Difluorophenyl)-carbamoyl]-3-methyl-1,2-thiazol-5-yl}amino)-N,N-dimethylpyridine-4-carboxamide | UPLC-MS (Method 1): Rt = 1.11 min; MS (Elneg): m/z = 416 [M − H]−. |
| Example 131 | 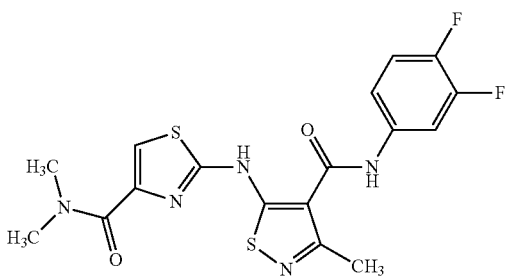<br>N-(3,4-Difluorophenyl)-5-{[4-(dimethylcarbamoyl)-1,3-thiazol-2-yl]amino}-3-methyl-1,2-thiazole-4-carboxamide | UPLC-MS (Method 1): Rt = 1.16 min; MS (Elneg): m/z = 422 [M − H]−. |
| Example 132 | 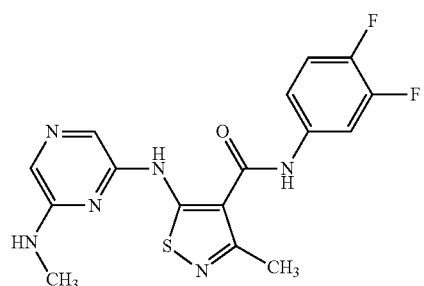<br>N-(3,4-Difluorophenyl)-3-methyl-5-{[6-(methylamino)pyrazin-2-yl]amino}-1,2-thiazole-4-carboxamide | UPLC-MS (Method 1): Rt = 1.13 min; MS (Elneg): m/z = 375 [M − H]−. |

TABLE B-continued

| Example No | Structure, Name | Analytical data |
|---|---|---|
| Example 133 | 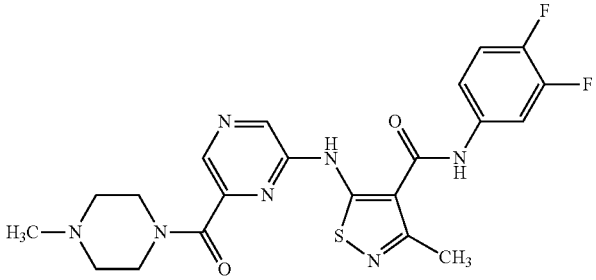<br>N-(3,4-Difluorophenyl)-3-methyl-5-({6-[(4-Methylpiperazin-1-yl)carbonyl]pyrazin-2-yl}amino)-1,2-thiazole-4-carboxamide | UPLC-MS (Method 1): Rt = 0.86 min; MS (Elneg): m/z = 472 [M − H]⁻. |
| Example 134 | 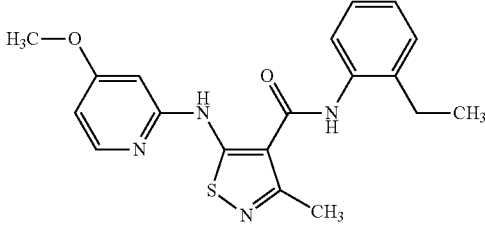<br>N-(2-Ethylphenyl)-5-[(4-methoxy-pyridin-2-yl)amino]-3-methyl-1,2-thiazole-4-carboxamide | UPLC-MS (Method 1): Rt = 1.38 min; MS (Elneg): m/z = 367 [M − H]⁻. |
| Example 135 | 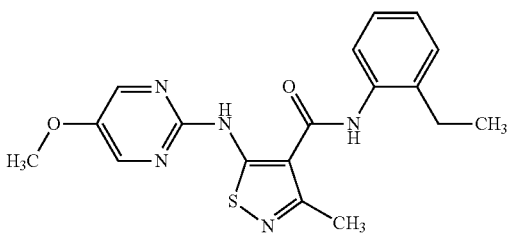<br>N-(2-Ethylphenyl)-5-[(5-methoxy-pyrimidin-2-yl)amino]-3-methyl-1,2-thiazole-4-carboxamide | UPLC-MS (Method 4): Rt = 1.26 min; MS (Elneg): m/z = 368 [M − H]⁻. |
| Example 136 | 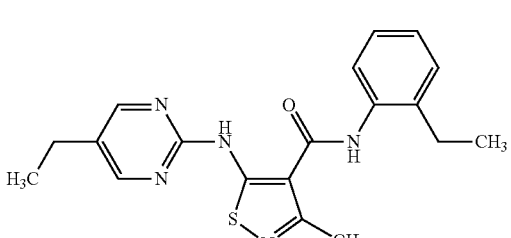<br>N-(2-Ethylphenyl)-5-[(5-ethyl-pyrimidin-2-yl)amino]-3-methyl-1,2-thiazole-4-carboxamide | UPLC-MS (Method 1): Rt = 1.39 min; MS (Elneg): m/z = 366 [M − H]⁻. |

TABLE B-continued

| Example No | Structure, Name | Analytical data |
|---|---|---|
| Example 137 | 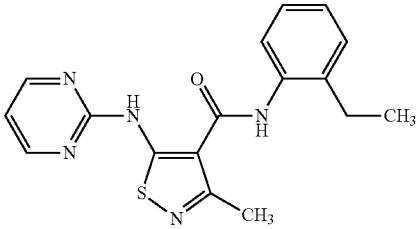<br>N-(2-Ethylphenyl)-3-methyl-5-(pyrimidin-2-ylamino)-1,2-thiazole-4-carboxamide | UPLC-MS (Method 1): Rt = 1.25 min; MS (Elneg): m/z = 338 [M − H]$^-$. |
| Example 138 | 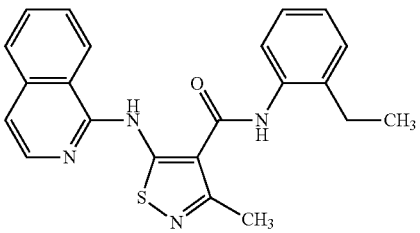<br>N-(2-Ethylphenyl)-5-(isoquinolin-1-ylamino)-3-methyl-1,2-thiazole-4-carboxamide | UPLC-MS (Method 1): Rt = 1.58 min; MS (Elneg): m/z = 387 [M − H]$^-$. |
| Example 139 | 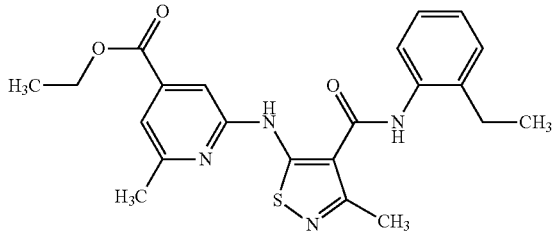<br>Ethyl 2-({4-[(2-ethylphenyl)carbamoyl]-3-methyl-1,2-thiazol-5-yl}amino)-6-methylpyridine-4-carboxylate | UPLC-MS (Method 3): Rt = 1.50 min; MS (Elneg): m/z = 423 [M − H]$^-$. |
| Example 140 | 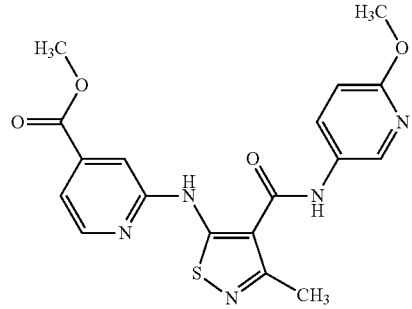<br>Methyl 2-({4-[(6-methoxypyridin-3-yl)carbamoyl]-3-methyl-1,2-thiazol-5-yl}amino)pyridine-4-carboxylate | UPLC-MS (Method 5): Rt = 1.11 min; MS (Elneg): m/z = 398 [M − H]$^-$. |

TABLE B-continued

| Example No | Structure, Name | Analytical data |
|---|---|---|
| Example 141 | 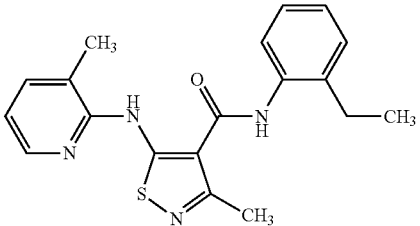<br>N-(2-Ethylphenyl)-3-methyl-5-[(3-methylpyridin-2-yl)amino]-1,2-thiazole-4-carboxamide | UPLC-MS (Method 1): Rt = 1.45 min; MS (Elneg): m/z = 351 [M − H]⁻. |
| Example 142 | 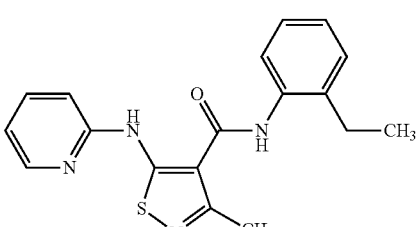<br>N-(2-Ethylphenyl)-3-methyl-5-(pyridin-2-ylamino)-1,2-thiazole-4-carboxamide | UPLC-MS (Method 1): Rt = 1.35 min; MS (Elneg): m/z = 337 [M − H]−. |
| Example 143 | 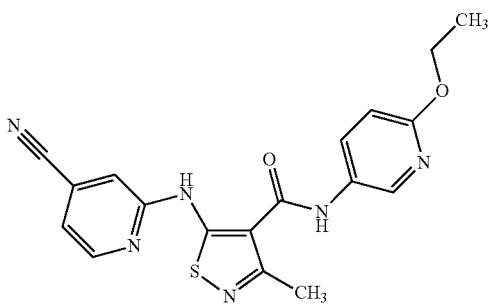<br>5-[(4-Cyanopyridin-2-yl)amino]-N-(6-ethoxypyridin-3-yl)-3-methyl-1,2-thiazole-4-carboxamide | UPLC-MS (Method 1): Rt = 1.19 min; MS (Elneg): m/z = 379 [M − H]⁻. |
| Example 144 | 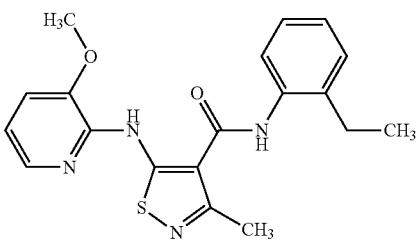<br>N-(2-Ethylphenyl)-5-[(3-methoxypyridin-2-yl)amino]-3-methyl-1,2-thiazole-4-carboxamide | UPLC-MS (Method 1): Rt = 1.39 min; MS (Elneg): m/z = 367 [M − H]⁻. |

TABLE B-continued

| Example No | Structure, Name | Analytical data |
|---|---|---|
| Example 145 | 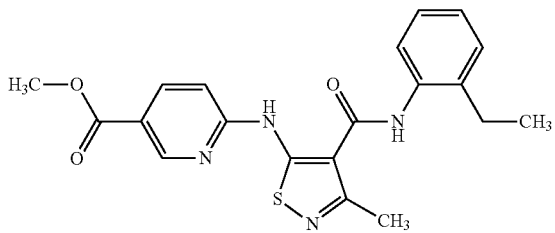<br>Methyl 6-({4-[(2-ethylphenyl)-carbamoyl]-3-methyl-1,2-thiazol-5-yl}amino)nicotinate | UPLC-MS (Method 1): Rt = 1.38 min; MS (EIneg): m/z = 395 [M − H]$^-$. |
| Example 146 | 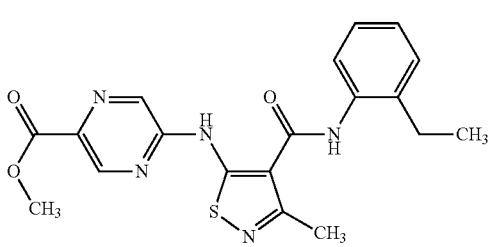<br>Methyl 5-({4-[(2-ethylphenyl)-carbamoyl]-3-methyl-1,2-thiazol-5-yl}amino)pyrazine-2-carboxylate | UPLC-MS (Method 1): Rt = 1.20 min; MS (EIneg): m/z = 396 [M − H]$^-$. |
| Example 147 | 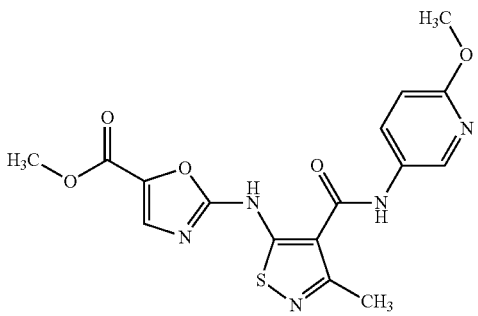<br>Methyl 2-({4-[(6-methoxypyridin-3-yl)carbamoyl]-3-methyl-1,2-thiazol-5-yl}amino)-1,3-oxazole-5-carboxylate | UPLC-MS (Method 1): Rt = 1.06 min; MS (EIneg): m/z = 388 [M − H]$^-$. |
| Example 148 | 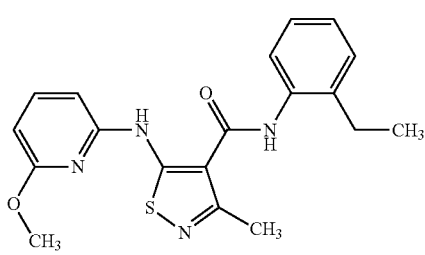<br>N-(2-Ethylphenyl)-5-[(6-methoxy-pyridin-2-yl)amino]-3-methyl-1,2-thiazole-4-carboxamide | UPLC-MS (Method 1): Rt = 1.44 min; MS (EIneg): m/z = 367 [M − H]$^-$. |

TABLE B-continued

| Example No | Structure, Name | Analytical data |
|---|---|---|
| Example 149 | 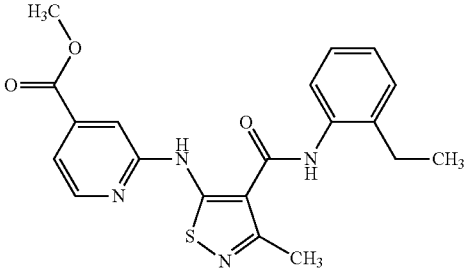<br>Methyl 2-({4-[(2-ethylphenyl)-carbamoyl]-3-methyl-1,2-thiazol-5-yl}amino)isonicotinate | UPLC-MS (Method 1): Rt = 1.38 min; MS (Elneg): m/z = 395 [M − H]⁻. |
| Example 150 | 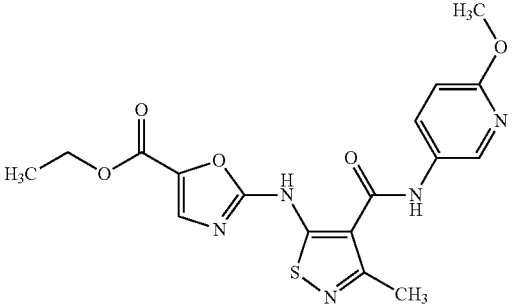<br>Ethyl 2-({4-[(6-methoxypyridin-3-yl)carbamoyl]-3-methyl-1,2-thiazol-5-yl}amino)-1,3-oxazole-5-carboxylate | UPLC-MS (Method 1): Rt = 1.14 min; MS (Elneg): m/z = 402 [M − H]⁻. |
| Example 151 | 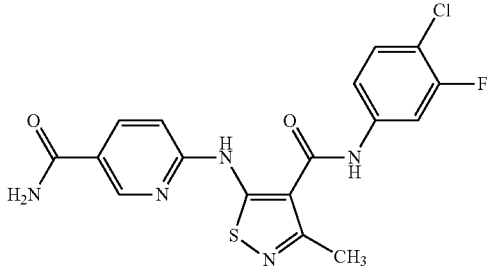<br>6-({4-[(4-Chloro-3-fluorophenyl)-carbamoyl]-3-methyl-1,2-thiazol-5-yl}amino)nicotinamide | UPLC-MS (Method 1): Rt = 1.11 min; MS (Elneg): m/z = 404 [M − H]⁻. |
| Example 152 | 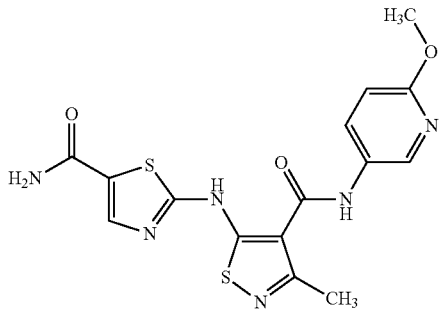<br>5-[(5-Carbamoyl-1,3-thiazol-2-yl)amino]-N-(6-methoxypyridin-3-yl)-3-methyl-1,2-thiazole-4-carboxamide | UPLC-MS (Method 2): Rt = 0.59 min; MS (Elneg): m/z = 389 [M − H]⁻. |

TABLE B-continued

| Example No | Structure, Name | Analytical data |
|---|---|---|
| Example 153 | 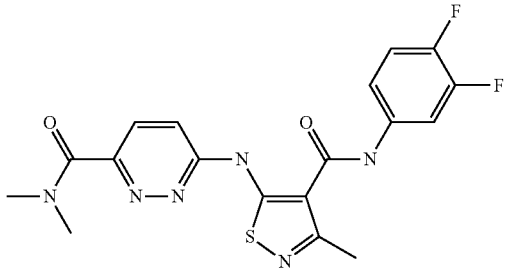<br>6-({4-[(3,4-Difluorophenyl)-carbamoyl]-3-methyl-1,2-thiazol-5-yl}amino)-N,N-dimethyl-pyridazine-3-carboxamide | UPLC-MS (Method 1): Rt = 1.04 min; MS (Elneg): m/z = 417 [M − H]−. |
| Example 154 | 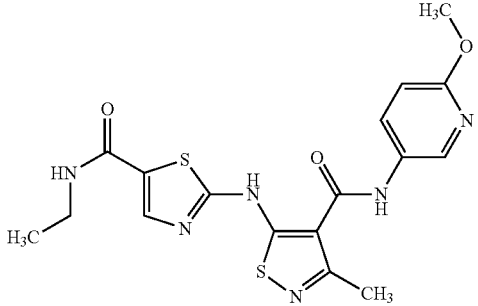<br>5-{[5-(Ethylcarbamoyl)-1,3-thiazol-2-yl]amino}-N-(6-methoxypyridin-3-yl)-3-methyl-1,2-thiazole-4-carboxamide | UPLC-MS (Method 1): Rt = 0.98 min; MS (Elneg): m/z = 417 [M − H]−. |
| Example 155 | 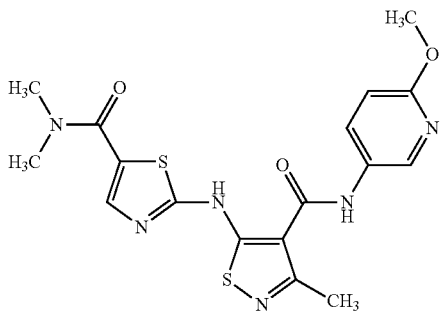<br>5-{[5-(Dimethylcarbamoyl)-1,3-thiazol-2-yl]amino}-N-(6-methoxy-pyridin-3-yl)-3-methyl-1,2-thiazole-4-carboxamide | UPLC-MS (Method 1): Rt = 0.98 min; MS (Elneg): m/z = 417 [M − H]−. |
| Example 156 | 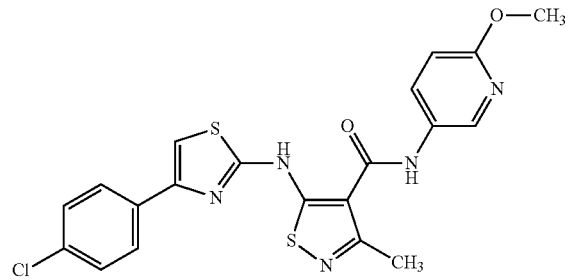<br>5-{[4-(4-Chlorophenyl)-1,3-thiazol-2-yl]amino}-N-(6-methoxypyridin-3-yl)-3-methyl-1,2-thiazole-4-carboxamide | UPLC-MS (Method 1): Rt = 1.46 min; MS (Elneg): m/z = 456 [M − H]-. |

TABLE B-continued

| Example No | Structure, Name | Analytical data |
|---|---|---|
| Example 157 | 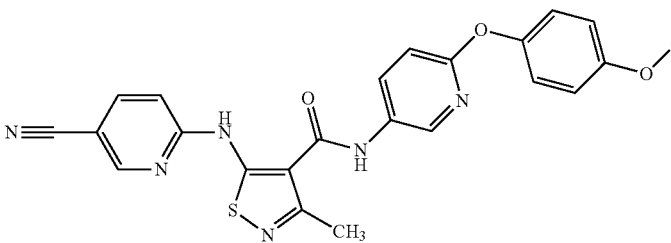  5-[(5-Cyanopyridin-2-yl)amino]-N-[6-(4-methoxyphenoxy)pyridin-3-yl]-3-methyl-1,2-thiazole-4-carboxamide | UPLC-MS (Method 2): Rt = 0.82 min; MS (Elneg): m/z = 457 [M − H]⁻. |
| Example 158 | 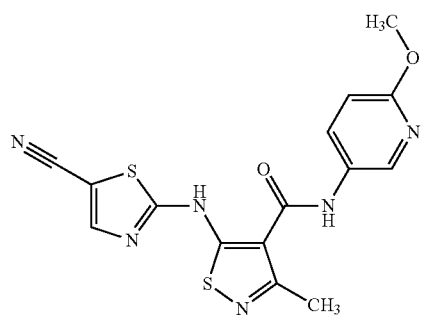  5-[(5-Cyano-1,3-thiazol-2-yl)amino]-N-(6-methoxypyridin-3-yl)-3-methyl-1,2-thiazole-4-carboxamide | UPLC-MS (Method 1): Rt = 1.13 min; MS (Elneg): m/z = 371 [M − H]−. |
| Example 159 | 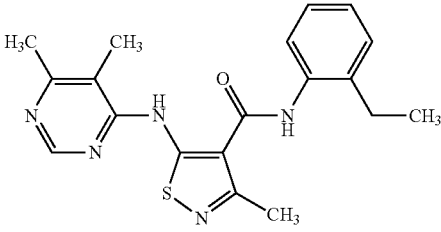  5-[(5,6-Ddimethylpyrimidin-4-yl)amino]-N-(2-ethylphenyl)-methyl-1,2-thiazole-4-carboxamide | UPLC-MS (Method 3): Rt = 1.17 min; MS (Elneg): m/z = 366 [M − H]⁻. |
| Example 160 | 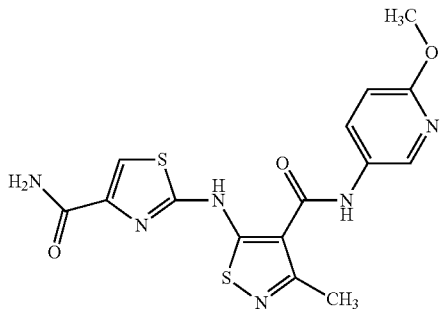  5-[(4-Carbamoyl-1,3-thiazol-2-yl)amino]-N-(6-methoxypyridin-3-yl)-3-methyl-1,2-thiazole-4-carboxamide | UPLC-MS (Method 2): Rt = 0.63 min; MS (Elneg): m/z = 389 [M − H]⁻. |

TABLE B-continued

| Example No | Structure, Name | Analytical data |
| --- | --- | --- |
| Example 161 | 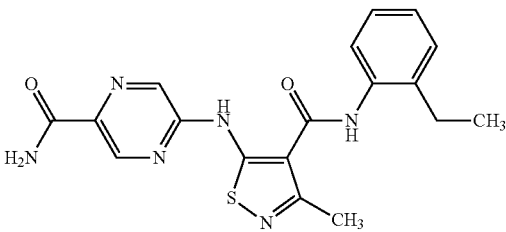<br>5-({4-[(2-Ethylphenyl)carbamoyl]-3-methyl-1,2-thiazol-5-yl}amino)-pyrazine-2-carboxamide | UPLC-MS (Method 1): Rt = 1.08 min; MS (Elneg): m/z = 381 [M − H]⁻. |
| Example 162 | 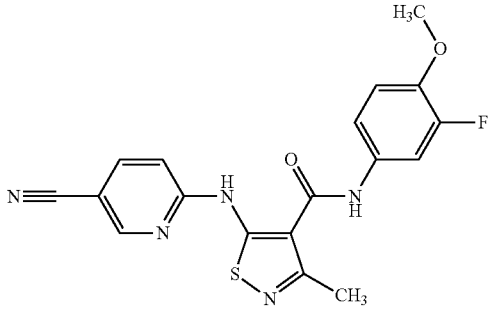<br>5-[(5-Cyanopyridin-2-yl)amino]-N-(3-fluoro-4-methoxyphenyl)-3-methyl-1,2-thiazole-4-carboxamide | UPLC-MS (Method 1): Rt = 1.21 min; MS (Elneg): m/z = 382 [M − H]⁻. |
| Example 163 | 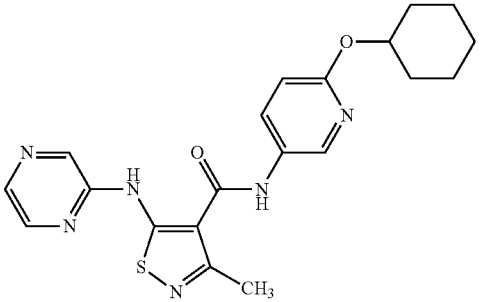<br>N-[6-(cyclohexyloxy)pyridin-3-yl]-3-methyl-5-(pyrazin-2-ylamino)-1,2-thiazole-4-carboxamide | UPLC-MS (Method 3): Rt = 1.34 min; MS (Elneg): m/z = 409 [M − H]⁻. |

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol.

The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference).

Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents (examples include but are not limited to nitrogen and argon), antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution:

A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 min.

Lyophilised Powder for IV Administration:

A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 min.

Intramuscular Suspension:

The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The term "chemotherapeutic anti-cancer agents", includes but is not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, copanlisib, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, 1-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-linked lintuzumab, EM-1421, HyperAcute vaccine, tucotuzumab celmoleukin, galiximab, HPV-16-E7, Javelin-prostate cancer, Javelin-melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

A compound of general formula (I) as defined herein can optionally be administered in combination with one or more of the following: ARRY-162, ARRY-300, ARRY-704, AS-703026, AZD-5363, AZD-8055, BEZ-235, BGT-226, BKM-120, BYL-719, CAL-101, CC-223, CH-5132799, deforolimus, E-6201, enzastaurin, GDC-0032, GDC-0068, GDC-0623, GDC-0941, GDC-0973, GDC-0980, GSK-2110183, GSK-2126458, GSK-2141795, MK-2206, novolimus, OSI-027, perifosine, PF-04691502, PF-05212384, PX-866, rapamycin, RG-7167, RO-4987655, RO-5126766, selumetinib, TAK-733, trametinib, triciribine, UCN-01, WX-554, XL-147, XL-765, zotarolimus, ZSTK-474.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit the spindle assembly checkpoint and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses are affected by inhibition of the spindle assembly checkpoint, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyperproliferative disorders include but are not limited to, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assays:

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Spindle Assembly Checkpoint (SAC) Assays

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Paclitaxel is a microtubule stabilizing compound. Thus, nocodazole as well as paclitaxel interfere with microtubule dynamics and mobilize the spindle assembly checkpoint. The cells arrest in mitosis at G2/M transition and exhibit phosphorylated histone H3 on serine 10. An inhibition of the spindle assembly checkpoint overrides the mitotic blockage in the presence of nocodazole or paclitaxel, the cells complete mitosis prematurely, and their nuclei typically exhibit a multilobed phenotype. The mitotic breakthrough can be detected by the decrease of cells with phosphorylation of histone H3 on serine 10. This decline is used as a marker to determine the capability of compounds of the present invention to induce a mitotic breakthrough. The typical morphological alteration of nuclei with a prematurely completed mitosis after SAC-inhibition can be monitored via image analysis routines supporting those findings.

The nocodazole and paclitaxel variations were used to focus on compounds that are capable of inhibiting a SAC induced by both microtubule destabilization as well as microtubule stabilization. When SAC inducing agents and compounds are given simultaneously, inhibitors that effectively block the SAC during formation or abrogation are identified. When cells are incubated with a SAC inducing agent and the SAC interfering compound is given after a defined time, inhibitors are identified that effectively block SAC abrogation.

SAC-Formation—Nocodazole-Induced Assay

Cultivated cells of the human cervical tumor cell line HeLa (ATCC CCL-2) were plated at a density of 1000 cells/well in a 1536-well microtiter plate in 2 µl PAA Ham's F12 Medium supplemented with 1% (v/v) glutamine, 1% (v/v) penicillin, 1% (v/v) streptomycin and 10% (v/v) fetal calf serum. After incubation overnight at 37° C., 10 µl/well nocodazole at a final concentration of 0.1 µg/ml were added to cells. Test compounds solubilized in dimethyl sulfoxide (DMSO) were added at various concentrations (0 µM, as well as in the range of 0.005 μM-20 μM; the final concentration of the solvent DMSO was 0.5% (v/v)). Cells were incubated for 24 h at 37° C. in the presence of test compounds in combination with nocodazole. Thereafter, cells were fixed in 4% (v/v) paraformaldehyde in phosphate buffered saline (PBS) at 4° C. overnight then permeabilized in 0.1% (v/v) Triton X™ 100 in PBS at room temperature for 20 min and blocked in 0.5% (v/v) bovine serum albumin (BSA) in PBS at room temperature for 15 min. After washing with PBS, 5 μl/well antibody solution (anti-phospho-histone H3 clone 3H10, FITC; Millipore, Cat #16-222; 1:1000 dilution) was added to cells, which were incubated for 2 h at room temperature. Afterwards, cells were washed with PBS and 5 μl/well solution of HOECHST 33342 dye (5 μg/ml) was added to cells and cells were incubated 15 min at room temperature in the dark. Cells were washed twice with PBS then covered with PBS and stored at 4° C. until analysis. Images were acquired with a PERKIN ELMER OPERA™ High-Content Analysis reader. Images were analyzed with image analysis software MetaXpress™ from Molecular devices utilizing the Mitotic Index application module. In this assay both labels HOECHST 33342 and phosphorylated Histone H3 on serine 10 were measured. HOECHST 33342 labels the DNA and is used to count the cell number. The staining of phosphorylated Histone H3 on serine 10 determines the number of mitotic cells. After 24 h incubation, inhibition of SAC in presence of nocodazole decreases the number of mitotic cells indicating an inappropriate mitotic progression. Otherwise cells were arrested at G2/M phase of the cell cycle progression. The raw assay data were further analyzed by four-parametric hill equation using Genedata's Assay Analyzer and Condoseo software.

TABLE 1

SAC-Formation - Nocodazole-Induced Assay

| Example No. | $IC_{50}$ [mol/l] |
| --- | --- |
| 1 | 1.8E−06 |
| 2 | 4.2E−06 |
| 3 | 3.0E−06 |
| 4 | 7.3E−07 |
| 5 | 1.2E−06 |
| 6 | 6.8E−07 |
| 7 | 8.3E−07 |
| 8 | 4.1E−06 |
| 9 | 1.3E−06 |
| 10 | 6.5E−06 |
| 11 | 1.8E−06 |
| 12 | 2.0E−06 |
| 13 | 5.9E−07 |
| 14 | 3.5E−07 |
| 15 | 1.6E−05 |
| 16 | 9.8E−06 |
| 17 | 6.0E−06 |
| 18 | 1.5E−07 |
| 19 | 5.1E−08 |
| 20 | 3.4E−07 |
| 21 | 2.8E−07 |
| 22 | 2.1E−07 |
| 23 | 2.8E−07 |
| 24 | 3.8E−06 |
| 25 | 2.2E−06 |
| 26 | 1.4E−07 |
| 27 | 1.1E−07 |
| 28 | 4.1E−08 |
| 29 | 3.1E−07 |
| 30 | 9.2E−08 |
| 31 | 5.5E−06 |
| 32 | 5.1E−07 |
| 33 | 2.0E−07 |
| 34 | 9.5E−07 |
| 35 | 2.6E−07 |

TABLE 1-continued

SAC-Formation - Nocodazole-Induced Assay

| Example No. | $IC_{50}$ [mol/l] |
| --- | --- |
| 36 | 1.6E−06 |
| 37 | 2.4E−06 |
| 38 | 6.9E−07 |
| 39 | 1.3E−06 |
| 40 | 4.5E−08 |
| 41 | 1.6E−07 |
| 42 | 2.6E−07 |
| 43 | 3.4E−08 |
| 44 | 2.0E−07 |
| 45 | 5.4E−08 |
| 46 | 6.1E−08 |
| 47 | 9.2E−08 |
| 48 | 1.3E−07 |
| 49 | 3.5E−07 |
| 50 | 5.6E−08 |
| 51 | 3.9E−08 |
| 52 | 3.4E−08 |
| 53 | 3.4E−07 |
| 54 | 1.9E−08 |
| 55 | 2.2E−07 |
| 56 | 6.7E−08 |
| 57 | 5.2E−07 |
| 58 | 2.8E−07 |
| 59 | 2.6E−07 |
| 60 | 4.0E−08 |
| 61 | 3.1E−07 |
| 62 | 8.2E−09 |
| 63 | 1.8E−07 |
| 64 | 9.7E−08 |
| 65 | 2.1E−07 |
| 66 | 3.7E−08 |
| 67 | 1.2E−08 |
| 68 | 4.9E−08 |
| 69 | 4.8E−08 |
| 70 | 9.9E−08 |
| 71 | 9.4E−08 |
| 72 | 3.5E−07 |
| 73 | 2.3E−07 |
| 74 | 2.9E−08 |
| 75 | 8.1E−08 |
| 76 | 5.2E−08 |
| 77 | 1.8E−08 |
| 78 | 3.9E−07 |
| 79 | 1.4E−07 |
| 80 | 1.9E−06 |
| 81 | 9.7E−09 |
| 82 | 2.1E−08 |
| 83 | 7.0E−09 |
| 84 | 5.8E−08 |
| 85 | 6.2E−09 |
| 86 | 5.3E−07 |
| 87 | 5.9E−07 |
| 88 | 8.2E−07 |
| 89 | 1.4E−06 |
| 90 | 4.2E−06 |
| 91 | 4.2E−06 |
| 92 | 1.2E−06 |
| 93 | 1.4E−06 |
| 94 | 8.1E−08 |
| 95 | 2.6E−07 |
| 96 | 1.2E−06 |
| 97 | 5.9E−06 |
| 98 | 3.0E−06 |
| 99 | 2.0E−05 |
| 100 | 5.5E−06 |
| 101 | 1.8E−06 |
| 102 | 2.2E−07 |
| 103 | 2.4E−07 |
| 104 | 5.3E−07 |
| 105 | 2.0E−06 |
| 106 | 2.6E−07 |
| 107 | 3.4E−07 |
| 108 | 1.8E−06 |
| 109 | 1.1E−06 |
| 110 | 6.5E−07 |
| 111 | 2.0E−07 |

TABLE 1-continued

SAC-Formation - Nocodazole-Induced Assay

| Example No. | IC$_{50}$ [mol/l] |
|---|---|
| 112 | 1.8E−08 |
| 113 | 4.7E−07 |
| 114 | 3.1E−08 |
| 115 | 9.0E−08 |
| 116 | 1.6E−06 |
| 117 | 2.7E−07 |
| 118 | 6.0E−08 |
| 119 | 8.8E−08 |
| 120 | 2.7E−07 |
| 121 | 1.3E−07 |
| 122 | 5.9E−08 |
| 123 | 2.2E−07 |
| 124 | 1.8E−05 |
| 125 | >2.0E−05 |
| 126 | 1.9E−05 |
| 127 | >2.0E−05 |
| 128 | 1.3E−05 |
| 129 | 1.4E−05 |
| 130 | >2.0E−05 |
| 131 | 1.1E−05 |
| 132 | 1.4E−05 |
| 133 | 1.5E−05 |
| 134 | >2.0E−05 |
| 135 | 1.6E−05 |
| 136 | 6.8E−06 |
| 137 | >2.0E−05 |
| 138 | 1.7E−05 |
| 139 | >2.0E−05 |
| 140 | >2.0E−05 |
| 141 | 1.9E−05 |
| 142 | 1.4E−05 |
| 143 | >2.0E−05 |
| 144 | >2.0E−05 |
| 145 | 7.2E−06 |
| 146 | 1.4E−06 |
| 147 | 1.3E−05 |
| 148 | >2.0E−05 |
| 149 | 4.1E−06 |
| 150 | 1.6E−05 |
| 151 | 1.7E−06 |
| 152 | >2.0E−05 |
| 153 | 1.5E−06 |
| 154 | 4.3E−06 |
| 155 | 5.8E−06 |
| 156 | 5.5E−07 |
| 157 | 2.8E−06 |
| 158 | 4.2E−06 |
| 159 | 1.5E−05 |
| 160 | 2.6E−06 |
| 161 | 1.5E−05 |
| 162 | >2.0E−05 |
| 163 | 1.3E−06 |

SAC-Formation—Paclitaxel-Induced Assay

Cultivated cells of the human cervical tumor cell line HeLa (ATCC CCL-2) were plated at a density of 1000 cells/well in a 1536-well microtiter plate in 2 µl PAA Ham's F12 Medium supplemented with 1% (v/v) glutamine, 1% (v/v) penicillin, 1% (v/v) streptomycin and 10% (v/v) fetal calf serum. After incubation overnight at 37° C., 10 µl/well paclitaxel at a final concentration of 0.05 µM were added to cells. Test compounds solubilized in dimethyl sulfoxide (DMSO) were added at various concentrations (0 µM, as well as in the range of 0.005 µM-20 µM; the final concentration of the solvent DMSO was 0.5% (v/v)). Cells were incubated for 24 h at 37° C. in the presence of test compounds in combination with paclitaxel. Thereafter, cells were fixed in 4% (v/v) paraformaldehyde in phosphate buffered saline (PBS) at 4° C. overnight then permeabilized in 0.1% (v/v) Triton X™ 100 in PBS at room temperature for 20 min and blocked in 0.5% (v/v) bovine serum albumin (BSA) in PBS at room temperature for 15 min. After washing with PBS, 5 µl/well antibody solution (anti-phospho-histone H3 clone 3H10, FITC; Millipore, Cat #16-222; 1:1000 dilution) was added to cells, which were incubated for 2 h at room temperature. Afterwards, cells were washed with PBS and 5 µl/well solution of HOECHST 33342 dye (5 µg/ml) was added to cells and cells were incubated 15 min at room temperature in the dark. Cells were washed twice with PBS then covered with PBS and stored at 4° C. until analysis. Images were acquired with a PERKIN ELMER OPERA™ High-Content Analysis reader. Images were analyzed with image analysis software MetaXpress™ from Molecular devices utilizing the Mitotic Index application module. In this assay both labels HOECHST 33342 and phosphorylated Histone H3 on serine 10 were measured. HOECHST 33342 labels the DNA and is used to count the cell number. The staining of phosphorylated Histone H3 on serine 10 determines the number of mitotic cells. After 24 h incubation, inhibition of SAC in presence of paclitaxel decreases the number of mitotic cells indicating an inappropriate mitotic progression. Otherwise cells were arrested at G2/M phase of the cell cycle progression. The raw assay data were further analyzed by four-parametric hill equation using Genedata's Assay Analyzer and Condoseo software.

TABLE 2

SAC-Formation - Paclitaxel-Induced Assay

| Example No. | IC$_{50}$ [mol/l] |
|---|---|
| 1 | 4.9E−06 |
| 2 | 1.1E−05 |
| 3 | 5.1E−06 |
| 4 | 1.7E−06 |
| 5 | >2.0E−05 |
| 6 | 1.2E−06 |
| 7 | 2.5E−06 |
| 8 | 1.8E−05 |
| 9 | 3.0E−06 |
| 10 | 1.1E−05 |
| 11 | 2.9E−06 |
| 12 | 6.9E−06 |
| 13 | 2.1E−06 |
| 14 | 7.6E−07 |
| 15 | >2.0E−05 |
| 16 | >2.0E−05 |
| 17 | 1.9E−05 |
| 18 | 2.0E−06 |
| 19 | 1.4E−07 |
| 20 | 4.0E−07 |
| 21 | 3.6E−06 |
| 22 | 2.6E−07 |
| 23 | 5.0E−07 |
| 24 | 8.5E−06 |
| 25 | 1.2E−06 |
| 26 | 2.5E−07 |
| 27 | 1.7E−07 |
| 28 | 7.2E−08 |
| 29 | 7.0E−07 |
| 30 | 3.2E−07 |
| 31 | >2.0E−05 |
| 32 | 1.2E−06 |
| 33 | 7.3E−07 |
| 34 | 1.6E−06 |
| 35 | 4.6E−06 |
| 36 | 3.7E−06 |
| 37 | 5.7E−07 |
| 38 | 5.8E−07 |
| 39 | 1.3E−06 |
| 40 | 1.2E−07 |
| 41 | 8.1E−07 |
| 42 | 8.9E−07 |
| 43 | 1.1E−06 |
| 44 | 4.9E−07 |
| 45 | 1.4E−07 |

TABLE 2-continued

SAC-Formation - Paclitaxel-Induced Assay

| Example No. | IC$_{50}$ [mol/l] |
|---|---|
| 46 | 3.4E−08 |
| 47 | 6.3E−08 |
| 48 | 1.4E−07 |
| 49 | 9.6E−07 |
| 50 | 2.8E−08 |
| 51 | 3.5E−08 |
| 52 | 1.6E−08 |
| 53 | 5.9E−07 |
| 54 | 3.0E−08 |
| 55 | 4.6E−07 |
| 56 | 2.5E−07 |
| 57 | 3.9E−07 |
| 58 | 2.9E−07 |
| 59 | 2.6E−07 |
| 60 | 4.2E−08 |
| 61 | 3.4E−07 |
| 62 | 3.3E−08 |
| 63 | 3.6E−07 |
| 64 | 1.1E−07 |
| 65 | 6.9E−07 |
| 66 | 9.0E−08 |
| 67 | 2.2E−07 |
| 68 | 3.0E−08 |
| 69 | 1.0E−08 |
| 70 | 9.4E−07 |
| 71 | 8.4E−08 |
| 72 | 2.0E−05 |
| 73 | 6.3E−08 |
| 74 | 3.1E−08 |
| 75 | 5.8E−08 |
| 76 | 1.3E−08 |
| 77 | 8.3E−09 |
| 78 | 9.1E−07 |
| 79 | 1.5E−07 |
| 80 | 4.7E−06 |
| 81 | 1.6E−08 |
| 82 | 7.7E−08 |
| 83 | 9.3E−09 |
| 84 | 6.5E−08 |
| 85 | 5.2E−08 |
| 86 | 4.9E−07 |
| 87 | 3.5E−07 |
| 88 | 1.1E−06 |
| 89 | 2.3E−06 |
| 90 | 2.3E−06 |
| 91 | 1.4E−06 |
| 92 | 5.6E−06 |
| 93 | 8.0E−06 |
| 94 | 5.6E−06 |
| 95 | 5.1E−07 |
| 96 | 1.4E−06 |
| 97 | 8.1E−06 |
| 98 | 7.9E−06 |
| 99 | 3.0E−07 |
| 100 | 3.4E−06 |
| 101 | 1.5E−06 |
| 102 | 7.9E−07 |
| 103 | 8.2E−07 |
| 104 | 7.5E−06 |
| 105 | 2.0E−05 |
| 106 | 3.2E−07 |
| 107 | 2.1E−07 |
| 108 | 2.0E−05 |
| 109 | 1.9E−06 |
| 110 | 3.8E−06 |
| 111 | 1.8E−06 |
| 112 | 5.7E−08 |
| 113 | 1.0E−06 |
| 114 | 1.2E−07 |
| 115 | 1.2E−07 |
| 116 | 4.8E−06 |
| 117 | 2.0E−06 |
| 118 | 5.6E−08 |
| 119 | 2.5E−06 |
| 120 | 1.2E−06 |
| 121 | 7.5E−07 |
| 122 | 8.8E−07 |

SAC-Multilobed Assay

Cultivated cells of the human cervical tumor cell line HeLa (ATCC CCL-2) were plated at a density of 1000 cells/well in a 1536-well microtiter plate in 2 µl PAA Ham's F12 Medium supplemented with 1% (v/v) glutamine, 1% (v/v) penicillin, 1% (v/v) streptomycin and 10% (v/v) fetal calf serum. After incubation overnight at 37° C., 10 µl/well nocodazole at a final concentration of 0.1 µg/ml were added to cells. Test compounds solubilized in dimethyl sulfoxide (DMSO) were added at various concentrations (0 µM, as well as in the range of 0.005 µM-20 µM; the final concentration of the solvent DMSO was 0.5% (v/v)). Cells were incubated for 24 h at 37° C. in the presence of test compounds in combination with nocodazole. Thereafter, cells were fixed in 4% (v/v) paraformaldehyde in phosphate buffered saline (PBS) at 4° C. overnight then permeabilized in 0.1% (v/v) Triton X™ 100 in PBS at room temperature for 20 min and blocked in 0.5% (v/v) bovine serum albumin (BSA) in PBS at room temperature for 15 min. Afterwards, cells were washed with PBS and 5 µl/well solution of HOECHST 33342 dye (5 µg/ml) was added to cells and cells were incubated 15 min at room temperature in the dark. Cells were washed twice with PBS then covered with PBS and stored at 4° C. until analysis. Images were acquired with a PERKIN ELMER OPERA™ High-Content Analysis reader. Images were analyzed with image analysis software MetaXpress™ from Molecular devices utilizing an image analysis routine that quantifies number of nuclei showing a multilobed shape. This number was related to the number of all nuclei counted with Count Nuclei application module resulting in a multilobed index. In this assay nuclei were identified via DNA staining with HOECHST 33342. After 24 h incubation, inhibition of SAC in presence of nocodazole increases the multilobed index i.e. number of nuclei with a multilobed shape related to all nuclei indicating an inappropriate mitotic progression. The raw assay data were further analyzed by four-parametric hill equation using Genedata's Assay Analyzer and Condoseo software.

SAC-Abrogation Assay

HeLa (cervical tumor; ATCC CCL-2) cells were plated at a density of 1000 cells/well in a 1536 well microtiter plate in 2 µl growth medium. After incubation overnight at 37° C., 2 µl/well nocodazole at a final concentration of 0.1 µg/ml was added to cells. After 24 h incubation, cells are arrested at G2/M phase of the cell cycle progression. Test compounds solubilized in DMSO were added at various concentrations (0 µM, as well as in the range of 0.005 µM-10 µM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilized in 0.1% (v/v) Triton X™ 100 in PBS at room temperature for 20 min and blocked in 0.5% (v/v) bovine serum albumin (BSA) in PBS at room temperature for 15 min. After washing with PBS, 5 µl/well antibody solution (anti-phospho-histone H3 clone 3H10, FITC; Millipore, Cat #16-222; 1:1000 dilution) was added to cells, which were incubated for 2 h at room temperature. Afterwards, cells were washed with PBS and 5 µl/well solution of HOECHST 33342 dye (5 µg/ml) was added to cells and cells were incubated 15 min at room temperature in the dark. Cells were washed twice with PBS then covered with PBS and stored at 4° C. until analysis. Images were acquired with a PERKIN ELMER OPERA™ High-Content Analysis reader. Images were analyzed with image analysis software MetaXpress™ from Molecular devices utilizing the Mitotic Index application module. In this assay both labels HOECHST 33342 and phosphorylated Histone H3 on serine 10 were measured. HOECHST 33342 labels the DNA and is used to count the cell number. The staining of phosphorylated Histone H3 on serine 10 determines the number of mitotic cells. After 24 h incubation, inhibition of SAC in presence of paclitaxel decreases the number of mitotic cells indicating an inappropriate mitotic progression. Otherwise cells were arrested at G2/M phase of the cell cycle progression. The raw assay data were further analyzed by four-parametric hill equation using Genedata's Assay Analyzer and Condoseo software.

M-Arrest-Assay

HeLa (cervical tumor; ATCC CCL-2) cells were plated at a density of 1000 cells/well in a 1536 well microtiter plate in 2 µl growth medium. After incubation overnight at 37° C., test compounds solubilized in DMSO were added at various concentrations (0 µM, as well as in the range of 0.005 µM-10 µM; the final concentration of the solvent DMSO was 0.5% (v/v)). Cells were incubated for 24 h at 37° C. in the presence of test compounds. Thereafter, cells were fixed in 4% (v/v) paraformaldehyde in phosphate buffered saline (PBS) at 4° C. overnight then permeabilized in 0.1% (v/v) Triton X™ 100 in PBS at room temperature for 20 min and blocked in 0.5% (v/v) bovine serum albumin (BSA) in PBS at room temperature for 15 min. After washing with PBS, 5 µl/well antibody solution (anti-phospho-histone H3 clone 3H10, FITC; Millipore, Cat #16-222; 1:1000 dilution) was added to cells, which were incubated for 2 h at room temperature. Afterwards, cells were washed with PBS and 5 µl/well solution of HOECHST 33342 dye (5 µg/ml) was added to cells and cells were incubated 15 min at room temperature in the dark. Cells were washed twice with PBS then covered with PBS and stored at 4° C. until analysis. Images were acquired with a PERKIN ELMER OPERA™ High-Content Analysis reader. Images were analyzed with image analysis software MetaXpress™ from Molecular devices utilizing the Mitotic Index application module. In this assay both labels HOECHST 33342 and phosphorylated Histone H3 on serine 10 were measured. HOECHST 33342 labels the DNA and is used to count the cell number. The staining of phosphorylated Histone H3 on serine 10 determines the number of mitotic cells. After 24 h incubation, the majority of the cells have entered mitosis. A compound that is able to arrest cells in M-phase will increase the number of nuclei with phosphorylated histone H3 on serine 10, which will be reflected by an increase of the Mitotic Index. The assay was used to exclude compounds that lead to a considerable G2/M-arrest after 24 h incubation. The raw assay data were further analyzed by four-parametric hill equation using Genedata's Assay Analyzer and Condoseo software.

Induction of Cellular Multinucleation by SAC Inhibition

An abnormal mitosis by abrogating the mitotic spindle checkpoint can result in polyploidy and multi-nucleation in cells. Inhibition of SAC function by competent compounds impairs checkpoint activity and induces failures during cytokinesis. This is consequently associated with nuclear enlargement, multilobulation of nuclei and multinucleated cells resulting in extreme cellular phenotypes after several cell cycle turns with blocked SAC activity as depicted. Osteosarcoma cells U-2 OS (ATCC: HTB-96) were plated at a density of 2500 cells/well in a 384 well microtiter plate in 20 µl growth medium. After incubation overnight at 37° C., 20 µl/well SAC inhibitors at varying concentrations were added to cells in triplicates. Cells were incubated for 0 h, 24 h, 48 h and 72 h at 37° C. in the presence of test compounds.

Thereafter, cells were fixed, then permeabilized and blocked. Nuclei were marked by a DNA label and alpha-tubulin structures were detected by antibody labeling. Images were acquired with a PERKIN ELMER OPERA™ High-Content Analysis reader. The images were used for a qualitative assessment of the multinucleation state in tested cells after SAC inhibition.

CDK2/CycE Kinase Assay

CDK2/CycE-inhibitory activity of compounds of the present invention was quantified employing the CDK2/CycE TR-FRET assay as described in the following paragraphs.

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.25 µM=>final conc. in the 5 µl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/ml. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit.

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence biotin-Ahx-PWDPDDADITEILG (C-terminus in amide form, purchased from Biosyntan GmbH, Berlin) was used.

For the assay 50 nl of a 100-fold concentrated solution of the test compound in DMSO was pipetted into a black low volume 384 well microtiter plate (Greiner Bio-One, Frickenhausen, Germany), 2 µl of a solution of Mps-1 in assay buffer [0.1 mM sodium-ortho-vanadate, 10 mM $MgCl_2$, 2 mM DTT, 25 mM Hepes pH 7.7, 0.05% BSA (w/v), 0.001% Pluronic F-127] were added and the mixture was incubated for 15 min at 22° C. to allow pre-binding of the test compounds to Mps-1 before the start of the kinase reaction. Then the kinase reaction was started by the addition of 3 µl of a solution of 16.7 µM adenosine-tri-phosphate (ATP, 16.7 µM=>final conc. in the 5 µl assay volume is 10 µM) and peptide substrate (1.67 µM=>final conc. in the 5 µl assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 0.5 nM (final conc. in the 5 µl assay volume). The reaction was stopped by the addition of 5 µl of a solution of TR-FRET detection reagents (100 mM Hepes pH 7.4, 0.1% BSA, 40 mM EDTA, 140 nM Streptavidin-XLent [#61GSTXLB, Fa. Cis Biointernational, Marcoule, France], 1.5 nM anti-phospho(Ser/Thr)-Europium-antibody [#AD0180, PerkinElmer LAS, Rodgau-Jugesheim, Germany]. Instead of the 1.5 nM anti-phospho(Ser/Thr)-Europium-antibody a mixture of 2 nM unlabeled anti-phospho ser/thr-pro antibody MPM-2 [Millipore cat. #05-368] and 1 nM LANCE EU-W1024 labeled anti-mouse IgG antibody [Perkin-Elmer, product no. AD0077] can be used).

The resulting mixture was incubated 1 h at 22° C. to allow the binding of the phosphorylated peptide to the anti-phospho(Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jugesheim, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit.

Bub1 Kinase Assay

Bub1-inhibitory activity of compounds of the present invention was quantified employing the Bub1 TR-FRET assay as described in the following paragraphs.

N-terminally His6-tagged recombinant catalytic domain of human Bub1 (amino acids 704-1085), expressed in insect cells (Hi5) and purified by Ni-NTA affinity chromatography and subsequent size exclusion chromatography, was used as enzyme. As substrate for the kinase reaction the biotinylated peptide biotin-Ahx-VLLPKKSFAEPG (C-terminus in amid form) was used which can be purchased e.g. form the company Biosyntan (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of Bub1 in aqueous assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Bub1 was adjusted depending of the activity of the enzyme lot and was chosen appropriate to have the assay in the linear range, typical concentrations were in the range of 200 ng/ml. The reaction was stopped by the addition of 5 µl of a solution of TR-FRET detection reagents (0.2 µM streptavidine-XL665 [Cisbio Bioassays, Codolet, France] and 1 nM anti-phosho-Serine antibody [Merck Millipore, cat. #35-001] and 0.4 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (50 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar or Pherastar (both from BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit.

TABLE 3

$IC_{50}$ data for Bub1, CDK2 and Mps1 kinase assays

| Example No. | Bub1 avg ($IC_{50}$ [mol/l]) | CDK2 avg ($IC_{50}$ [mol/l]) | Mps1 avg ($IC_{50}$ [mol/l]) |
| --- | --- | --- | --- |
| 1 | >2.00E−05 | >2.00E−05 | >2.00E−05 |
| 2 | >2.00E−05 | >2.00E−05 | >2.00E−05 |
| 3 | >2.00E−05 | >2.00E−05 | >2.00E−05 |
| 4 | >2.00E−05 | >2.00E−05 | >2.00E−05 |
| 5 | >2.00E−05 | >2.00E−05 | >2.00E−05 |
| 6 | >2.00E−05 | >2.00E−05 | >2.00E−05 |
| 7 | >2.00E−05 | >2.00E−05 | >2.00E−05 |
| 8 | >2.00E−05 | >2.00E−05 | >2.00E−05 |
| 9 | >2.00E−05 | >2.00E−05 | >2.00E−05 |
| 10 | >2.00E−05 | >2.00E−05 | >2.00E−05 |
| 11 | 3.80E−06 | >2.00E−05 | >2.00E−05 |
| 12 | >2.00E−05 | >2.00E−05 | >2.00E−05 |
| 13 | >2.00E−05 | >2.00E−05 | >2.00E−05 |
| 14 | 8.59E−06 | >2.00E−05 | >2.00E−05 |
| 15 | >2.00E−05 | >2.00E−05 | >2.00E−05 |
| 16 | >2.00E−05 | >2.00E−05 | >2.00E−05 |
| 17 | >2.00E−05 | >2.00E−05 | >2.00E−05 |
| 18 | >2.00E−05 | >2.00E−05 | >2.00E−05 |
| 19 | >2.00E−05 | >2.00E−05 | >2.00E−05 |
| 20 | >2.00E−05 | >2.00E−05 | >2.00E−05 |
| 21 | >2.00E−05 | >2.00E−05 | >2.00E−05 |
| 22 | >2.00E−05 | >2.00E−05 | >2.00E−05 |
| 23 | >2.00E−05 | >2.00E−05 | >2.00E−05 |
| 24 | 3.10E−06 | >2.00E−05 | >2.00E−05 |
| 25 | >2.00E−05 | >2.00E−05 | >2.00E−05 |
| 26 | >2.00E−05 | >2.00E−05 | >2.00E−05 |
| 27 | >2.00E−05 | >2.00E−05 | >2.00E−05 |
| 28 | >2.00E−05 | >2.00E−05 | >2.00E−05 |
| 29 | >2.00E−05 | >2.00E−05 | >2.00E−05 |
| 30 | >2.00E−05 | >2.00E−05 | >2.00E−05 |
| 31 | >2.00E−05 | >2.00E−05 | >2.00E−05 |
| 32 | >2.00E−05 | >2.00E−05 | >2.00E−05 |
| 33 | >2.00E−05 | >2.00E−05 | >2.00E−05 |
| 34 | >2.00E−05 | >2.00E−05 | >2.00E−05 |
| 35 | >2.00E−05 | >2.00E−05 | >2.00E−05 |
| 36 | | >2.00E−05 | >2.00E−05 |
| 37 | >2.00E−05 | >2.00E−05 | >2.00E−05 |
| 38 | >2.00E−05 | >2.00E−05 | >2.00E−05 |
| 39 | >2.00E−05 | >2.00E−05 | >2.00E−05 |
| 40 | >2.0E−05 | >2.0E−05 | >2.0E−05 |
| 41 | >2.0E−05 | >2.0E−05 | >2.0E−05 |
| 42 | >2.0E−05 | >2.0E−05 | >2.0E−05 |
| 43 | >2.0E−05 | >2.0E−05 | >2.0E−05 |
| 44 | >2.0E−05 | >2.0E−05 | >2.0E−05 |
| 45 | >2.0E−05 | >2.0E−05 | >2.0E−05 |
| 46 | >2.0E−05 | >2.0E−05 | >2.0E−05 |
| 47 | >2.0E−05 | >2.0E−05 | >2.0E−05 |
| 48 | >2.0E−05 | >2.0E−05 | >2.0E−05 |
| 49 | >2.0E−05 | >2.0E−05 | >2.0E−05 |
| 50 | >2.0E−05 | >2.0E−05 | >2.0E−05 |
| 51 | >2.0E−05 | >2.0E−05 | >2.0E−05 |
| 52 | >2.0E−05 | >2.0E−05 | >2.0E−05 |
| 53 | >2.0E−05 | >2.0E−05 | >2.0E−05 |
| 54 | >2.0E−05 | >2.0E−05 | >2.0E−05 |
| 55 | >2.0E−05 | >2.0E−05 | >2.0E−05 |
| 56 | >2.0E−05 | >2.0E−05 | >2.0E−05 |
| 57 | >2.0E−05 | >2.0E−05 | 1.8E−05 |
| 58 | >2.0E−05 | >2.0E−05 | 1.9E−05 |
| 59 | >2.0E−05 | >2.0E−05 | >2.0E−05 |
| 60 | >2.0E−05 | >2.0E−05 | >2.0E−05 |
| 61 | >2.0E−05 | >2.0E−05 | >2.0E−05 |
| 62 | >2.0E−05 | 6.5E−06 | >2.0E−05 |
| 63 | >2.0E−05 | >2.0E−05 | >2.0E−05 |
| 64 | 1.5E−05 | 8.4E−06 | >2.0E−05 |
| 65 | >2.0E−05 | >2.0E−05 | >2.0E−05 |
| 66 | >2.0E−05 | >2.0E−05 | >2.0E−05 |
| 67 | >2.0E−05 | | |
| 68 | >2.0E−05 | >2.0E−05 | >2.0E−05 |
| 69 | >2.0E−05 | >2.0E−05 | >2.0E−05 |
| 70 | 1.7E−06 | >2.0E−05 | >2.0E−05 |
| 71 | >2.0E−05 | 8.6E−06 | >2.0E−05 |
| 72 | >2.0E−05 | >2.0E−05 | >2.0E−05 |
| 73 | 6.2E−06 | >2.0E−05 | >2.0E−05 |
| 74 | >2.0E−05 | >2.0E−05 | >2.0E−05 |
| 75 | >2.0E−05 | >2.0E−05 | >2.0E−05 |
| 76 | >2.0E−05 | >2.0E−05 | >2.0E−05 |
| 77 | >2.0E−05 | >2.0E−05 | >2.0E−05 |
| 78 | >2.0E−05 | >2.0E−05 | 1.6E−05 |
| 79 | >2.0E−05 | >2.0E−05 | >2.0E−05 |
| 80 | >2.0E−05 | >2.0E−05 | >2.0E−05 |
| 81 | >2.0E−05 | >2.0E−05 | >2.0E−05 |
| 82 | 1.5E−05 | | >2.0E−05 |
| 83 | >2.0E−05 | >2.0E−05 | >2.0E−05 |
| 84 | >2.0E−05 | >2.0E−05 | >2.0E−05 |
| 85 | >2.0E−05 | >2.0E−05 | >2.0E−05 |
| 86 | >2.0E−05 | >2.0E−05 | >2.0E−05 |
| 87 | 1.1E−05 | >2.0E−05 | |
| 88 | 1.7E−05 | >2.0E−05 | |
| 89 | 2.1E−07 | >2.0E−05 | >2.0E−05 |
| 90 | >2.0E−05 | >2.0E−05 | >2.0E−05 |
| 91 | >2.0E−05 | >2.0E−05 | |
| 92 | >2.0E−05 | >2.0E−05 | >2.0E−05 |
| 93 | >2.0E−05 | >2.0E−05 | >2.0E−05 |
| 94 | >2.0E−05 | >2.0E−05 | >2.0E−05 |
| 95 | >2.0E−05 | >2.0E−05 | >2.0E−05 |
| 96 | >2.0E−05 | >2.0E−05 | >2.0E−05 |
| 97 | >2.0E−05 | >2.0E−05 | >2.0E−05 |
| 98 | >2.0E−05 | >2.0E−05 | 1.8E−05 |
| 99 | >2.0E−05 | >2.0E−05 | >2.0E−05 |
| 100 | >2.0E−05 | >2.0E−05 | >2.0E−05 |
| 101 | >2.0E−05 | >2.0E−05 | >2.0E−05 |
| 102 | >2.0E−05 | >2.0E−05 | >2.0E−05 |
| 103 | >2.0E−05 | >2.0E−05 | >2.0E−05 |
| 104 | >2.0E−05 | >2.0E−05 | >2.0E−05 |
| 105 | >2.0E−05 | >2.0E−05 | 1.2E−05 |
| 106 | >2.0E−05 | >2.0E−05 | >2.0E−05 |
| 107 | >2.0E−05 | >2.0E−05 | >2.0E−05 |
| 108 | >2.0E−05 | >2.0E−05 | >2.0E−05 |
| 109 | >2.0E−05 | >2.0E−05 | >2.0E−05 |
| 110 | >2.0E−05 | >2.0E−05 | >2.0E−05 |
| 111 | >2.0E−05 | >2.0E−05 | |
| 112 | >2.0E−05 | >2.0E−05 | >2.0E−05 |
| 113 | >2.0E−05 | >2.0E−05 | >2.0E−05 |
| 114 | >2.0E−05 | >2.0E−05 | >2.0E−05 |
| 115 | >2.0E−05 | >2.0E−05 | >2.0E−05 |
| 116 | >2.0E−05 | >2.0E−05 | 3.6E−06 |
| 117 | >2.0E−05 | >2.0E−05 | >2.0E−05 |
| 118 | >2.0E−05 | >2.0E−05 | >2.0E−05 |
| 119 | >2.0E−05 | >2.0E−05 | >2.0E−05 |
| 120 | >2.0E−05 | >2.0E−05 | >2.0E−05 |
| 121 | >2.0E−05 | >2.0E−05 | >2.0E−05 |
| 122 | >2.0E−05 | >2.0E−05 | >2.0E−05 |

Kinase Profiling (KINOMEscan™)

The KINOMEscan™ screening platform offered as a service by DiscoveRx Corporation (42501 Albrae Street, Fremont, Calif. 94538-3142, USA) employs an active site-directed competition binding assay to quantitatively measure interactions between test compounds and more than 450 human kinases and disease relevant mutant variants. Compounds that bind the kinase active site and directly (sterically) or indirectly (allosterically) prevent kinase binding to the immobilized ligand, will reduce the amount of kinase captured on the solid support. Conversely, test molecules that do not bind the kinase have no effect on the amount of kinase captured on the solid support. Screening "hits" are identified by measuring the amount of kinase captured in test versus control samples by using a quantitative, precise and ultra-sensitive qPCR method that detects the associated DNA label attached to the kinase. In a similar manner, dissociation constants (Kds) for test compound/kinase interactions are calculated by measuring the amount of kinase captured on the solid support as a function of the test compound concentration. The compounds of the present invention were tested at DiscoveRx Corporation (42501 Albrae Street, Fremont, Calif. 94538-3142, USA) using the following protocol (also described in Fabian et al. A small molecule-kinase interaction map for clinical kinase inhibitors. Nat. Biotechnol. 23, 329-336 (2005) and Karaman, M. W. et al. A quantitative analysis of kinase inhibitor selectivity. Nat. Biotechnol. 26, 127-132 (2008))

For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR. The compounds were tested at the indicated concentration, and results for primary screen binding interactions are reported as '% Ctrl', where lower numbers indicate stronger inhibition. The calculation of % Ctrl values is given by the following equation: 100× (test compound signal−positive control signal)/(negative control signal−positive control signal) with negative control being DMSO and positive control being a control compound for the respective kinases.

TABLE 4

Data from profiling of Example 20 against a total of 456 kinases (of these 395 non-mutant kinases).

| KINOMEscan Gene Symbol | Entrez Gene ID | Example 20 % Ctrl @ 10 μM |
|---|---|---|
| AAK1 | 22848 | 68 |
| ABL1(E255K)-phosphorylated | 25 | 100 |
| ABL1(F317I)-nonphosphorylated | 25 | 100 |
| ABL1(F317I)-phosphorylated | 25 | 86 |
| ABL1(F317L)-nonphosphorylated | 25 | 100 |
| ABL1(F317L)-phosphorylated | 25 | 100 |
| ABL1(H396P)-nonphosphorylated | 25 | 100 |
| ABL1(H396P)-phosphorylated | 25 | 92 |
| ABL1(M351T)-phosphorylated | 25 | 90 |
| ABL1(Q252H)-nonphosphorylated | 25 | 100 |
| ABL1(Q252H)-phosphorylated | 25 | 100 |
| ABL1(T315I)-nonphosphorylated | 25 | 100 |
| ABL1(T315I)-phosphorylated | 25 | 87 |
| ABL1(Y253F)-phosphorylated | 25 | 100 |
| ABL1-nonphosphorylated | 25 | 100 |
| ABL1-phosphorylated | 25 | 100 |
| ABL2 | 27 | 100 |
| ACVR1 | 90 | 77 |
| ACVR1B | 91 | 100 |
| ACVR2A | 92 | 94 |
| ACVR2B | 93 | 91 |
| ACVRL1 | 94 | 100 |
| ADCK3 | 56997 | 64 |
| ADCK4 | 79934 | 100 |
| AKT1 | 207 | 100 |
| AKT2 | 208 | 90 |
| AKT3 | 10000 | 100 |
| ALK | 238 | 77 |
| ALK(C1156Y) | 238 | 100 |
| ALK(L1196M) | 238 | 100 |
| AMPK-alpha1 | 5562 | 92 |
| AMPK-alpha2 | 5563 | 100 |
| ANKK1 | 255239 | 100 |
| ARK5 | 9891 | 85 |
| ASK1 | 4217 | 90 |
| ASK2 | 9064 | 73 |
| AURKA | 6790 | 100 |
| AURKB | 9212 | 100 |
| AURKC | 6795 | 73 |
| AXL | 558 | 90 |
| BIKE | 55589 | 62 |
| BLK | 640 | 100 |
| BMPR1A | 657 | 100 |
| BMPR1B | 658 | 95 |
| BMPR2 | 659 | 100 |
| BMX | 660 | 95 |
| BRAF | 673 | 82 |
| BRAF(V600E) | 673 | 100 |
| BRK | 5753 | 55 |
| BRSK1 | 84446 | 90 |
| BRSK2 | 9024 | 100 |
| BTK | 695 | 98 |
| BUB1 | 699 | 100 |
| CAMK1 | 8536 | 68 |
| CAMK1D | 57118 | 87 |
| CAMK1G | 57172 | 86 |
| CAMK2A | 815 | 88 |
| CAMK2B | 816 | 82 |
| CAMK2D | 817 | 89 |
| CAMK2G | 818 | 75 |
| CAMK4 | 814 | 100 |
| CAMKK1 | 84254 | 80 |
| CAMKK2 | 10645 | 74 |
| CASK | 8573 | 87 |
| CDC2L1 | 984 | 92 |
| CDC2L2 | 985 | 85 |
| CDC2L5 | 8621 | 100 |
| CDK11 | 23097 | 100 |
| CDK2 | 1017 | 100 |
| CDK3 | 1018 | 100 |
| CDK4-cyclinD1 | 1019 | 85 |
| CDK4-cyclinD3 | 1019 | 93 |
| CDK5 | 1020 | 100 |
| CDK7 | 1022 | 92 |

TABLE 4-continued

Data from profiling of Example 20 against a total of 456 kinases (of these 395 non-mutant kinases).

| KINOMEscan Gene Symbol | Entrez Gene ID | Example 20 % Ctrl @ 10 μM |
|---|---|---|
| CDK8 | 1024 | 100 |
| CDK9 | 1025 | 100 |
| CDKL1 | 8814 | 100 |
| CDKL2 | 8999 | 100 |
| CDKL3 | 51265 | 66 |
| CDKL5 | 6792 | 100 |
| CHEK1 | 1111 | 73 |
| CHEK2 | 11200 | 100 |
| CIT | 11113 | 80 |
| CLK1 | 1195 | 58 |
| CLK2 | 1196 | 77 |
| CLK3 | 1198 | 74 |
| CLK4 | 57396 | 100 |
| CSF1R | 1436 | 100 |
| CSF1R-autoinhibited | 1436 | 91 |
| CSK | 1445 | 100 |
| CSNK1A1 | 1452 | 92 |
| CSNK1A1L | 122011 | 100 |
| CSNK1D | 1453 | 86 |
| CSNK1E | 1454 | 74 |
| CSNK1G1 | 53944 | 90 |
| CSNK1G2 | 1455 | 95 |
| CSNK1G3 | 1456 | 70 |
| CSNK2A1 | 1457 | 85 |
| CSNK2A2 | 1459 | 100 |
| CTK | 4145 | 61 |
| DAPK1 | 1612 | 88 |
| DAPK2 | 23604 | 73 |
| DAPK3 | 1613 | 72 |
| DCAMKL1 | 9201 | 92 |
| DCAMKL2 | 166614 | 98 |
| DCAMKL3 | 85443 | 100 |
| DDR1 | 780 | 77 |
| DDR2 | 4921 | 100 |
| DLK | 7786 | 94 |
| DMPK | 1760 | 84 |
| DMPK2 | 55561 | 79 |
| DRAK1 | 9263 | 100 |
| DRAK2 | 9262 | 93 |
| DYRK1A | 1859 | 100 |
| DYRK1B | 9149 | 100 |
| DYRK2 | 8445 | 96 |
| EGFR | 1956 | 98 |
| EGFR(E746-A750del) | 1956 | 100 |
| EGFR(G719C) | 1956 | 95 |
| EGFR(G719S) | 1956 | 97 |
| EGFR(L747-E749del, A750P) | 1956 | 94 |
| EGFR(L747-S752del, P753S) | 1956 | 100 |
| EGFR(L747-T751del,Sins) | 1956 | 100 |
| EGFR(L858R) | 1956 | 96 |
| EGFR(L858R,T790M) | 1956 | 96 |
| EGFR(L861Q) | 1956 | 100 |
| EGFR(S752-I759del) | 1956 | 100 |
| EGFR(T790M) | 1956 | 100 |
| EIF2AK1 | 27102 | 100 |
| EPHA1 | 2041 | 95 |
| EPHA2 | 1969 | 88 |
| EPHA3 | 2042 | 95 |
| EPHA4 | 2043 | 100 |
| EPHA5 | 2044 | 99 |
| EPHA6 | 285220 | 85 |
| EPHA7 | 2045 | 100 |
| EPHA8 | 2046 | 96 |
| EPHB1 | 2047 | 96 |
| EPHB2 | 2048 | 77 |
| EPHB3 | 2049 | 82 |
| EPHB4 | 2050 | 96 |
| EPHB6 | 2051 | 92 |
| ERBB2 | 2064 | 77 |
| ERBB3 | 2065 | 99 |
| ERBB4 | 2066 | 100 |
| ERK1 | 5595 | 100 |
| ERK2 | 5594 | 96 |
| ERK3 | 5597 | 68 |
| ERK4 | 5596 | 88 |
| ERK5 | 5598 | 100 |
| ERK8 | 225689 | 82 |
| ERN1 | 2081 | 100 |
| FAK | 5747 | 94 |
| FER | 2241 | 100 |
| FES | 2242 | 94 |
| FGFR1 | 2260 | 94 |
| FGFR2 | 2263 | 80 |
| FGFR3 | 2261 | 85 |
| FGFR3(G697C) | 2261 | 87 |
| FGFR4 | 2264 | 77 |
| FGR | 2268 | 80 |
| FLT1 | 2321 | 74 |
| FLT3 | 2322 | 80 |
| FLT3(D835H) | 2322 | 83 |
| FLT3(D835Y) | 2322 | 100 |
| FLT3(ITD) | 2322 | 67 |
| FLT3(K663Q) | 2322 | 75 |
| FLT3(N841I) | 2322 | 84 |
| FLT3(R834Q) | 2322 | 93 |
| FLT3-autoinhibited | 2322 | 100 |
| FLT4 | 2324 | 87 |
| FRK | 2444 | 66 |
| FYN | 2534 | 57 |
| GAK | 2580 | 96 |
| GCN2(Kin.Dom.2,S808G) | 440275 | 100 |
| GRK1 | 6011 | 100 |
| GRK4 | 2868 | 77 |
| GRK7 | 131890 | 94 |
| GSK3A | 2931 | 68 |
| GSK3B | 2932 | 100 |
| HASPIN | 83903 | 100 |
| HCK | 3055 | 59 |
| HIPK1 | 204851 | 100 |
| HIPK2 | 28996 | 100 |
| HIPK3 | 10114 | 96 |
| HIPK4 | 147746 | 97 |
| HPK1 | 11184 | 60 |
| HUNK | 30811 | 93 |
| ICK | 22858 | 100 |
| IGF1R | 3480 | 100 |
| IKK-alpha | 1147 | 84 |
| IKK-beta | 3551 | 90 |
| IKK-epsilon | 9641 | 100 |
| INSR | 3643 | 98 |
| INSRR | 3645 | 76 |
| IRAK1 | 3654 | 100 |
| IRAK3 | 11213 | 100 |
| IRAK4 | 51135 | 100 |
| ITK | 3702 | 100 |
| JAK1(JH1domain-catalytic) | 3716 | 100 |
| JAK1(JH2domain-pseudokinase) | 3716 | 71 |
| JAK2(JH1domain-catalytic) | 3717 | 100 |
| JAK3(JH1domain-catalytic) | 3718 | 82 |
| JNK1 | 5599 | 100 |
| JNK2 | 5601 | 100 |
| JNK3 | 5602 | 100 |
| KIT | 3815 | 98 |
| KIT(A829P) | 3815 | 94 |
| KIT(D816H) | 3815 | 97 |
| KIT(D816V) | 3815 | 61 |
| KIT(L576P) | 3815 | 100 |
| KIT(V559D) | 3815 | 61 |
| KIT(V559D,T670I) | 3815 | 100 |
| KIT(V559D,V654A) | 3815 | 96 |
| KIT-autoinhibited | 3815 | 100 |
| LATS1 | 9113 | 100 |
| LATS2 | 26524 | 94 |
| LCK | 3932 | 94 |
| LIMK1 | 3984 | 90 |
| LIMK2 | 3985 | 94 |
| LKB1 | 6794 | 100 |
| LOK | 6793 | 100 |

TABLE 4-continued

Data from profiling of Example 20 against a total of 456 kinases (of these 395 non-mutant kinases).

| KINOMEscan Gene Symbol | Entrez Gene ID | Example 20 % Ctrl @ 10 μM |
|---|---|---|
| LRRK2 | 120892 | 95 |
| LRRK2(G2019S) | 120892 | 92 |
| LTK | 4058 | 68 |
| LYN | 4067 | 76 |
| LZK | 9175 | 88 |
| MAK | 4117 | 100 |
| MAP3K1 | 4214 | 84 |
| MAP3K15 | 389840 | 100 |
| MAP3K2 | 10746 | 100 |
| MAP3K3 | 4215 | 100 |
| MAP3K4 | 4216 | 84 |
| MAP4K2 | 5871 | 99 |
| MAP4K3 | 8491 | 83 |
| MAP4K4 | 9448 | 100 |
| MAP4K5 | 11183 | 89 |
| MAPKAPK2 | 9261 | 89 |
| MAPKAPK5 | 8550 | 100 |
| MARK1 | 4139 | 97 |
| MARK2 | 2011 | 83 |
| MARK3 | 4140 | 93 |
| MARK4 | 57787 | 100 |
| MAST1 | 22983 | 67 |
| MEK1 | 5604 | 97 |
| MEK2 | 5605 | 100 |
| MEK3 | 5606 | 100 |
| MEK4 | 6416 | 67 |
| MEK5 | 5607 | 100 |
| MEK6 | 5608 | 95 |
| MELK | 9833 | 100 |
| MERTK | 10461 | 98 |
| MET | 4233 | 100 |
| MET(M1250T) | 4233 | 100 |
| MET(Y1235D) | 4233 | 77 |
| MINK | 50488 | 100 |
| MKK7 | 5609 | 100 |
| MKNK1 | 8569 | 100 |
| MKNK2 | 2872 | 100 |
| MLCK | 91807 | 88 |
| MLK1 | 4293 | 100 |
| MLK2 | 4294 | 78 |
| MLK3 | 4296 | 90 |
| MRCKA | 8476 | 92 |
| MRCKB | 9578 | 61 |
| MST1 | 6789 | 79 |
| MST1R | 4486 | 100 |
| MST2 | 6788 | 100 |
| MST3 | 8428 | 75 |
| MST4 | 51765 | 100 |
| MTOR | 2475 | 100 |
| MUSK | 4593 | 91 |
| MYLK | 4638 | 87 |
| MYLK2 | 85366 | 100 |
| MYLK4 | 340156 | 100 |
| MYO3A | 53904 | 86 |
| MYO3B | 140469 | 100 |
| NDR1 | 11329 | 100 |
| NDR2 | 23012 | 75 |
| NEK1 | 4750 | 100 |
| NEK10 | 152110 | 84 |
| NEK11 | 79858 | 92 |
| NEK2 | 4751 | 100 |
| NEK3 | 4752 | 97 |
| NEK4 | 6787 | 99 |
| NEK5 | 341676 | 100 |
| NEK6 | 10783 | 100 |
| NEK7 | 140609 | 79 |
| NEK9 | 91754 | 78 |
| NIK | 9020 | 96 |
| NIM1 | 167359 | 77 |
| NLK | 51701 | 100 |
| OSR1 | 9943 | 97 |
| p38-alpha | 1432 | 90 |
| p38-beta | 5600 | 100 |
| p38-delta | 5603 | 100 |
| p38-gamma | 6300 | 58 |
| PAK1 | 5058 | 100 |
| PAK2 | 5062 | 100 |
| PAK3 | 5063 | 100 |
| PAK4 | 10298 | 100 |
| PAK6 | 56924 | 100 |
| PAK7 | 57144 | 94 |
| PCTK1 | 5127 | 100 |
| PCTK2 | 5128 | 100 |
| PCTK3 | 5129 | 82 |
| PDGFRA | 5156 | 100 |
| PDGFRB | 5159 | 89 |
| PDPK1 | 5170 | 86 |
| PFCDPK1(*P. falciparum*) | 812762 | 100 |
| PFPK5(*P. falciparum*) | 813841 | 100 |
| PFTAIRE2 | 65061 | 84 |
| PFTK1 | 5218 | 93 |
| PHKG1 | 5260 | 70 |
| PHKG2 | 5261 | 99 |
| PIK3C2B | 5287 | 100 |
| PIK3C2G | 5288 | 86 |
| PIK3CA | 5290 | 100 |
| PIK3CA(C420R) | 5290 | 96 |
| PIK3CA(E542K) | 5290 | 81 |
| PIK3CA(E545A) | 5290 | 95 |
| PIK3CA(E545K) | 5290 | 84 |
| PIK3CA(H1047L) | 5290 | 56 |
| PIK3CA(H1047Y) | 5290 | 100 |
| PIK3CA(I800L) | 5290 | 93 |
| PIK3CA(M1043I) | 5290 | 76 |
| PIK3CA(Q546K) | 5290 | 66 |
| PIK3CB | 5291 | 83 |
| PIK3CD | 5293 | 100 |
| PIK3CG | 5294 | 99 |
| PIK4CB | 5298 | 78 |
| PIM1 | 5292 | 100 |
| PIM2 | 11040 | 100 |
| PIM3 | 415116 | 100 |
| PIP5K1A | 8394 | 100 |
| PIP5K1C | 23396 | 100 |
| PIP5K2B | 8396 | 86 |
| PIP5K2C | 79837 | 100 |
| PKAC-alpha | 5566 | 91 |
| PKAC-beta | 5567 | 82 |
| PKMYT1 | 9088 | 100 |
| PKN1 | 5585 | 61 |
| PKN2 | 5586 | 100 |
| PKNB(*M. tuberculosis*) | 887072 | 100 |
| PLK1 | 5347 | 87 |
| PLK2 | 10769 | 90 |
| PLK3 | 1263 | 92 |
| PLK4 | 10733 | 100 |
| PRKCD | 5580 | 85 |
| PRKCE | 5581 | 75 |
| PRKCH | 5583 | 100 |
| PRKCI | 5584 | 100 |
| PRKCQ | 5588 | 76 |
| PRKD1 | 5587 | 88 |
| PRKD2 | 25865 | 91 |
| PRKD3 | 23683 | 97 |
| PRKG1 | 5592 | 90 |
| PRKG2 | 5593 | 100 |
| PRKR | 5610 | 100 |
| PRKX | 5613 | 75 |
| PRP4 | 8899 | 87 |
| PYK2 | 2185 | 100 |
| QSK | 23387 | 91 |
| RAF1 | 5894 | 100 |
| RET | 5979 | 88 |
| RET(M918T) | 5979 | 78 |
| RET(V804L) | 5979 | 89 |
| RET(V804M) | 5979 | 100 |
| RIOK1 | 83732 | 100 |
| RIOK2 | 55781 | 77 |

TABLE 4-continued

Data from profiling of Example 20 against a total of 456 kinases (of these 395 non-mutant kinases).

| KINOMEscan Gene Symbol | Entrez Gene ID | Example 20 % Ctrl @ 10 μM |
|---|---|---|
| RIOK3 | 8780 | 91 |
| RIPK1 | 8737 | 99 |
| RIPK2 | 8767 | 66 |
| RIPK4 | 54101 | 100 |
| RIPK5 | 25778 | 100 |
| ROCK1 | 6093 | 81 |
| ROCK2 | 9475 | 100 |
| ROS1 | 6098 | 89 |
| RPS6KA4(Kin.Dom.1-N-terminal) | 8986 | 93 |
| RPS6KA4(Kin.Dom.2-C-terminal) | 8986 | 88 |
| RPS6KA5(Kin.Dom.1-N-terminal) | 9252 | 100 |
| RPS6KA5(Kin.Dom.2-C-terminal) | 9252 | 100 |
| RSK1(Kin.Dom.1-N-terminal) | 6195 | 95 |
| RSK1(Kin.Dom.2-C-terminal) | 6195 | 86 |
| RSK2(Kin.Dom.1-N-terminal) | 6197 | 100 |
| RSK2(Kin.Dom.2-C-terminal) | 6197 | 100 |
| RSK3(Kin.Dom.1-N-terminal) | 6196 | 72 |
| RSK3(Kin.Dom.2-C-terminal) | 6196 | 79 |
| RSK4(Kin.Dom.1-N-terminal) | 27330 | 100 |
| RSK4(Kin.Dom.2-C-terminal) | 27330 | 75 |
| S6K1 | 6198 | 100 |
| SBK1 | 388228 | 91 |
| SGK | 6446 | 100 |
| SgK110 | 100130827 | 100 |
| SGK2 | 10110 | 100 |
| SGK3 | 23678 | 100 |
| SIK | 150094 | 100 |
| SIK2 | 23235 | 84 |
| SLK | 9748 | 95 |
| SNARK | 81788 | 100 |
| SNRK | 54861 | 100 |
| SRC | 6714 | 100 |
| SRMS | 6725 | 100 |
| SRPK1 | 6732 | 86 |
| SRPK2 | 6733 | 100 |
| SRPK3 | 26576 | 87 |
| STK16 | 8576 | 100 |
| STK33 | 65975 | 100 |
| STK35 | 140901 | 84 |
| STK36 | 27148 | 75 |
| STK39 | 27347 | 100 |
| SYK | 6850 | 90 |
| TAK1 | 6885 | 100 |
| TAOK1 | 57551 | 100 |
| TAOK2 | 9344 | 100 |
| TAOK3 | 51347 | 100 |
| TBK1 | 29110 | 91 |
| TEC | 7006 | 100 |
| TESK1 | 7016 | 78 |
| TGFBR1 | 7046 | 100 |
| TGFBR2 | 7048 | 100 |
| TIE1 | 7075 | 100 |
| TIE2 | 7010 | 100 |
| TLK1 | 9874 | 84 |
| TLK2 | 11011 | 94 |
| TNIK | 23043 | 100 |
| TNK1 | 8711 | 86 |
| TNK2 | 10188 | 93 |
| TNNI3K | 51086 | 85 |
| TRKA | 4914 | 100 |
| TRKB | 4915 | 90 |
| TRKC | 4916 | 93 |
| TRPM6 | 140803 | 83 |
| TSSK1B | 83942 | 100 |
| TTK | 7272 | 72 |
| TXK | 7294 | 71 |
| TYK2(JH1domain-catalytic) | 7297 | 100 |
| TYK2(JH2domain-pseudokinase) | 7297 | 100 |
| TYRO3 | 7301 | 56 |
| ULK1 | 8408 | 100 |
| ULK2 | 9706 | 100 |
| ULK3 | 25989 | 100 |
| VEGFR2 | 3791 | 100 |
| VRK2 | 7444 | 100 |
| WEE1 | 7465 | 100 |
| WEE2 | 494551 | 100 |
| WNK1 | 65125 | 100 |
| WNK3 | 65267 | 100 |
| YANK1 | 202374 | 100 |
| YANK2 | 55351 | 100 |
| YANK3 | 282974 | 67 |
| YES | 7525 | 90 |
| YSK1 | 10494 | 100 |
| YSK4 | 80122 | 100 |
| ZAK | 51776 | 78 |
| ZAP70 | 7535 | 88 |

Proliferation Assay:

Cultivated tumor cells (cells were ordered from ATCC, except HeLa-MaTu and HeLa-MaTu-ADR, which were ordered from EPO-GmbH, Berlin) were plated at a density of 1000 to 5000 cells/well, depending on the growth rate of the respective cell line, in a 96-well multititer plate in 200 μL of their respective growth medium supplemented 10% fetal calf serum. After 24 hours, the cells of one plate (zero-point plate) were stained with crystal violet (see below), while the medium of the other plates was replaced by fresh culture medium (200 μl), to which the test substances were added in various concentrations (0 μM, as well as in the range of 0.001-10 μM; the final concentration of the solvent dimethyl sulfoxide was 0.5%). The cells were incubated for 4 days in the presence of test substances. Cell proliferation was determined by staining the cells with crystal violet: the cells were fixed by adding 20 μl/measuring point of an 11% glutaric aldehyde solution for 15 minutes at room temperature. After three washing cycles of the fixed cells with water, the plates were dried at room temperature. The cells were stained by adding 100 μl/measuring point of a 0.1% crystal violet solution (pH 3.0). After three washing cycles of the stained cells with water, the plates were dried at room temperature. The dye was dissolved by adding 100 μl/measuring point of a 10% acetic acid solution. Absorption was determined by photometry at a wavelength of 595 nm. The change of cell number, in percent, was calculated by normalization of the measured values to the absorption values of the zero-point plate (=0%) and the absorption of the untreated (0 μm) cells (=100%). The $IC_{50}$ values were determined by means of a 4 parameter fit.

TABLE 5

Compounds had been evaluated in the following cell lines, which exemplify the sub-indications listed

| Tumor indication | Cell line |
|---|---|
| Cervical cancer | HeLa |
|  | HeLa-MaTu-ADR |
| Non-small cell lung cancer (NSCLC) | NCI-H460 |
| Prostate cancer | DU145 |
| Colon cancer | Caco2 |
| Melanoma | B16F10 |

TABLE 6

Inhibition of proliferation of HeLa, HeLa-MaTu-ADR, NCI-H460, DU145, Caco-2 and B16F10 cells by compounds according to the present invention. All $IC_{50}$ (inhibitory concentration at 50% of maximal effect) values are indicated in [mol/L].

| Example No. | HeLa | HeLa-MaTu-ADR | NCI-H460 | DU145 | Caco2 | B16F10 |
|---|---|---|---|---|---|---|
| 1 | 8.8E−06 | | | | | |
| 2 | >1.0E−05 | | | | | |
| 3 | 7.7E−06 | | | | | |
| 4 | 3.2E−06 | 1.8E−06 | 2.0E−06 | 6.9E−06 | 2.4E−06 | 2.7E−06 |
| 5 | >1.0E−05 | | | | | |
| 6 | 3.2E−06 | 1.9E−06 | 2.1E−06 | 3.0E−06 | 2.3E−06 | 2.3E−06 |
| 7 | 3.0E−06 | | | | | |
| 8 | >1.0E−05 | | | | | |
| 9 | 2.4E−06 | | | | | |
| 10 | 7.2E−06 | | | | | |
| 11 | 3.7E−06 | | | | | |
| 12 | 9.5E−06 | | | | | |
| 13 | >1.0E−05 | | | | | |
| 14 | 1.0E−06 | | | | | |
| 15 | >1.0E−05 | | | | | |
| 16 | >1.0E−05 | | | | | |
| 17 | >1.0E−05 | | | | | |
| 18 | 7.5E−06 | | | | | |
| 19 | 2.5E−06 | 4.1E−07 | 1.5E−06 | 2.5E−06 | 9.7E−07 | 1.8E−06 |
| 20 | 1.1E−06 | 5.0E−07 | 4.4E−07 | 6.0E−07 | 5.5E−07 | 5.3E−07 |
| 21 | >1.0E−05 | | | | | |
| 22 | 1.3E−06 | 7.6E−07 | 7.9E−07 | 2.2E−06 | 1.6E−06 | 9.5E−07 |
| 23 | 1.8E−06 | 2.7E−06 | 2.2E−06 | 9.4E−06 | 2.4E−06 | 8.4E−06 |
| 24 | >1.0E−05 | | | | | |
| 25 | >1.0E−05 | | | | | |
| 26 | 4.4E−06 | | | | | |
| 27 | 2.0E−06 | 2.4E−07 | 2.2E−07 | 3.5E−07 | 4.5E−07 | 2.2E−07 |
| 28 | 1.6E−06 | 1.2E−07 | 9.9E−08 | 3.2E−07 | 2.1E−07 | 1.3E−07 |
| 29 | 2.8E−06 | | | | | |
| 30 | 1.6E−06 | | | | | |
| 31 | >1.0E−05 | | | | | |
| 32 | 8.3E−06 | | | | | |
| 33 | 2.2E−06 | 8.5E−07 | 1.2E−06 | 1.3E−06 | 7.4E−07 | 1.4E−06 |
| 34 | 6.7E−06 | | | | | |
| 35 | 1.2E−06 | 6.1E−07 | 1.6E−06 | 2.4E−06 | 1.6E−06 | 1.7E−06 |
| 36 | 9.9E−06 | | | | | |
| 37 | >1.0E−05 | | | | | |
| 38 | 5.3E−06 | | | | | |
| 39 | 6.7E−06 | | | | | |
| 40 | 5.6E−07 | 3.3E−07 | 2.9E−07 | 5.9E−07 | 4.7E−07 | 4.4E−07 |
| 41 | 1.3E−06 | 6.4E−07 | 3.5E−07 | 7.5E−07 | 1.7E−07 | 6.8E−07 |
| 42 | 1.2E−06 | | | | | |
| 43 | 4.2E−07 | 2.6E−07 | 1.3E−07 | 4.2E−07 | 3.8E−07 | 2.3E−07 |
| 44 | 2.4E−06 | | | | | |
| 45 | 3.4E−07 | 3.0E−07 | 1.0E−07 | 4.6E−07 | 3.8E−07 | 1.9E−07 |
| 46 | 1.3E−07 | 1.1E−07 | 8.6E−08 | 1.8E−07 | 1.1E−07 | 1.2E−07 |
| 47 | 3.7E−07 | 8.3E−08 | 1.8E−07 | 4.9E−08 | 3.6E−07 | 1.1E−07 |
| 48 | 5.8E−07 | 3.5E−07 | 2.1E−07 | 6.0E−07 | 4.3E−07 | 4.3E−07 |
| 49 | 4.4E−06 | | | | | |
| 50 | 4.5E−07 | 2.1E−07 | 5.2E−07 | 4.1E−07 | 2.7E−07 | 3.0E−07 |
| 51 | 5.7E−07 | 3.7E−07 | 2.8E−07 | 1.6E−07 | 6.9E−08 | 4.7E−07 |
| 52 | 2.4E−07 | 1.3E−07 | 1.3E−07 | 3.1E−07 | 1.9E−07 | 2.3E−07 |
| 53 | 1.0E−06 | 3.1E−07 | 5.2E−07 | 9.8E−07 | 2.0E−07 | 2.2E−07 |
| 54 | 8.0E−07 | 6.5E−07 | 2.1E−07 | 1.2E−06 | 1.3E−06 | 8.6E−07 |
| 55 | 9.2E−07 | 1.4E−07 | 3.0E−07 | 3.9E−07 | 1.5E−07 | 3.8E−07 |
| 56 | 7.9E−07 | 3.7E−07 | 3.7E−07 | 5.4E−07 | 5.6E−07 | 4.7E−07 |
| 57 | 2.9E−06 | | | | | |
| 58 | 1.5E−06 | | | | | |
| 59 | 9.9E−07 | | | | | |
| 60 | 7.3E−07 | 2.4E−07 | 2.3E−07 | 4.3E−07 | 2.2E−07 | 2.5E−07 |
| 61 | 7.7E−06 | | | | | |
| 62 | 4.2E−07 | | 1.4E−07 | 2.9E−07 | 1.9E−07 | 1.4E−07 |
| 63 | 4.1E−06 | | | | | |

TABLE 6-continued

Inhibition of proliferation of HeLa, HeLa-MaTu-ADR, NCI-H460, DU145, Caco-2 and B16F10 cells by compounds according to the present invention. All $IC_{50}$ (inhibitory concentration at 50% of maximal effect) values are indicated in [mol/L].

| Example No. | HeLa | HeLa-MaTu-ADR | NCI-H460 | DU145 | Caco2 | B16F10 |
|---|---|---|---|---|---|---|
| 64 | 1.6E−06 | 2.7E−07 | 2.6E−07 | 4.7E−07 | 7.2E−07 | 4.7E−07 |
| 65 | 2.8E−06 | | | | | |
| 66 | 2.6E−06 | | | | | |
| 67 | 7.7E−07 | 1.8E−07 | 2.1E−07 | 3.2E−07 | 2.1E−07 | 1.6E−07 |
| 68 | 1.0E−06 | 3.2E−07 | 3.5E−07 | 5.7E−07 | 2.4E−07 | 3.3E−07 |
| 69 | 7.0E−06 | | | | | |
| 70 | 6.4E−06 | | | | | |
| 71 | 3.8E−07 | 2.3E−07 | 1.8E−07 | 4.3E−07 | 2.4E−07 | 2.2E−07 |
| 72 | 1.7E−06 | | | | | |
| 73 | 1.2E−06 | 1.0E−07 | 6.2E−07 | 5.1E−07 | 3.2E−07 | 3.9E−07 |
| 74 | 2.6E−07 | 1.3E−07 | 1.2E−07 | 1.9E−07 | 1.6E−07 | 1.7E−07 |
| 75 | 1.9E−06 | 5.3E−07 | 2.9E−06 | 2.9E−06 | 1.3E−06 | 3.0E−06 |
| 76 | 2.6E−06 | | | | | |
| 77 | 2.0E−07 | 9.4E−08 | 1.8E−07 | 2.8E−07 | 1.8E−07 | 2.2E−07 |
| 78 | 2.5E−06 | 1.1E−06 | 3.0E−06 | 3.0E−06 | 1.5E−06 | 2.0E−06 |
| 79 | 8.0E−07 | 3.5E−07 | 3.4E−07 | 6.5E−07 | 3.5E−07 | 5.1E−07 |
| 80 | 4.4E−06 | | | | | |
| 81 | 3.8E−07 | 2.3E−07 | 2.4E−07 | 6.8E−07 | 2.1E−07 | 2.0E−07 |
| 82 | 1.1E−07 | 1.3E−07 | 5.6E−08 | 2.7E−07 | 1.7E−07 | 1.4E−07 |
| 83 | 9.2E−07 | 3.7E−07 | 2.6E−07 | 7.4E−07 | 3.5E−07 | 2.5E−07 |
| 84 | 2.9E−07 | 3.3E−07 | 1.8E−07 | 8.4E−07 | 2.4E−07 | 2.9E−07 |
| 85 | 1.0E−06 | 3.6E−07 | 4.2E−07 | 7.0E−07 | 3.7E−07 | 5.0E−07 |
| 86 | 1.0E−06 | 2.6E−07 | 1.7E−07 | 5.1E−07 | 3.1E−07 | 3.2E−07 |
| 87 | 2.8E−06 | | | | | |
| 88 | 2.1E−06 | | | | | |
| 89 | 3.6E−06 | | | | | |
| 90 | 1.0E−05 | | | | | |
| 91 | 9.7E−06 | | | | | |
| 92 | 1.0E−05 | | | | | |
| 93 | 1.0E−05 | | | | | |
| 94 | 1.0E−05 | | | | | |
| 95 | 1.2E−06 | | | | | |
| 96 | 1.0E−05 | | | | | |
| 97 | 1.0E−05 | | | | | |
| 98 | 1.0E−05 | | | | | |
| 99 | 3.3E−06 | | | | | |
| 100 | 1.0E−05 | | | | | |
| 101 | 7.2E−06 | | | | | |
| 102 | 7.3E−06 | | | | | |
| 103 | 2.9E−06 | | | | | |
| 104 | 1.0E−05 | | | | | |
| 105 | 1.0E−05 | | | | | |
| 106 | 3.7E−06 | | | | | |
| 107 | 4.9E−06 | | | | | |
| 108 | 1.0E−05 | | | | | |
| 109 | 5.0E−06 | | | | | |
| 110 | 1.5E−06 | | | | | |
| 111 | 2.1E−06 | | | | | |
| 112 | 2.0E−06 | | | | | |
| 113 | 8.8E−07 | | | | | |
| 114 | 1.1E−06 | 6.9E−07 | 5.2E−07 | 1.3E−06 | 9.8E−07 | 1.2E−06 |
| 115 | 1.3E−06 | | | | | |
| 116 | 3.2E−06 | | | | | |
| 117 | 3.2E−06 | | | | | |
| 118 | 1.7E−06 | | | | | |
| 119 | 3.3E−06 | | | | | |
| 120 | 1.9E−06 | | | | | |
| 121 | 3.3E−06 | | | | | |
| 122 | 1.8E−06 | | | | | |

Thus the compounds of the present invention effectively inhibit the spindle assembly checkpoint and tumor cell proliferation and are therefore suitable for the treatment or prophylaxis of diseases of uncontrolled cell growth, proliferation and/or survival, inappropriate cellular immune responses, or inappropriate cellular inflammatory responses, particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The invention claimed is:
1. A compound of formula (I)

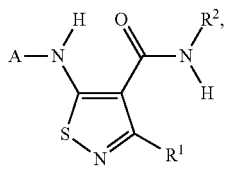

in which:
A represents a heteroaryl group selected from:

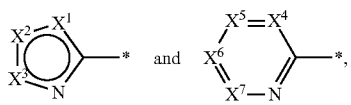

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, COORS, CONR$^4$R$^5$, NR$^4$R$^5$,
said phenyl and 5-membered heteroaryl being optionally substituted, one or two times, identically or differently, with a substituent selected from:
a halogen atom, or a $C_1$-$C_3$-alkyl-, or a $C_1$-$C_3$-alkoxy-group,
$R^1$ represents a $C_1$-$C_3$-alkyl-group,
$R^2$ represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkyloxy, hydroxy, a halogen atom, phenyl, phenyloxy,
said phenyl and phenyloxy group being optionally substituted, one or two times, identically or differently, with a substituent selected from:
a halogen atom, or a $C_1$-$C_3$-alkyl-, or a $C_1$-$C_3$-alkoxy-group, $R^3$ represents:
a hydrogen atom, or a group selected from $C_1$-$C_6$-alkyl,
$R^4$ represents:
a hydrogen atom, or a group selected from $C_1$-$C_6$-alkyl,
$R^5$ represents:
a hydrogen atom, or a group selected from $C_1$-$C_6$-alkyl,
or,
$R^4$ and $R^5$ together with the nitrogen to which they are attached represent:
a 5- to 6-membered heterocycloalkyl which optionally contains one further heteroatom selected from the group consisting of O, N and S,
or a stereoisomer, a tautomer, an N-oxide, a hydrate, a solvate, or a salt thereof, or a mixture of same.

2. The compound according to claim 1, wherein:
A represents a heteroaryl group selected from:

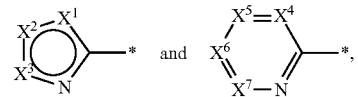

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, COORS, CONR$^4$R$^5$, NR$^4$R$^5$,
said phenyl and 5-membered heteroaryl being optionally substituted, one or two times, identically or differently, with a substituent selected from:
a halogen atom, or a $C_1$-$C_3$-alkyl-, or a $C_1$-$C_3$-alkoxy-group,
$R^1$ represents a methyl group,
$R^2$ represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkyloxy, hydroxy, a halogen atom, phenyl, phenyloxy,
said phenyl and phenyloxy group being optionally substituted, one or two times, identically or differently, with a substituent selected from:
a halogen atom, or a $C_1$-$C_3$-alkyl-, or a $C_1$-$C_3$-alkoxy-group,
$R^3$ represents:
a hydrogen atom, or a group selected from $C_1$-$C_6$-alkyl, $R^4$ represents:
a hydrogen atom, or a group selected from $C_1$-$C_6$-alkyl,
$R^5$ represents:
a hydrogen atom, or a group selected from $C_1$-$C_6$-alkyl, or,
$R^4$ and $R^5$ together with the nitrogen to which they are attached represent:
a 5- to 6-membered heterocycloalkyl which optionally contains one further heteroatom selected from the group consisting of O, N and S,
or a stereoisomer, a tautomer, an N-oxide, a hydrate, a solvate, or a salt thereof, or a mixture of same.

3. The compound according to claim 1, wherein:
A represents a heteroaryl group selected from:

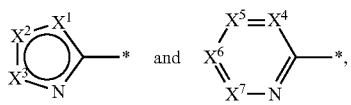

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, $C_3$-$C_6$-cycloalkyl, $C_3$-$C_6$-cycloalkyloxy, hydroxy, a halogen atom, cyano, phenyl, 5-membered heteroaryl, COORS, $CONR^4R^5$, $NR^4R^5$,
said phenyl and 5-membered heteroaryl being optionally substituted, one or two times, identically or differently, with a substituent selected from:
a halogen atom, or a $C_1$-$C_3$-alkyl-, or a $C_1$-$C_3$-alkoxy-group,
$R^1$ represents a methyl group,
$R^2$ represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-alkoxy, $C_3$-$C_6$-cycloalkyloxy, a halogen atom, phenyloxy,
said phenyloxy group being optionally substituted, one or two times, identically or differently, with a substituent selected from:
a halogen atom, or a $C_1$-$C_3$-alkoxy-group,
$R^3$ represents:
a hydrogen atom, or a group selected from $C_1$-$C_6$-alkyl,
$R^4$ represents:
a hydrogen atom, or a group selected from $C_1$-$C_6$-alkyl,
$R^5$ represents:
a hydrogen atom, or a group selected from $C_1$-$C_6$-alkyl, or,
$R^4$ and $R^5$ together with the nitrogen to which they are attached represent:
a 5- to 6-membered heterocycloalkyl which optionally contains one further heteroatom selected from the group consisting of O, N and S, or a stereoisomer, a tautomer, an N-oxide, a hydrate, a solvate, or a salt thereof, or a mixture of same.

4. The compound according to claim 1, wherein:
A represents a heteroaryl group selected from:

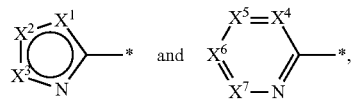

wherein one of $X^1$, $X^2$ and $X^3$ represents an N, O or S as ring atom and the others of $X^1$, $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^1$ and $X^2$ or $X^2$ and $X^3$ or $X^4$ and $X^5$ or $X^5$ and $X^6$ or $X^6$ and $X^7$ optionally form part of an additional 5-membered or 6-membered ring, which optionally contains one further heteroatom selected from the group consisting of O, N and S, and which ring is unsaturated or partially saturated, and
wherein * indicates the point of attachment of said groups with the rest of the molecule,
said heteroaryl group, which is monocyclic or bicyclic, being optionally substituted, one or two times, identically or differently, with a substituent selected from:
$C_1$-$C_6$-alkyl, $C_1$-$C_6$-haloalkyl, $C_1$-$C_6$-alkoxy, a halogen atom, cyano, phenyl, 5-membered heteroaryl, COORS, $CONR^4R^5$, $NR^4R^5$,
$R^1$ represents a methyl group,
$R^2$ represents a group selected from:
phenyl or pyridinyl,
said phenyl and pyridinyl being optionally substituted, one or two times, identically or differently, with a substituent selected from:
$C_1$-$C_6$-alkyl, $C_1$-$C_6$-alkoxy, $C_3$-$C_6$-cycloalkyloxy, a halogen atom, phenyloxy,
said phenyloxy group being optionally substituted, one or two times, identically or differently, with a substituent selected from:
a halogen atom, or a $C_1$-$C_3$-alkoxy-group,
$R^3$ represents:
a group selected from $C_1$-$C_6$-alkyl,
$R^4$ represents:
a hydrogen atom, or a group selected from $C_1$-$C_6$-alkyl,
$R^5$ represents:
a hydrogen atom, or a group selected from $C_1$-$C_6$-alkyl, or,
$R^4$ and $R^5$ together with the nitrogen to which they are attached represent:
a 5- to 6-membered heterocycloalkyl which 6-membered heterocycloalkyl contains one further heteroatom which is O,
or a stereoisomer, a tautomer, an N-oxide, a hydrate, a solvate, or a salt thereof, or a mixture of same.

5. The compound according to claim 1, wherein:
A represents a heteroaryl group selected from:

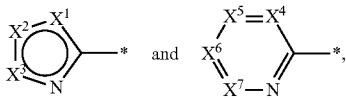

wherein $X^1$ represents an O or S as ring atom and $X^2$ and $X^3$ represent carbon as ring atoms, and
wherein $X^4$, $X^5$, $X^6$ and $X^7$ represent carbon as ring atoms or one of $X^4$, $X^5$, $X^6$ and $X^7$ represent an N atom, and the others of $X^4$, $X^5$, $X^6$ and $X^7$ represent carbon as ring atoms, and
wherein $X^2$ and $X^3$ or $X^4$ and $X^5$ or $X^6$ and $X^7$ optionally form part of an additional 5-membered or 6-membered ring, said 5-membered ring optionally containing one further heteroatom which is selected from the group consisting of N and S, and being unsaturated, and said 6-membered ring optionally containing one further heteroatom which is N, and being unsaturated,
wherein * indicates the point of attachment of said groups with the rest of the molecule,
said heteroaryl group, which is monocyclic or bicyclic, being optionally substituted, one or two times, identically or differently, with a substituent selected from:
a chlorine, a fluorine or a bromine atom, or a methyl, ethyl, trifluoromethyl, methoxy, cyano, phenyl, imidazol-1-yl, 1,3-oxazol-2-yl, pyrazol-1-yl, COORS, CONR⁴R⁵, NR⁴R⁵-group,
$R^1$ represents a methyl group,
$R^2$ represents a group selected from:
  phenyl or pyridin-3-yl,
    said phenyl and pyridinyl being optionally substituted, one or two times, identically or differently, with a substituent selected from:
      methyl, ethyl, methoxy, ethoxy, isopropoxy, cyclohexyloxy, a chlorine or a fluorine atom, phenyloxy,
      said phenyloxy group being optionally substituted, one or two times, identically or differently, with a substituent selected from:
        a fluorine atom, or methoxy,
$R^3$ represents a group selected from:
  methyl or ethyl,
$R^4$ represents:
  a hydrogen atom, or a methyl group,
$R^5$ represents:
  a hydrogen atom, or a methyl group, or an ethyl group, or,
$R^4$ and $R^5$ together with the nitrogen to which they are attached represent:
  a pyrrolidine ring, or a morpholine ring,
or a stereoisomer, a tautomer, an N-oxide, a hydrate, a solvate, or a salt thereof, or a mixture of same.

6. The compound according to claim 1, which is selected from the group consisting of:
N-(2-Ethylphenyl)-3-methyl-5-(pyrazin-2-ylamino)-1,2-thiazole-4-carboxamide;
N-(2-Ethylphenyl)-3-methyl-5-(pyrimidin-4-ylamino)-1,2-thiazole-4-carboxamide;
N-(2-Ethylphenyl)-3-methyl-5-{[3-(trifluoromethyl)pyridin-2-yl]amino}-1,2-thiazole-4-carboxamide;
5-[(4-Cyanopyridin-2-yl)amino]-N-(2-ethylphenyl)-3-methyl-1,2-thiazole-4-carboxamide;
N-(2-Ethylphenyl)-3-methyl-5-[(4-phenylpyrimidin-2-yl)amino]-1,2-thiazole-4-carboxamide;
5-[(2-Cyanopyrimidin-4-yl)amino]-N-(2-ethylphenyl)-3-methyl-1,2-thiazole-4-carboxamide;
5-[(5-Cyanopyridin-2-yl)amino]-N-(2-ethylphenyl)-3-methyl-1,2-thiazole-4-carboxamide;
5-[(3-Cyanopyridin-2-yl)amino]-N-(2-ethylphenyl)-3-methyl-1,2-thiazole-4-carboxamide;
N-(2-Ethylphenyl)-5-{[6-(1H-imidazol-1-yl)pyrimidin-4-yl]amino}-3-methyl-1,2-thiazole-4-carboxamide;
N-(2-Ethylphenyl)-3-methyl-5-(quinazolin-4-ylamino)-1,2-thiazole-4-carboxamide;
5-(1,3-Benzoxazol-2-ylamino)-N-(2-ethylphenyl)-3-methyl-1,2-thiazole-4-carboxamide;
N-(2-Ethylphenyl)-3-methyl-5-(thieno[2,3-d]pyrimidin-4-ylamino)-1,2-thiazole-4-carboxamide;
N-(2-Ethylphenyl)-3-methyl-5-(thieno[3,2-d]pyrimidin-4-ylamino)-1,2-thiazole-4-carboxamide;
5-(1,3-Benzothiazol-2-ylamino)-N-(2-ethylphenyl)-3-methyl-1,2-thiazole-4-carboxamide;
N-(2-Ethylphenyl)-3-methyl-5-{[6-(methylamino)pyrimidin-4-yl]amino}-1,2-thiazole-4-carboxamide;
N-(2-Ethylphenyl)-5-[(4-methoxypyrimidin-2-yl)amino]-3-methyl-1,2-thiazole-4-carboxamide;
N-(2-Ethylphenyl)-5-[(4-ethylpyrimidin-2-yl)amino]-3-methyl-1,2-thiazole-4-carboxamide;
N-(2-Ethylphenyl)-3-methyl-5-{[4-(trifluoromethyl)pyridin-2-yl]amino}-1,2-thiazole-4-carboxamide;
N-(2-Ethylphenyl)-3-methyl-5-(quinoxalin-2-ylamino)-1,2-thiazole-4-carboxamide;
N-(2-Ethylphenyl)-5-[(6-fluoroquinoxalin-2-yl)amino]-3-methyl-1,2-thiazole-4-carboxamide;
N-(2-Ethylphenyl)-3-methyl-5-[(3-methylquinoxalin-2-yl)amino]-1,2-thiazole-4-carboxamide;
N-(6-methoxypyridin-3-yl)-3-methyl-5-[(8-methylquinoxalin-2-yl)amino]-1,2-thiazole-4-carboxamide;
5-[(6-Chloroquinoxalin-2-yl)amino]-N-(6-methoxypyridin-3-yl)-3-methyl-1,2-thiazole-4-carboxamide;
5-[(3-Cyanopyrazin-2-yl)amino]-N-(6-methoxypyridin-3-yl)-3-methyl-1,2-thiazole-4-carboxamide;
5-[(4-Cyanopyridin-2-yl)amino]-N-(6-methoxypyridin-3-yl)-3-methyl-1,2-thiazole-4-carboxamide;
Ethyl 2-({4-[(2-ethylphenyl)carbamoyl]-3-methyl-1,2-thiazol-5-yl}amino)-4-methyl-1,3-thiazole-5-carboxylate;
5-[(4-Cyanopyridin-2-yl)amino]-N-(3,4-difluorophenyl)-3-methyl-1,2-thiazole-4-carboxamide;
5-[(5-Cyanopyridin-2-yl)amino]-N-(3,4-difluorophenyl)-3-methyl-1,2-thiazole-4-carboxamide;
Ethyl 2-({4-[(6-methoxypyridin-3-yl)carbamoyl]-3-methyl-1,2-thiazol-5-yl}amino)-1,3-thiazole-5-carboxylate;
Ethyl 2-({4-[(6-methoxypyridin-3-yl)carbamoyl]-3-methyl-1,2-thiazol-5-yl}amino)-4-methyl-1,3-thiazole-5-carboxylate;
Methyl 6-({4-[(6-methoxypyridin-3-yl)carbamoyl]-3-methyl-1,2-thiazol-5-yl}amino)-nicotinate;
Methyl 5-({4-[(6-methoxypyridin-3-yl)carbamoyl]-3-methyl-1,2-thiazol-5-yl}amino)-pyrazine-2-carboxylate;
N-(2-Ethylphenyl)-3-methyl-5-[(8-methylquinoxalin-2-yl)amino]-1,2-thiazole-4-carboxamide;
5-[(3-Cyanopyrazin-2-yl)amino]-N-(2-ethylphenyl)-3-methyl-1,2-thiazole-4-carboxamide;
N-(2-Ethylphenyl)-3-methyl-5-[(2-methylquinazolin-4-yl)amino]-1,2-thiazole-4-carboxamide;

5-[(3-Cyanopyridin-2-yl)amino]-N-(6-methoxypyridin-3-yl)-3-methyl-1,2-thiazole-4-carboxamide;
5-[(6-Cyanopyridin-2-yl)amino]-N-(6-methoxypyridin-3-yl)-3-methyl-1,2-thiazole-4-carboxamide;
N-(2-Ethylphenyl)-3-methyl-5-[(2-methylthieno[2,3-d]pyrimidin-4-yl)amino]-1,2-thiazole-4-carboxamide;
5-[(5-Cyanopyridin-2-yl)amino]-N-(6-methoxypyridin-3-yl)-3-methyl-1,2-thiazole-4-carboxamide;
N-(4-Chloro-3-fluorophenyl)-3-methyl-5-(quinoxalin-2-ylamino)-1,2-thiazole-4-carboxamide;
5-[(7-Chloroquinoxalin-2-yl)amino]-N-(2-ethylphenyl)-3-methyl-1,2-thiazole-4-carboxamide;
5-[(7-Chloroquinoxalin-2-yl)amino]-N-(6-methoxypyridin-3-yl)-3-methyl-1,2-thiazole-4-carboxamide;
5-[(5,6-Difluoroquinoxalin-2-yl)amino]-N-(6-methoxypyridin-3-yl)-3-methyl-1,2-thiazole-4-carboxamide;
5-[(7-Fluoroquinoxalin-2-yl)amino]-N-(6-methoxypyridin-3-yl)-3-methyl-1,2-thiazole-4-carboxamide;
N-(6-Methoxypyridin-3-yl)-3-methyl-5-{[6-(trifluoromethyl)quinoxalin-2-yl]amino}-1,2-thiazole-4-carboxamide;
N-(3,4-Difluorophenyl)-5-[(6-fluoroquinoxalin-2-yl)amino]-3-methyl-1,2-thiazole-4-carboxamide;
N-(3-Fluoro-4-methoxyphenyl)-3-methyl-5-{[4-(trifluoromethyl)-1,3-benzothiazol-2-yl]amino}-1,2-thiazole-4-carboxamide;
N-(6-Methoxypyridin-3-yl)-3-methyl-5-{[4-(trifluoromethyl)-1,3-benzothiazol-2-yl]-amino}-1,2-thiazole-4-carboxamide;
N-(3,4-Difluorophenyl)-5-{[5-(dimethylcarbamoyl)-1,3-thiazol-2-yl]amino}-3-methyl-1,2-thiazole-4-carboxamide;
N-(3,4-Difluorophenyl)-3-methyl-5-(quinoxalin-2-ylamino)-1,2-thiazole-4-carboxamide;
N-(3,4-Difluorophenyl)-3-methyl-5-{[4-(trifluoromethyl)-1,3-benzothiazol-2-yl]amino}-1,2-thiazole-4-carboxamide;
N-(4-Chloro-3-fluorophenyl)-5-[(5-cyanopyridin-2-yl)amino]-3-methyl-1,2-thiazole-4-carboxamide;
N-(4-Chloro-3-fluorophenyl)-3-methyl-5-{[4-(trifluoromethyl)-1,3-benzothiazol-2-yl]amino}-1,2-thiazole-4-carboxamide;
N-(4-Chloro-3-fluorophenyl)-5-[(4-cyanopyridin-2-yl)amino]-3-methyl-1,2-thiazole-4-carboxamide;
Ethyl 5-({4-[(3,4-difluorophenyl)carbamoyl]-3-methyl-1,2-thiazol-5-yl}amino)-pyrazolo[1,5-a]pyrimidine-3-carboxylate;
N-(4-Chloro-3-fluorophenyl)-3-methyl-5-(pyrazin-2-ylamino)-1,2-thiazole-4-carboxamide;
N-(3,4-Difluorophenyl)-3-methyl-5-(pyrazolo[1,5-a]pyrimidin-5-ylamino)-1,2-thiazole-4-carboxamide;
N-(3,4-Difluorophenyl)-3-methyl-5-{[7-(trifluoromethyl)[1,3]thiazolo[5,4-b]pyridin-2-yl]amino}-1,2-thiazole-4-carboxamide;
Methyl 5-({4-[(3,4-difluorophenyl)carbamoyl]-3-methyl-1,2-thiazol-5-yl}amino)-pyrazine-2-carboxylate;
N-(3,4-Difluorophenyl)-3-methyl-5-{[6-(trifluoromethyl)quinoxalin-2-yl]amino}-1,2-thiazole-4-carboxamide;
N-(3,4-Dichlorophenyl)-3-methyl-5-{[6-(trifluoromethyl)quinoxalin-2-yl]amino}-1,2-thiazole-4-carboxamide;
5-[(5-Cyanopyridin-2-yl)amino]-N-(3,4-dichlorophenyl)-3-methyl-1,2-thiazole-4-carboxamide;
N-(4-Chloro-3-fluorophenyl)-3-methyl-5-{[6-(1,3-oxazol-2-yl)pyrazin-2-yl]amino}-1,2-thiazole-4-carboxamide;
N-(3,4-Difluorophenyl)-3-methyl-5-{[6-(1H-pyrazol-1-yl)pyrazin-2-yl]amino}-1,2-thiazole-4-carboxamide;
N-(3,4-Difluorophenyl)-3-methyl-5-(pyrazin-2-ylamino)-1,2-thiazole-4-carboxamide;
Methyl 6-({4-[(3,4-difluorophenyl)carbamoyl]-3-methyl-1,2-thiazol-5-yl}amino)-pyrazine-2-carboxylate;
N-(4-Chloro-3-fluorophenyl)-3-methyl-5-{[6-(1H-pyrazol-1-yl)pyrazin-2-yl]amino}-1,2-thiazole-4-carboxamide;
N-(4-Chloro-3-fluorophenyl)-3-methyl-5-{[6-(trifluoromethyl)quinoxalin-2-yl]amino}-1,2-thiazole-4-carboxamide;
N-(4-Chloro-3-fluorophenyl)-3-methyl-5-[(6-methylpyrazin-2-yl)amino]-1,2-thiazole-4-carboxamide;
6-({4-[(3,4-Difluorophenyl)carbamoyl]-3-methyl-1,2-thiazol-5-yl}amino)-N-methylpyrazine-2-carboxamide;
5-[(6-Chloropyrazin-2-yl)amino]-N-(3,4-difluorophenyl)-3-methyl-1,2-thiazole-4-carboxamide;
N-(3,4-Difluorophenyl)-5-[(6-methoxypyrazin-2-yl)amino]-3-methyl-1,2-thiazole-4-carboxamide;
6-({4-[(3,4-Difluorophenyl)carbamoyl]-3-methyl-1,2-thiazol-5-yl}amino)-N-ethylpyrazine-2-carboxamide;
5-[(5-Chloropyrazin-2-yl)amino]-N-(3,4-difluorophenyl)-3-methyl-1,2-thiazole-4-carboxamide;
5-({4-[(3,4-Difluorophenyl)carbamoyl]-3-methyl-1,2-thiazol-5-yl}amino)-N-methylpyrazine-2-carboxamide;
N-(3,4-Difluorophenyl)-5-[(6-ethylpyrazin-2-yl)amino]-3-methyl-1,2-thiazole-4-carboxamide;
5-[(5-Bromopyrazin-2-yl)amino]-N-(3,4-difluorophenyl)-3-methyl-1,2-thiazole-4-carboxamide;
N-(3,4-Difluorophenyl)-5-{[6-(ethylamino)pyrazin-2-yl]amino}-3-methyl-1,2-thiazole-4-carboxamide;
N-(3,4-Difluorophenyl)-5-[(5-ethylpyrazin-2-yl)amino]-3-methyl-1,2-thiazole-4-carboxamide;
6-({4-[(3,4-Difluorophenyl)carbamoyl]-3-methyl-1,2-thiazol-5-yl}amino)-N-methylpyridazine-3-carboxamide;
N-(3,4-Difluorophenyl)-3-methyl-5-{[5-(trifluoromethyl)pyrazin-2-yl]amino}-1,2-thiazole-4-carboxamide;
N-(3,4-Difluorophenyl)-3-methyl-5-{[6-(trifluoromethyl)pyrazin-2-yl]amino}-1,2-thiazole-4-carboxamide;
N-(3,4-Difluorophenyl)-3-methyl-5-{[6-(trifluoromethyl)pyridazin-3-yl]amino}-1,2-thiazole-4-carboxamide;
N-(6-methoxypyridin-3-yl)-3-methyl-5-{[6-(trifluoromethyl)pyrazin-2-yl]amino}-1,2-thiazole-4-carboxamide;
N-(6-methoxypyridin-3-yl)-3-methyl-5-{[5-(trifluoromethyl)pyrazin-2-yl]amino}-1,2-thiazole-4-carboxamide;
5-[(6-Chloroquinoxalin-2-yl)amino]-N-(2-ethylphenyl)-3-methyl-1,2-thiazole-4-carboxamide;
5-[(6-Methoxy-1,3-benzothiazol-2-yl)amino]-N-(6-methoxypyridin-3-yl)-3-methyl-1,2-thiazole-4-carboxamide;
5-[(6-Fluoro-1,3-benzothiazol-2-yl)amino]-N-(6-methoxypyridin-3-yl)-3-methyl-1,2-thiazole-4-carboxamide;
N-(6-Methoxypyridin-3-yl)-3-methyl-5-([1,3]thiazolo[5,4-b]pyridin-2-ylamino)-1,2-thiazole-4-carboxamide;
N-(6-Methoxypyridin-3-yl)-3-methyl-5-[(6-methyl-1,3-benzothiazol-2-yl)amino]-1,2-thiazole-4-carboxamide;
Methyl 2-({4-[(2-ethylphenyl)carbamoyl]-3-methyl-1,2-thiazol-5-yl}amino)-1,3-oxazole-4-carboxylate;
Ethyl 2-({4-[(2-ethylphenyl)-carbamoyl]-3-methyl-1,2-thiazol-5-yl}amino)-1,3-thiazole-5-carboxylate;

N-(3-Fluoro-4-methoxyphenyl)-3-methyl-5-{[5-(morpholin-4-ylcarbonyl)-1,3-thiazol-2-yl]amino}-1,2-thiazole-4-carboxamide;
N-(6-Methoxypyridin-3-yl)-3-methyl-5-(quinoxalin-2-ylamino)-1,2-thiazole-4-carboxamide;
Ethyl 2-({4-[(4-chloro-3-fluoro-phenyl)carbamoyl]-3-methyl-1,2-thiazol-5-yl}amino)-4-methyl-1,3-thiazole-5-carboxylate;
Ethyl 2-({4-[(3,4-difluorophenyl)carbamoyl]-3-methyl-1,2-thiazol-5-yl}amino)-1,3-oxazole-5-carboxylate;
Methyl 2-({4-[(3,4-difluoro-phenyl)carbamoyl]-3-methyl-1,2-thiazol-5-yl}amino)-1,3-oxazole-5-carboxylate;
Ethyl 2-({4-[(3,4-difluoro-phenyl)carbamoyl]-3-methyl-1,2-thiazol-5-yl}amino)-1,3-oxazole-4-carboxylate;
N-(3,4-Difluorophenyl)-5-{[4-(ethylcarbamoyl)-1,3-thiazol-2-yl]amino}-3-methyl-1,2-thiazole-4-carboxamide;
Ethyl 2-({4-[(6-methoxypyridin-3-yl)carbamoyl]-3-methyl-1,2-thiazol-5-yl}amino)-1,3-oxazole-4-carboxylate;
Methyl 6-({4-[(6-methoxypyridin-3-yl)carbamoyl]-3-methyl-1,2-thiazol-5-yl}amino)-pyrazine-2-carboxylate;
N-(3,4-Dichlorophenyl)-3-methyl-5-{[4-(trifluoromethyl)-1,3-benzothiazol-2-yl]amino}-1,2-thiazole-4-carboxamide;
N-(4-Chloro-3-fluorophenyl)-3-methyl-5-{[7-(trifluoromethyl)[1,3]thiazolo[5,4-b]-pyridin-2-yl]amino}-1,2-thiazole-4-carboxamide;
6-({4-[(3,4-Difluorophenyl)-carbamoyl]-3-methyl-1,2-thiazol-5-yl}amino)-N,N-dimethylpyrazine-2-carboxamide;
N-(3,4-Difluorophenyl)-5-{[6-(dimethylamino)pyrazin-2-yl]amino}-3-methyl-1,2-thiazole-4-carboxamide;
N-(3,4-Difluorophenyl)-3-methyl-5-{[6-(pyrrolidin-1-ylcarbonyl)pyrazin-2-yl]amino}-1,2-thiazole-4-carboxamide;
N-(3,4-Difluorophenyl)-3-methyl-5-{[6-(morpholin-4-ylcarbonyl)pyrazin-2-yl]amino}-1,2-thiazole-4-carboxamide;
2-({4-[(3,4-Difluorophenyl)-carbamoyl]-3-methyl-1,2-thiazol-5-yl}amino)-N-methyliso-nicotinamide;
5-({4-[(3,4-Difluorophenyl)carbamoyl]-3-methyl-1,2-thiazol-5-yl}amino)-N,N-dimethylpyrazine-2-carboxamide;
5-[(5-Cyanopyridin-2-yl)amino]-N-(6-isopropoxypyridin-3-yl)-3-methyl-1,2-thiazole-4-carboxamide;
5-[(4-Cyanopyridin-2-yl)amino]-3-methyl-N-(6-phenoxypyridin-3-yl)-1,2-thiazole-4-carboxamide;
3-Methyl-N-(6-phenoxypyridin-3-yl)-5-(quinoxalin-2-ylamino)-1,2-thiazole-4-carboxamide;
N-[6-(2,4-Difluorophenoxy)pyridin-3-yl]-3-methyl-5-(quinoxalin-2-ylamino)-1,2-thiazole-4-carboxamide;
5-[(4-Cyanopyridin-2-yl)amino]-N-[6-(2,4-difluorophenoxy)pyridin-3-yl]-3-methyl-1,2-thiazole-4-carboxamide;
N-[6-(Cyclohexyloxy)pyridin-3-yl]-3-methyl-5-(quinoxalin-2-ylamino)-1,2-thiazole-4-carboxamide;
N-[6-(4-Methoxyphenoxy)pyridin-3-yl]-3-methyl-5-(quinoxalin-2-ylamino)-1,2-thiazole-4-carboxamide;
5-[(4-Cyanopyridin-2-yl)amino]-N-[6-(4-methoxyphenoxy)pyridin-3-yl]-3-methyl-1,2-thiazole-4-carboxamide;
5-[(4-Cyanopyridin-2-yl)amino]-N-[6-(cyclohexyloxy)pyridin-3-yl]-3-methyl-1,2-thiazole-4-carboxamide;
N-(6-Ethoxypyridin-3-yl)-3-methyl-5-(quinoxalin-2-ylamino)-1,2-thiazole-4-carboxamide;
5-[(5-Cyanopyridin-2-yl)amino]-N-(6-methoxy-5-methylpyridin-3-yl)-3-methyl-1,2-thiazole-4-carboxamide;
N-(6-Methoxy-5-methylpyridin-3-yl)-3-methyl-5-(quinoxalin-2-ylamino)-1,2-thiazole-4-carboxamide; and
N-(6-Isopropoxypyridin-3-yl)-3-methyl-5-(quinoxalin-2-ylamino)-1,2-thiazole-4-carboxamide.

7. The compound according to claim 1, wherein:
A represents a heteroaryl group selected from:

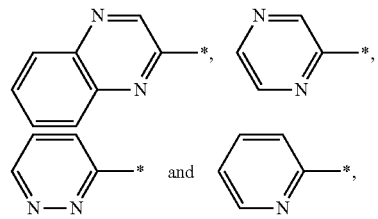

wherein * indicates the point of attachment of said groups with the rest of the molecule,
said heteroaryl group being substituted with a substituent selected from:
a trifluoromethyl, cyano, or a $CONR^4R^5$-group,
$R^1$ represents a methyl group,
$R^2$ represents a group selected from:
phenyl or pyridin-3-yl,
said phenyl and pyridinyl being substituted, one or two times, identically or differently, with a substituent selected from:
methoxy, a chlorine or a fluorine atom,
$R^4$ represents:
a hydrogen atom,
$R^5$ represents:
a methyl group,
or a stereoisomer, a tautomer, an N-oxide, a hydrate, a solvate, or a salt thereof, or a mixture of same.

8. The compound according to claim 1, wherein:
A represents a heteroaryl group selected from:

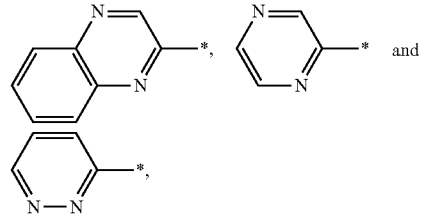

wherein * indicates the point of attachment of said groups with the rest of the molecule,
said heteroaryl group being substituted with a substituent selected from:
a trifluoromethyl, or a $CONR^4R^5$-group,
or,
A represents a:

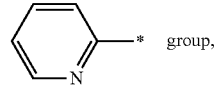 group, wherein * indicates the point of attachment of said group with the rest of the molecule,
said group being substituted with a cyano -group,
$R^1$ represents a methyl group,
$R^2$ represents a group selected from:
phenyl or pyridin-3-yl,
said phenyl being substituted, two times, identically or differently, with a substituent selected from:
a chlorine or a fluorine atom,
and,
said pyridinyl being substituted with a substituent selected from:
methoxy,
$R^4$ represents:
a hydrogen atom,
$R^5$ represents:
a methyl group,
or a stereoisomer, a tautomer, an N-oxide, a hydrate, a solvate, or a salt thereof, or a mixture of same.

9. The compound according to claim 1, which is selected from the group consisting of:
N-(3,4-Difluorophenyl)-3-methyl-5-{[6-(trifluoromethyl)quinoxalin-2-yl]amino}-1,2-thiazole-4-carboxamide;
5-({4-[(3,4-Difluorophenyl)carbamoyl]-3-methyl-1,2-thiazol-5-yl}amino)-N-methylpyrazine-2-carboxamide;
N-(3,4-Difluorophenyl)-3-methyl-5-{[5-(trifluoromethyl)pyrazin-2-yl]amino}-1,2-thiazole-4-carboxamide;
N-(6-methoxypyridin-3-yl)-3-methyl-5-{[6-(trifluoromethyl)pyrazin-2-yl]amino}-1,2-thiazole-4-carboxamide;
N-(3,4-Difluorophenyl)-3-methyl-5-{[6-(trifluoromethyl)pyridazin-3-yl]amino}-1,2-thiazole-4-carboxamide;
N-(6-methoxypyridin-3-yl)-3-methyl-5-{[5-(trifluoromethyl)pyrazin-2-yl]amino}-1,2-thiazole-4-carboxamide;
N-(4-Chloro-3-fluorophenyl)-5-[(4-cyanopyridin-2-yl)amino]-3-methyl-1,2-thiazole-4-carboxamide; and
N-(3,4-Dichlorophenyl)-3-methyl-5-{[6-(trifluoromethyl)quinoxalin-2-yl]amino}-1,2-thiazole-4-carboxamide.

10. A method of preparing a compound of formula (I) according to claim 1, said method comprising reacting an intermediate compound of formula (II):

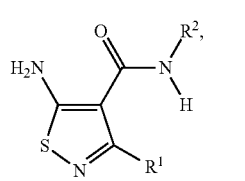
(II)

in which R1 and R2 are as defined in claim 1, with a compound of formula (III):

A-X    (III), in which A is as defined in claim 1, and X represents a halogen atom, or a perfluoroalkylsulfonate group, or a boronic acid, thereby giving a compound of formula (I):

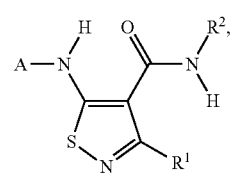
(I)

in which A, R1 and R2 are as defined in claim 1.

11. A pharmaceutical composition comprising a compound of formula (I), or a stereoisomer, a tautomer, an N-oxide, a hydrate, a solvate, or a pharmaceutically acceptable salt thereof, or a mixture of same, according to claim 1, and a pharmaceutically acceptable diluent or carrier.

12. A pharmaceutical combination comprising:
a compound of formula (I), or a stereoisomer, a tautomer, an N-oxide, a hydrate, a solvate, or a pharmaceutically acceptable salt thereof, according to claim 1, and
one or more chemotherapeutic anti-cancer agents.

13. A method for the treatment of a disease of uncontrolled cell growth, proliferation or survival, an inappropriate cellular immune response, or an inappropriate cellular inflammatory response, comprising administering to a patient in need thereof a therapeutically effective amount of a compound of formula (I), or a stereoisomer, a tautomer, an N-oxide, a hydrate, a solvate, or a pharmaceutically acceptable salt thereof, according to claim 1.

14. The method according to claim 13, wherein the disease of uncontrolled cell growth, proliferation or survival, inappropriate cellular immune response, or inappropriate cellular inflammatory response is a haematological tumour, a solid tumour or metastases thereof.

15. The method according to claim 14, wherein the haematological tumour, solid tumour or metastases thereof is selected from leukaemias and myelodysplastic syndrome, malignant lymphomas, head and neck tumours, brain tumours and brain metastases, tumours of the thorax, non-small cell and small cell lung tumours, gastrointestinal tumours, endocrine tumours, mammary and other gynaecological tumours, urological tumours, renal, bladder and prostate tumours, skin tumours, and sarcomas, and metastases thereof.

* * * * *